(12) United States Patent
de Vicente Fidalgo et al.

(10) Patent No.: US 8,618,103 B2
(45) Date of Patent: Dec. 31, 2013

(54) INHIBITORS OF JAK

(75) Inventors: Javier de Vicente Fidalgo, Glen Ridge, NJ (US); Johannes Cornelius Hermann, Jersey City, NJ (US); Remy Lemoine, San Francisco, CA (US); Hongju Li, Edison, NJ (US); Allen John Lovey, North Caldwell, NJ (US); Eric Brian Sjogren, Mountain View, CA (US); Michael Soth, Glen Rock, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 281 days.

(21) Appl. No.: 12/878,048

(22) Filed: Sep. 9, 2010

(65) Prior Publication Data

US 2011/0059118 A1   Mar. 10, 2011

Related U.S. Application Data

(60) Provisional application No. 61/241,095, filed on Sep. 10, 2009, provisional application No. 61/367,639, filed on Jul. 26, 2010.

(51) Int. Cl.
| | | |
|---|---|---|
| C07D 487/04 | (2006.01) | |
| A61K 31/4985 | (2006.01) | |
| C07D 239/04 | (2006.01) | |
| A61K 31/506 | (2006.01) | |
| A61P 29/00 | (2006.01) | |
| A61P 35/00 | (2006.01) | |

(52) U.S. Cl.
USPC ........... 514/249; 544/350; 544/295; 544/317; 544/324; 544/327; 544/117; 514/210.21; 514/234.2

(58) Field of Classification Search
USPC .......................................... 544/350; 514/249
See application file for complete search history.

(56) References Cited

U.S. PATENT DOCUMENTS

| 6,235,740 B1 | 5/2001 | Barrish et al. |
| 2005/0234064 A1 | 10/2005 | Bemis et al. |
| 2007/0135466 A1 | 6/2007 | Ledeboer et al. |

FOREIGN PATENT DOCUMENTS

| WO | 9945009 | 9/1999 |
| WO | 2007/070514 | 6/2007 |
| WO | 2008079965 | 7/2008 |
| WO | 2009/106441 | 9/2009 |
| WO | 2009152133 | 12/2009 |

OTHER PUBLICATIONS

Annu. Rev. Immunol. 16 (1998) pp. 293-322.
Leonard et al., (2000) J. Allergy Clin. Immunol. 105:877-888.
Oncogene 19 (2000) pp. 5662-5679.
Demoulin et al., (1996) Mol. Cell. Biol. 16 4710-6.
Jurlander et al. (1997) Blood 89:4146-52.
Kaneko et al. (1997) Clin. Exp. Immun. 109:185-193.
Nakamura et al., (1996) J. Biol. Chem 271:19483-8.
Kudlacz et al., (2004) Am. J. Transplant 4:51-57.
Changelian (2003) Science 302:875-878.
Suzuki et al., (2000) Blood 96 2172-2180.
Malaviya et al., (1999) Biochem. Biophys. Res. Commun. 257:807-813.
Malaviya et al. (1999) J. Biol. Chem. 274:27028-27038.
Kirken (2001) Transpl. Proc. 33:3268-3270.
Muller-Ladner et al., (2000) J. Immunol. 164:3894-3901.
Trieu et al., (2000) Biochem. Biophys. Res. Commun. 267:22-25.
Sudbeck et al. (1999) Clin. Cancer Res. 5:1569-1582.
Nielsen et al. (1997) Prac. Natl. Acad. Sci. USA 94:6764-6769.
Yu et al. (1997) J. Immunol. 159 5206-5210.
Catlett-Falcone et al. (1999) Immunity 10:105-115.
J. Immunal. 168 (2002) pp. 2475-2482.
Blood 103 (2004) pp. 2009-2018.
J. Investig. Med. 44(1996) pp. 304-311.
Curr. Opin. Cell Biol. 9 (1997) pp. 233-239.
(Taiwanese Search Report in Corres Appl 099130224 Jan. 15, 2013).
Internaitonal Search Report dated Nov. 11, 2010.

*Primary Examiner* — Susanna Moore

(57) ABSTRACT

The present invention relates to the use of novel compounds of Formula I,

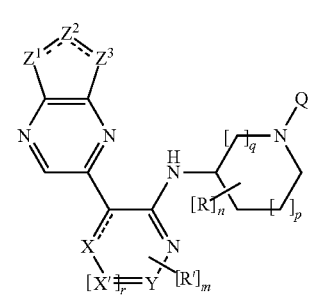

wherein the variables m, n, p, q, Q, r, R, R', X, X', Y, $Z^1$, $Z^2$, and $Z^3$ are defined as described herein, which inhibit JAK and are useful for the treatment of auto-immune and inflammatory diseases.

27 Claims, No Drawings

INHIBITORS OF JAK

CROSS-REFERENCE TO RELATED APPLICATIONS

This application is entitled to the benefit of U.S. provisional patent application Ser. No. 61/241,095 filed on Sep. 10, 2009, and 61/367,639 filed on Jul. 26, 2010, the disclosures of which are incorporated herein by reference.

FIELD OF THE INVENTION

The present invention relates to the use of novel compounds which are JAK inhibitors and selectively inhibit JAK3 and are useful for the treatment of auto-immune and inflammatory diseases.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Oncogene* 19 (2000), pp. 5662-5679), which indicates the difficulty of specifically targeting one element of the JAK-STAT pathway without interfering with other signal transduction pathways.

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

However, in contrast to the relatively ubiquitous expression of JAK1, JAK2 and Tyk2, JAK3 has a more restricted and regulated expression. Whereas some JAKs (JAK1, JAK2, Tyk2) are used by a variety of cytokine receptors, JAK3 is used only by cytokines that contain a yc in their receptor. JAK3, therefore, plays a role in cytokine signaling for cytokines which receptor was shown to date to use the common gamma chain; IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-alpha. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad.

Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (*J. Immunol.* 168 (2002), pp. 2475-2482). Because bone marrow transplants for SCID are curative (*Blood* 103 (2004), pp. 2009-2018), it seems unlikely that JAK3 has essential non-redundant functions in other tissues or organs. Hence, in contrast with other targets of immunosuppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ strains (*J. Investig. Med.* 44 (1996), pp. 304-311; *Curr. Opin. Cell Biol.* 9 (1997), pp. 233-239), the ubiquitous distribution of STATs and the fact that those molecules lack enzymatic activity that could be targeted with small-molecule inhibitors has contributed to their non-selection as key targets for immunosuppression.

In view of the numerous conditions that are contemplated to benefit by treatment involving modulation of the JAK pathways it is immediately apparent that new compounds that modulate JAK pathways and methods of using these compounds should provide substantial therapeutic benefits to a wide variety of patients. Provided herein are novel compounds for use in the treatment of conditions in which targeting of the JAK pathways or inhibition of JAK kinases, particularly JAK3, and are therapeutically useful for the treatment of auto-immune and inflammatory diseases.

SUMMARY OF THE INVENTION

The novel compounds provided herein selectively inhibit JAK3 and are useful for the treatment of auto-immune and inflammatory diseases. The compounds of the invention modulate the JAK pathways and are useful novel compounds for the treatment of auto-immune and inflammatory diseases, wherein preferred compounds selectively inhibit JAK3. For example, the compounds of the invention may inhibit JAK3, wherein preferred compounds are selective for JAK3 of the JAK kinases and are useful novel compounds for the treatment of auto-immune and inflammatory diseases. Furthermore, the compounds of the invention may inhibit JAK3 and JAK2, wherein preferred compounds are selective for JAK3 of the JAK kinases, and are useful novel compounds for the treatment of auto-immune and inflammatory diseases. Similarly, the compounds of the invention may inhibit JAK3 and JAK1, wherein preferred compounds are selective for JAK3 of the JAK kinases, and are useful novel compounds for the treatment of auto-immune and inflammatory diseases.

The application provides a compound of Formula I'

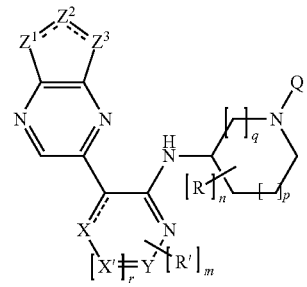

wherein:
R is lower alkyl;
n is 0 or 1;
$Z^1$ is CH, NH, or S;
$Z^2$ is CH or N;
$Z^3$ is $CR^1$, N, or $NR^2$;
  $R^1$ is H, lower alkyl, or halogen;
  $R^2$ is H or lower alkyl;
X is CH, CR', or N;
X' is CH, CR', or N;
  r is 0 or 1;
Y is CH, CR', or N;
R' is halogen, lower alkyl, OR", SR", or NR"R";
m is 0 or 1;
  R" is H or lower alkyl;
Q is H, S(=O)$_2$Q$^1$, C(=O)Q$^2$, C(=O)OQ$^3$, or Q$^4$;
  $Q^1$ is lower alkyl, cycloalkyl lower alkyl, or cycloalkyl, optionally substituted with one or more $Q^{1'}$;
    each $Q^{1'}$ is independently halogen, lower alkyl, cyano, or lower alkoxy;
  $Q^2$ is lower alkyl, cycloalkyl lower alkyl, or cycloalkyl, optionally substituted with one or more $Q^{2'}$;
    each $Q^{2'}$ is independently halogen, lower alkyl, or lower alkoxy;
  $Q^3$ is lower alkyl, cycloalkyl lower alkyl, or cycloalkyl, optionally substituted with one or more $Q^{3'}$;
    each $Q^{3'}$ is independently halogen, lower alkyl, or lower alkoxy;
  $Q^4$ is lower alkyl, cycloalkyl lower alkyl, or cycloalkyl, optionally substituted with one or more $Q^{4'}$;
    each $Q^{4'}$ is independently halogen, lower alkyl, or lower alkoxy;
p is 0, 1, or 2;
q is 1 or 2;
each ==== represents a single bond or a double bond; and
with the proviso that the bonds between $Z^1$ and $Z^2$ and $Z^2$ and $Z^3$ are not both double bonds and are not both single bonds;
or a pharmaceutically acceptable salt thereof.

The application provides a method for treating an inflammatory or autoimmune condition comprising administering to a patient in need thereof a therapeutically effective amount of the compound of any one of Formulae I-V, as described herein.

The application provides a pharmaceutical composition comprising the compound of any one of Formulae I-V, as described herein, admixed with at least one pharmaceutically acceptable carrier, excipient or diluent.

The application provides a use of the compound of any one of Formulae I-V, as described herein, in the manufacture of a medicament for the treatment of an inflammatory disorder.

The application provides a use of the compound of any one of Formulae I-V, as described herein, in the manufacture of a medicament for the treatment of a metabolic disorder.

DETAILED DESCRIPTION OF THE INVENTION

The application provides a compound of Formula I

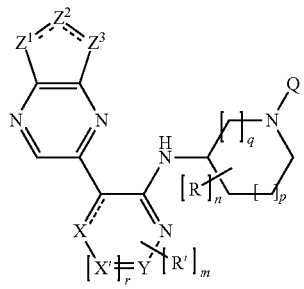

I wherein:
R is lower alkyl, lower haloalkyl, lower alkoxy, hydroxy lower alkyl, hydroxy, or halogen;
n is 0 or 1;
$Z^1$ is CH, NH, or S;
$Z^2$ is CH or N;
$Z^3$ is $CR^1$, N, or $NR^2$;
$R^1$ is H, lower alkyl, cycloalkyl, cyano, cyano lower alkyl, or halogen;
$R^2$ is H or lower alkyl;
X is CH, CR', or N;
X' is CH, CR', or N;
r is 0 or 1;
Y is CH, CR', or N;
R' is $R'^a$ or $R'^b$;
   $R'^a$ is halogen or cyano;
   $R'^b$ is lower alkyl, cycloalkyl, heterocycloalkyl, OR", SR", $S(=O)_2R"$, or NR"R", optionally substituted with one or more $R'^c$;
      $R'^c$ is hydroxy, halogen, oxo, cyano, lower alkyl, cycloalkyl, heterocycloalkyl, heteroaryl, carboxy lower alkyl, amino, amino carboxy lower alkyl, lower alkyl amino, lower dialkyl amino, lower haloalkyl, or lower alkoxy;
m is 0 or 1;
R" is H, lower alkyl, hydroxy lower alkyl, heteroaryl, or lower alkoxy;
Q is H, $S(=O)_2Q^1$, $C(=O)Q^2$, $C(=O)OQ^3$, or $Q^4$;
   $Q^1$ is lower alkyl, cycloalkyl lower alkyl, lower alkyl amino, lower dialkyl amino, or cycloalkyl, optionally substituted with one or more $Q^{1'}$;
      each $Q^{1'}$ is independently halogen, lower alkyl, cyano, or lower alkoxy;
   $Q^2$ is lower alkyl, cycloalkyl lower alkyl, or cycloalkyl, optionally substituted with one or more $Q^{2'}$;
      each $Q^{2'}$ is independently halogen, lower alkyl, cyano, or lower alkoxy;
   $Q^3$ is lower alkyl, cycloalkyl lower alkyl, or cycloalkyl, optionally substituted with one or more $Q^{3'}$;
      each $Q^{3'}$ is independently halogen, lower alkyl, or lower alkoxy;
   $Q^4$ is lower alkyl, cycloalkyl lower alkyl, heterocycloalkyl, or cycloalkyl, optionally substituted with one or more $Q^{4'}$;
      each $Q^{4'}$ is independently halogen, cyano, cyano lower alkyl, lower alkyl, or lower alkoxy;
p is 0, 1, or 2;
q is 1 or 2;
each ═══ represents a single bond or a double bond; and with the proviso that the bonds between $Z^1$ and $Z^2$ and $Z^2$ and $Z^3$ are not both double bonds and are not both single bonds;
or a pharmaceutically acceptable salt thereof.

In one variation, the above compound has the formula II


II wherein:
R is lower alkyl;
n is 0 or 1;
$Z^3$ is $CR^1$, N, or $NR^2$;
$R^1$ is H, lower alkyl, or halogen;
$R^2$ is H or lower alkyl;
X is CH, CR', or N;
r is 0 or 1;
Y is CH, CR', or N;
R' is $R'^a$ or $R'^b$;
   $R'^a$ is halogen or cyano;
   $R'^b$ is lower alkyl, cycloalkyl, heterocycloalkyl, OR", SR", $S(=O)_2R"$, or NR"R", optionally substituted with one or more $R'^c$;
      $R'^c$ is hydroxy, halogen, oxo, cyano, lower alkyl, cycloalkyl, heterocycloalkyl, heteroaryl, carboxy lower alkyl, amino, amino carboxy lower alkyl, lower alkyl amino, lower dialkyl amino, lower haloalkyl, or lower alkoxy;
m is 0 or 1;
R" is H, lower alkyl, hydroxy lower alkyl, heteroaryl, or lower alkoxy;
Q is H, $S(=O)_2Q^1$, $C(=O)Q^2$, $C(=O)OQ^3$, or $Q^4$;
   Q is H, $S(=O)_2Q^1$, $C(=O)Q^2$, $C(=O)OQ^3$, or $Q^4$;
   $Q^1$ is lower alkyl, cycloalkyl lower alkyl, lower alkyl amino, lower dialkyl amino, or cycloalkyl, optionally substituted with one or more $Q^{1'}$;
      each $Q^{1'}$ is independently halogen, lower alkyl, cyano, or lower alkoxy;
   $Q^2$ is lower alkyl, cycloalkyl lower alkyl, or cycloalkyl, optionally substituted with one or more $Q^{2'}$;
      each $Q^{2'}$ is independently halogen, lower alkyl, cyano, or lower alkoxy;
   $Q^3$ is lower alkyl, cycloalkyl lower alkyl, or cycloalkyl, optionally substituted with one or more $Q^{3'}$;
      each $Q^{3'}$ is independently halogen, lower alkyl, or lower alkoxy;
   $Q^4$ is lower alkyl, cycloalkyl lower alkyl, heterocycloalkyl, or cycloalkyl, optionally substituted with one or more $Q^{4'}$;
      each $Q^{4'}$ is independently halogen, cyano, cyano lower alkyl, lower alkyl, or lower alkoxy;
p is 0, 1, or 2;
q is 1 or 2; and
or a pharmaceutically acceptable salt thereof.

In one variation of Formula II, $Z^3$ is CH.
In one variation of Formula II, $Z^3$ is CH.
In one variation of Formula II, X is CH and Y is CH.
In one variation of Formula II, $Z^3$ is CH, X is CH, and Y is CH.
In one variation of Formula II, m is 0 and n is 0.
In one variation of Formula II, m is 0, n is 0, X is CH, and Y is CH.
In one variation of Formula II, m is 0, n is 0, and $Z^3$ is CH.
In one variation of Formula II, m is 0, n is 0, $Z^3$ is CH, X is CH, and Y is CH.
In one variation of Formula II, p is 1 and q is 1.
In one variation of Formula II, p is 1, q is 1, and $Z^3$ is CH.
In one variation of Formula II, p is 1, q is 1, X is CH, and Y is CH.
In one variation of Formula II, p is 1, q is 1, $Z^3$ is CH, X is CH, and Y is CH.
In one variation of Formula II, p is 1, q is 1, m is 0, and n is 0.
In one variation of Formula II, p is 1, q is 1, m is 0, n is 0, and $Z^3$ is CH.
In one variation of Formula II, p is 1, q is 1, m is 0, n is 0, X is CH, and Y is CH.
In one variation of Formula II, p is 1, q is 1, m is 0, n is 0, $Z^3$ is CH, X is CH, and Y is CH.
In one variation of Formula II, Q is $S(=O)_2Q^1$.
In one variation of Formula II, p is 1, q is 1, and Q is $S(=O)_2Q^1$.
In one variation of Formula II, p is 1, q is 1, Q is $S(=O)_2Q^1$, X is CH, and Y is CH.
In one variation of Formula II, p is 1, q is 1, Q is $S(=O)_2Q^1$ and $Z^3$ is CH.
In one variation of Formula II, p is 1, q is 1, Q is $S(=O)_2Q^1$, X is CH, and Y is CH, and $Z^3$ is CH.
In one variation of Formula II, Q is $S(=O)_2Q^1$ and $Q^1$ is lower alkyl.
In one variation of Formula II, p is 1, q is 1, Q is $S(=O)_2Q^1$, and $Q^1$ is lower alkyl.
In one variation of Formula II, p is 1, q is 1, Q is $S(=O)_2Q^1$, X is CH, Y is CH, and $Q^1$ is lower alkyl.
In one variation of Formula II, p is 1, q is 1, Q is $S(=O)_2Q^1$, $Z^3$ is CH, and $Q^1$ is lower alkyl.
In one variation of Formula II, p is 1, q is 1, Q is $S(=O)_2Q^1$, X is CH, Y is CH, $Z^3$ is CH, and $Q^1$ is lower alkyl.
In one variation of Formula II, p is 1, q is 1, Q is $S(=O)_2Q^1$, X is CH, Y is CH, $Z^3$ is CH, $Q^1$ is lower alkyl, m is 0, and n is 0.
In one variation of Formula II, p is 1, q is 1, Q is $S(=O)_2Q^1$, X is CH, Y is CH, $Z^3$ is CH, $Q^1$ is lower alkyl, m is 1, n is 0, and R' is lower alkyl.
In one variation of Formula II, p is 1, q is 1, Q is $S(=O)_2Q^1$, X is CH, Y is CH, $Z^3$ is CH, $Q^1$ is lower alkyl, m is 0, n is 1, and R" is lower alkyl.
In one variation of Formula II, p is 1, q is 1, Q is $S(=O)_2Q^1$, X is CH, Y is CH, $Z^3$ is CH, $Q^1$ is lower alkyl, m is 1, n is 1, R" is lower alkyl, and R" is lower alkyl.
In one variation of Formula II, Q is $S(=O)_2Q^1$ and $Q^1$ is cycloalkyl lower alkyl.
In one variation of Formula II, p is 1, q is 1, Q is $S(=O)_2Q^1$, and $Q^1$ is cycloalkyl lower alkyl.
In one variation of Formula II, p is 1, q is 1, Q is $S(=O)_2Q^1$, X is CH, Y is CH, and $Q^1$ is cycloalkyl lower alkyl.
In one variation of Formula II, p is 1, q is 1, Q is $S(=O)_2Q^1$, $Z^3$ is CH, and $Q^1$ is cycloalkyl lower alkyl.
In one variation of Formula II, p is 1, q is 1, Q is $S(=O)_2Q^1$, X is CH, Y is CH, $Z^3$ is CH, and $Q^1$ is cycloalkyl lower alkyl.
In one variation of Formula II, p is 1, q is 1, Q is $S(=O)_2Q^1$, X is CH, Y is CH, $Z^3$ is CH, $Q^1$ is cycloalkyl lower alkyl, m is 0, and n is 0.
In one variation of Formula II, p is 1, q is 1, Q is $S(=O)_2Q^1$, X is CH, Y is CH, $Z^3$ is CH, $Q^1$ is cycloalkyl lower alkyl, m is 1, n is 0, and R' is lower alkyl.
In one variation of Formula II, p is 1, q is 1, Q is $S(=O)_2Q^1$, X is CH, Y is CH, $Z^3$ is CH, $Q^1$ is cycloalkyl lower alkyl, m is 0, n is 1, and R" is lower alkyl.
In one variation of Formula II, p is 1, q is 1, Q is $S(=O)_2Q^1$, X is CH, Y is CH, $Z^3$ is CH, $Q^1$ is cycloalkyl lower alkyl, m is 1, n is 1, R" is lower alkyl, and R" is lower alkyl.
In one variation of Formula II, Q is $C(=O)Q^2$ and $Q^2$ is lower alkyl.
In one variation of Formula II, p is 1, q is 1, Q is $C(=O)Q^2$, $Q^2$ is lower alkyl, X is CH, Y is CH, and $Z^3$ is CH.
In one variation of Formula II, p is 1, q is 1, Q is $C(=O)Q^2$, $Q^2$ is lower alkyl, X is CH, Y is CH, $Z^3$ is CH, m is 1, n is 0, and R' is lower alkyl.
In one variation of Formula II, p is 1, q is 1, Q is $C(=O)Q^2$, $Q^2$ is lower alkyl, X is CH, Y is CH, $Z^3$ is CH, m is 0, n is 1, and R" is lower alkyl.
In one variation of Formula II, p is 1, q is 1, Q is $C(=O)Q^2$, $Q^2$ is lower alkyl, X is CH, Y is CH, $Z^3$ is CH, m is 0, and n is 0.
In one variation of Formula II, Q is $C(=O)OQ^3$ and $Q^3$ is lower alkyl.
In one variation of Formula II, p is 1, q is 1, Q is $C(=O)OQ^3$, $Q^3$ is lower alkyl, X is CH, Y is CH, and $Z^3$ is CH.
In one variation of Formula II, p is 1, q is 1, Q is $C(=O)OQ^3$, $Q^3$ is lower alkyl, X is CH, Y is CH, $Z^3$ is CH, m is 0, and n is 0.
In one variation of Formula II, p is 1, q is 1, Q is $C(=O)OQ^3$, $Q^3$ is lower alkyl, X is CH, Y is CH, $Z^3$ is CH, m is 1, n is 0, and R' is lower alkyl.
In one variation of Formula II, p is 1, q is 1, Q is $C(=O)OQ^3$, $Q^3$ is lower alkyl, X is CH, Y is CH, $Z^3$ is CH, m is 0, n is 1, and R" is lower alkyl.
In one variation of Formula II, p is 0 and q is 1.
In one variation of Formula II, p is 0, q is 1, and $Z^3$ is CH.
In one variation of Formula II, p is 0, q is 1, X is CH, and Y is CH.
In one variation of Formula II, p is 0, q is 1, $Z^3$ is CH, X is CH, and Y is CH.
In one variation of Formula II, p is 0, q is 1, m is 0, and n is 0.
In one variation of Formula II, p is 0, q is 1, m is 0, n is 0, and $Z^3$ is CH.
In one variation of Formula II, p is 0, q is 1, m is 0, n is 0, X is CH, and Y is CH.
In one variation of Formula II, p is 0, q is 1, m is 0, n is 0, $Z^3$ is CH, X is CH, and Y is CH.
In one variation of Formula II, p is 0, q is 1, and Q is $S(=O)_2Q^1$.
In one variation of Formula II, p is 0, q is 1, Q is $S(=O)_2Q^1$, X is CH, and Y is CH.
In one variation of Formula II, p is 0, q is 1, Q is $S(=O)_2Q^1$ and $Z^3$ is CH.
In one variation of Formula II, p is 0, q is 1, Q is $S(=O)_2Q^1$, X is CH, and Y is CH, and $Z^3$ is CH.
In one variation of Formula II, p is 0, q is 1, Q is $S(=O)_2Q^1$, and $Q^1$ is lower alkyl.
In one variation of Formula II, p is 0, q is 1, Q is $S(=O)_2Q^1$, X is CH, Y is CH, and $Q^1$ is lower alkyl.
In one variation of Formula II, p is 0, q is 1, Q is $S(=O)_2Q^1$, $Z^3$ is CH, and $Q^1$ is lower alkyl.

In one variation of Formula II, p is 0, q is 1, Q is S(=O)$_2$Q$^1$, X is CH, Y is CH, Z$^3$ is CH, and Q$^1$ is lower alkyl.

In one variation of Formula II, p is 0, q is 1, Q is S(=O)$_2$Q$^1$, and Q$^1$ is cycloalkyl lower alkyl.

In one variation of Formula II, p is 0, q is 1, Q is S(=O)$_2$Q$^1$, X is CH, Y is CH, and Q$^1$ is cycloalkyl lower alkyl.

In one variation of Formula II, p is 0, q is 1, Q is S(=O)$_2$Q$^1$, Z$^3$ is CH, and Q$^1$ is cycloalkyl lower alkyl.

In one variation of Formula II, p is 0, q is 1, Q is S(=O)$_2$Q$^1$, X is CH, Y is CH, Z$^3$ is CH, and Q$^1$ is cycloalkyl lower alkyl.

In one variation of Formula II, p is 0, q is 1, Q is C(=O)Q$^2$, Q$^2$ is lower alkyl, X is CH, Y is CH, and Z$^3$ is CH.

In one variation of Formula II, p is 0, q is 1, Q is C(=O)Q$^2$, Q$^2$ is lower alkyl, X is CH, Y is CH, Z$^3$ is CH, m is 0, and n is 0.

In one variation of Formula II, p is 0, q is 1, Q is C(=O)OQ$^3$, Q$^3$ is lower alkyl, X is CH, Y is CH, and Z$^3$ is CH.

In one variation of Formula II, p is 0, q is 1, Q is C(=O)OQ$^3$, Q$^3$ is lower alkyl, X is CH, Y is CH, Z$^3$ is CH, m is 0, and n is 0.

In one variation of Formula II, p is 0, q is 1, Q is S(=O)$_2$Q$^1$, X is CH, Y is CH, Z$^3$ is CH, Q$^1$ is lower alkyl, m is 1, n is 0, and R' is lower alkyl.

In one variation of Formula II, p is 0, q is 1, Q is S(=O)$_2$Q$^1$, X is CH, Y is CH, Z$^3$ is CH, Q$^1$ is lower alkyl, m is 0, n is 1, and R" is lower alkyl.

In one variation of Formula II, p is 0, q is 1, Q is S(=O)$_2$Q$^1$, X is CH, Y is CH, Z$^3$ is CH, Q$^1$ is lower alkyl, m is 1, n is 1, R" is lower alkyl, and R" is lower alkyl.

The application provides a compound of Formula III

III wherein:
R is lower alkyl;
n is 0 or 1;
R$^3$ is H or lower alkyl;
X is CH, CR', or N;
   r is 0 or 1;
Y is CH, CR', or N;
R' is R'$^a$ or R'$^b$;
   R'$^a$ is halogen or cyano;
   R'$^b$ is lower alkyl, cycloalkyl, heterocycloalkyl, OR", SR", or NR"R", optionally substituted with one or more R'$^c$;
      R'$^c$ is hydroxy, halogen, oxo, cyano, lower alkyl, cycloalkyl, heterocycloalkyl, heteroaryl, carboxy lower alkyl, amino, lower alkyl amino, lower dialkyl amino, lower haloalkyl, or lower alkoxy;
m is 0 or 1;
Q is H, S(=O)$_2$Q$^1$, C(=O)Q$^2$, C(=O)OQ$^3$, or Q$^4$;
   Q$^1$ is lower alkyl, cycloalkyl lower alkyl, or cycloalkyl, optionally substituted with one or more Q$^{1'}$;
      each Q$^{1'}$ is independently halogen, lower alkyl, cyano, or lower alkoxy;

Q$^2$ is lower alkyl, cycloalkyl lower alkyl, or cycloalkyl, optionally substituted with one or more Q$^{2'}$;
   each Q$^{2'}$ is independently halogen, lower alkyl, or lower alkoxy;
Q$^3$ is lower alkyl, cycloalkyl lower alkyl, or cycloalkyl, optionally substituted with one or more Q$^{3'}$;
   each Q$^{3'}$ is independently halogen, lower alkyl, or lower alkoxy;
Q$^4$ is lower alkyl, cycloalkyl lower alkyl, or cycloalkyl, optionally substituted with one or more Q$^{4'}$;
   each Q$^{4'}$ is independently halogen, lower alkyl, or lower alkoxy;
p is 0, 1, or 2;
q is 1 or 2; and
or a pharmaceutically acceptable salt thereof.

In one variation of Formula III, R$^3$ is H.
In one variation of Formula III, X is CH and Y is CH.
In one variation of Formula III, R$^3$ is H, X is CH and Y is CH.
In one variation of Formula III, m is 0 and n is 0.
In one variation of Formula III, m is 0, n is 0, and R$^3$ is H.
In one variation of Formula III, m is 0, n is 0, X is CH, Y is CH, and R$^3$ is H.
In one variation of Formula III, p is 1 and q is 1.
In one variation of Formula III, m is 0, n is 0, X is CH, Y is CH, R$^3$ is H, p is 1 and q is 1.
In one variation of Formula III, Q is S(=O)$_2$Q$^1$.
In one variation of Formula III, Q$^1$ is lower alkyl.
In one variation of Formula III, Q$^1$ is cycloalkyl lower alkyl.
In one variation of Formula III, Q is S(=O)$_2$Q$^1$ and Q$^1$ is lower alkyl.
In one variation of Formula III, m is 0, n is 0, X is CH, Y is CH, R$^3$ is H, p is 1, and q is 1, Q is S(=O)$_2$Q$^1$ and Q$^1$ is lower alkyl.
In one variation of Formula III, Q is S(=O)$_2$Q$^1$ and Q$^1$ is cycloalkyl lower alkyl.
In one variation of Formula III, m is 0, n is 0, X is CH, Y is CH, R$^3$ is H, p is 1, q is 1, Q is S(=O)$_2$Q$^1$, and Q$^1$ is cycloalkyl lower alkyl.
In one variation of Formula III, p is 0 and q is 1.
In one variation of Formula III, m is 0, n is 0, X is CH, Y is CH, R$^3$ is H, p is 0 and q is 1.

The application provides a compound of Formula IV

IV wherein:
R is lower alkyl;
n is 0 or 1;
X is CH, CR', or N;
   r is 0 or 1;
Y is CH, CR', or N;
R' is R'$^a$ or R'$^b$;
   R'$^a$ is halogen or cyano;

$R^{tb}$ is lower alkyl, cycloalkyl, heterocycloalkyl, OR", SR", or NR"R", optionally substituted with one or more $R^{tc}$;

$R^{tc}$ is hydroxy, halogen, oxo, cyano, lower alkyl, cycloalkyl, heterocycloalkyl, heteroaryl, carboxy lower alkyl, amino, lower alkyl amino, lower dialkyl amino, lower haloalkyl, or lower alkoxy;

m is 0 or 1;

Q is H, S(=O)$_2$Q$^1$, C(=O)Q$^2$, C(=O)OQ$^3$, or Q$^4$;

Q$^1$ is lower alkyl, cycloalkyl lower alkyl, or cycloalkyl, optionally substituted with one or more Q$^{1'}$;

each Q$^{1'}$ is independently halogen, lower alkyl, cyano, or lower alkoxy;

Q$^2$ is lower alkyl, cycloalkyl lower alkyl, or cycloalkyl, optionally substituted with one or more Q$^{2'}$;

each Q$^{2'}$ is independently halogen, lower alkyl, or lower alkoxy;

Q$^3$ is lower alkyl, cycloalkyl lower alkyl, or cycloalkyl, optionally substituted with one or more Q$^{3'}$;

each Q$^{3'}$ is independently halogen, lower alkyl, or lower alkoxy;

Q$^4$ is lower alkyl, cycloalkyl lower alkyl, or cycloalkyl, optionally substituted with one or more Q$^{4'}$;

each Q$^{4'}$ is independently halogen, lower alkyl, or lower alkoxy;

p is 0, 1, or 2;

q is 1 or 2; and or a pharmaceutically acceptable salt thereof.

In one variation of Formula IV, X is CH and Y is CH.

In one variation of Formula IV, m is 0 and n is 0.

In one variation of Formula IV, X is CH, Y is CH, m is 0, and n is 0.

In one variation of Formula IV, p is 1 and q is 1.

In one variation of Formula IV, p is 1, q is 1, X is CH, Y is CH, m is 0, and n is 0.

In one variation of Formula IV, p is 0 and q is 1.

In one variation of Formula IV, p is 0 and q is 1, X is CH, Y is CH, m is 0, and n is 0.

In one variation of Formula IV, Q is S(=O)$_2$Q$^1$.

In one variation of Formula IV, Q$^1$ is lower alkyl.

In one variation of Formula IV, Q is S(=O)$_2$Q$^1$ and Q$^1$ is lower alkyl.

In one variation of Formula IV, Q is S(=O)$_2$Q$^1$, Q$^1$ is lower alkyl, p is 0, q is 1, X is CH, Y is CH, m is 0, and n is 0.

In one variation of Formula IV, Q$^1$ is cycloalkyl lower alkyl.

In one variation of Formula IV, Q is S(=O)$_2$Q$^1$ and Q$^1$ is cycloalkyl lower alkyl.

In one variation of Formula IV, Q is S(=O)$_2$Q$^1$, Q$^1$ is cycloalkyl lower alkyl, p is 0, q is 1, X is CH, Y is CH, m is 0, and n is 0.

The application provides a compound of Formula V

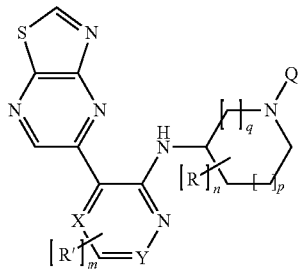

V wherein:

R is lower alkyl;

n is 0 or 1;

X is CH, CR', or N;

r is 0 or 1;

Y is CH, CR', or N;

R' is $R^{ta}$ or $R^{tb}$;

$R^{ta}$ is halogen or cyano;

$R^{tb}$ is lower alkyl, cycloalkyl, heterocycloalkyl, OR", SR", or NR"R", optionally substituted with one or more $R^{tc}$;

$R^{tc}$ is hydroxy, halogen, oxo, cyano, lower alkyl, cycloalkyl, heterocycloalkyl, heteroaryl, carboxy lower alkyl, amino, lower alkyl amino, lower dialkyl amino, lower haloalkyl, or lower alkoxy;

m is 0 or 1;

Q is H, S(=O)$_2$Q$^1$, C(=O)Q$^2$, C(=O)OQ$^3$, or Q$^4$;

Q$^1$ is lower alkyl, cycloalkyl lower alkyl, or cycloalkyl, optionally substituted with one or more Q$^{1'}$;

each Q$^{1'}$ is independently halogen, lower alkyl, cyano, or lower alkoxy;

Q$^2$ is lower alkyl, cycloalkyl lower alkyl, or cycloalkyl, optionally substituted with one or more Q$^{2'}$;

each Q$^{2'}$ is independently halogen, lower alkyl, or lower alkoxy;

Q$^3$ is lower alkyl, cycloalkyl lower alkyl, or cycloalkyl, optionally substituted with one or more Q$^{3'}$;

each Q$^{3'}$ is independently halogen, lower alkyl, or lower alkoxy;

Q$^4$ is lower alkyl, cycloalkyl lower alkyl, or cycloalkyl, optionally substituted with one or more Q$^{4'}$;

each Q$^{4'}$ is independently halogen, lower alkyl, or lower alkoxy;

p is 0, 1, or 2;

q is 1 or 2; and or a pharmaceutically acceptable salt thereof.

In one variation of Formula V, X is CH and Y is CH.

In one variation of Formula V, m is 0 and n is 0.

In one variation of Formula V, m is 0, n is 0, X is CH, and Y is CH.

In one variation of Formula V, p is 1 and q is 1.

In one variation of Formula V, m is 0, n is 0, X is CH, Y is CH, p is 1, and q is 1.

In one variation of Formula V, p is 0 and q is 1.

In one variation of Formula V, m is 0, n is 0, X is CH, Y is CH, p is 0 and q is 1.

In one variation of Formula V, Q is S(=O)$_2$Q$^1$.

In one variation of Formula V, Q$^1$ is lower alkyl.

In one variation of Formula V, Q is S(=O)$_2$Q$^1$ and Q$^1$ is lower alkyl.

In one variation of Formula V, m is 0, n is 0, X is CH, Y is CH, p is 1, q is 1, Q is S(=O)$_2$Q$^1$ and Q$^1$ is lower alkyl.

In one variation of Formula V, Q$^1$ is cycloalkyl lower alkyl.

In one variation of Formula V, Q is S(=O)$_2$Q$^1$ and Q$^1$ is cycloalkyl lower alkyl.

In one variation of Formula V, m is 0, n is 0, X is CH, Y is CH, p is 1, q is 1, Q is S(=O)$_2$Q$^1$ and Q$^1$ is cycloalkyl lower alkyl.

The application provides compound selected from the group consisting of:

((S)-1-Methanesulfonyl-piperidin-3-yl)-[3-(5H-pyrrolo[2,3-b]pyrazin-2-yl)-pyridin-2-yl]-amine;

((R)-1-Methanesulfonyl-piperidin-3-yl)-[3-(5H-pyrrolo[2,3-b]pyrazin-2-yl)-pyridin-2-yl]-amine;

1-{(R)-3-[3-(5H-Pyrrolo[2,3-b]pyrazin-2-yl)-pyridin-2-ylamino]-pyrrolidin-1-yl}-ethanone;

(R)-3-[3-(5H-Pyrrolo[2,3-b]pyrazin-2-yl)-pyridin-2-ylamino]-pyrrolidine-1-carboxylic acid methyl ester;

((R)-1-Methanesulfonyl-pyrrolidin-3-yl)-[3-(5H-pyrrolo[2,3-b]pyrazin-2-yl)-pyridin-2-yl]-amine;
1-{(R)-3-[3-(5H-Pyrrolo[2,3-b]pyrazin-2-yl)-pyridin-2-ylamino]-piperidin-1-yl}-ethanone;
4-[3-(5H-Pyrrolo[2,3-b]pyrazin-2-yl)-pyridin-2-ylamino]-piperidine-1-carboxylic acid methyl ester;
1-{4-[3-(5H-Pyrrolo[2,3-b]pyrazin-2-yl)-pyridin-2-ylamino]-piperidin-1-yl}-ethanone;
1-{(S)-3-[3-(5H-Pyrrolo[2,3-b]pyrazin-2-yl)-pyridin-2-ylamino]-pyrrolidin-1-yl}-ethanone;
(S)-3-[3-(5H-Pyrrolo[2,3-b]pyrazin-2-yl)-pyridin-2-ylamino]-pyrrolidine-1-carboxylic acid methyl ester;
((S)-1-Methanesulfonyl-pyrrolidin-3-yl)-[3-(5H-pyrrolo[2,3-b]pyrazin-2-yl)-pyridin-2-yl]-amine;
1-{3-[3-(5H-Pyrrolo[2,3-b]pyrazin-2-yl)-pyridin-2-ylamino]-azepan-1-yl}-ethanone;
3-[3-(5H-Pyrrolo[2,3-b]pyrazin-2-yl)-pyridin-2-ylamino]-azepane-1-carboxylic acid methyl ester;
(1-Methanesulfonyl-azepan-3-yl)-[3-(5H-pyrrolo[2,3-b]pyrazin-2-yl)-pyridin-2-yl]-amine;
[(R)-1-(Propane-2-sulfonyl)-piperidin-3-yl]-[3-(5H-pyrrolo[2,3-b]pyrazin-2-yl)-pyridin-2-yl]-amine;
((R)-1-Ethanesulfonyl-pyrrolidin-3-yl)-[3-(5H-pyrrolo[2,3-b]pyrazin-2-yl)-pyridin-2-yl]-amine;
[(R)-1-(Propane-1-sulfonyl)-pyrrolidin-3-yl]-[3-(5H-pyrrolo[2,3-b]pyrazin-2-yl)-pyridin-2-yl]-amine;
[(R)-1-(Propane-2-sulfonyl)-pyrrolidin-3-yl]-[3-(5H-pyrrolo[2,3-b]pyrazin-2-yl)-pyridin-2-yl]-amine;
[(R)-1-(2-Methyl-propane-1-sulfonyl)-pyrrolidin-3-yl]-[3-(5H-pyrrolo[2,3-b]pyrazin-2-yl)-pyridin-2-yl]-amine;
1-{(R)-3-[3-(5H-Pyrrolo[2,3-b]pyrazin-2-yl)-pyridin-2-ylamino]-pyrrolidin-1-yl}-propan-1-one;
1-{(R)-3-[3-(5H-Pyrrolo[2,3-b]pyrazin-2-yl)-pyridin-2-ylamino]-pyrrolidin-1-yl}-butan-1-one;
2-Methyl-1-{(R)-3-[3-(5H-pyrrolo[2,3-b]pyrazin-2-yl)-pyridin-2-ylamino]-pyrrolidin-1-yl}-propan-1-one;
3-Methyl-1-{(R)-3-[3-(5H-pyrrolo[2,3-b]pyrazin-2-yl)-pyridin-2-ylamino]-pyrrolidin-1-yl}-butan-1-one;
((3S,5S)-1-Methanesulfonyl-5-methyl-piperidin-3-yl)-[3-(5H-pyrrolo[2,3-b]pyrazin-2-yl)-pyridin-2-yl]-amine;
[(3S,5S)-5-Methyl-1-(propane-1-sulfonyl)-piperidin-3-yl]-[3-(5H-pyrrolo[2,3-b]pyrazin-2-yl)-pyridin-2-yl]-amine;
[(3S,5S)-5-Methyl-1-(2-methyl-propane-1-sulfonyl)-piperidin-3-yl]-[3-(5H-pyrrolo[2,3-b]pyrazin-2-yl)-pyridin-2-yl]-amine;
[(R)-1-(3-Methyl-butane-1-sulfonyl)-pyrrolidin-3-yl]-[3-(5H-pyrrolo[2,3-b]pyrazin-2-yl)-pyridin-2-yl]-amine;
[(3S,5S)-5-Methyl-1-(propane-2-sulfonyl)-piperidin-3-yl]-[3-(5H-pyrrolo[2,3-b]pyrazin-2-yl)-pyridin-2-yl]-amine;
[(S)-1-(2-Methyl-propane-1-sulfonyl)-piperidin-3-yl]-[3-(5H-pyrrolo[2,3-b]pyrazin-2-yl)-pyridin-2-yl]-amine;
1-{3-[6-Methyl-3-(5H-pyrrolo[2,3-b]pyrazin-2-yl)-pyridin-2-ylamino]-piperidin-1-yl}-ethanone;
(1-Methanesulfonyl-piperidin-3-yl)-[6-methyl-3-(5H-pyrrolo[2,3-b]pyrazin-2-yl)-pyridin-2-yl]-amine;
[(S)-1-(2,2-Dimethyl-propane-1-sulfonyl)-piperidin-3-yl]-[3-(5H-pyrrolo[2,3-b]pyrazin-2-yl)-pyridin-2-yl]-amine;
[3-(5H-Pyrrolo[2,3-b]pyrazin-2-yl)-pyridin-2-yl]-[(S)-1-(2,2,2-trifluoro-ethyl)-piperidin-3-yl]-amine;
(1-Ethanesulfonyl-piperidin-3-yl)-[6-methyl-3-(5H-pyrrolo[2,3-b]pyrazin-2-yl)-pyridin-2-yl]-amine;
(1-Cyclopropylmethanesulfonyl-piperidin-3-yl)-[6-methyl-3-(5H-pyrrolo[2,3-b]pyrazin-2-yl)-pyridin-2-yl]-amine;
[1-(2,2-Dimethyl-propane-1-sulfonyl)-piperidin-3-yl]-[6-methyl-3-(5H-pyrrolo[2,3-b]pyrazin-2-yl)-pyridin-2-yl]-amine;
(1-Methanesulfonyl-azepan-4-yl)-[3-(5H-pyrrolo[2,3-b]pyrazin-2-yl)-pyridin-2-yl]-amine;
((S)-1-Cyclopropylmethanesulfonyl-piperidin-3-yl)-[3-(5H-pyrrolo[2,3-b]pyrazin-2-yl)-pyridin-2-yl]-amine;
1-{3-[3-(7-Chloro-5H-pyrrolo[2,3-b]pyrazin-2-yl)-6-methyl-pyridin-2-ylamino]-piperidin-1-yl}-ethanone;
[3-(7-Chloro-5H-pyrrolo[2,3-b]pyrazin-2-yl)-6-methyl-pyridin-2-yl]-(1-cyclopropylmethanesulfonyl-piperidin-3-yl)-amine;
((S)-1-Methanesulfonyl-piperidin-3-yl)-[3-(5H-pyrrolo[2,3-b]pyrazin-2-yl)-pyrazin-2-yl]-amine;
{(S)-3-[3-(5H-Pyrrolo[2,3-b]pyrazin-2-yl)-pyridin-2-ylamino]-piperidine-1-sulfonyl}-acetonitrile;
((S)-1-Methanesulfonyl-piperidin-3-yl)-[3-(5-methyl-5H-pyrrolo[2,3-b]pyrazin-3-yl)-pyridin-2-yl]-amine;
[3-(1H-Imidazo[4,5-b]pyrazin-5-yl)-pyridin-2-yl]-((S)-1-methanesulfonyl-piperidin-3-yl)-amine;
((S)-1-Methanesulfonyl-piperidin-3-yl)-[3-(1H-pyrazolo[3,4-b]pyrazin-5-yl)-pyridin-2-yl]-amine;
[(S)-1-(Propane-1-sulfonyl)-piperidin-3-yl]-[3-(1H-pyrazolo[3,4-b]pyrazin-5-yl)-pyridin-2-yl]-amine;
[(S)-1-(2-Methyl-propane-1-sulfonyl)-piperidin-3-yl]-[3-(1H-pyrazolo[3,4-b]pyrazin-5-yl)-pyridin-2-yl]-amine;
[(S)-1-(Propane-1-sulfonyl)-piperidin-3-yl]-[3-(5H-pyrrolo[2,3-b]pyrazin-3-yl)-pyridin-2-yl]-amine;
[3-(5-Methyl-5H-pyrrolo[2,3-b]pyrazin-3-yl)-pyridin-2-yl]-[(S)-1-(propane-1-sulfonyl)-piperidin-3-yl]-amine;
[(S)-1-(2-Methyl-propane-1-sulfonyl)-piperidin-3-yl]-[3-(5-methyl-5H-pyrrolo[2,3-b]pyrazin-3-yl)-pyridin-2-yl]-amine;
[3-(1H-Imidazo[4,5-b]pyrazin-5-yl)-pyridin-2-yl]-[(S)-1-(propane-1-sulfonyl)-piperidin-3-yl]-amine;
[3-(1H-Imidazo[4,5-b]pyrazin-5-yl)-pyridin-2-yl]-[(S)-1-(2-methyl-propane-1-sulfonyl)-piperidin-3-yl]-amine;
1-{(S)-3-[3-(1H-Pyrazolo[3,4-b]pyrazin-5-yl)-pyridin-2-ylamino]-piperidin-1-yl}-ethanone;
((S)-1-Methanesulfonyl-piperidin-3-yl)-[3-(5H-pyrrolo[2,3-b]pyrazin-3-yl)-pyridin-2-yl]-amine;
1-{(S)-3-[3-(5-Methyl-5H-pyrrolo[2,3-b]pyrazin-3-yl)-pyridin-2-ylamino]-piperidin-1-yl}-ethanone;
[(S)-1-(2-Methyl-propane-1-sulfonyl)-piperidin-3-yl]-[3-(5H-pyrrolo[2,3-b]pyrazin-2-yl)-pyrazin-2-yl]-amine;
[(S)-1-(2-Methyl-propane-1-sulfonyl)-piperidin-3-yl]-[3-(5H-pyrrolo[2,3-b]pyrazin-3-yl)-pyrazin-2-yl]-amine;
1-{(S)-3-[3-(5H-Pyrrolo[2,3-b]pyrazin-2-yl)-pyridin-2-ylamino]-piperidin-1-yl}-ethanone;
1-{3-[3-(1H-Imidazo[4,5-b]pyrazin-5-yl)-pyridin-2-ylamino]-piperidin-1-yl}-ethanone;
2-[2-((S)-1-Methanesulfonyl-piperidin-3-ylamino)-pyridin-3-yl]-5H-pyrrolo[2,3-b]pyrazine-7-carbonitrile;
((S)-1-Methanesulfonyl-piperidin-3-yl)-[3-(7-methyl-5H-pyrrolo[2,3-b]pyrazin-2-yl)-pyridin-2-yl]-amine;
[3-(7-Cyclopropyl-5H-pyrrolo[2,3-b]pyrazin-2-yl)-pyridin-2-yl]-((S)-1-methanesulfonyl-piperidin-3-yl)-amine;
[3-(7-Chloro-5H-pyrrolo[2,3-b]pyrazin-2-yl)-pyridin-2-yl]-((S)-1-methanesulfonyl-piperidin-3-yl)-amine;
(3R,4R)-1-(2-Methyl-propane-1-sulfonyl)-3-[3-(5H-pyrrolo[2,3-b]pyrazin-2-yl)-pyridin-2-ylamino]-piperidin-4-ol;
(3R,4R)-1-Methanesulfonyl-3-[3-(5H-pyrrolo[2,3-b]pyrazin-2-yl)-pyridin-2-ylamino]-piperidin-4-ol;
(S)-3-[3-(5H-Pyrrolo[2,3-b]pyrazin-2-yl)-pyridin-2-ylamino]-piperidine-1-sulfonic acid dimethylamide;
(S)-3-[3-(5H-Pyrrolo[2,3-b]pyrazin-2-yl)-pyridin-2-ylamino]-piperidine-1-sulfonic acid tert-butylamide;
((S)-1-Methanesulfonyl-piperidin-3-yl)-[5-(5H-pyrrolo[2,3-b]pyrazin-2-yl)-pyrimidin-4-yl]-amine;

[(S)-1-(2-Methyl-propane-1-sulfonyl)-piperidin-3-yl]-[5-(5H-pyrrolo[2,3-b]pyrazin-2-yl)-pyrimidin-4-yl]-amine;
N4-[(S)-1-(2-Methyl-propane-1-sulfonyl)-piperidin-3-yl]-5-(5H-pyrrolo[2,3-b]pyrazin-2-yl)-pyrimidine-2,4-diamine;
N2,N2-Dimethyl-N-4-[(S)-1-(2-methyl-propane-1-sulfonyl)-piperidin-3-yl]-5-(5H-pyrrolo[2,3-b]pyrazin-2-yl)-pyrimidine-2,4-diamine;
[2-Methanesulfonyl-5-(5H-pyrrolo[2,3-b]pyrazin-2-yl)-pyrimidin-4-yl]-[(S)-1-(2-methyl-propane-1-sulfonyl)-piperidin-3-yl]-amine;
[(S)-1-(2-Methyl-propane-1-sulfonyl)-piperidin-3-yl]-[2-methylsulfanyl-5-(5H-pyrrolo[2,3-b]pyrazin-2-yl)-pyrimidin-4-yl]-amine;
[(S)-1-(2-Methyl-propane-1-sulfonyl)-piperidin-3-yl]-[2-morpholin-4-yl-5-(5H-pyrrolo[2,3-b]pyrazin-2-yl)-pyrimidin-4-yl]-amine;
((S)-1-Methanesulfonyl-piperidin-3-yl)-[2-methylsulfanyl-5-(5H-pyrrolo[2,3-b]pyrazin-2-yl)-pyrimidin-4-yl]-amine;
N4-((S)-1-Methanesulfonyl-piperidin-3-yl)-N2,N2-dimethyl-5-(5H-pyrrolo[2,3-b]pyrazin-2-yl)-pyrimidine-2,4-diamine;
N4-((S)-1-Methanesulfonyl-piperidin-3-yl)-5-(5H-pyrrolo[2,3-b]pyrazin-2-yl)-pyrimidine-2,4-diamine;
2-[2-Dimethylamino-4-((S)-1-methanesulfonyl-piperidin-3-ylamino)-pyrimidin-5-yl]-5H-pyrrolo[2,3-b]pyrazine-7-carbonitrile;
[(S)-1-(3,3-Dimethyl-butane-1-sulfonyl)-piperidin-3-yl]-[2-methylsulfanyl-5-(5H-pyrrolo[2,3-b]pyrazin-2-yl)-pyrimidin-4-yl]-amine;
((S)-1-Methanesulfonyl-piperidin-3-yl)-[2-methoxy-5-(5H-pyrrolo[2,3-b]pyrazin-2-yl)-pyrimidin-4-yl]-amine;
[2-Chloro-5-(5H-pyrrolo[2,3-b]pyrazin-2-yl)-pyrimidin-4-yl]-((S)-1-methanesulfonyl-piperidin-3-yl)-amine;
((S)-1-Methanesulfonyl-piperidin-3-yl)-[2-(4-methyl-piperazin-1-yl)-5-(5H-pyrrolo[2,3-b]pyrazin-2-yl)-pyrimidin-4-yl]-amine;
4-((S)-1-Methanesulfonyl-piperidin-3-ylamino)-5-(5H-pyrrolo[2,3-b]pyrazin-2-yl)-pyrimidin-2-ol;
[2-Ethoxy-5-(5H-pyrrolo[2,3-b]pyrazin-2-yl)-pyrimidin-4-yl]-((S)-1-methanesulfonyl-piperidin-3-yl)-amine;
2-[4-((S)-1-Methanesulfonyl-piperidin-3-ylamino)-5-(5H-pyrrolo[2,3-b]pyrazin-2-yl)-pyrimidin-2-ylamino]-ethanol;
N4-((S)-1-Methanesulfonyl-piperidin-3-yl)-N2-(2-methoxy-ethyl)-5-(5H-pyrrolo[2,3-b]pyrazin-2-yl)-pyrimidine-2,4-diamine;
((S)-1-Methanesulfonyl-piperidin-3-yl)-[2-morpholin-4-yl-5-(5H-pyrrolo[2,3-b]pyrazin-2-yl)-pyrimidin-4-yl]-amine;
3-{(S)-3-[2-Methylsulfanyl-5-(5H-pyrrolo[2,3-b]pyrazin-2-yl)-pyrimidin-4-ylamino]-piperidin-1-yl}-3-oxo-propionitrile;
1-[4-((S)-1-Methanesulfonyl-piperidin-3-ylamino)-5-(5H-pyrrolo[2,3-b]pyrazin-2-yl)-pyrimidin-2-ylamino]-2-methyl-propan-2-ol;
[2-(1,1-Dioxo-1λ6-thiomorpholin-4-yl)-5-(5H-pyrrolo[2,3-b]pyrazin-2-yl)-pyrimidin-4-yl]-((S)-1-methanesulfonyl-piperidin-3-yl)-amine;
((S)-1-Methanesulfonyl-piperidin-3-yl)-[2-(4-methoxy-piperidin-1-yl)-5-(5H-pyrrolo[2,3-b]pyrazin-2-yl)-pyrimidin-4-yl]-amine;
N2-(2-Amino-ethyl)-N4-((S)-1-methanesulfonyl-piperidin-3-yl)-5-(5H-pyrrolo[2,3-b]pyrazin-2-yl)-pyrimidine-2,4-diamine;
2-{1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetamide;
(S)-2-[4-((S)-1-Methanesulfonyl-piperidin-3-ylamino)-5-(5H-pyrrolo[2,3-b]pyrazin-2-yl)-pyrimidin-2-ylamino]-butan-1-ol;
(R)-2-[4-((S)-1-Methanesulfonyl-piperidin-3-ylamino)-5-(5H-pyrrolo[2,3-b]pyrazin-2-yl)-pyrimidin-2-ylamino]-butan-1-ol;
N4-((S)-1-Methanesulfonyl-piperidin-3-yl)-N2-(1-methyl-piperidin-4-yl)-5-(5H-pyrrolo[2,3-b]pyrazin-2-yl)-pyrimidine-2,4-diamine;
[(S)-1-(3,3-Dimethyl-butane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine;
[2-(4-Dimethylamino-piperidin-1-yl)-5-(5H-pyrrolo[2,3-b]pyrazin-2-yl)-pyrimidin-4-yl]-((S)-1-methanesulfonyl-piperidin-3-yl)-amine;
4-((S)-1-Methanesulfonyl-piperidin-3-ylamino)-5-(5H-pyrrolo[2,3-b]pyrazin-2-yl)-pyrimidine-2-carbonitrile;
(S)-1-[4-((S)-1-Methanesulfonyl-piperidin-3-ylamino)-5-(5H-pyrrolo[2,3-b]pyrazin-2-yl)-pyrimidin-2-yl]-pyrrolidin-3-ol;
(R)-1-[4-((S)-1-Methanesulfonyl-piperidin-3-ylamino)-5-(5H-pyrrolo[2,3-b]pyrazin-2-yl)-pyrimidin-2-yl]-pyrrolidin-3-ol;
1-[4-((S)-1-Methanesulfonyl-piperidin-3-ylamino)-5-(5H-pyrrolo[2,3-b]pyrazin-2-yl)-pyrimidin-2-yl]-azetidine-3-carbonitrile;
4-[4-((S)-1-Methanesulfonyl-piperidin-3-ylamino)-5-(5H-pyrrolo[2,3-b]pyrazin-2-yl)-pyrimidin-2-ylamino]-cyclohexanecarbonitrile;
((S)-1-Methanesulfonyl-piperidin-3-yl)-[2-(4-pyridin-2-yl-piperazin-1-yl)-5-(5H-pyrrolo[2,3-b]pyrazin-2-yl)-pyrimidin-4-yl]-amine;
{1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetic acid;
N4-((S)-1-Methanesulfonyl-piperidin-3-yl)-N2-pyridin-4-yl-5-(5H-pyrrolo[2,3-b]pyrazin-2-yl)-pyrimidine-2,4-diamine;
N2-(2-Dimethylamino-ethyl)-N4-((S)-1-methanesulfonyl-piperidin-3-yl)-5-(5H-pyrrolo[2,3-b]pyrazin-2-yl)-pyrimidine-2,4-diamine;
[2-(4-Ethyl-piperazin-1-yl)-5-(5H-pyrrolo[2,3-b]pyrazin-2-yl)-pyrimidin-4-yl]-((S)-1-methanesulfonyl-piperidin-3-yl)-amine;
[2-((R)-3-Dimethylamino-pyrrolidin-1-yl)-5-(5H-pyrrolo[2,3-b]pyrazin-2-yl)-pyrimidin-4-yl]-((S)-1-methanesulfonyl-piperidin-3-yl)-amine;
[2-(4-Methyl-piperazin-1-yl)-5-(5H-pyrrolo[2,3-b]pyrazin-2-yl)-pyrimidin-4-yl]-[(S)-1-(2-methyl-propane-1-sulfonyl)-piperidin-3-yl]-amine;
[(3S,5S)-5-Methyl-1-(2-methyl-propane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine;
{(3S,5S)-3-Methyl-5-[2-(4-methyl-piperazin-1-yl)-5-(5H-pyrrolo[2,3-b]pyrazin-2-yl)-pyrimidin-4-ylamino]-piperidine-1-sulfonyl}-acetonitrile;
((3S,5S)-1-Methanesulfonyl-5-methyl-piperidin-3-yl)-[2-(4-methyl-piperazin-1-yl)-5-(5H-pyrrolo[2,3-b]pyrazin-2-yl)-pyrimidin-4-yl]-amine;
((3S,5S)-1-Methanesulfonyl-5-trifluoromethyl-piperidin-3-yl)-[3-(5H-pyrrolo[2,3-b]pyrazin-2-yl)-pyridin-2-yl]-amine;

[(3S,5S)-1-(2-Methyl-propane-1-sulfonyl)-5-trifluoromethyl-piperidin-3-yl]-[3-(5H-pyrrolo[2,3-b]pyrazin-2-yl)-pyridin-2-yl]-amine;

(3-{(S)-3-[3-(5H-Pyrrolo[2,3-b]pyrazin-2-yl)-pyridin-2-ylamino]-piperidin-1-yl}-oxetan-3-yl)-acetonitrile;

(3-{(3S,5S)-3-Methyl-5-[3-(5H-pyrrolo[2,3-b]pyrazin-2-yl)-pyridin-2-ylamino]-piperidin-1-yl}-oxetan-3-yl)-acetonitrile;

{(3S,5S)-3-Methyl-5-[3-(5H-pyrrolo[2,3-b]pyrazin-2-yl)-pyridin-2-ylamino]-piperidine-1-sulfonyl}-acetonitrile; and 4,4,4-Trifluoro-3-{(S)-3-[3-(5H-pyrrolo[2,3-b]pyrazin-2-yl)-pyridin-2-ylamino]-piperidin-1-yl}-butyronitrile.

The application provides a method for treating an inflammatory or autoimmune condition comprising administering to a patient in need thereof a therapeutically effective amount of the compound of any one of Formulae I-V.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of any one of Formulae I-V.

The application provides a method for inhibiting T-cell proliferative disorder comprising administering to a patient in need thereof a therapeutically effective amount of the compound of any one of Formulae I-V.

The application provides a method for inhibiting T-cell proliferative disorder comprising administering to a patient in need thereof a therapeutically effective amount of the compound of any one of Formulae I-V.

The application provides the above method, wherein the proliferative disorder is cancer.

The application provides a method for treating a B-cell proliferative disorder comprising administering to a patient in need thereof a therapeutically effective amount of the compound of any one of Formulae I-V.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of any one of Formulae I-V.

The application provides a method for preventing or treating all forms of organ rejection, including acute allograft or xenograft rejection and chronic allograft or xenograft rejection, of vascularized or non-vascularized transplants, comprising administering to a patient in need thereof the compound of any one of Formulae I-V.

The application provides a method for inhibiting JAK3 activity comprising administering the compound of any one of Formulae I-V, wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

The application provides a method for treating an inflammatory condition comprising co-administering to a patient in need thereof a therapeutically effective amount of an anti-inflammatory compound in combination with the compound of any one of Formulae I-V.

The application provides a method for treating an immune disorder comprising co-administering to a patient in need thereof a therapeutically effective amount of an immunosuppressant compound in combination with the compound of any one of Formulae I-V.

The application provides a pharmaceutical composition comprising the compound of any one of Formulae I-V, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides a use of the compound of any one of Formulae I-V in the manufacture of a medicament for the treatment of an inflammatory disorder.

The application provides a use of the compound of any one of Formulae I-V in the manufacture of a medicament for the treatment of an autoimmune disorder.

The application provides a method for treating rheumatoid arthritis comprising administering to a patient in need thereof a therapeutically effective amount of the compound of any one of Formulae I-V.

The application provides a method for treating asthma comprising administering to a patient in need thereof a therapeutically effective amount of the compound of any one of Formulae I-V.

The application provides a compound or method as described herein.

The application provides a compound of Formula I'

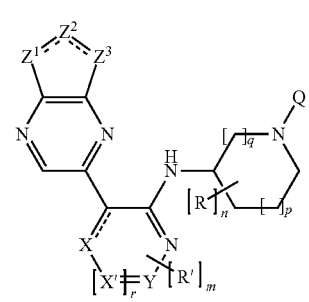

I' wherein:
R is lower alkyl;
n is 0 or 1;
$Z^1$ is CH, NH, or S;
$Z^2$ is CH or N;
$Z^3$ is CR', N, or $NR^2$;
$R^1$ is H, lower alkyl, or halogen;
$R^2$ is H or lower alkyl;
X is CH, CR', or N;
X' is CH, CR', or N;
r is 0 or 1;

Y is CH, CR', or N;
R' is halogen, lower alkyl, OR", SR", or NR"R";
m is 0 or 1;
R" is H or lower alkyl;
Q is H, S(=O)$_2$Q$^1$, C(=O)Q$^2$, C(=O)OQ$^3$, or Q$^4$;
Q$^1$ is lower alkyl, cycloalkyl lower alkyl, or cycloalkyl, optionally substituted with one or more Q$^{1'}$;
each Q$^{1'}$ is independently halogen, lower alkyl, cyano, or lower alkoxy;
Q$^2$ is lower alkyl, cycloalkyl lower alkyl, or cycloalkyl, optionally substituted with one or more Q$^{2'}$;
each Q$^{2'}$ is independently halogen, lower alkyl, or lower alkoxy;
Q$^3$ is lower alkyl, cycloalkyl lower alkyl, or cycloalkyl, optionally substituted with one or more Q$^{3'}$;
each Q$^{3'}$ is independently halogen, lower alkyl, or lower alkoxy;
Q$^4$ is lower alkyl, cycloalkyl lower alkyl, or cycloalkyl, optionally substituted with one or more Q$^{4'}$;
each Q$^{4'}$ is independently halogen, lower alkyl, or lower alkoxy;
p is 0, 1, or 2;
q is 1 or 2;
each === represents a single bond or a double bond; and
with the proviso that the bonds between Z$^1$ and Z$^2$ and Z$^2$ and Z$^3$ are not both double bonds and are not both single bonds;
or a pharmaceutically acceptable salt thereof.

The application provides a compound of Formula II'

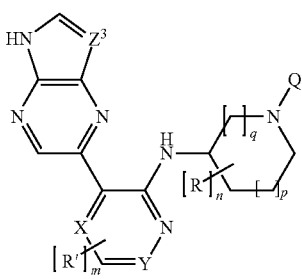

II' wherein:
R is lower alkyl;
n is 0 or 1;
Z$^3$ is CR$^1$, N, or NR$^2$;
R$^1$ is H, lower alkyl, or halogen;
R$^2$ is H or lower alkyl;
X is CH, CR', or N;
X' is CH, CR', or N;
r is 0 or 1;
Y is CH, CR', or N;
R' is halogen, lower alkyl, OR", SR", or NR"R";
m is 0 or 1;
R" is H or lower alkyl;
Q is H, S(=O)$_2$Q$^1$, C(=O)Q$^2$, C(=O)OQ$^3$, or Q$^4$;
Q$^1$ is lower alkyl, cycloalkyl lower alkyl, or cycloalkyl, optionally substituted with one or more Q$^{1'}$;
each Q$^{1'}$ is independently halogen, lower alkyl, cyano, or lower alkoxy;
Q$^2$ is lower alkyl, cycloalkyl lower alkyl, or cycloalkyl, optionally substituted with one or more Q$^{2'}$;
each Q$^{2'}$ is independently halogen, lower alkyl, or lower alkoxy;
Q$^3$ is lower alkyl, cycloalkyl lower alkyl, or cycloalkyl, optionally substituted with one or more Q$^{3'}$;
each Q$^{3'}$ is independently halogen, lower alkyl, or lower alkoxy;
Q$^4$ is lower alkyl, cycloalkyl lower alkyl, or cycloalkyl, optionally substituted with one or more Q$^{4'}$;
each Q$^{4'}$ is independently halogen, lower alkyl, or lower alkoxy;
p is 0, 1, or 2;
q is 1 or 2; and
or a pharmaceutically acceptable salt thereof.

In one variation of Formula II', Z$^3$ is CH.
In one variation of Formula II', Z$^3$ is CH.
In one variation of Formula II', X is CH and Y is CH.
In one variation of Formula II', Z$^3$ is CH, X is CH, and Y is CH.
In one variation of Formula II', m is 0 and n is 0.
In one variation of Formula II', m is 0, n is 0, X is CH, and Y is CH.
In one variation of Formula II', m is 0, n is 0, and Z$^3$ is CH.
In one variation of Formula II', m is 0, n is 0, Z$^3$ is CH, X is CH, and Y is CH.
In one variation of Formula II', p is 1 and q is 1.
In one variation of Formula II', p is 1, q is 1, and Z$^3$ is CH.
In one variation of Formula II', p is 1, q is 1, X is CH, and Y is CH.
In one variation of Formula II', p is 1, q is 1, Z$^3$ is CH, X is CH, and Y is CH.
In one variation of Formula II', p is 1, q is 1, m is 0, and n is 0.
In one variation of Formula II', p is 1, q is 1, m is 0, n is 0, and Z$^3$ is CH.
In one variation of Formula II', p is 1, q is 1, m is 0, n is 0, X is CH, and Y is CH.
In one variation of Formula II', p is 1, q is 1, m is 0, n is 0, Z$^3$ is CH, X is CH, and Y is CH.
In one variation of Formula II', Q is S(=O)$_2$Q$^1$.
In one variation of Formula II', p is 1, q is 1, and Q is S(=O)$_2$Q$^1$.
In one variation of Formula II', p is 1, q is 1, Q is S(=O)$_2$Q$^1$, X is CH, and Y is CH.
In one variation of Formula II', p is 1, q is 1, Q is S(=O)$_2$Q$^1$ and Z$^3$ is CH.
In one variation of Formula II', p is 1, q is 1, Q is S(=O)$_2$Q$^1$, X is CH, and Y is CH, and Z$^3$ is CH.
In one variation of Formula II', Q is S(=O)$_2$Q$^1$ and Q$^1$ is lower alkyl.
In one variation of Formula II', p is 1, q is 1, Q is S(=O)$_2$Q$^1$, and Q$^1$ is lower alkyl.
In one variation of Formula II', p is 1, q is 1, Q is S(=O)$_2$Q$^1$, X is CH, Y is CH, and Q$^1$ is lower alkyl.
In one variation of Formula II', p is 1, q is 1, Q is S(=O)$_2$Q$^1$, Z$^3$ is CH, and Q$^1$ is lower alkyl.
In one variation of Formula II', p is 1, q is 1, Q is S(=O)$_2$Q$^1$, X is CH, Y is CH, Z$^3$ is CH, and Q$^1$ is lower alkyl.
In one variation of Formula II', p is 1, q is 1, Q is S(=O)$_2$Q$^1$, X is CH, Y is CH, Z$^3$ is CH, Q$^1$ is lower alkyl, m is 0, and n is 0.
In one variation of Formula II', p is 1, q is 1, Q is S(=O)$_2$Q$^1$, X is CH, Y is CH, Z$^3$ is CH, Q$^1$ is lower alkyl, m is 1, n is 0, and R' is lower alkyl.
In one variation of Formula II', p is 1, q is 1, Q is S(=O)$_2$Q$^1$, X is CH, Y is CH, Z$^3$ is CH, Q$^1$ is lower alkyl, m is 0, n is 1, and R" is lower alkyl.
In one variation of Formula II', p is 1, q is 1, Q is S(=O)$_2$Q$^1$, X is CH, Y is CH, Z$^3$ is CH, Q$^1$ is lower alkyl, m is 1, n is 1, R" is lower alkyl, and R" is lower alkyl.
In one variation of Formula II', Q is S(=O)$_2$Q$^1$ and Q$^1$ is cycloalkyl lower alkyl.

In one variation of Formula II', p is 1, q is 1, Q is S(=O)$_2$ Q$^1$, and Q$^1$ is cycloalkyl lower alkyl.

In one variation of Formula II', p is 1, q is 1, Q is S(=O)$_2$ Q$^1$, X is CH, Y is CH, and Q$^1$ is cycloalkyl lower alkyl.

In one variation of Formula II', p is 1, q is 1, Q is S(=O)$_2$ Q$^1$, Z$^3$ is CH, and Q$^1$ is cycloalkyl lower alkyl.

In one variation of Formula II', p is 1, q is 1, Q is S(=O)$_2$ Q$^1$, X is CH, Y is CH, Z$^3$ is CH, and Q$^1$ is cycloalkyl lower alkyl.

In one variation of Formula II', p is 1, q is 1, Q is S(=O)$_2$ Q$^1$, X is CH, Y is CH, Z$^3$ is CH, Q$^1$ is cycloalkyl lower alkyl, m is 0, and n is 0.

In one variation of Formula II', p is 1, q is 1, Q is S(=O)$_2$ Q$^1$, X is CH, Y is CH, Z$^3$ is CH, Q$^1$ is cycloalkyl lower alkyl, m is 1, n is 0, and R' is lower alkyl.

In one variation of Formula II', p is 1, q is 1, Q is S(=O)$_2$ Q$^1$, X is CH, Y is CH, Z$^3$ is CH, Q$^1$ is cycloalkyl lower alkyl, m is 0, n is 1, and R" is lower alkyl.

In one variation of Formula II', p is 1, q is 1, Q is S(=O)$_2$ Q$^1$, X is CH, Y is CH, Z$^3$ is CH, Q$^1$ is cycloalkyl lower alkyl, m is 1, n is 1, R" is lower alkyl, and R" is lower alkyl.

In one variation of Formula II', Q is C(=O)Q$^2$ and Q$^2$ is lower alkyl.

In one variation of Formula II', p is 1, q is 1, Q is C(=O)Q$^2$, Q$^2$ is lower alkyl, X is CH, Y is CH, and Z$^3$ is CH.

In one variation of Formula II', p is 1, q is 1, Q is C(=O)Q$^2$, Q$^2$ is lower alkyl, X is CH, Y is CH, Z$^3$ is CH, m is 1, n is 0, and R' is lower alkyl.

In one variation of Formula II', p is 1, q is 1, Q is C(=O)Q$^2$, Q$^2$ is lower alkyl, X is CH, Y is CH, Z$^3$ is CH, m is 0, n is 1, and R" is lower alkyl.

In one variation of Formula II', p is 1, q is 1, Q is C(=O)Q$^2$, Q$^2$ is lower alkyl, X is CH, Y is CH, Z$^3$ is CH, m is 0, and n is 0.

In one variation of Formula II', Q is C(=O)OQ$^3$ and Q$^3$ is lower alkyl.

In one variation of Formula II', p is 1, q is 1, Q is C(=O) OQ$^3$, Q$^3$ is lower alkyl, X is CH, Y is CH, and Z$^3$ is CH.

In one variation of Formula II', p is 1, q is 1, Q is C(=O) OQ$^3$, Q$^3$ is lower alkyl, X is CH, Y is CH, Z$^3$ is CH, m is 0, and n is 0.

In one variation of Formula II', p is 1, q is 1, Q is C(=O) OQ$^3$, Q$^3$ is lower alkyl, X is CH, Y is CH, Z$^3$ is CH, m is 1, n is 0, and R' is lower alkyl.

In one variation of Formula II', p is 1, q is 1, Q is C(=O) OQ$^3$, Q$^3$ is lower alkyl, X is CH, Y is CH, Z$^3$ is CH, m is 0, n is 1, and R" is lower alkyl.

In one variation of Formula II', p is 0 and q is 1.

In one variation of Formula II', p is 0, q is 1, and Z$^3$ is CH.

In one variation of Formula II', p is 0, q is 1, X is CH, and Y is CH.

In one variation of Formula II', p is 0, q is 1, Z$^3$ is CH, X is CH, and Y is CH.

In one variation of Formula II', p is 0, q is 1, m is 0, and n is 0.

In one variation of Formula II', p is 0, q is 1, m is 0, n is 0, and Z$^3$ is CH.

In one variation of Formula II', p is 0, q is 1, m is 0, n is 0, X is CH, and Y is CH.

In one variation of Formula II', p is 0, q is 1, m is 0, n is 0, Z$^3$ is CH, X is CH, and Y is CH.

In one variation of Formula II', p is 0, q is 1, and Q is S(=O)$_2$Q$^1$.

In one variation of Formula II', p is 0, q is 1, Q is S(=O)$_2$ Q$^1$, X is CH, and Y is CH.

In one variation of Formula II', p is 0, q is 1, Q is S(=O)$_2$Q$^1$ and Z$^3$ is CH.

In one variation of Formula II', p is 0, q is 1, Q is S(=O)$_2$ Q$^1$, X is CH, and Y is CH, and Z$^3$ is CH.

In one variation of Formula II', p is 0, q is 1, Q is S(=O)$_2$ Q$^1$, and Q$^1$ is lower alkyl.

In one variation of Formula II', p is 0, q is 1, Q is S(=O)$_2$ Q$^1$, X is CH, Y is CH, and Q$^1$ is lower alkyl.

In one variation of Formula II', p is 0, q is 1, Q is S(=O)$_2$ Q$^1$, Z$^3$ is CH, and Q$^1$ is lower alkyl.

In one variation of Formula II', p is 0, q is 1, Q is S(=O)$_2$ Q$^1$, X is CH, Y is CH, Z$^3$ is CH, and Q$^1$ is lower alkyl.

In one variation of Formula II', p is 0, q is 1, Q is S(=O)$_2$ Q$^1$, and Q$^1$ is cycloalkyl lower alkyl.

In one variation of Formula II', p is 0, q is 1, Q is S(=O)$_2$ Q$^1$, X is CH, Y is CH, and Q$^1$ is cycloalkyl lower alkyl.

In one variation of Formula II', p is 0, q is 1, Q is S(=O)$_2$ Q$^1$, Z$^3$ is CH, and Q$^1$ is cycloalkyl lower alkyl.

In one variation of Formula II', p is 0, q is 1, Q is S(=O)$_2$ Q$^1$, X is CH, Y is CH, Z$^3$ is CH, and Q$^1$ is cycloalkyl lower alkyl.

In one variation of Formula II', p is 0, q is 1, Q is C(=O)Q$^2$, Q$^2$ is lower alkyl, X is CH, Y is CH, and Z$^3$ is CH.

In one variation of Formula II', p is 0, q is 1, Q is C(=O)Q$^2$, Q$^2$ is lower alkyl, X is CH, Y is CH, Z$^3$ is CH, m is 0, and n is 0.

In one variation of Formula II', p is 0, q is 1, Q is C(=O) OQ$^3$, Q$^3$ is lower alkyl, X is CH, Y is CH, and Z$^3$ is CH.

In one variation of Formula II', p is 0, q is 1, Q is C(=O) OQ$^3$, Q$^3$ is lower alkyl, X is CH, Y is CH, Z$^3$ is CH, m is 0, and n is 0.

In one variation of Formula II', p is 0, q is 1, Q is S(=O)$_2$ Q$^1$, X is CH, Y is CH, Z$^3$ is CH, Q$^1$ is lower alkyl, m is 1, n is 0, and R' is lower alkyl.

In one variation of Formula II', p is 0, q is 1, Q is S(=O)$_2$ Q$^1$, X is CH, Y is CH, Z$^3$ is CH, Q$^1$ is lower alkyl, m is 0, n is 1, and R" is lower alkyl.

In one variation of Formula II', p is 0, q is 1, Q is S(=O)$_2$ Q$^1$, X is CH, Y is CH, Z$^3$ is CH, Q$^1$ is lower alkyl, m is 1, n is 1, R" is lower alkyl, and R" is lower alkyl.

The application provides a compound of Formula III'

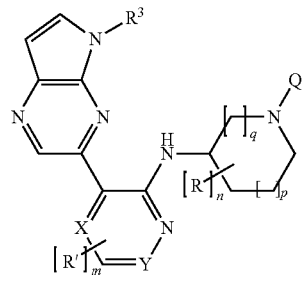

wherein:
R is lower alkyl;
n is 0 or 1;
R$^3$ is H or lower alkyl;
X is CH, CR', or N;
X' is CH, CR', or N;
r is 0 or 1;
Y is CH, CR', or N;
R' is halogen, lower alkyl, OR", SR", or NR"R";
m is 0 or 1;
R" is H or lower alkyl;
Q is H, S(=O)$_2$Q$^1$, C(=O)Q$^2$, C(=O)OQ$^3$, or Q$^4$;

$Q^1$ is lower alkyl, cycloalkyl lower alkyl, or cycloalkyl, optionally substituted with one or more $Q^{1'}$;

each $Q^{1'}$ is independently halogen, lower alkyl, cyano, or lower alkoxy;

$Q^2$ is lower alkyl, cycloalkyl lower alkyl, or cycloalkyl, optionally substituted with one or more $Q^{2'}$;

each $Q^{2'}$ is independently halogen, lower alkyl, or lower alkoxy;

$Q^3$ is lower alkyl, cycloalkyl lower alkyl, or cycloalkyl, optionally substituted with one or more $Q^{3'}$;

each $Q^{3'}$ is independently halogen, lower alkyl, or lower alkoxy;

$Q^4$ is lower alkyl, cycloalkyl lower alkyl, or cycloalkyl, optionally substituted with one or more $Q^{4'}$;

each $Q^{4'}$ is independently halogen, lower alkyl, or lower alkoxy;

p is 0, 1, or 2;
q is 1 or 2; and
or a pharmaceutically acceptable salt thereof.

In one variation of Formula III', $R^3$ is H.
In one variation of Formula III', X is CH and Y is CH.
In one variation of Formula III', $R^3$ is H, X is CH and Y is CH.
In one variation of Formula III', m is 0 and n is 0.
In one variation of Formula III', m is 0, n is 0, and $R^3$ is H.
In one variation of Formula III', m is 0, n is 0, X is CH, Y is CH, and $R^3$ is H.
In one variation of Formula III', p is 1 and q is 1.
In one variation of Formula III', m is 0, n is 0, X is CH, Y is CH, $R^3$ is H, p is 1 and q is 1.
In one variation of Formula III', Q is $S(=O)_2Q^1$.
In one variation of Formula III', $Q^1$ is lower alkyl.
In one variation of Formula III', $Q^1$ is cycloalkyl lower alkyl.
In one variation of Formula III', Q is $S(=O)_2Q^1$ and $Q^1$ is lower alkyl.
In one variation of Formula III', m is 0, n is 0, X is CH, Y is CH, $R^3$ is H, p is 1, and q is 1, Q is $S(=O)_2Q^1$ and $Q^1$ is lower alkyl.
In one variation of Formula III', Q is $S(=O)_2Q^1$ and $Q^1$ is cycloalkyl lower alkyl.
In one variation of Formula III', m is 0, n is 0, X is CH, Y is CH, $R^3$ is H, p is 1, q is 1, Q is $S(=O)_2Q^1$, and $Q^1$ is cycloalkyl lower alkyl.
In one variation of Formula III', p is 0 and q is 1.
In one variation of Formula III', m is 0, n is 0, X is CH, Y is CH, $R^3$ is H, p is 0 and q is 1.

The application provides a compound of Formula IV'

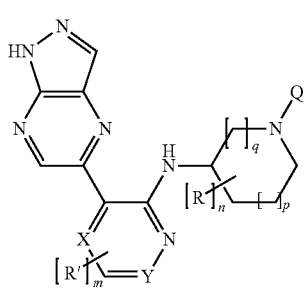

IV' wherein:
R is lower alkyl;
n is 0 or 1;
X is CH, CR', or N;
X' is CH, CR', or N;
r is 0 or 1;
Y is CH, CR', or N;
R' is halogen, lower alkyl, OR", SR", or NR"R";
m is 0 or 1;
R" is H or lower alkyl;
Q is H, $S(=O)_2Q^1$, $C(=O)Q^2$, $C(=O)OQ^3$, or $Q^4$;

$Q^1$ is lower alkyl, cycloalkyl lower alkyl, or cycloalkyl, optionally substituted with one or more $Q^{1'}$;

each $Q^{1'}$ is independently halogen, lower alkyl, cyano, or lower alkoxy;

$Q^2$ is lower alkyl, cycloalkyl lower alkyl, or cycloalkyl, optionally substituted with one or more $Q^{2'}$;

each $Q^{2'}$ is independently halogen, lower alkyl, or lower alkoxy;

$Q^3$ is lower alkyl, cycloalkyl lower alkyl, or cycloalkyl, optionally substituted with one or more $Q^{3'}$;

each $Q^{3'}$ is independently halogen, lower alkyl, or lower alkoxy;

$Q^4$ is lower alkyl, cycloalkyl lower alkyl, or cycloalkyl, optionally substituted with one or more $Q^{4'}$;

each $Q^{4'}$ is independently halogen, lower alkyl, or lower alkoxy;

p is 0, 1, or 2;
q is 1 or 2; and
or a pharmaceutically acceptable salt thereof.

In one variation of Formula IV', X is CH and Y is CH.
In one variation of Formula IV', m is 0 and n is 0.
In one variation of Formula IV', X is CH, Y is CH, m is 0, and n is 0.
In one variation of Formula IV', p is 1 and q is 1.
In one variation of Formula IV', p is 1, q is 1, X is CH, Y is CH, m is 0, and n is 0.
In one variation of Formula IV', p is 0 and q is 1.
In one variation of Formula IV', p is 0 and q is 1, X is CH, Y is CH, m is 0, and n is 0.
In one variation of Formula IV', Q is $S(=O)_2Q^1$.
In one variation of Formula IV', $Q^1$ is lower alkyl.
In one variation of Formula IV', Q is $S(=O)_2Q^1$ and $Q^1$ is lower alkyl.
In one variation of Formula IV', Q is $S(=O)_2Q^1$, $Q^1$ is lower alkyl, p is 0, q is 1, X is CH, Y is CH, m is 0, and n is 0.
In one variation of Formula IV', $Q^1$ is cycloalkyl lower alkyl.
In one variation of Formula IV', Q is $S(=O)_2Q^1$ and $Q^1$ is cycloalkyl lower alkyl.
In one variation of Formula IV', Q is $S(=O)_2Q^1$, $Q^1$ is cycloalkyl lower alkyl, p is 0, q is 1, X is CH, Y is CH, m is 0, and n is 0.

The application provides a compound of Formula V'

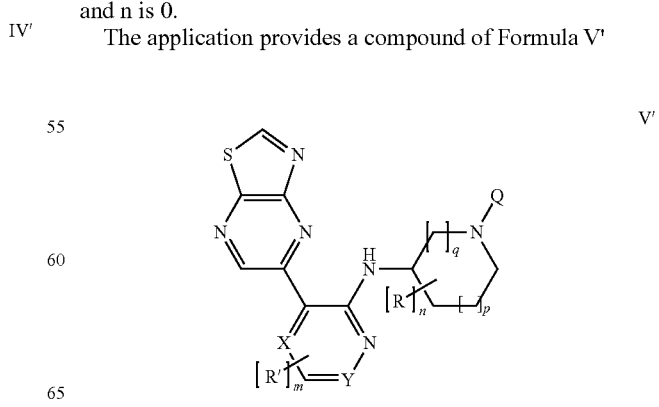

V' wherein:
R is lower alkyl;
n is 0 or 1;
X is CH, CR', or N;
X' is CH, CR', or N;
r is 0 or 1;
Y is CH, CR', or N;
R' is halogen, lower alkyl, OR", SR", or NR"R";
m is 0 or 1;
R" is H or lower alkyl;
Q is H, S(=O)$_2$Q$^1$, C(=O)Q$^2$, C(=O)OQ$^3$, or Q$^4$;
Q$^1$ is lower alkyl, cycloalkyl lower alkyl, or cycloalkyl, optionally substituted with one or more Q$^{1'}$;
each Q$^{1'}$ is independently halogen, lower alkyl, cyano, or lower alkoxy;
Q$^2$ is lower alkyl, cycloalkyl lower alkyl, or cycloalkyl, optionally substituted with one or more Q$^{2'}$;
each Q$^{2'}$ is independently halogen, lower alkyl, or lower alkoxy;
Q$^3$ is lower alkyl, cycloalkyl lower alkyl, or cycloalkyl, optionally substituted with one or more Q$^{3'}$;
each Q$^{3'}$ is independently halogen, lower alkyl, or lower alkoxy;
Q$^4$ is lower alkyl, cycloalkyl lower alkyl, or cycloalkyl, optionally substituted with one or more Q$^{4'}$;
each Q$^{4'}$ is independently halogen, lower alkyl, or lower alkoxy;
p is 0, 1, or 2;
q is 1 or 2; and
or a pharmaceutically acceptable salt thereof.

In one variation of Formula V', X is CH and Y is CH.
In one variation of Formula V', m is 0 and n is 0.
In one variation of Formula V', m is 0, n is 0, X is CH, and Y is CH.
In one variation of Formula V', p is 1 and q is 1.
In one variation of Formula V', m is 0, n is 0, X is CH, Y is CH, p is 1, and q is 1.
In one variation of Formula V', p is 0 and q is 1.
In one variation of Formula V', m is 0, n is 0, X is CH, Y is CH, p is 0 and q is 1.
In one variation of Formula V', Q is S(=O)$_2$Q$^1$.
In one variation of Formula V', Q$^1$ is lower alkyl.
In one variation of Formula V', Q is S(=O)$_2$Q$^1$ and Q$^1$ is lower alkyl.
In one variation of Formula V', m is 0, n is 0, X is CH, Y is CH, p is 1, q is 1, Q is S(=O)$_2$Q$^1$ and Q$^1$ is lower alkyl.
In one variation of Formula V', Q$^1$ is cycloalkyl lower alkyl.
In one variation of Formula V', Q is S(=O)$_2$Q$^1$ and Q$^1$ is cycloalkyl lower alkyl.
In one variation of Formula V', m is 0, n is 0, X is CH, Y is CH, p is 1, q is 1, Q is S(=O)$_2$Q$^1$ and Q$^1$ is cycloalkyl lower alkyl.

The application provides a compound selected from the group consisting of:
((S)-1-Methanesulfonyl-piperidin-3-yl)-[3-(5H-pyrrolo[2,3-b]pyrazin-2-yl)-pyridin-2-yl]-amine;
((R)-1-Methanesulfonyl-piperidin-3-yl)-[3-(5H-pyrrolo[2,3-b]pyrazin-2-yl)-pyridin-2-yl]-amine;
1-{(R)-3-[3-(5H-Pyrrolo[2,3-b]pyrazin-2-yl)-pyridin-2-ylamino]-pyrrolidin-1-yl}-ethanone;
(R)-3-[3-(5H-Pyrrolo[2,3-b]pyrazin-2-yl)-pyridin-2-ylamino]-pyrrolidine-1-carboxylic acid methyl ester;
((R)-1-Methanesulfonyl-pyrrolidin-3-yl)-[3-(5H-pyrrolo[2,3-b]pyrazin-2-yl)-pyridin-2-yl]-amine;
1-{(R)-3-[3-(5H-Pyrrolo[2,3-b]pyrazin-2-yl)-pyridin-2-ylamino]-piperidin-1-yl}-ethanone;
4-[3-(5H-Pyrrolo[2,3-b]pyrazin-2-yl)-pyridin-2-ylamino]-piperidine-1-carboxylic acid methyl ester;
1-{4-[3-(5H-Pyrrolo[2,3-b]pyrazin-2-ylamino]-piperidin-1-yl}-ethanone;
1-{(S)-3-[3-(5H-Pyrrolo[2,3-b]pyrazin-2-yl)-pyridin-2-ylamino]-pyrrolidin-1-yl}-ethanone;
(S)-3-[3-(5H-Pyrrolo[2,3-b]pyrazin-2-yl)-pyridin-2-ylamino]-pyrrolidine-1-carboxylic acid methyl ester;
((S)-1-Methanesulfonyl-pyrrolidin-3-yl)-[3-(5H-pyrrolo[2,3-b]pyrazin-2-yl)-pyridin-2-yl]-amine;
1-{3-[3-(5H-Pyrrolo[2,3-b]pyrazin-2-yl)-pyridin-2-ylamino]-azepan-1-yl}-ethanone;
3-[3-(5H-Pyrrolo[2,3-b]pyrazin-2-yl)-pyridin-2-ylamino]-azepane-1-carboxylic acid methyl ester;
(1-Methanesulfonyl-azepan-3-yl)-[3-(5H-pyrrolo[2,3-b]pyrazin-2-yl)-pyridin-2-yl]-amine;
[(R)-1-(Propane-2-sulfonyl)-piperidin-3-yl]-[3-(5H-pyrrolo[2,3-b]pyrazin-2-yl)-pyridin-2-yl]-amine;
((R)-1-Ethanesulfonyl-pyrrolidin-3-yl)-[3-(5H-pyrrolo[2,3-b]pyrazin-2-yl)-pyridin-2-yl]-amine;
[(R)-1-(Propane-1-sulfonyl)-pyrrolidin-3-yl]-[3-(5H-pyrrolo[2,3-b]pyrazin-2-yl)-pyridin-2-yl]-amine;
[(R)-1-(Propane-2-sulfonyl)-pyrrolidin-3-yl]-[3-(5H-pyrrolo[2,3-b]pyrazin-2-yl)-pyridin-2-yl]-amine;
[(R)-1-(2-Methyl-propane-1-sulfonyl)-pyrrolidin-3-yl]-[3-(5H-pyrrolo[2,3-b]pyrazin-2-yl)-pyridin-2-yl]-amine;
1-{(R)-3-[3-(5H-Pyrrolo[2,3-b]pyrazin-2-yl)-pyridin-2-ylamino]-pyrrolidin-1-yl}-propan-1-one;
1-{(R)-3-[3-(5H-Pyrrolo[2,3-b]pyrazin-2-yl)-pyridin-2-ylamino]-pyrrolidin-1-yl}-butan-1-one;
2-Methyl-1-{(R)-3-[3-(5H-pyrrolo[2,3-b]pyrazin-2-yl)-pyridin-2-ylamino]-pyrrolidin-1-yl}-propan-1-one;
3-Methyl-1-{(R)-3-[3-(5H-pyrrolo[2,3-b]pyrazin-2-yl)-pyridin-2-ylamino]-pyrrolidin-1-yl}-butan-1-one;
((3S,5S)-1-Methanesulfonyl-5-methyl-piperidin-3-yl)-[3-(5H-pyrrolo[2,3-b]pyrazin-2-yl)-pyridin-2-yl]-amine;
[(3S,5S)-5-Methyl-1-(propane-1-sulfonyl)-piperidin-3-yl]-[3-(5H-pyrrolo[2,3-b]pyrazin-2-yl)-pyridin-2-yl]-amine;
[(3S,5S)-5-Methyl-1-(2-methyl-propane-1-sulfonyl)-piperidin-3-yl]-[3-(5H-pyrrolo[2,3-b]pyrazin-2-yl)-pyridin-2-yl]-amine;
[(R)-1-(3-Methyl-butane-1-sulfonyl)-pyrrolidin-3-yl]-[3-(5H-pyrrolo[2,3-b]pyrazin-2-yl)-pyridin-2-yl]-amine;
[(3S,5S)-5-Methyl-1-(propane-2-sulfonyl)-piperidin-3-yl]-[3-(5H-pyrrolo[2,3-b]pyrazin-2-yl)-pyridin-2-yl]-amine;
[(S)-1-(2-Methyl-propane-1-sulfonyl)-piperidin-3-yl]-[3-(5H-pyrrolo[2,3-b]pyrazin-2-yl)-pyridin-2-yl]-amine;
1-{3-[6-Methyl-3-(5H-pyrrolo[2,3-b]pyrazin-2-yl)-pyridin-2-ylamino]-piperidin-1-yl}-ethanone;
(1-Methanesulfonyl-piperidin-3-yl)-[6-methyl-3-(5H-pyrrolo[2,3-b]pyrazin-2-yl)-pyridin-2-yl]-amine;
[(S)-1-(2,2-Dimethyl-propane-1-sulfonyl)-piperidin-3-yl]-[3-(5H-pyrrolo[2,3-b]pyrazin-2-yl)-pyridin-2-yl]-amine;
[3-(5H-Pyrrolo[2,3-b]pyrazin-2-yl)-pyridin-2-yl]-[(S)-1-(2,2,2-trifluoro-ethyl)-piperidin-3-yl]-amine;
(1-Ethanesulfonyl-piperidin-3-yl)-[6-methyl-3-(5H-pyrrolo[2,3-b]pyrazin-2-yl)-pyridin-2-yl]-amine;
(1-Cyclopropylmethanesulfonyl-piperidin-3-yl)-[6-methyl-3-(5H-pyrrolo[2,3-b]pyrazin-2-yl)-pyridin-2-yl]-amine;
[1-(2,2-Dimethyl-propane-1-sulfonyl)-piperidin-3-yl]-[6-methyl-3-(5H-pyrrolo[2,3-b]pyrazin-2-yl)-pyridin-2-yl]-amine;
(1-Methanesulfonyl-azepan-4-yl)-[3-(5H-pyrrolo[2,3-b]pyrazin-2-yl)-pyridin-2-yl]-amine;
((S)-1-Cyclopropylmethanesulfonyl-piperidin-3-yl)-[3-(5H-pyrrolo[2,3-b]pyrazin-2-yl)-pyridin-2-yl]-amine;

1-{3-[3-(7-Chloro-5H-pyrrolo[2,3-b]pyrazin-2-yl)-6-methyl-pyridin-2-ylamino]-piperidin-1-yl}-ethanone;

[3-(7-Chloro-5H-pyrrolo[2,3-b]pyrazin-2-yl)-6-methyl-pyridin-2-yl]-(1-cyclopropylmethanesulfonyl-piperidin-3-yl)-amine;

((S)-1-Methanesulfonyl-piperidin-3-yl)-[3-(5H-pyrrolo[2,3-b]pyrazin-2-yl)-pyrazin-2-yl]-amine; and {(S)-3-[3-(5H-Pyrrolo[2,3-b]pyrazin-2-yl)-pyridin-2-ylamino]-piperidine-1-sulfonyl}-acetonitrile.

The application provides a method for treating an inflammatory or autoimmune condition comprising administering to a patient in need thereof a therapeutically effective amount of the compound of any one of Formulae I'-V'.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of any one of Formulae I'-V'.

The application provides a method for inhibiting T-cell proliferative disorder comprising administering to a patient in need thereof a therapeutically effective amount of the compound of any one of Formulae I'-V'.

The application provides a method for inhibiting T-cell proliferative disorder comprising administering to a patient in need thereof a therapeutically effective amount of the compound of any one of Formulae I'-V'.

The application provides the above method, wherein the proliferative disorder is cancer.

The application provides a method for treating a B-cell proliferative disorder comprising administering to a patient in need thereof a therapeutically effective amount of the compound of any one of Formulae I'-V'.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of any one of Formulae I'-V'.

The application provides a method for preventing or treating all forms of organ rejection, including acute allograft or xenograft rejection and chronic allograft or xenograft rejection, of vascularized or non-vascularized transplants, comprising administering to a patient in need thereof the compound of any one of Formulae I'-V'.

The application provides a method for inhibiting JAK3 activity comprising administering the compound of any one of Formulae I'-V', wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

The application provides a method for treating an inflammatory condition comprising co-administering to a patient in need thereof a therapeutically effective amount of an anti-inflammatory compound in combination with the compound of any one of Formulae I'-V'.

The application provides a method for treating an immune disorder comprising co-administering to a patient in need thereof a therapeutically effective amount of an immunosuppressant compound in combination with the compound of any one of Formulae I'-V'.

The application provides a pharmaceutical composition comprising the compound of any one of Formulae I'-V', admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides a use of the compound of any one of Formulae I-V in the manufacture of a medicament for the treatment of an inflammatory disorder.

The application provides a use of the compound of any one of Formulae I-V in the manufacture of a medicament for the treatment of an autoimmune disorder.

The application provides a method for treating rheumatoid arthritis comprising administering to a patient in need thereof a therapeutically effective amount of the compound of any one of Formulae I'-V'.

The application provides a method for treating asthma comprising administering to a patient in need thereof a therapeutically effective amount of the compound of any one of Formulae I'-V'.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, R', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

MeC(=O)OR$^4$ wherein

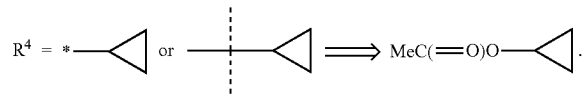

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

In Formula I,

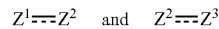

indicate that the bonds between $Z^1$ and $Z^2$, as well as $Z^2$ and $Z^3$, may be single or double, but both may not be single bonds and both may not be double bonds. Thus, intended bond configurations include:

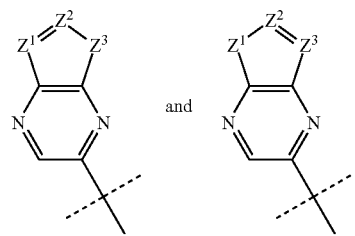

In Formula I, X═══ indicates that the bond between X and the carbon atom is either a single bond or a double bond. Thus, intended bond configurations include:

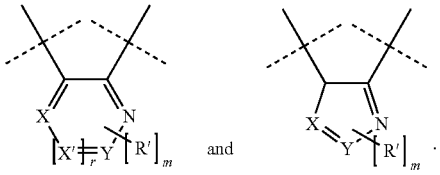

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "halogen" or "halo" as used herein means fluorine, chlorine, bromine, or iodine.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocycloalkyl", "heterocyclyl" or "heterocycle" as used herein denotes a monovalent saturated cyclic radical, consisting of one or more rings, preferably one to two rings, of three to eight atoms per ring, incorporating one or more ring carbon atoms and one or more ring heteroatoms (chosen from N, O or $S(=O)_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

Commonly used abbreviations include: acetyl (Ac), azobis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), trimethylsilanyl-ethoxymethyl (SEM), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tent-) and neo have their customary meaning when used with an alkyl moiety. (J. Rigaudy and D. P. Klesney, *Nomenclature in Organic Chemistry*, IUPAC 1979 Pergamon Press, Oxford.).

COMPOUNDS AND PREPARATION

Examples of representative compounds encompassed by the present invention and within the scope of the invention are provided in the following Table I. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| COMPOUND | SYSTEMATIC NAME | STRUCTURE | MS (M + H) | MP |
|---|---|---|---|---|
| I-1 | ((S)-1-Methanesulfonyl-piperidin-3-yl)-[3-(5H-pyrrolo[2,3-b]pyrazin-2-yl)-pyridin-2-yl]-amine | 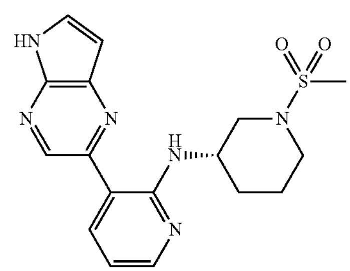 [SMILES: CS(=O)(=O)N1CCC[C@H](Nc2ncccc2-c2cnc3[nH]ccc3n2)C1] | 373 | 174.0-177.0 |
| I-2 | ((R)-1-Methanesulfonyl-piperidin-3-yl)-[3-(5H-pyrrolo[2,3-b]pyrazin-2-yl)-pyridin-2-yl]-amine | 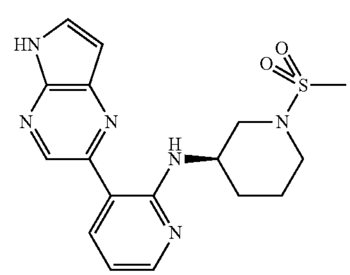 [SMILES: CS(=O)(=O)N1CCC[C@@H](Nc2ncccc2-c2cnc3[nH]ccc3n2)C1] | 373 | |
| I-3 | 1-{(R)-3-[3-(5H-Pyrrolo[2,3-b]pyrazin-2-yl)-pyridin-2-ylamino]-pyrrolidin-1-yl}-ethanone | 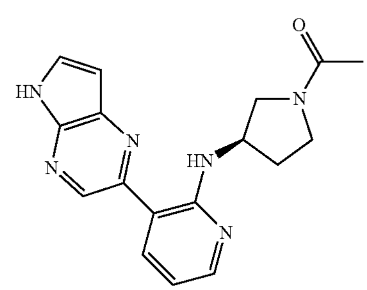 [SMILES: CC(=O)N1CC[C@@H](Nc2ncccc2-c2cnc3[nH]ccc3n2)C1] | 323 | 105.0-110.0 |

TABLE I-continued

| COMPOUND | SYSTEMATIC NAME | STRUCTURE | MS (M + H) | MP |
|---|---|---|---|---|
| I-4 | (R)-3-[3-(5H-Pyrrolo[2,3-b]pyrazin-2-yl)-pyridin-2-ylamino]-pyrrolidine-1-carboxylic acid methyl ester | 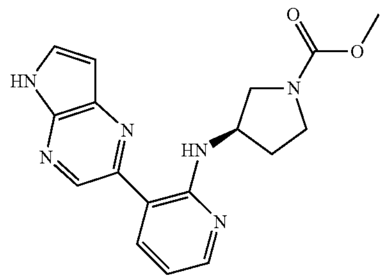 [SMILES: COC(=O)N1CC[C@@H](Nc2ncccc2-c2cnc3[nH]ccc3n2)C1] | 339 | 221.0-224.0 |
| I-5 | ((R)-1-Methanesulfonyl-pyrrolidin-3-yl)-[3-(5H-pyrrolo[2,3-b]pyrazin-2-yl)-pyridin-2-yl]-amine | 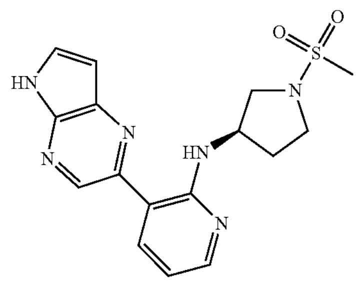 [SMILES: CS(=O)(=O)N1CC[C@@H](Nc2ncccc2-c2cnc3[nH]ccc3n2)C1] | 359 | 224.0-226.0 |
| I-6 | 1-{(R)-3-[3-(5H-Pyrrolo[2,3-b]pyrazin-2-yl)-pyridin-2-ylamino]-piperidin-1-yl}-ethanone | 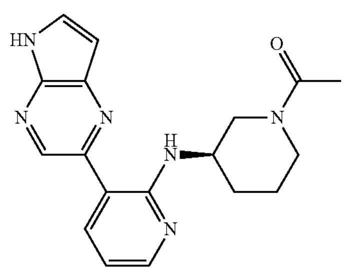 [SMILES: CC(=O)N1CCC[C@@H](Nc2ncccc2-c2cnc3[nH]ccc3n2)C1] | 337 | |
| I-7 | 4-[3-(5H-Pyrrolo[2,3-b]pyrazin-2-yl)-pyridin-2-ylamino]-piperidine-1-carboxylic acid methyl ester | 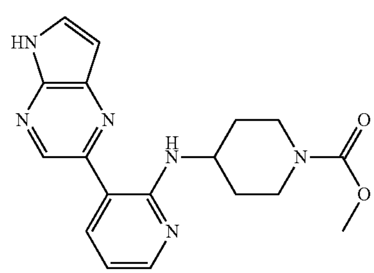 [SMILES: COC(=O)N1CCC(Nc2ncccc2-c2cnc3[nH]ccc3n2)CC1] | 353 | |
| I-8 | 1-{4-[3-(5H-Pyrrolo[2,3-b]pyrazin-2-yl)-pyridin-2-ylamino]-piperidin-1-yl}-ethanone | 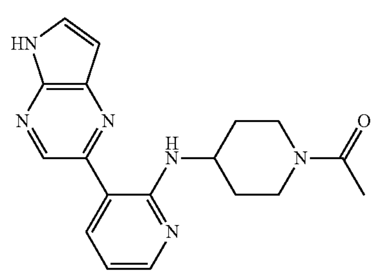 [SMILES: CC(=O)N1CCC(Nc2ncccc2-c2cnc3[nH]ccc3n2)CC1] | 337 | |

TABLE I-continued

| COMPOUND | SYSTEMATIC NAME | STRUCTURE | MS (M + H) | MP |
|---|---|---|---|---|
| I-9 | 1-{(S)-3-[3-(5H-Pyrrolo[2,3-b]pyrazin-2-yl)-pyridin-2-ylamino]-pyrrolidin-1-yl}-ethanone | 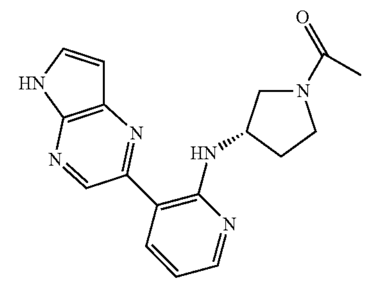 [SMILES: CC(=O)N1CC[C@H](Nc2ncccc2-c2cnc3[nH]ccc3n2)C1] | 323 | 115.0-120.0 |
| I-10 | (S)-3-[3-(5H-Pyrrolo[2,3-b]pyrazin-2-yl)-pyridin-2-ylamino]-pyrrolidine-1-carboxylic acid methyl ester | 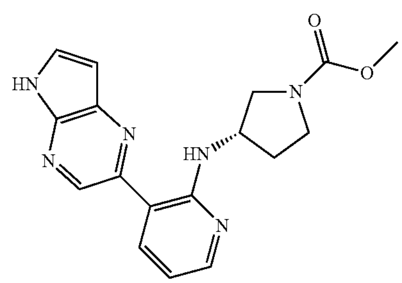 [SMILES: COC(=O)N1CC[C@H](Nc2ncccc2-c2cnc3[nH]ccc3n2)C1] | 339 | 222.0-225.0 |
| I-11 | ((S)-1-Methanesulfonyl-pyrrolidin-3-yl)-[3-(5H-pyrrolo[2,3-b]pyrazin-2-yl)-pyridin-2-yl]-amine | 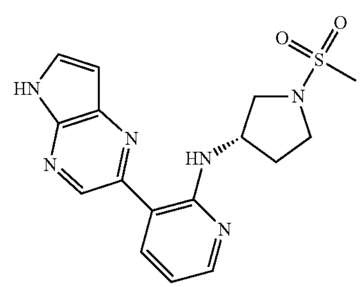 [SMILES: CS(=O)(=O)N1CC[C@H](Nc2ncccc2-c2cnc3[nH]ccc3n2)C1] | 359 | 222.0-224.0 |
| I-12 | 1-{3-[3-(5H-Pyrrolo[2,3-b]pyrazin-2-yl)-pyridin-2-ylamino]-azepan-1-yl}-ethanone | 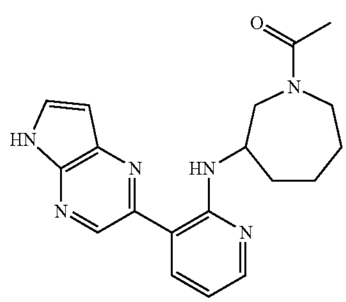 [SMILES: CC(=O)N1CCCCC(Nc2ncccc2-c2cnc3[nH]ccc3n2)C1] | 351 | 100.0-110.0 |
| I-13 | 3-[3-(5H-Pyrrolo[2,3-b]pyrazin-2-yl)-pyridin-2-ylamino]-azepane-1-carboxylic acid methyl ester | 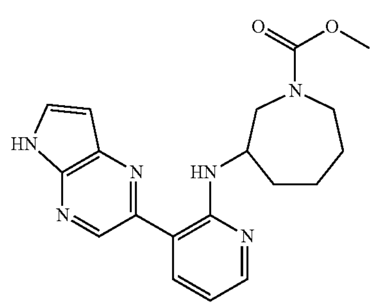 [SMILES: COC(=O)N1CCCCC(Nc2ncccc2-c2cnc3[nH]ccc3n2)C1] | 367 | 90.0-100.0 |

TABLE I-continued

| COMPOUND | SYSTEMATIC NAME | STRUCTURE | MS (M + H) | MP |
|---|---|---|---|---|
| I-14 | (1-Methane-sulfonyl-azepan-3-yl)-[3-(5H-pyrrolo[2,3-b]pyrazin-2-yl)-pyridin-2-yl]-amine | 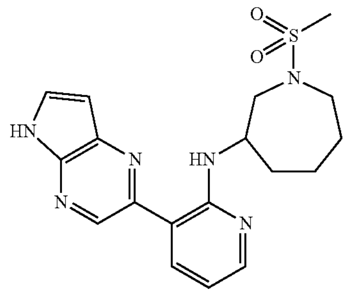 [SMILES: CS(=O)(=O)N1CCCCC(Nc2ncccc2-c2cnc3[nH]ccc3n2)C1] | 387 | 213.0-216.0 |
| I-15 | [(R)-1-(Propane-2-sulfonyl)-piperidin-3-yl]-[3-(5H-pyrrolo[2,3-b]pyrazin-2-yl)-pyridin-2-yl]-amine | 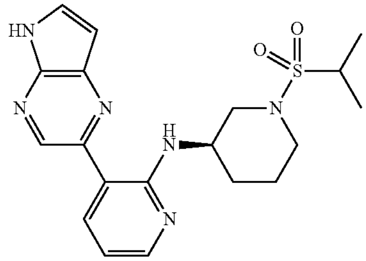 [SMILES: CC(C)S(=O)(=O)N1CCC[C@@H](Nc2ncccc2-c2cnc3[nH]ccc3n2)C1] | 401 | |
| I-16 | ((R)-1-Ethanesulfonyl-pyrrolidin-3-yl)-[3-(5H-pyrrolo[2,3-b]pyrazin-2-yl)-pyridin-2-yl]-amine | 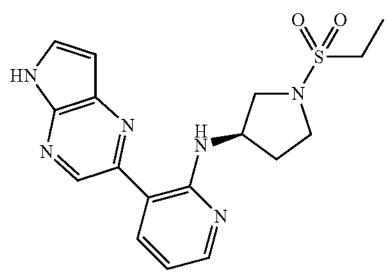 [SMILES: CCS(=O)(=O)N1CC[C@@H](Nc2ncccc2-c2cnc3[nH]ccc3n2)C1] | 373 | 230.0-232.0 |
| I-17 | [(R)-1-(Propane-1-sulfonyl)-pyrrolidin-3-yl]-[3-(5H-pyrrolo[2,3-b]pyrazin-2-yl)-pyridin-2-yl]-amine | 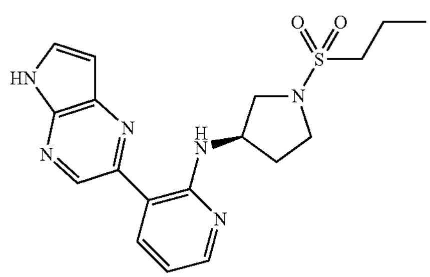 [SMILES: CCCS(=O)(=O)N1CC[C@@H](Nc2ncccc2-c2cnc3[nH]ccc3n2)C1] | 387 | 198.0-200.0 |
| I-18 | [(R)-1-(Propane-2-sulfonyl)-pyrrolidin-3-yl]-[3-(5H-pyrrolo[2,3-b]pyrazin-2-yl)-pyridin-2-yl]-amine | 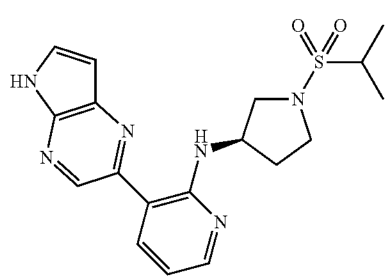 [SMILES: CC(C)S(=O)(=O)N1CC[C@@H](Nc2ncccc2-c2cnc3[nH]ccc3n2)C1] | 387 | 187.0-189.0 |

TABLE I-continued

| COMPOUND | SYSTEMATIC NAME | STRUCTURE | MS (M + H) | MP |
|---|---|---|---|---|
| I-19 | [(R)-1-(2-Methyl-propane-1-sulfonyl)-pyrrolidin-3-yl]-[3-(5H-pyrrolo[2,3-b]pyrazin-2-yl)-pyridin-2-yl]-amine | 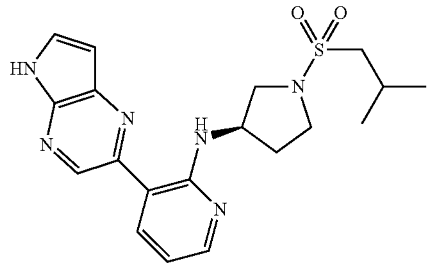 [SMILES: CC(C)CS(=O)(=O)N1CC[C@@H](Nc2ncccc2-c2cnc3[nH]ccc3n2)C1] | 401 | 134.0-137.0 |
| I-20 | 1-{(R)-3-[3-(5H-Pyrrolo[2,3-b]pyrazin-2-yl)-pyridin-2-ylamino]-pyrrolidin-1-yl}-propan-1-one | 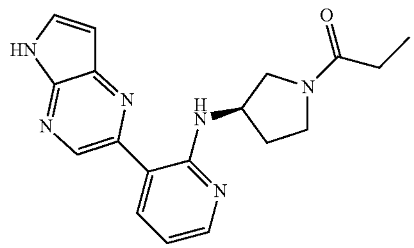 [SMILES: CCC(=O)N1CC[C@@H](Nc2ncccc2-c2cnc3[nH]ccc3n2)C1] | 337 | 105.0-110.0 |
| I-21 | 1-{(R)-3-[3-(5H-Pyrrolo[2,3-b]pyrazin-2-yl)-pyridin-2-ylamino]-pyrrolidin-1-yl}-butan-1-one | 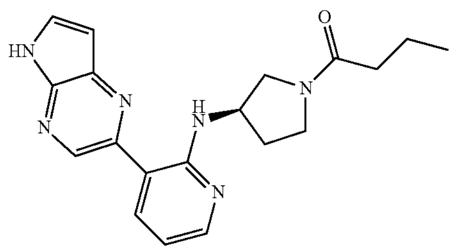 [SMILES: CCCC(=O)N1CC[C@@H](Nc2ncccc2-c2cnc3[nH]ccc3n2)C1] | 351 | 115.0-120.0 |
| I-22 | 2-Methyl-1-{(R)-3-[3-(5H-pyrrolo[2,3-b]pyrazin-2-yl)-pyridin-2-ylamino]-pyrrolidin-1-yl}-propan-1-one | 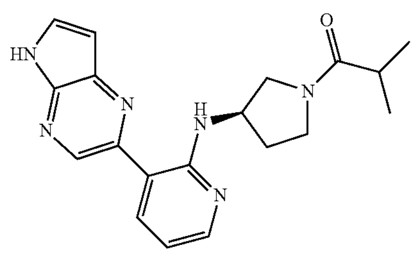 [SMILES: CC(C)C(=O)N1CC[C@@H](Nc2ncccc2-c2cnc3[nH]ccc3n2)C1] | 351 | 100.0-105.0 |
| I-23 | 3-Methyl-1-{(R)-3-[3-(5H-pyrrolo[2,3-b]pyrazin-2-yl)-pyridin-2-ylamino]-pyrrolidin-1-yl}-butan-1-one | 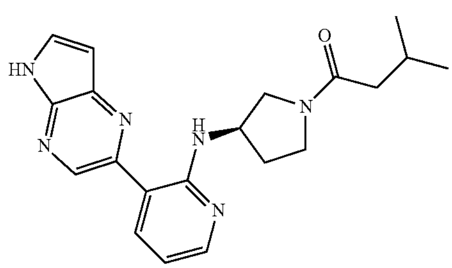 [SMILES: CC(C)CC(=O)N1CC[C@@H](Nc2ncccc2-c2cnc3[nH]ccc3n2)C1] | 365 | 100.0-105.0 |
| I-24 | ((3S,5S)-1-Methanesulfonyl-5-methyl-piperidin-3-yl)-[3-(5H-pyrrolo[2,3-b]pyrazin-2-yl)-pyridin-2-yl]-amine | 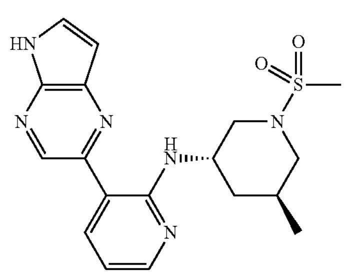 [SMILES: C[C@H]1C[C@H](Nc2ncccc2-c2cnc3[nH]ccc3n2)CN(S(C)(=O)=O)C1] | 387 | |

TABLE I-continued

| COMPOUND | SYSTEMATIC NAME | STRUCTURE | MS (M + H) | MP |
|---|---|---|---|---|
| I-25 | [(3S,5S)-5-Methyl-1-(propane-1-sulfonyl)-piperidin-3-yl]-[3-(5H-pyrrolo[2,3-b]pyrazin-2-yl)-pyridin-2-yl]-amine | 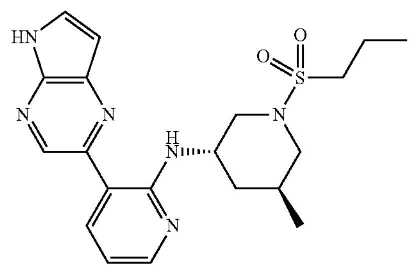 [SMILES: CCCS(=O)(=O)N1C[C@@H](C)C[C@H](Nc2ncccc2-c2cnc3[nH]ccc3n2)C1] | 415 | 178.0-180.0 |
| I-26 | [(3S,5S)-5-Methyl-1-(2-methyl-propane-1-sulfonyl)-piperidin-3-yl]-[3-(5H-pyrrolo[2,3-b]pyrazin-2-yl)-pyridin-2-yl]-amine | 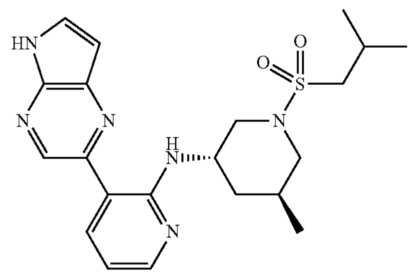 [SMILES: CC(C)CS(=O)(=O)N1C[C@@H](C)C[C@H](Nc2ncccc2-c2cnc3[nH]ccc3n2)C1] | 429 | 215.0-218.0 |
| I-27 | [(R)-1-(3-Methyl-butane-1-sulfonyl)-pyrrolidin-3-yl]-[3-(5H-pyrrolo[2,3-b]pyrazin-2-yl)-pyridin-2-yl]-amine | 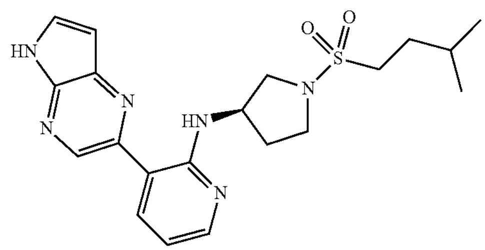 [SMILES: CC(C)CCS(=O)(=O)N1CC[C@@H](Nc2ncccc2-c2cnc3[nH]ccc3n2)C1] | 415 | 160.0-162.0 |
| I-28 | [(3S,5S)-5-Methyl-1-(propane-2-sulfonyl)-piperidin-3-yl]-[3-(5H-pyrrolo[2,3-b]pyrazin-2-yl)-pyridin-2-yl]-amine | 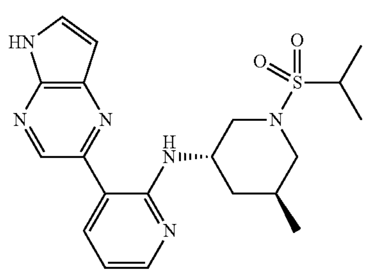 [SMILES: CC(C)S(=O)(=O)N1C[C@@H](C)C[C@H](Nc2ncccc2-c2cnc3[nH]ccc3n2)C1] | 415 | |
| I-29 | [(S)-1-(2-Methyl-propane-1-sulfonyl)-piperidin-3-yl]-[3-(5H-pyrrolo[2,3-b]pyrazin-2-yl)-pyridin-2-yl]-amine | 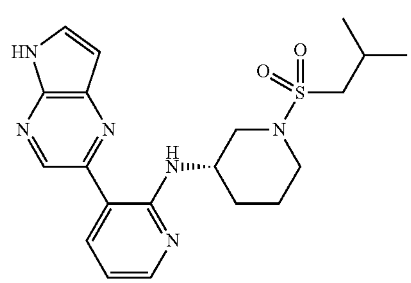 [SMILES: CC(C)CS(=O)(=O)N1CCC[C@H](Nc2ncccc2-c2cnc3[nH]ccc3n2)C1] | 415 | 150.0-152.0 |

TABLE I-continued

| COMPOUND | SYSTEMATIC NAME | STRUCTURE | MS (M + H) | MP |
|---|---|---|---|---|
| I-30 | 1-{3-[6-Methyl-3-(5H-pyrrolo[2,3-b]pyrazin-2-yl)-pyridin-2-ylamino]-piperidin-1-yl}-ethanone | 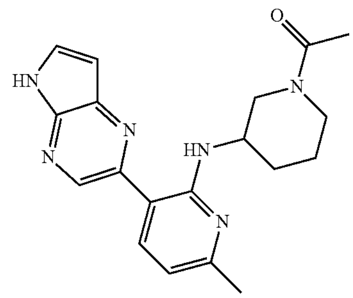 [SMILES: CC(=O)N1CCCC(Nc2nc(C)ccc2-c2cnc3[nH]ccc3n2)C1] | 351 | 213.0-215.0 |
| I-31 | (1-Methane-sulfonyl-piperidin-3-yl)-[6-methyl-3-(5H-pyrrolo[2,3-b]pyrazin-2-yl)-pyridin-2-yl]-amine | 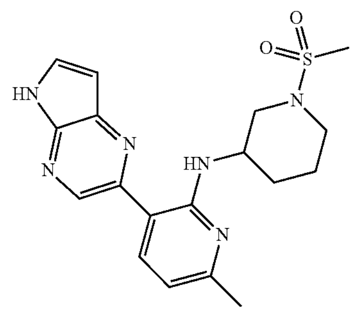 [SMILES: Cc1ccc(-c2cnc3[nH]ccc3n2)c(NC2CCCN(S(C)(=O)=O)C2)n1] | 387 | 253.0-255.0 |
| I-32 | [(S)-1-(2,2-Dimethyl-propane-1-sulfonyl)-piperidin-3-yl]-[3-(5H-pyrrolo[2,3-b]pyrazin-2-yl)-pyridin-2-yl]-amine | 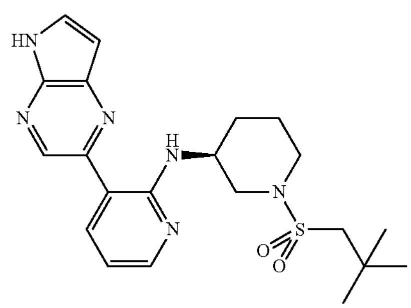 [SMILES: CC(C)(C)CS(=O)(=O)N1CCC[C@H](Nc2ncccc2-c2cnc3[nH]ccc3n2)C1] | 429 | 120.0-125.0 |
| I-33 | [3-(5H-Pyrrolo[2,3-b]pyrazin-2-yl)-pyridin-2-yl]-[(S)-1-(2,2,2-trifluoro-ethyl)-piperidin-3-yl]-amine | 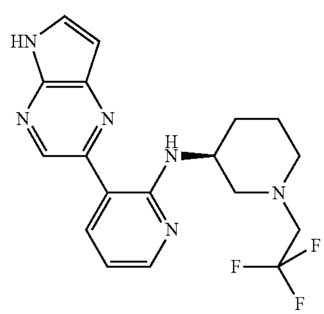 [SMILES: FC(F)(F)CN1CCC[C@H](Nc2ncccc2-c2cnc3[nH]ccc3n2)C1] | 377 | 207.0-209.0 |
| I-34 | (1-Ethane-sulfonyl-piperidin-3-yl)-[6-methyl-3-(5H-pyrrolo[2,3-b]pyrazin-2-yl)-pyridin-2-yl]-amine | 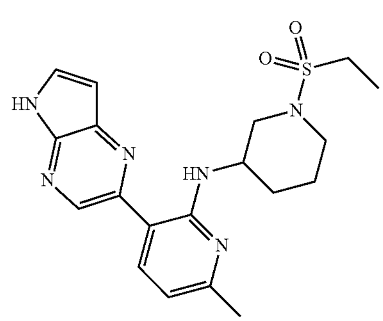 [SMILES: CCS(=O)(=O)N1CCCC(Nc2nc(C)ccc2-c2cnc3[nH]ccc3n2)C1] | 401 | 204.0-207.0 |

TABLE I-continued

| COMPOUND | SYSTEMATIC NAME | STRUCTURE | MS (M + H) | MP |
|---|---|---|---|---|
| I-35 | (1-Cyclopropyl-methanesulfonyl-piperidin-3-yl)-[6-methyl-3-(5H-pyrrolo[2,3-b]pyrazin-2-yl)-pyridin-2-yl]-amine | 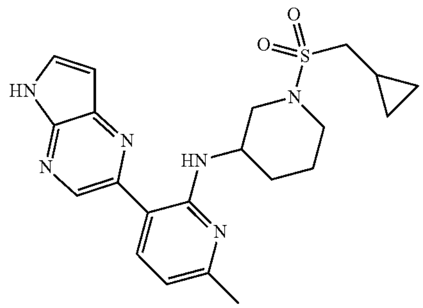 [SMILES: Cc1ccc(-c2cnc3[nH]ccc3n2)c(NC2CCCN(S(=O)(=O)CC3CC3)C2)n1] | 427 | 112.0-116.0 |
| I-36 | [1-(2,2-Dimethyl-propane-1-sulfonyl)-piperidin-3-yl]-[6-methyl-3-(5H-pyrrolo[2,3-b]pyrazin-2-yl)-pyridin-2-yl]-amine | 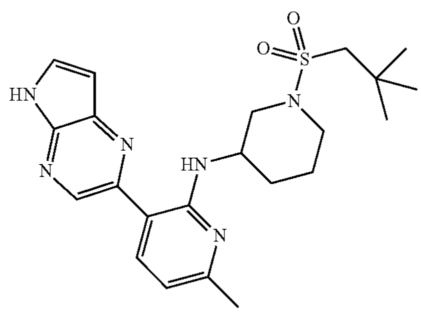 [SMILES: Cc1ccc(-c2cnc3[nH]ccc3n2)c(NC2CCCN(S(=O)(=O)CC(C)(C)C)C2)n1] | 443 | 218.0-220.0 |
| I-37 | (1-Methane-sulfonyl-azepan-4-yl)-[3-(5H-pyrrolo[2,3-b]pyrazin-2-yl)-pyridin-2-yl]-amine | 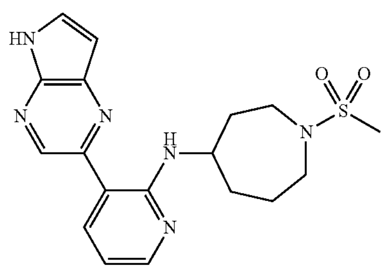 [SMILES: CS(=O)(=O)N1CCCC(Nc2ncccc2-c2cnc3[nH]ccc3n2)CC1] | 387 | 215.0-217.0 |
| I-38 | ((S)-1-Cyclopropyl-methanesulfonyl-piperidin-3-yl)-[3-(5H-pyrrolo[2,3-b]pyrazin-2-yl)-pyridin-2-yl]-amine | 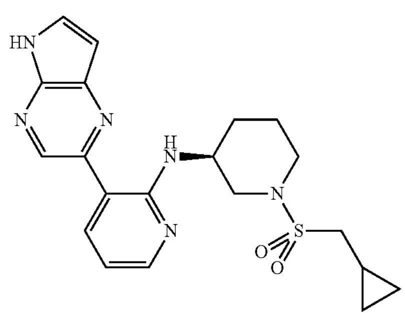 [SMILES: O=S(=O)(CC1CC1)N1CCC[C@H](Nc2ncccc2-c2cnc3[nH]ccc3n2)C1] | 413 | 209.0-212.0 |
| I-39 | 1-{3-[3-(7-Chloro-5H-pyrrolo[2,3-b]pyrazin-2-yl)-6-methyl-pyridin-2-ylamino]-piperidin-1-yl}-ethanone | 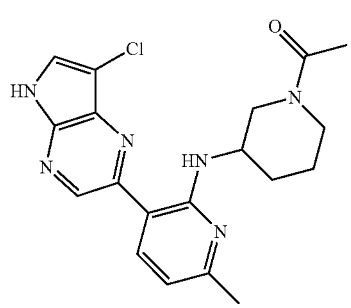 [SMILES: CC(=O)N1CCCC(Nc2nc(C)ccc2-c2cnc3[nH]cc(Cl)c3n2)C1] | 385 | 254.0-259.0 |

TABLE I-continued

| COMPOUND | SYSTEMATIC NAME | STRUCTURE | MS (M + H) | MP |
|---|---|---|---|---|
| I-40 | [3-(7-Chloro-5H-pyrrolo[2,3-b]pyrazin-2-yl)-6-methyl-pyridin-2-yl]-(1-cyclopropyl-methanesulfonyl-piperidin-3-yl)-amine | 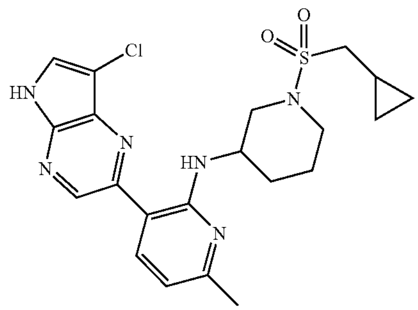 [SMILES: Cc1ccc(-c2cnc3[nH]cc(Cl)c3n2)c(NC2CCCN(S(=O)(=O)CC3CC3)C2)n1] | 461 | 255.0-258.0 |
| I-41 | ((S)-1-Methanesulfonyl-piperidin-3-yl)-[3-(5H-pyrrolo[2,3-b]pyrazin-2-yl)-pyrazin-2-yl]-amine | 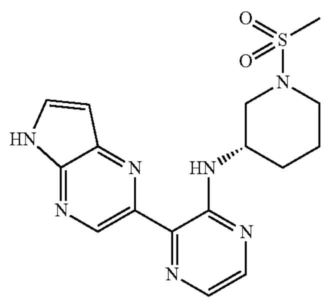 [SMILES: CS(=O)(=O)N1CCC[C@H](Nc2nccnc2-c2cnc3[nH]ccc3n2)C1] | 374 | |
| I-42 | {(S)-3-[3-(5H-Pyrrolo[2,3-b]pyrazin-2-yl)-pyridin-2-ylamino]-piperidine-1-sulfonyl}-acetonitrile | 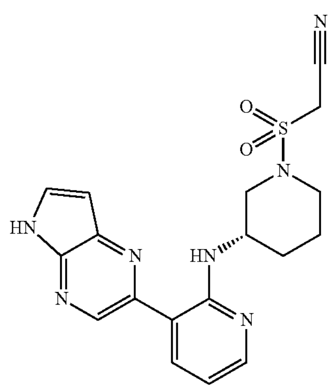 [SMILES: N#CCS(=O)(=O)N1CCC[C@H](Nc2ncccc2-c2cnc3[nH]ccc3n2)C1] | 398 | |
| I-43 | ((S)-1-Methanesulfonyl-piperidin-3-yl)-[3-(5-methyl-5H-pyrrolo[2,3-b]pyrazin-3-yl)-pyridin-2-yl]-amine | 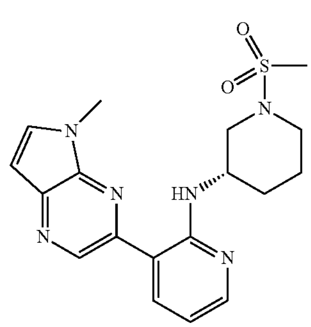 [SMILES: Cn1ccc2ncc(-c3cccnc3N[C@H]3CCCN(S(C)(=O)=O)C3)nc21] | 387 | |

TABLE I-continued

| COMPOUND | SYSTEMATIC NAME | STRUCTURE | MS (M + H) | MP |
|---|---|---|---|---|
| I-44 | [3-(1H-Imidazo[4,5-b]pyrazin-5-yl)-pyridin-2-yl]-((S)-1-methanesulfonyl-piperidin-3-yl)-amine | 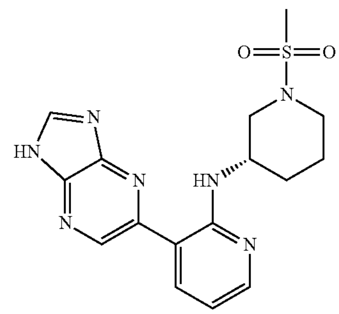 [SMILES: CS(=O)(=O)N1CCC[C@H](Nc2ncccc2-c2cnc3[nH]cnc3n2)C1] | 374 | |
| I-45 | ((S)-1-Methanesulfonyl-piperidin-3-yl)-[3-(1H-pyrazolo[3,4-b]pyrazin-5-yl)-pyridin-2-yl]-amine | 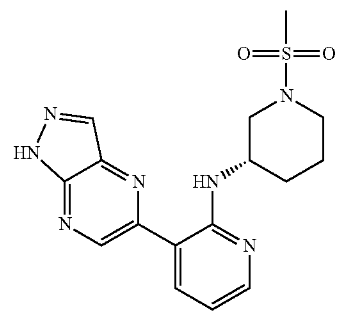 [SMILES: CS(=O)(=O)N1CCC[C@H](Nc2ncccc2-c2cnc3[nH]ncc3n2)C1] | 374 | |
| I-46 | [(S)-1-(Propane-1-sulfonyl)-piperidin-3-yl]-[3-(1H-pyrazolo[3,4-b]pyrazin-5-yl)-pyridin-2-yl]-amine | 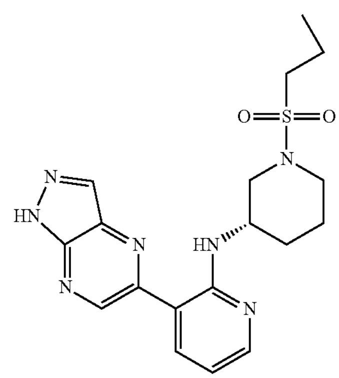 [SMILES: CCCS(=O)(=O)N1CCC[C@H](Nc2ncccc2-c2cnc3[nH]ncc3n2)C1] | 402 | |
| I-47 | [(S)-1-(2-Methyl-propane-1-sulfonyl)-piperidin-3-yl]-[3-(1H-pyrazolo[3,4-b]pyrazin-5-yl)-pyridin-2-yl]-amine | 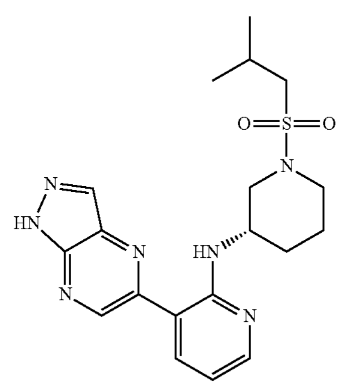 [SMILES: CC(C)CS(=O)(=O)N1CCC[C@H](Nc2ncccc2-c2cnc3[nH]ncc3n2)C1] | 416 | |

TABLE I-continued

| COMPOUND | SYSTEMATIC NAME | STRUCTURE | MS (M + H) | MP |
|---|---|---|---|---|
| I-48 | [(S)-1-(Propane-1-sulfonyl)-piperidin-3-yl]-[3-(5H-pyrrolo[2,3-b]pyrazin-3-yl)-pyridin-2-yl]-amine | 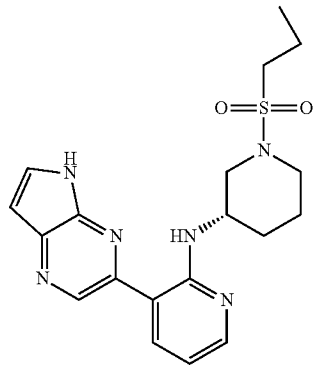 [SMILES: CCCS(=O)(=O)N1CCC[C@H](Nc2ncccc2-c2cnc3cc[nH]c3n2)C1] | 401 | |
| I-49 | [3-(5-Methyl-5H-pyrrolo[2,3-b]pyrazin-3-yl)-pyridin-2-yl]-[(S)-1-(propane-1-sulfonyl)-piperidin-3-yl]-amine | 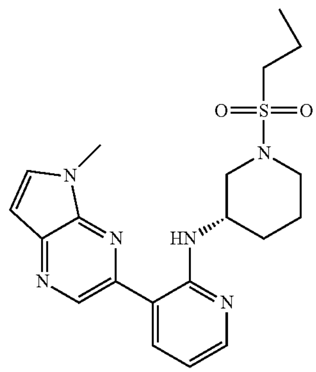 [SMILES: CCCS(=O)(=O)N1CCC[C@H](Nc2ncccc2-c2cnc3ccn(C)c3n2)C1] | 415 | |
| I-50 | [(S)-1-(2-Methyl-propane-1-sulfonyl)-piperidin-3-yl]-[3-(5-methyl-5H-pyrrolo[2,3-b]pyrazin-3-yl)-pyridin-2-yl]-amine | 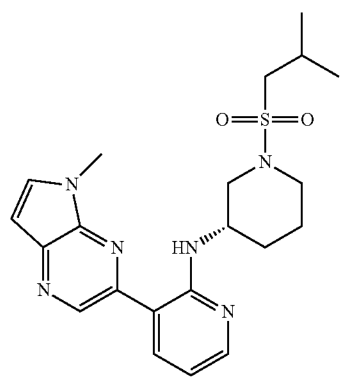 [SMILES: CC(C)CS(=O)(=O)N1CCC[C@H](Nc2ncccc2-c2cnc3ccn(C)c3n2)C1] | 429 | |
| I-51 | [3-(1H-Imidazo[4,5-b]pyrazin-5-yl)-pyridin-2-yl]-[(S)-1-(propane-1-sulfonyl)-piperidin-3-yl]-amine | 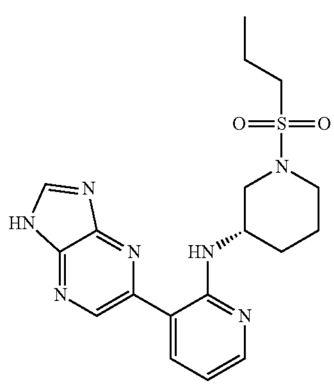 [SMILES: CCCS(=O)(=O)N1CCC[C@H](Nc2ncccc2-c2cnc3[nH]cnc3n2)C1] | 402 | |

TABLE I-continued

| COMPOUND | SYSTEMATIC NAME | STRUCTURE | MS (M + H) | MP |
|---|---|---|---|---|
| I-52 | [3-(1H-Imidazo[4,5-b]pyrazin-5-yl)-pyridin-2-yl]-[(S)-1-(2-methyl-propane-1-sulfonyl)-piperidin-3-yl]-amine | 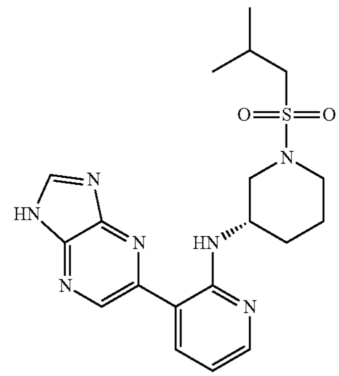 [SMILES: CC(C)CS(=O)(=O)N1CCC[C@H](Nc2ncccc2-c2cnc3[nH]cnc3n2)C1] | 416 | |
| I-53 | 1-{(S)-3-[3-(1H-Pyrazolo[3,4-b]pyrazin-5-yl)-pyridin-2-ylamino]-piperidin-1-yl}-ethanone | 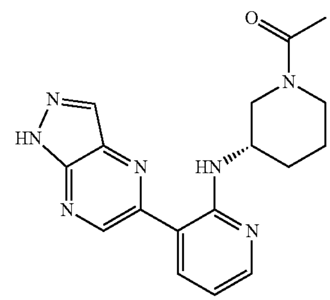 [SMILES: CC(=O)N1CCC[C@H](Nc2ncccc2-c2cnc3[nH]ncc3n2)C1] | 338 | |
| I-54 | ((S)-1-Methanesulfonyl-piperidin-3-yl)-[3-(5H-pyrrolo[2,3-b]pyrazin-3-yl)-pyridin-2-yl]-amine | 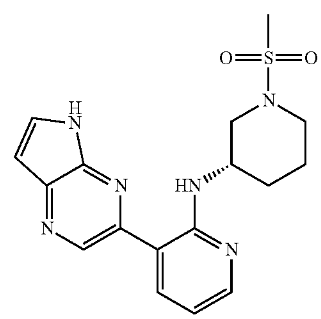 [SMILES: CS(=O)(=O)N1CCC[C@H](Nc2ncccc2-c2cnc3cc[nH]c3n2)C1] | 373 | |
| I-55 | 1-{(S)-3-[3-(5-Methyl-5H-pyrrolo[2,3-b]pyrazin-3-yl)-pyridin-2-ylamino]-piperidin-1-yl}-ethanone | 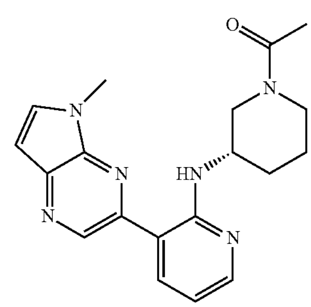 [SMILES: CC(=O)N1CCC[C@H](Nc2ncccc2-c2cnc3ccn(C)c3n2)C1] | 351 | |

TABLE I-continued

| COMPOUND | SYSTEMATIC NAME | STRUCTURE | MS (M + H) | MP |
|---|---|---|---|---|
| I-56 | [(S)-1-(2-Methyl-propane-1-sulfonyl)-piperidin-3-yl]-[3-(5H-pyrrolo[2,3-b]pyrazin-2-yl)-pyrazin-2-yl]-amine | 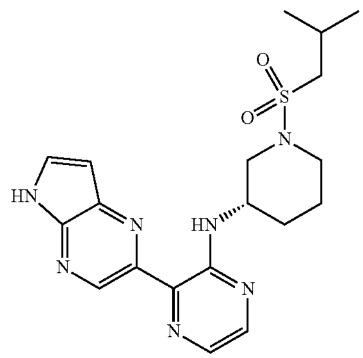 [SMILES: CC(C)CS(=O)(=O)N1CCC[C@H](Nc2nccnc2-c2cnc3[nH]ccc3n2)C1] | 416 | |
| I-57 | [(S)-1-(2-Methyl-propane-1-sulfonyl)-piperidin-3-yl]-[3-(5H-pyrrolo[2,3-b]pyrazin-3-yl)-pyridin-2-yl]-amine | 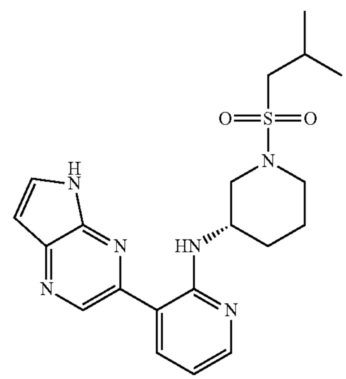 [SMILES: CC(C)CS(=O)(=O)N1CCC[C@H](Nc2ncccc2-c2cnc3cc[nH]c3n2)C1] | 415 | |
| I-58 | 1-{(S)-3-[3-(5H-Pyrrolo[2,3-b]pyrazin-3-yl)-pyridin-2-ylamino]-piperidin-1-yl}-ethanone | 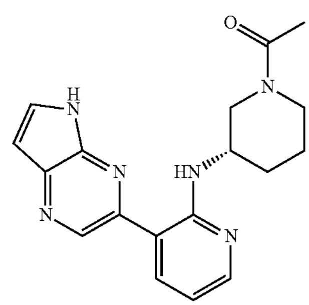 [SMILES: CC(=O)N1CCC[C@H](Nc2ncccc2-c2cnc3cc[nH]c3n2)C1] | 337 | |
| I-59 | 1-{3-[3-(1H-Imidazo[4,5-b]pyrazin-5-yl)-pyridin-2-ylamino]-piperidin-1-yl}-ethanone | 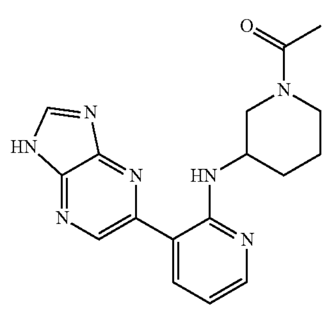 [SMILES: CC(=O)N1CCCC(Nc2ncccc2-c2cnc3[nH]cnc3n2)C1] | 338 | |

TABLE I-continued

| COMPOUND | SYSTEMATIC NAME | STRUCTURE | MS (M + H) | MP |
|---|---|---|---|---|
| I-60 | 2-[2-((S)-1-Methanesulfonyl-piperidin-3-ylamino)-pyridin-3-yl]-5H-pyrrolo[2,3-b]pyrazine-7-carbonitrile | 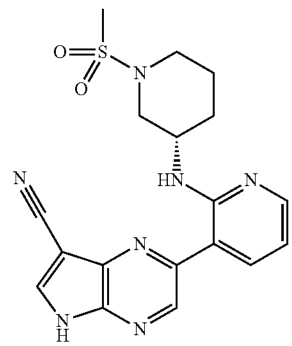 [SMILES: CS(=O)(=O)N1CCC[C@H](Nc2ncccc2-c2cnc3[nH]cc(C#N)c3n2)C1] | 398 | |
| I-61 | ((S)-1-Methanesulfonyl-piperidin-3-yl)-[3-(7-methyl-5H-pyrrolo[2,3-b]pyrazin-2-yl)-pyridin-2-yl]-amine | 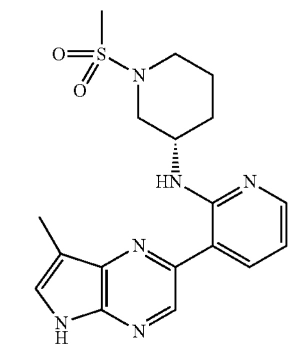 [SMILES: Cc1c[nH]c2ncc(-c3cccnc3N[C@H]3CCCN(S(C)(=O)=O)C3)nc12] | 387 | |
| I-62 | [3-(7-Cyclopropyl-5H-pyrrolo[2,3-b]pyrazin-2-yl)-pyridin-2-yl]-((S-1-methanesulfonyl-piperidin-3-yl)-amine | 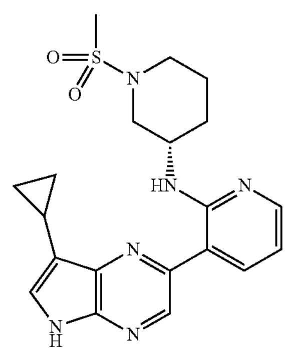 [SMILES: CS(=O)(=O)N1CCC[C@H](Nc2ncccc2-c2cnc3[nH]cc(C4CC4)c3n2)C1] | 413 | |
| I-63 | [3-(7-Chloro-5H-pyrrolo[2,3-b]pyrazin-2-yl)-pyridin-2-yl]-((S)-1-methanesulfonyl-piperidin-3-yl)-amine | 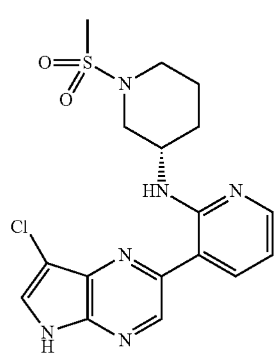 [SMILES: CS(=O)(=O)N1CCC[C@H](Nc2ncccc2-c2cnc3[nH]cc(Cl)c3n2)C1] | 407 | |

TABLE I-continued

| COMPOUND | SYSTEMATIC NAME | STRUCTURE | MS (M + H) | MP |
|---|---|---|---|---|
| I-64 | (3R,4R)-1-(2-Methyl-propane-1-sulfonyl)-3-[3-(5H-pyrrolo[2,3-b]pyrazin-2-yl)-pyridin-2-ylamino]-piperidin-4-ol | 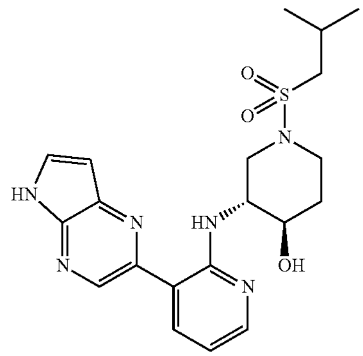 [SMILES: CC(C)CS(=O)(=O)N1CC[C@@H](O)[C@H](Nc2ncccc2-c2cnc3[nH]ccc3n2)C1] | 431 | |
| I-65 | (3R,4R)-1-Methanesulfonyl-3-[3-(5H-pyrrolo[2,3-b]pyrazin-2-yl)-pyridin-2-ylamino]-piperidin-4-ol | 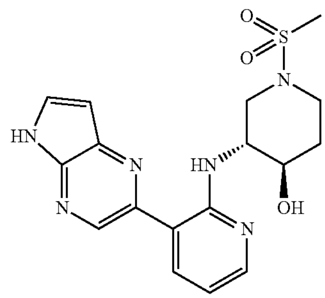 [SMILES: CS(=O)(=O)N1CC[C@@H](O)[C@H](Nc2ncccc2-c2cnc3[nH]ccc3n2)C1] | 389 | |
| I-66 | (S)-3-[3-(5H-Pyrrolo[2,3-b]pyrazin-2-yl)-pyridin-2-ylamino]-piperidine-1-sulfonic acid dimethylamide | 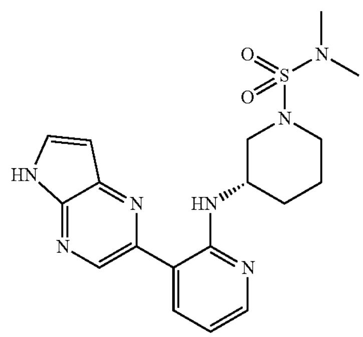 [SMILES: CN(C)S(=O)(=O)N1CCC[C@H](Nc2ncccc2-c2cnc3[nH]ccc3n2)C1] | 402 | |
| I-67 | (S)-3-[3-(5H-Pyrrolo[2,3-b]pyrazin-2-yl)-pyridin-2-ylamino]-piperidine-1-sulfonic acid tert-butylamide | 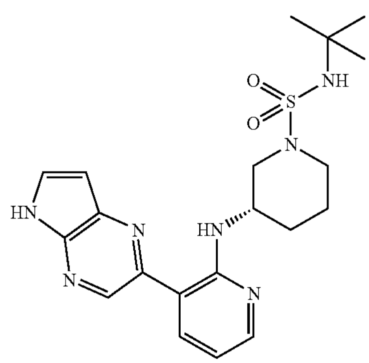 [SMILES: CC(C)(C)NS(=O)(=O)N1CCC[C@H](Nc2ncccc2-c2cnc3[nH]ccc3n2)C1] | 430 | |
| I-68 | ((S)-1-Methanesulfonyl-piperidin-3-yl)-[5-(5H-pyrrolo[2,3-b]pyrazin-2-yl)-pyrimidin-4-yl]-amine | 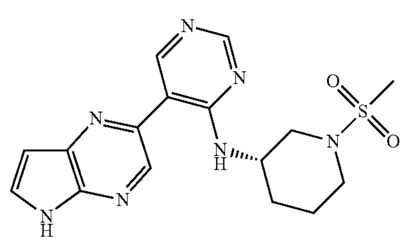 [SMILES: CS(=O)(=O)N1CCC[C@H](Nc2ncncc2-c2cnc3[nH]ccc3n2)C1] | 374 | |

TABLE I-continued

| COMPOUND | SYSTEMATIC NAME | STRUCTURE | MS (M + H) | MP |
|---|---|---|---|---|
| I-69 | [(S)-1-(2-Methyl-propane-1-sulfonyl)-piperidin-3-yl]-[5-(5H-pyrrolo[2,3-b]pyrazin-2-yl)-pyrimidin-4-yl]-amine | 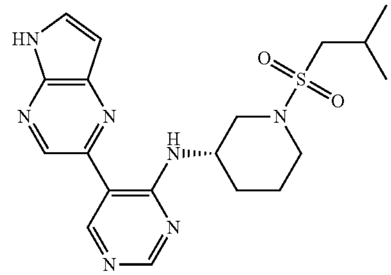 [SMILES: CC(C)CS(=O)(=O)N1CCC[C@H](Nc2ncncc2-c2cnc3[nH]ccc3n2)C1] | 416 | |
| I-70 | N4-[(S)-1-(2-Methyl-propane-1-sulfonyl)-piperidin-3-yl]-5-(5H-pyrrolo[2,3-b]pyrazin-2-yl)-pyrimidine-2,4-diamine | 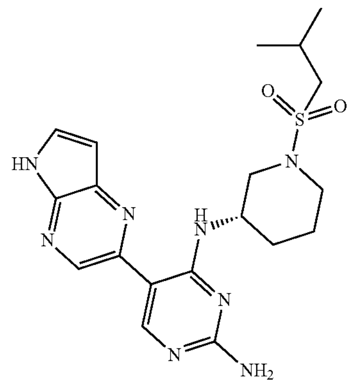 [SMILES: CC(C)CS(=O)(=O)N1CCC[C@H](Nc2nc(N)ncc2-c2cnc3[nH]ccc3n2)C1] | 431 | |
| I-71 | N2,N2-Dimethyl-N4-[(S)-1-(2-methyl-propane-1-sulfonyl)-piperidin-3-yl]-5-(5H-pyrrolo[2,3-b]pyrazin-2-yl)-pyrimidine-2,4-diamine | 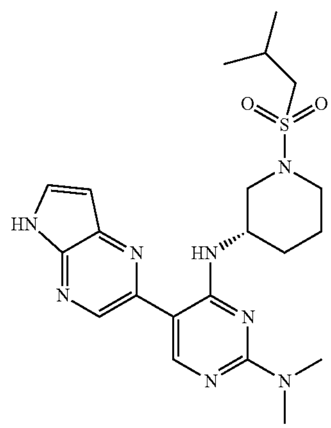 [SMILES: CC(C)CS(=O)(=O)N1CCC[C@H](Nc2nc(N(C)C)ncc2-c2cnc3[nH]ccc3n2)C1] | 459 | |
| I-72 | [2-Methanesulfonyl-5-(5H-pyrrolo[2,3-b]pyrazin-2-yl)-pyrimidin-4-yl]-[(S)-1-(2-methyl-propane-1-sulfonyl)-piperidin-3-yl]-amine | 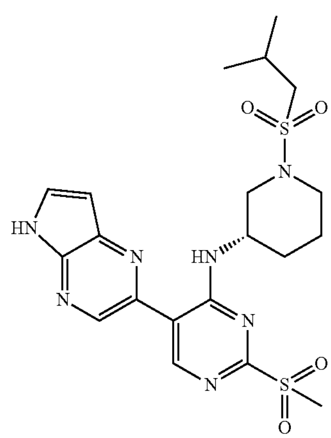 [SMILES: CC(C)CS(=O)(=O)N1CCC[C@H](Nc2nc(S(C)(=O)=O)ncc2-c2cnc3[nH]ccc3n2)C1] | 494 | |

TABLE I-continued

| COMPOUND | SYSTEMATIC NAME | STRUCTURE | MS (M + H) | MP |
|---|---|---|---|---|
| I-73 | [(S)-1-(2-Methyl-propane-1-sulfonyl)-piperidin-3-yl]-[2-methylsulfanyl-5-(5H-pyrrolo[2,3-b]pyrazin-2-yl)-pyrimidin-4-yl]-amine | 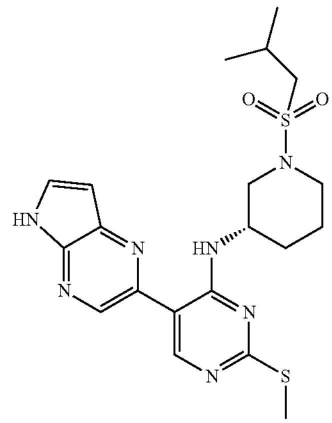 [SMILES: CSc1ncc(-c2cnc3[nH]ccc3n2)c(N[C@H]2CCCN(S(=O)(=O)CC(C)C)C2)n1] | 462 | |
| I-74 | [(S)-1-(2-Methyl-propane-1-sulfonyl)-piperidin-3-yl]-[2-morpholin-4-yl-5-(5H-pyrrolo[2,3-b]pyrazin-2-yl)-pyrimidin-4-yl]-amine | 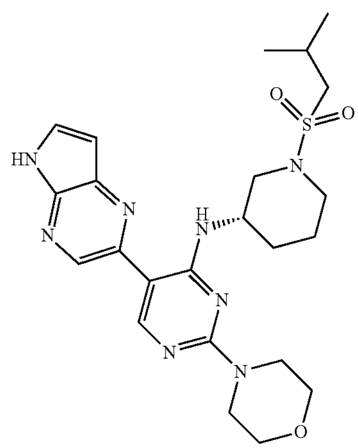 [SMILES: CC(C)CS(=O)(=O)N1CCC[C@H](Nc2nc(N3CCOCC3)ncc2-c2cnc3[nH]ccc3n2)C1] | 501 | |
| I-75 | ((S)-1-Methanesulfonyl-piperidin-3-yl)-[2-methylsulfanyl-5-(5H-pyrrolo[2,3-b]pyrazin-2-yl)-pyrimidin-4-yl]-amine | 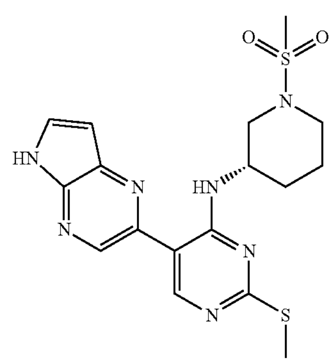 [SMILES: CSc1ncc(-c2cnc3[nH]ccc3n2)c(N[C@H]2CCCN(S(C)(=O)=O)C2)n1] | 420 | |
| I-76 | N4-((S)-1-Methanesulfonyl-piperidin-3-yl)-N2,N2-dimethyl-5-(5H-pyrrolo[2,3-b]pyrazin-2-yl)-pyrimidine-2,4-diamine | 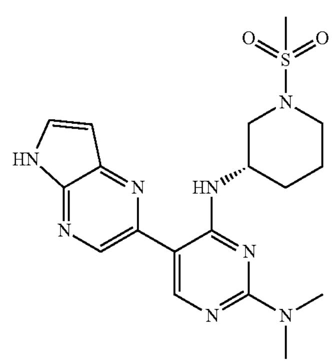 [SMILES: CN(C)c1ncc(-c2cnc3[nH]ccc3n2)c(N[C@H]2CCCN(S(C)(=O)=O)C2)n1] | 417 | |

TABLE I-continued

| COMPOUND | SYSTEMATIC NAME | STRUCTURE | MS (M + H) | MP |
|---|---|---|---|---|
| I-77 | N-((S)-1-Methanesulfonyl-piperidin-3-yl)-5-(5H-pyrrolo[2,3-b]pyrazin-2-yl)-pyrimidine-2,4-diamine | 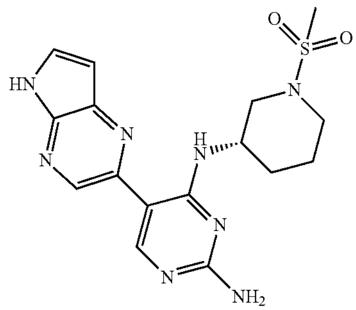 [SMILES: CS(=O)(=O)N1CCC[C@H](Nc2nc(N)ncc2-c2cnc3[nH]ccc3n2)C1] | 389 | |
| I-78 | 2-[2-Dimethylamino-4-((S)-1-methanesulfonyl-piperidin-3-ylamino)-pyrimidin-5-yl]-5H-pyrrolo[2,3-b]pyrazine-7-carbonitrile | 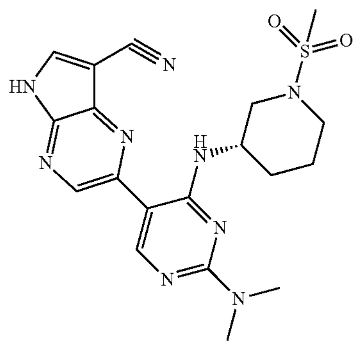 [SMILES: CN(C)c1ncc(-c2cnc3[nH]cc(C#N)c3n2)c(N[C@H]2CCCN(S(C)(=O)=O)C2)n1] | 442 | |
| I-79 | [(S)-1-(3,3-Dimethyl-butane-1-sulfonyl)-piperidin-3-yl]-[2-methylsulfanyl-5-(5H-pyrrolo[2,3-b]pyrazin-2-yl)-pyrimidin-4-yl]-amine | 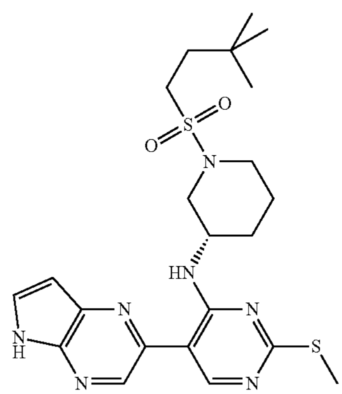 [SMILES: CSc1ncc(-c2cnc3[nH]ccc3n2)c(N[C@H]2CCCN(S(=O)(=O)CCC(C)(C)C)C2)n1] | 490 | |
| I-80 | ((S)-1-Methanesulfonyl-piperidin-3-yl)-[2-methoxy-5-(5H-pyrrolo[2,3-b]pyrazin-2-yl)-pyrimidin-4-yl]-amine | 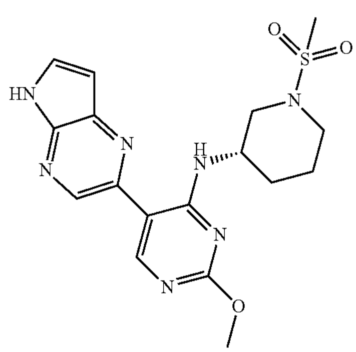 [SMILES: COc1ncc(-c2cnc3[nH]ccc3n2)c(N[C@H]2CCCN(S(C)(=O)=O)C2)n1] | 404 | |

TABLE I-continued

| COMPOUND | SYSTEMATIC NAME | STRUCTURE | MS (M + H) | MP |
|---|---|---|---|---|
| I-81 | [2-Chloro-5-(5H-pyrrolo[2,3-b]pyrazin-2-yl)-pyrimidin-4-yl]-((S)-1-methanesulfonyl-piperidin-3-yl)-amine | 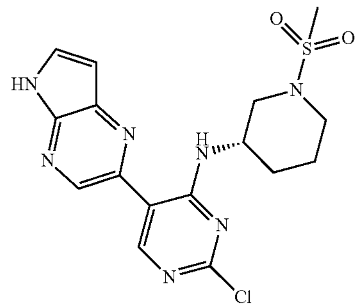 [SMILES: CS(=O)(=O)N1CCC[C@H](Nc2nc(Cl)ncc2-c2cnc3[nH]ccc3n2)C1] | 408 | |
| I-82 | ((S)-1-Methanesulfonyl-piperidin-3-yl)-[2-(4-methyl-piperazin-1-yl)-5-(5H-pyrrolo[2,3-b]pyrazin-2-yl)-pyrimidin-4-yl]-amine | 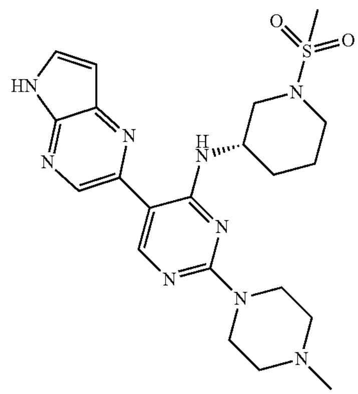 [SMILES: CN1CCN(c2ncc(-c3cnc4[nH]ccc4n3)c(N[C@H]3CCCN(S(C)(=O)=O)C3)n2)CC1] | 472 | |
| I-83 | 4-((S)-1-Methanesulfonyl-piperidin-3-ylamino)-5-(5H-pyrrolo[2,3-b]pyrazin-2-yl)-pyrimidin-2-ol | 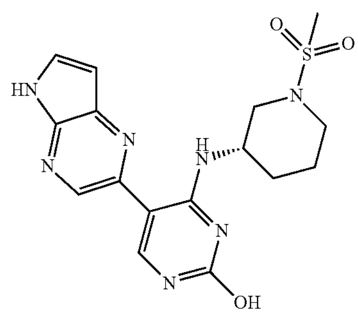 [SMILES: CS(=O)(=O)N1CCC[C@H](Nc2nc(O)ncc2-c2cnc3[nH]ccc3n2)C1] | 390 | |
| I-84 | [2-Ethoxy-5-(5H-pyrrolo[2,3-b]pyrazin-2-yl)-pyrimidin-4-yl]-((S)-1-methanesulfonyl-piperidin-3-yl)-amine | 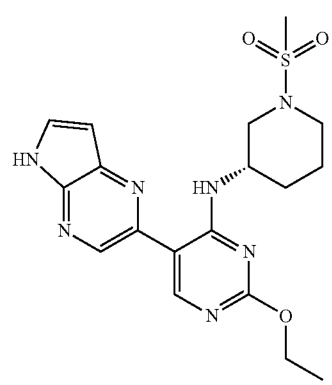 [SMILES: CCOc1ncc(-c2cnc3[nH]ccc3n2)c(N[C@H]2CCCN(S(C)(=O)=O)C2)n1] | 418 | |

TABLE I-continued

| COMPOUND | SYSTEMATIC NAME | STRUCTURE | MS (M + H) | MP |
|---|---|---|---|---|
| I-85 | 2-[4-((S)-1-Methanesulfonyl-piperidin-3-ylamino)-5-(5H-pyrrolo[2,3-b]pyrazin-2-yl)-pyrimidin-2-ylamino]-ethanol | 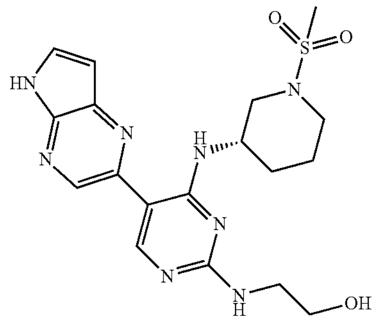 [SMILES: CS(=O)(=O)N1CCC[C@H](Nc2nc(NCCO)ncc2-c2cnc3[nH]ccc3n2)C1] | 433 | |
| I-86 | N4-((S)-1-Methanesulfonyl-piperidin-3-yl)-N2-(2-methoxy-ethyl)-5-(5H-pyrrolo[2,3-b]pyrazin-2-yl)-pyrimidine-2,4-diamine | 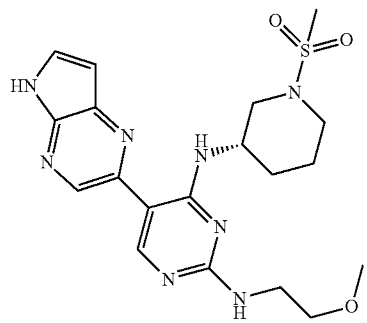 [SMILES: COCCNc1ncc(-c2cnc3[nH]ccc3n2)c(N[C@H]2CCCN(S(C)(=O)=O)C2)n1] | 447 | |
| I-87 | ((S)-1-Methanesulfonyl-piperidin-3-yl)-[2-morpholin-4-yl-5-(5H-pyrrolo[2,3-b]pyrazin-2-yl)-pyrimidin-4-yl]-amine | 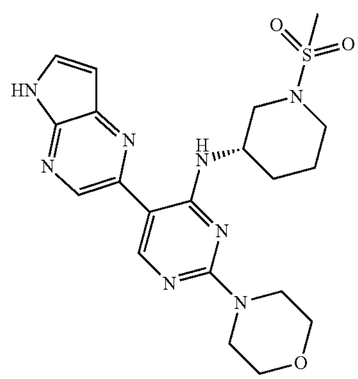 [SMILES: CS(=O)(=O)N1CCC[C@H](Nc2nc(N3CCOCC3)ncc2-c2cnc3[nH]ccc3n2)C1] | 459 | |
| I-88 | 3-{(S)-3-[2-Methylsulfanyl-5-(5H)-pyrrolo[2,3-b]pyrazin-2-yl)-pyrimidin-4-ylamino]-piperidin-1-yl}-3-oxo-propionitrile | 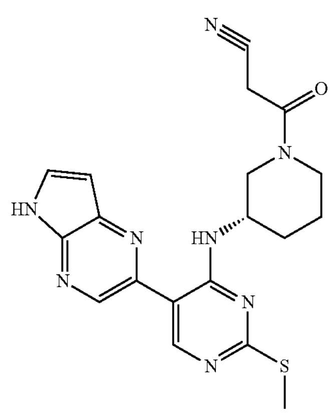 [SMILES: CSc1ncc(-c2cnc3[nH]ccc3n2)c(N[C@H]2CCCN(C(=O)CC#N)C2)n1] | 409 | |

TABLE I-continued

| COMPOUND | SYSTEMATIC NAME | STRUCTURE | MS (M + H) | MP |
|---|---|---|---|---|
| I-89 | 1-[4-((S)-1-Methanesulfonyl-piperidin-3-ylamino)-5-(5H-pyrrolo[2,3-b]pyrazin-2-yl)-pyrimidin-2-ylamino]-2-methyl-propan-2-ol | 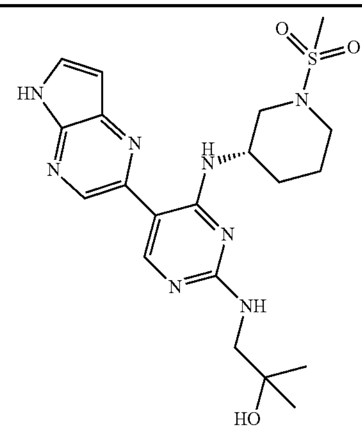 | 461 | |
| I-90 | [2-(1,1-Dioxo-1λ6-thiomorpholin-4-yl)-5-(5H-pyrrolo[2,3-b]pyrazin-2-yl)-pyrimidin-4-yl]-((S)-1-methanesulfonyl-piperidin-3-yl)-amine | 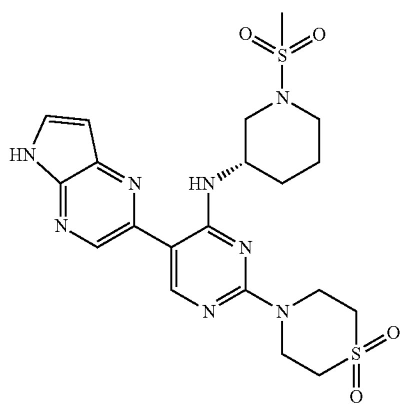 [SMILES: CS(=O)(=O)N1CCC[C@H](Nc2nc(N3CCS(=O)(=O)CC3)ncc2-c2cnc3[nH]ccc3n2)C1] | 507 | |
| I-91 | ((S)-1-Methanesulfonyl-piperidin-3-yl)-[2-(4-methoxy-piperidin-1-yl)-5-(5H-pyrrolo[2,3-b]pyrazin-2-yl)-pyrimidin-4-yl]-amine | 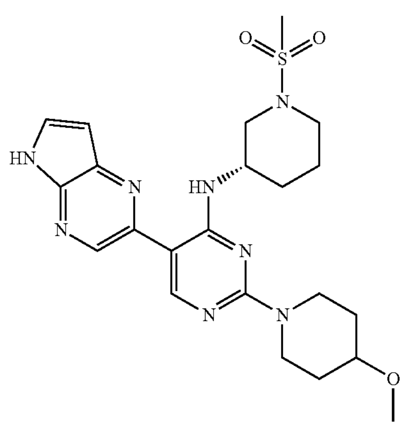 [SMILES: COC1CCN(c2ncc(-c3cnc4[nH]ccc4n3)c(N[C@H]3CCCN(S(C)(=O)=O)C3)n2)CC1] | 487 | |

TABLE I-continued

| COMPOUND | SYSTEMATIC NAME | STRUCTURE | MS (M + H) | MP |
|---|---|---|---|---|
| I-92 | N2-(2-Amino-ethyl)-N4-((S)-1-methanesulfonyl-piperidin-3-yl)-5-(5H-pyrrolo[2,3-b]pyrazin-2-yl)-pyrimidine-2,4-diamine | 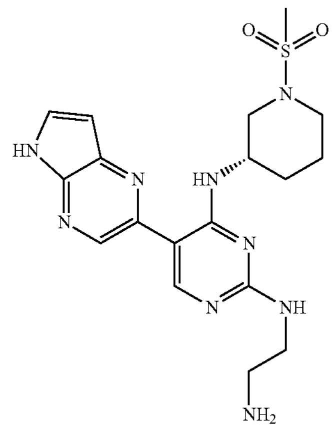 [SMILES: CS(=O)(=O)N1CCC[C@H](Nc2nc(NCCN)ncc2-c2cnc3[nH]ccc3n2)C1] | 432 | |
| I-93 | 2-{1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetamide | 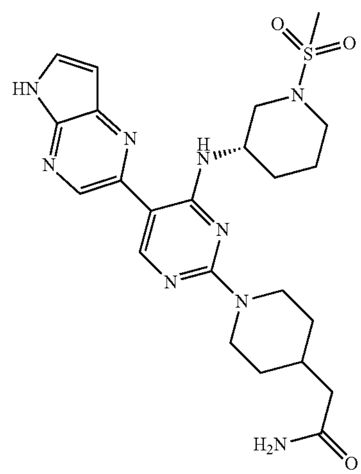 [SMILES: CS(=O)(=O)N1CCC[C@H](Nc2nc(N3CCC(CC(N)=O)CC3)ncc2-c2cnc3[nH]ccc3n2)C1] | 514 | |
| I-94 | (S)-2-[4-((S)-1-Methanesulfonyl-piperidin-3-ylamino)-5-(5H-pyrrolo[2,3-b]pyrazin-2-yl)-pyrimidin-2-ylamino]-butan-1-ol | 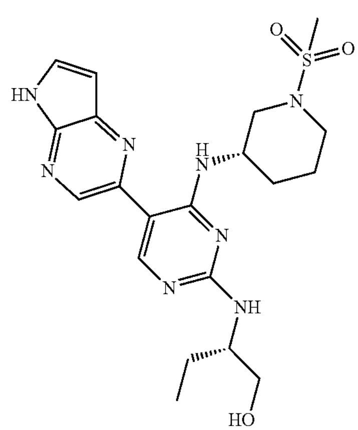 [SMILES: CC[C@@H](CO)Nc1ncc(-c2cnc3[nH]ccc3n2)c(N[C@H]2CCCN(S(C)(=O)=O)C2)n1] | 461 | |

TABLE I-continued

| COMPOUND | SYSTEMATIC NAME | STRUCTURE | MS (M + H) | MP |
|---|---|---|---|---|
| I-95 | (R)-2-[4-((S)-1-Methanesulfonyl-piperidin-3-ylamino)-5-(5H-pyrrolo[2,3-b]pyrazin-2-yl)-pyrimidin-2-ylamino]-butan-1-ol | 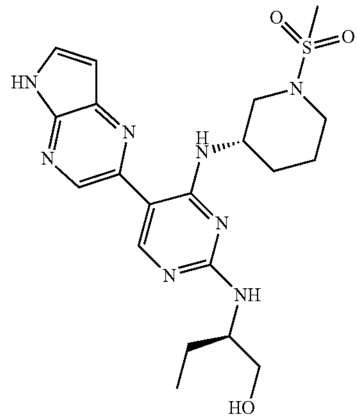 [SMILES: CC[C@H](CO)Nc1ncc(-c2cnc3[nH]ccc3n2)c(N[C@H]2CCCN(S(C)(=O)=O)C2)n1] | 461 | |
| I-96 | N4-((S)-1-Methanesulfonyl-piperidin-3-yl)-N2-(1-methyl-piperidin-4-yl)-5-(5H-pyrrolo[2,3-b]pyrazin-2-yl)-pyrimidine-2,4-diamine | 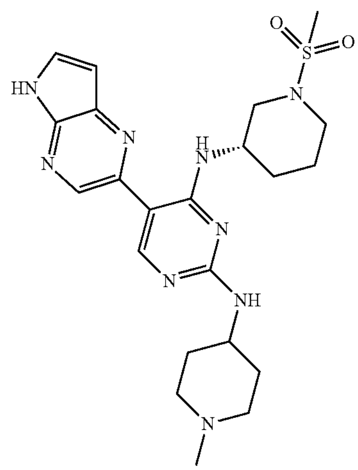 [SMILES: CN1CCC(Nc2ncc(-c3cnc4[nH]ccc4n3)c(N[C@H]3CCCN(S(C)(=O)=O)C3)n2)CC1] | 486 | |
| I-97 | [(S)-1-(3,3-Dimethyl-butane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine | 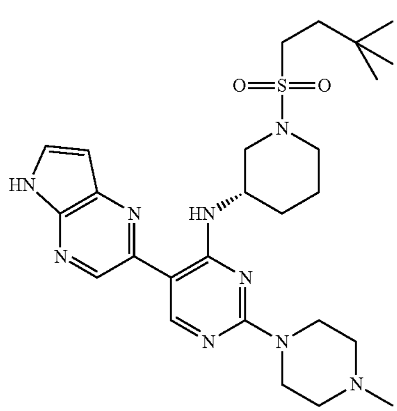 [SMILES: CN1CCN(c2ncc(-c3cnc4[nH]ccc4n3)c(N[C@H]3CCCN(S(=O)(=O)CCC(C)(C)C)C3)n2)CC1] | 542 | |

TABLE I-continued

| COMPOUND | SYSTEMATIC NAME | STRUCTURE | MS (M + H) | MP |
|---|---|---|---|---|
| I-98 | [2-(4-Dimethylamino-piperidin-1-yl)-5-(5H-pyrrolo(2,3-b]pyrazin-2-yl)-pyrimidin-4-yl]-((S)-1-methanesulfonyl-piperidin-3-yl)-amine | 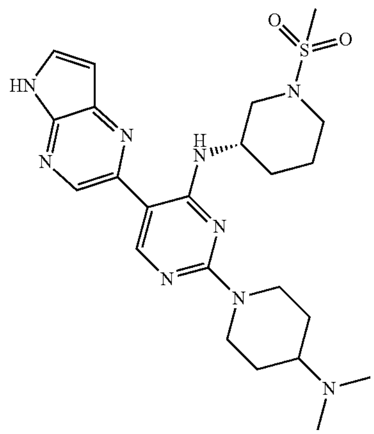 [SMILES: CN(C)C1CCN(c2ncc(-c3cnc4[nH]ccc4n3)c(N[C@H]3CCCN(S(C)(=O)=O)C3)n2)CC1] | 500 | |
| I-99 | 4-((S)-1-Methanesulfonyl-piperidin-3-ylamino)-5-(5H-pyrrolo[2,3-b]pyrazin-2-yl)-pyrimidine-2-carbonitrile | 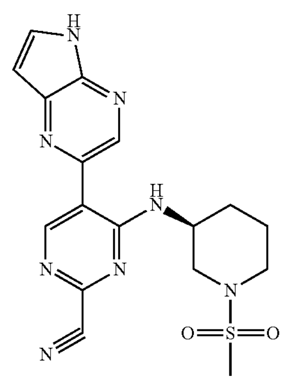 [SMILES: CS(=O)(=O)N1CCC[C@H](Nc2nc(C#N)ncc2-c2cnc3[nH]ccc3n2)C1] | 399 | |
| I-100 | (S)-1-[4-((S)-1-Methanesulfonyl-piperidin-3-ylamino)-5-(5H-pyrrolo[2,3-b]pyrazin-2-yl)-pyrimidin-2-yl]-pyrrolidin-3-ol | 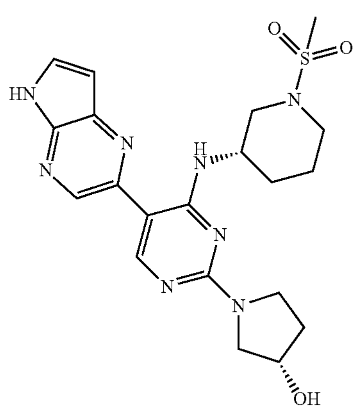 [SMILES: CS(=O)(=O)N1CCC[C@H](Nc2nc(N3CC[C@H](O)C3)ncc2-c2cnc3[nH]ccc3n2)C1] | 459 | |

TABLE I-continued

| COMPOUND | SYSTEMATIC NAME | STRUCTURE | MS (M + H) | MP |
|---|---|---|---|---|
| I-101 | (R)-1-[4-((S)-1-Methanesulfonyl-piperidin-3-ylamino)-5-(5H-pyrrolo[2,3-b]pyrazin-2-yl)-pyrimidin-2-yl]-pyrrolidin-3-ol | 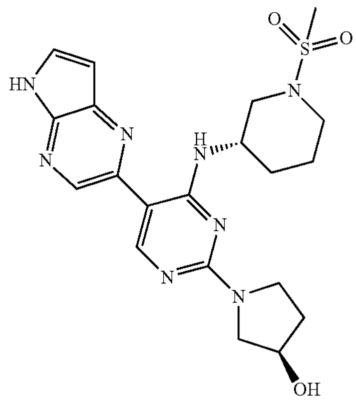 [SMILES: CS(=O)(=O)N1CCC[C@H](Nc2nc(N3CC[C@@H](O)C3)ncc2-c2cnc3[nH]ccc3n2)C1] | 459 | |
| I-102 | 1-[4-((S)-1-Methanesulfonyl-piperidin-3-ylamino)-5-(5H-pyrrolo[2,3-b]pyrazin-2-yl)-pyrimidin-2-yl]-azetidine-3-carbonitrile | 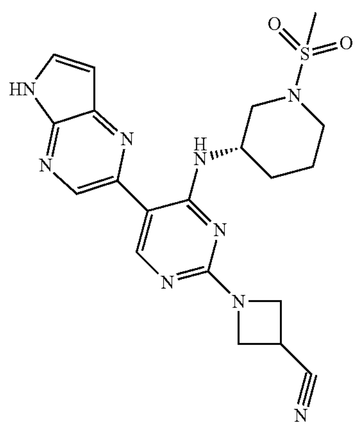 [SMILES: CS(=O)(=O)N1CCC[C@H](Nc2nc(N3CC(C#N)C3)ncc2-c2cnc3[nH]ccc3n2)C1] | 454 | |
| I-103 | 4-[4-((S)-1-Methanesulfonyl-piperidin-3-ylamino)-5-(5H-pyrrolo[2,3-b]pyrazin-2-yl)-pyrimidin-2-ylamino]-cyclohexane-carbonitrile | 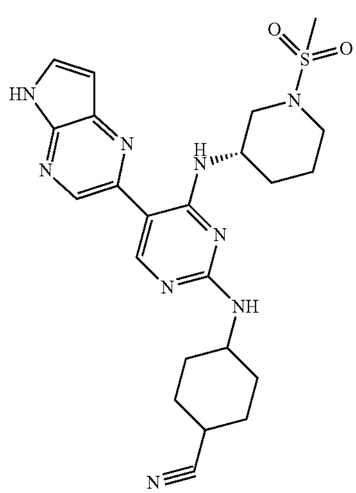 [SMILES: CS(=O)(=O)N1CCC[C@H](Nc2nc(NC3CCC(C#N)CC3)ncc2-c2cnc3[nH]ccc3n2)C1] | 496 | |

TABLE I-continued

| COMPOUND | SYSTEMATIC NAME | STRUCTURE | MS (M + H) | MP |
|---|---|---|---|---|
| I-104 | ((S)-1-Methanesulfonyl-piperidin-3-yl)-[2-(4-pyridin-2-yl-piperazin-1-yl)-5-(5H-pyrrolo[2,3-b]pyrazin-2-yl)-pyrimidin-4-yl]-amine | 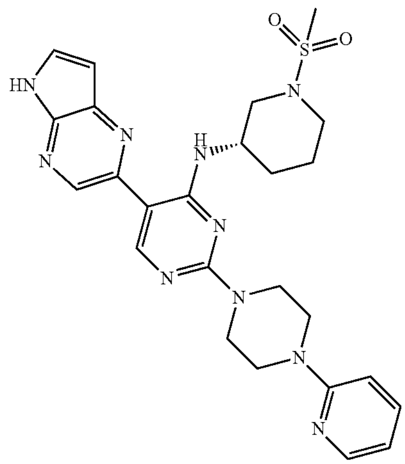 [SMILES: CS(=O)(=O)N1CCC[C@H](Nc2nc(N3CCN(c4ccccn4)CC3)ncc2-c2cnc3[nH]ccc3n2)C1] | 535 | |
| I-105 | {1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetic acid | 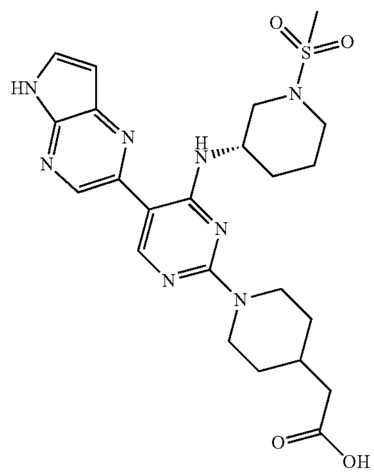 [SMILES: CS(=O)(=O)N1CCC[C@H](Nc2nc(N3CCC(CC(=O)O)CC3)ncc2-c2cnc3[nH]ccc3n2)C1] | 515 | |
| I-106 | N4-((S)-1-Methanesulfonyl-piperidin-3-yl)-N2-pyridin-4-yl-5-(5H-pyrrolo[2,3-b]pyrazin-2-yl)-pyrimidine-2,4-diamine | 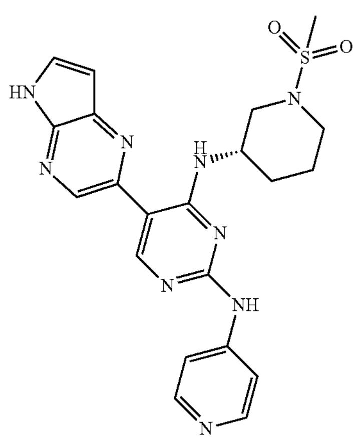 [SMILES: CS(=O)(=O)N1CCC[C@H](Nc2nc(Nc3ccncc3)ncc2-c2cnc3[nH]ccc3n2)C1] | 466 | |

TABLE I-continued

| COMPOUND | SYSTEMATIC NAME | STRUCTURE | MS (M + H) | MP |
|---|---|---|---|---|
| I-107 | N2-(2-Dimethylamino-ethyl)-N4-((S)-1-methanesulfonyl-piperidin-3-yl)-5-(5H-pyrrolo[2,3-b]pyrazin-2-yl)-pyrimidine-2,4-diamine | 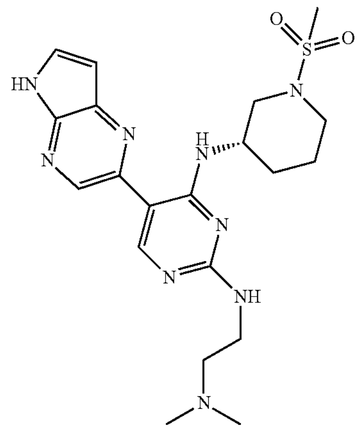 [SMILES: CN(C)CCNc1ncc(-c2cnc3[nH]ccc3n2)c(N[C@H]2CCCN(S(C)(=O)=O)C2)n1] | 460 | |
| I-108 | [2-(4-Ethyl-piperazin-1-yl)-5-(5H-pyrrolo[2,3-b]pyrazin-2-yl)-pyrimidin-4-yl]-((S)-1-methanesulfonyl-piperidin-3-yl)-amine | 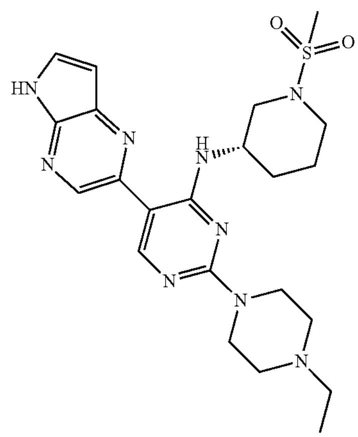 [SMILES: CCN1CCN(c2ncc(-c3cnc4[nH]ccc4n3)c(N[C@H]3CCCN(S(C)(=O)=O)C3)n2)CC1] | 486 | |
| I-109 | [2-((R)-3-Dimethylamino-pyrrolidin-1-yl)-5-(5H-pyrrolo[2,3-b]pyrazin-2-yl)-pyrimidin-4-yl]-((S))-1-methanesulfonyl-piperidin-3-yl)-amine | 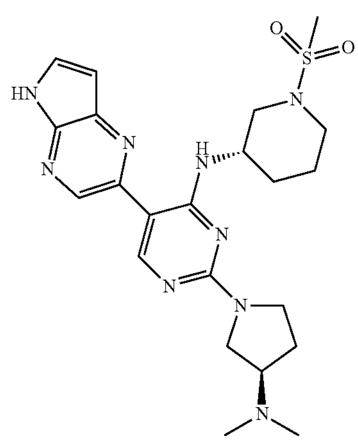 [SMILES: CN(C)[C@@H]1CCN(c2ncc(-c3cnc4[nH]ccc4n3)c(N[C@H]3CCCN(S(C)(=O)=O)C3)n2)C1] | 486 | |

| COMPOUND | SYSTEMATIC NAME | STRUCTURE | MS (M + H) | MP |
|---|---|---|---|---|
| I-110 | [2-(4-Methyl-piperazin-1-yl)-5-(5H-pyrrolo(2,3-b]pyrazin-2-yl)-pyrimidin-4-yl]-[(S)-1-(2-methyl-propane-1-sulfonyl)-piperidin-3-yl]-amine | 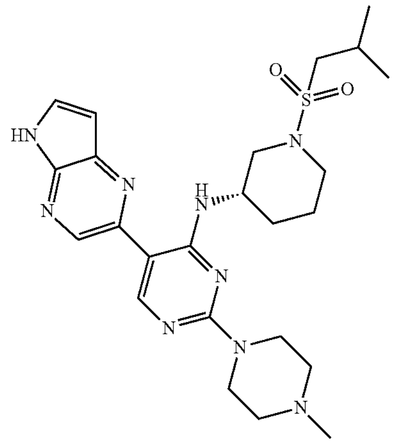 [SMILES: CC(C)CS(=O)(=O)N1CCC[C@H](Nc2nc(N3CCN(C)CC3)ncc2-c2cnc3[nH]ccc3n2)C1] | 514 | |
| I-111 | [(3S,5S)-5-Methyl-1-(2-methyl-propane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine | 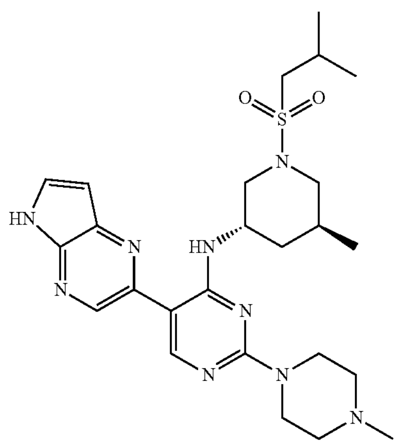 [SMILES: CC(C)CS(=O)(=O)N1C[C@@H](C)C[C@H](Nc2nc(N3CCN(C)CC3)ncc2-c2cnc3[nH]ccc3n2)C1] | 418 | |
| I-112 | {(3S,5S)-3-Methyl-5-[2-(4-methyl-piperazin-1-yl)-5-(5H-pyrrolo[2,3-b]pyrazin-2-yl)-pyrimidin-4-ylamino]-piperidine-1-sulfonyl}-acetonitrile | 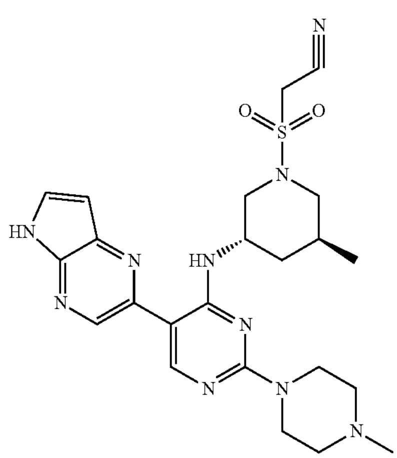 [SMILES: C[C@H]1C[C@H](Nc2nc(N3CCN(C)CC3)ncc2-c2cnc3[nH]ccc3n2)CN(S(=O)(=O)CC#N)C1] | 511 | |

TABLE I-continued

| COMPOUND | SYSTEMATIC NAME | STRUCTURE | MS (M + H) | MP |
|---|---|---|---|---|
| I-113 | ((3S,5S)-1-Methanesulfonyl-5-methyl-piperidin-3-yl)-[2-(4-methyl-piperazin-1-yl)-5-(5H-pyrrolo[2,3-b]pyrazin-2-yl)-pyrimidin-4-yl]-amine | 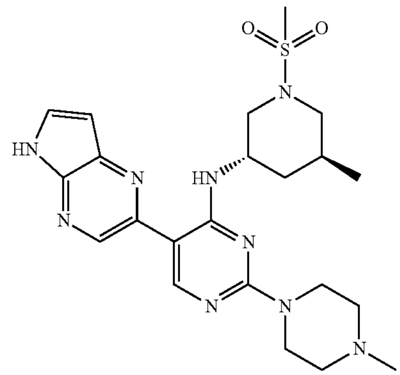 [SMILES: C[C@H]1C[C@H](Nc2nc(N3CCN(C)CC3)ncc2-c2cnc3[nH]ccc3n2)CN(S(C)(=O)=O)C1] | 486 | |
| I-114 | ((3S,5S)-1-Methanesulfonyl-5-trifluoromethyl-piperidin-3-yl)-[3-(5H-pyrrolo[2,3-b]pyrazin-2-yl)-pyridin-2-yl]-amine | 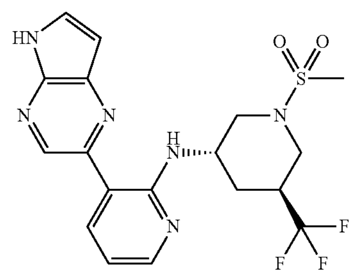 [SMILES: CS(=O)(=O)N1C[C@@H](Nc2ncccc2-c2cnc3[nH]ccc3n2)C[C@H](C(F)(F)F)C1] | 441 | |
| I-115 | [(3S,5S)-1-(2-Methyl-propane-1-sulfonyl)-5-trifluoromethyl-piperidin-3-yl]-[3-(5H-pyrrolo[2,3-b]pyrazin-2-yl)-pyridin-2-yl]-amine | 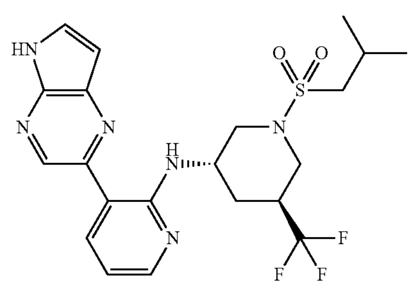 [SMILES: CC(C)CS(=O)(=O)N1C[C@@H](Nc2ncccc2-c2cnc3[nH]ccc3n2)C[C@H](C(F)(F)F)C1] | 483 | |
| I-116 | (3-{(S)-3-[3-(5H-Pyrrolo[2,3-b]pyrazin-2-yl)-pyridin-2-ylamino]-piperidin-1-yl}-oxetan-3-yl)-acetonitrile | 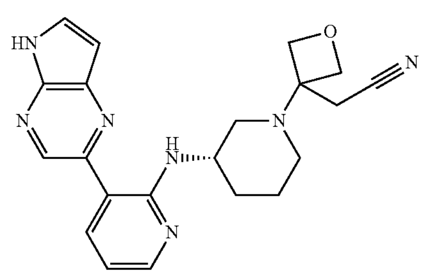 [SMILES: N#CCC1(N2CCC[C@H](Nc3ncccc3-c3cnc4[nH]ccc4n3)C2)COC1] | 390 | |
| I-117 | (3-{(3S,5S)-3-Methyl-5-[3-(5H-pyrrolo[2,3-b]pyrazin-2-yl)-pyridin-2-ylamino]-piperidin-1-yl}-oxetan-3-yl)-acetonitrile | 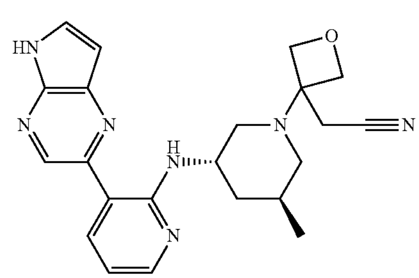 [SMILES: C[C@H]1C[C@H](Nc2ncccc2-c2cnc3[nH]ccc3n2)CN(C2(CC#N)COC2)C1] | 404 | |

TABLE I-continued

| COMPOUND | SYSTEMATIC NAME | STRUCTURE | MS (M + H) | MP |
|---|---|---|---|---|
| I-118 | {(3S,5S)-3-Methyl-5-[3-(5H-pyrrolo[2,3-b]pyrazin-2-yl)-pyridin-2-ylamino]-piperidine-1-sulfonyl}-acetonitrile | 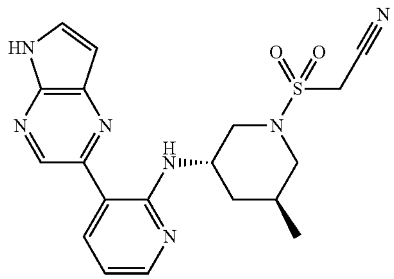 [SMILES: C[C@H]1C[C@H](Nc2ncccc2-c2cnc3[nH]ccc3n2)CN(S(=O)(=O)CC#N)C1] | 412 | |
| I-119 | 4,4,4-Trifluoro-3-{(S)-3-[3-(5H-pyrrolo[2,3-b]pyrazin-2-yl)-pyridin-2-ylamino]-piperidin-1-yl}-butyronitrile | 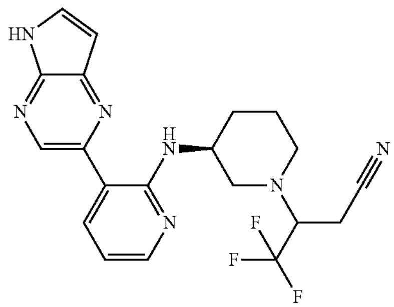 [SMILES: N#CCC(N1CCC[C@H](Nc2ncccc2-c2cnc3[nH]ccc3n2)C1)C(F)(F)F] | 416 | |

DOSAGE AND ADMINISTRATION

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

General Procedures

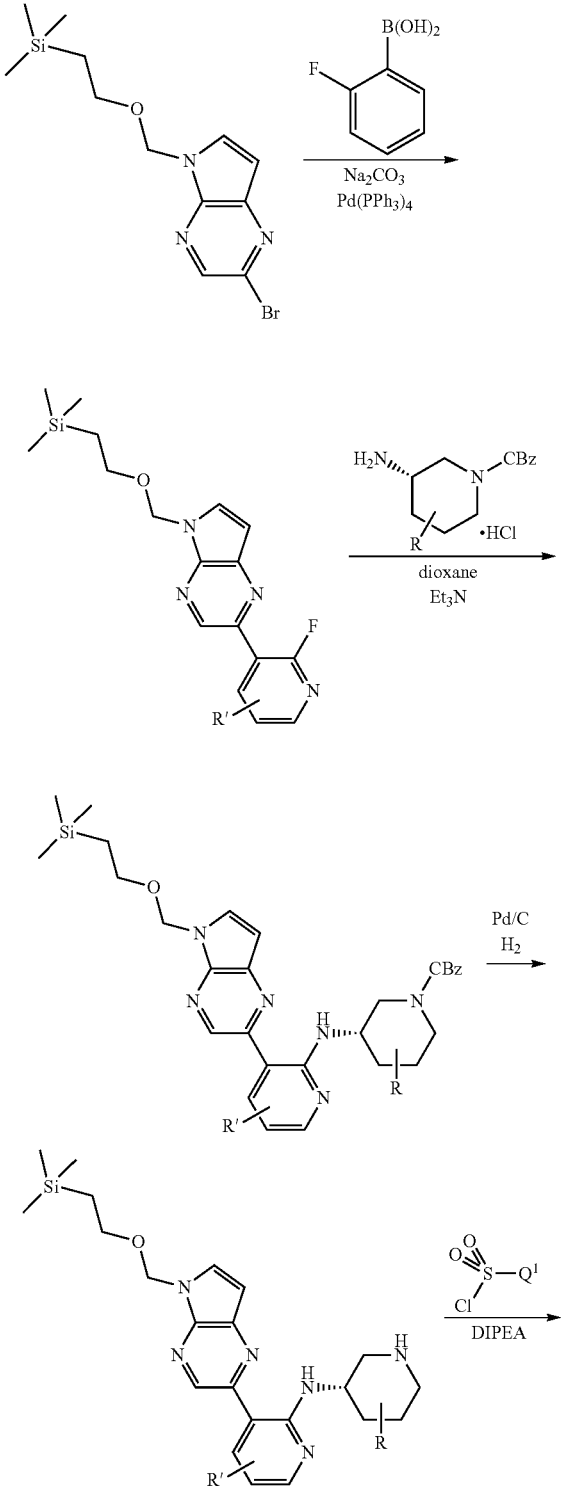

Scheme 1.

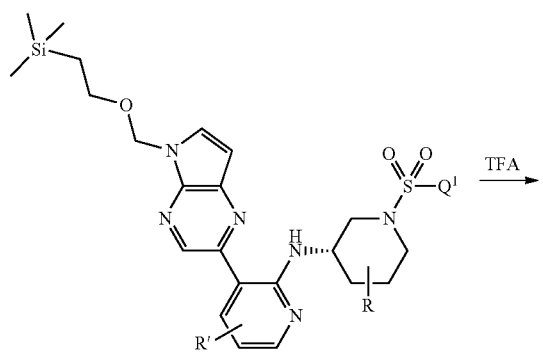

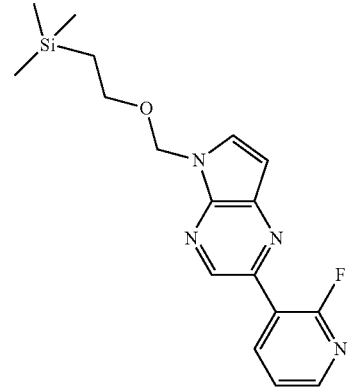

According to Scheme 1, R can be lower alkyl, n can be 0 or 1, R' can be $R'^a$ or $R'^b$, $R'^a$ can be halogen or cyano, $R'^b$ can be lower alkyl, cycloalkyl, heterocycloalkyl, OR", SR", or NR"R", optionally substituted with one or more $R'^c$, $R'^c$ can be hydroxy, halogen, oxo, cyano, lower alkyl, cycloalkyl, heterocycloalkyl, heteroaryl, carboxy lower alkyl, amino, lower alkyl amino, lower dialkyl amino, lower haloalkyl, or lower alkoxy, m can be 0 or 1, and R" can be H, lower alkyl, hydroxy lower alkyl, heteroaryl, or lower alkoxy, Q can be S(=O)$_2$Q$^1$, Q$^1$ can be lower alkyl, cycloalkyl lower alkyl, or cycloalkyl, optionally substituted with one or more Q$^{1'}$, and each Q$^{1'}$ can be independently halogen, lower alkyl, cyano, or lower alkoxy.

Preparation of Fluoro-Pyridine Intermediate 2

2-Bromo-5-(2-trimethylsilanyl-ethoxymethyl)-5H-pyrrolo[2,3-b]pyrazine (9.26 mmol, 3.04 g, 1.0 eq.), 2-Fluoro-3-pyridine boronic acid (13.8 mmol, 1.94 g, 1.5 eq.) and sodium carbonate (27.6 mmol, 2.925 g, 3.0 eq.) were dissolved in a 4:2:1 mixture of toluene/water/ethanol under argon. The reaction mixture was degassed with nitrogen for 20 minutes before the addition of palladium tetrakis triphenyphoshine (0.93 mmol, 1.075 g, 10 mol %). The reaction was sealed and stirred at 120° C. overnight. The reaction was subsequently cooled to room temperature and diluted with water and ethyl acetate. The biphasic mixture was extracted with ethyl acetate twice and the combined organic layers were dried over MgSO$_4$, filtered and concentrated in vacuo. The crude product was purified via flash column chromatography (0→35% EtOAc in hexanes over 25 minutes). The desired product was isolated as a yellow oil, 1.8764 g, 59% yield. MS (E/I): 345 (M+H).

General Procedure for the Preparation of Sulfonamide Coupling Partners—Standard Procedure A

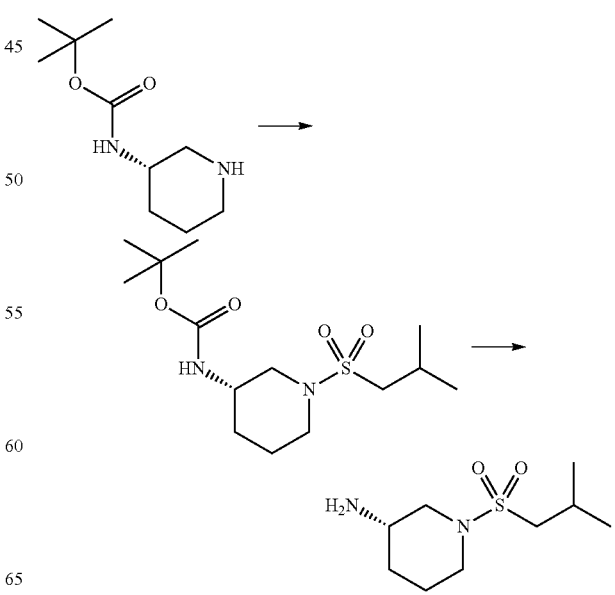

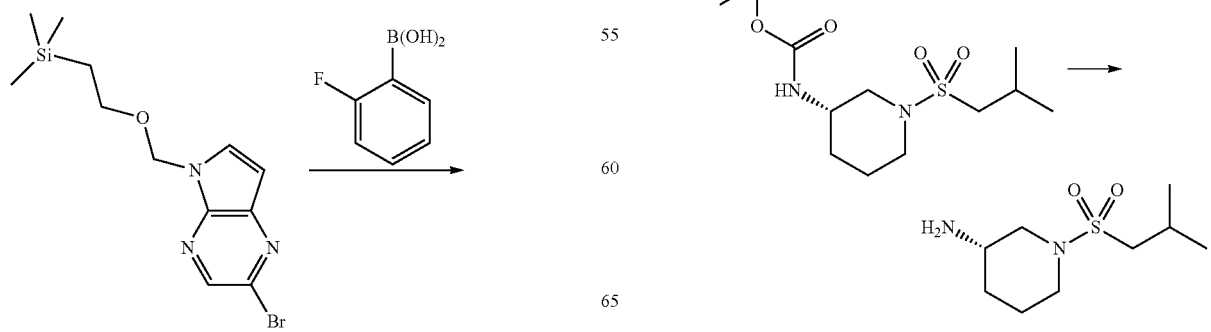

To a solution of (S)-Piperidin-3-yl-carbamic acid tert-butyl ester (3.746 mmol, 0.75 g) in 40 mL of dichloromethane was added triethylamine (0.626 mL, 0.454 g, 4.49 mmol, 1.2 eq.). The reaction mixture was subsequently cooled to 0° C. and isobutene sulfonyl chloride (0.587 mL, 0.704 g, 4.49 mmol, 1.2 eq.) was added. The reaction mixture was slowly warmed to ambient temperature and stirred overnight. The reaction mixture was diluted with water/dichloromethane and extracted with dichloromethane twice. The combined organics were dried over MgSO₄, filtered and concentrated in vacuo. The product was isolated as a yellow oil, 1.11 g, 93% yield and was used without further purification.

[(S)-1-(2-Methyl-propane-1-sulfonyl)-piperidin-3-yl]-carbamic acid tert-butyl ester (1.11 g, 3.46 mmol) was dissolved in 5 mL of hexafluoroisopropanol and transferred to a microwave vial with excess head space. The reaction was stirred under microwave heating at 150° C. for 90 minutes before being concentrated in vacuo. The product was isolated as an slightly orange solid, quantitative yield.

Synthesis of 1-((3R,5R)-3-amino-5-methyl-piperidin-1-yl)-ethanone hydrochloride

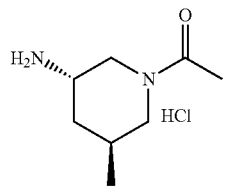

Step 1

To ((3R,5R)-1-benzyl-5-methyl-piperidin-3-yl)-carbamic acid tert-butyl ester (prepared as described in WO2004014893) (0.6 g, 1.971 mmol) Pd(OH)₂ on carbon (0.1 g) and EtOH (10 ml) were added and the reaction mixture was stirred at RT under 1 atm of H₂. After 2 hours the palladium was filtered off and the solvent was evaporated to give 0.45 g of ((3R,5R)-5-methyl-piperidin-3-yl)-carbamic acid tert-butyl ester as a colorless oil (>95% yield).

Step 2

((3R,5R)-5-Methyl-piperidin-3-yl)-carbamic acid tert-butyl ester (0.422 g, 1.971 mmol) was dissolved in DCM. Pyridine (0.2 ml, 2.56 mmol) was added, followed by acetic anhydride (0.24 ml, 2.56 mmol). The resulting colorless solution was stirred at RT overnight. 1 ml of MeOH was added and the mixture was stirred for about 30 minutes before being evaporated. The residue was partitioned between EtOAc and aqueous 1M HCl. The aqueous layer was extracted with EtOAc. The combined organic layers were washed with brine, dried (Na2SO4), filtered, and evaporated. The remaining oil was dried under high vacuum to give 0.51 g of ((3R,5R)-1-acetyl-5-methyl-piperidin-3-yl)-carbamic acid tert-butyl ester as an off-white solid (>95% yield).

Step 3

((3R,5R)-1-Acetyl-5-methyl-piperidin-3-yl)-carbamic acid tert-butyl ester (0.5 g, 1.971 mmol) was dissolved in DCM (15 ml) and HCl 4M in dioxane (2.5 ml, 10 mmol) was added. The resulting colorless solution was stirred at RT until precipitation of a solid was observed. The solvent was evaporated and the residue was dried under high vacuum. To give 0.45 g of 1-((3R,5R)-3-amino-5-methyl-piperidin-1-yl)-ethanone hydrochloride as an off-white solid (>95% yield).

Synthesis of (3S,5S)-3-amino-5-methyl-piperidine-1-carboxylic acid benzyl ester hydrochloride

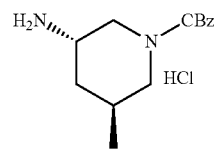

Step 1

To ((3R,5R)-1-benzyl-5-methyl-piperidin-3-yl)-carbamic acid tert-butyl ester (prepared as described in WO2004014893) (4.6 g, 15.11 mmol) Pd(OH)₂ on carbon (0.46 g) and EtOH (80 ml) were added and the reaction mixture stirred at RT under 1 atm of H2. After 3 hours the palladium was filtered off and the solvent was evaporated. The remaining oil was dried under high vacuum to give 2.9 g of ((3R,5R)-5-methyl-piperidin-3-yl)-carbamic acid tert-butyl ester as an off-white crystalline solid (89% yield).

Step 2

((3R,5R)-5-Methyl-piperidin-3-yl)-carbamic acid tert-butyl ester (2.9 g, 13.53 mmol) was dissolved in 70 mL of a 1:1 mixture of dioxane and H₂O and NaHCO₃ (4.55 g, 54.13 mmol) was added. To the resulting suspension benzyl chloroformate (2.2 ml, 14.2 mmol) was added slowly. After 2 hours the reaction mixture was extracted with EtOAc. The combined organic layers were washed with saturated aqueous NaHCO₃, dried (Na₂SO₄), filtered, and evaporated. The remaining oil was purified by SiO₂ chromatography (150 g SiO₂, hexanes/EtOAc 0-20% EtOAc) to give 3.6 g of (3R,5R)-3-tert-butoxycarbonylamino-5-methyl-piperidine-1-carboxylic acid benzyl ester as a colorless oil (76% yield).

Step 3

(3R,5R)-3-tert-Butoxycarbonylamino-5-methyl-piperidine-1-carboxylic acid benzyl ester (3.25 g, 9.327 mmol) was dissolved in DCM (50 ml) and HCl 4M in dioxane (20 ml, 80 mmol) was added. The resulting colorless solution stirred at RT for 4 hours before being evaporated. The residue was dried under high vacuum overnight to give 2.89 g of (3R,5R)-3-amino-5-methyl-piperidine-1-carboxylic acid benzyl ester hydrochloride as a white foam (>95% yield).

General Procedure for the Coupling of Fluoro-Pyridine 2 with Amines—Standard Procedure B

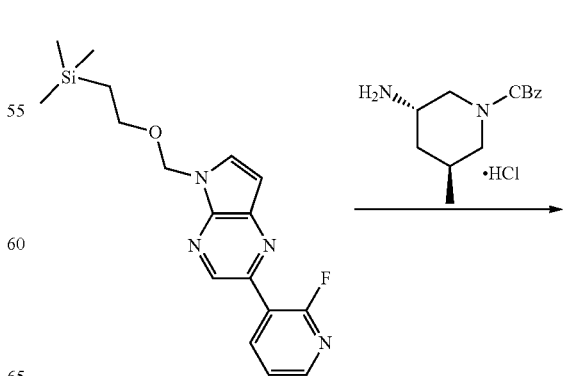

2

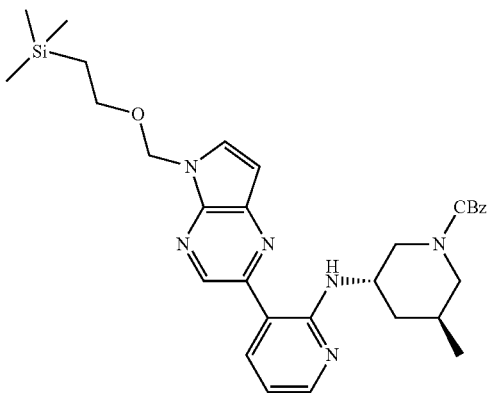

To a solution of 2-Bromo-5-(2-trimethylsilanyl-ethoxymethyl)-5H-pyrrolo[2,3-b]pyrazine (2.96 mmol, 1.02 g, 1.0 eq.) and amine (10.5 mmol, 3.0 g, 3.6 eq.) in 1,4-dioxane (30 mL) was added triethylamine (23.6 mmol, 2.4 g, 3.3 mL, 8 eq.). The reaction was sealed and stirred for 4 days at 140° C. The reaction was subsequently cooled to ambient temperature and concentrated in vacuo. The crude product was purified by flash column chromatography (0→60% EtOAc in hexanes over 25 minutes). The desired product was isolated as a yellow oil, 0.4812 g, 28% yield. MS (E/I): 573 (M+H).

General Procedure for the Removal of CBz Protecting Groups—Standard Procedure C

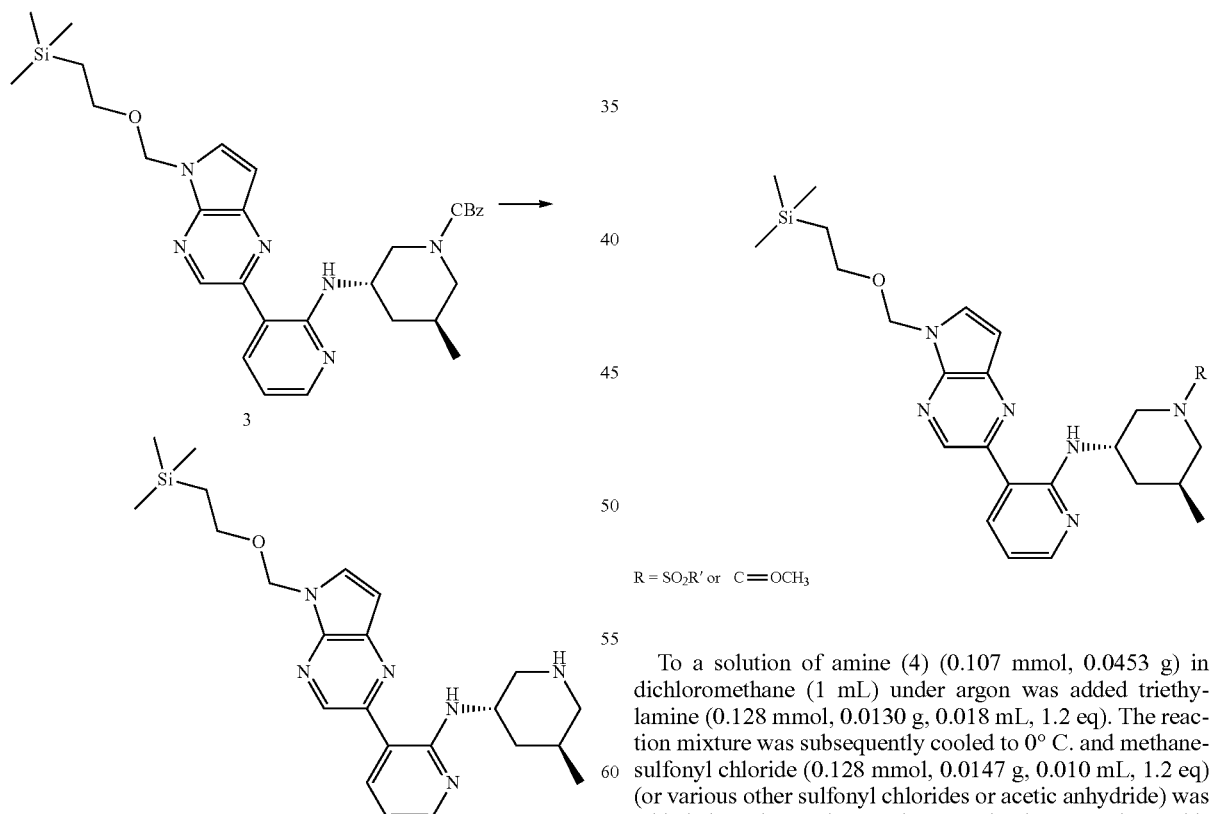

3

To a solution of 3 (0.2153 g, 0.385 mmol) in 5 mL of ethanol was and 0.25 g of palladium on activated carbon. The reaction vessel was subsequently evacuated (×3) and filled with hydrogen gas (via balloon). The reaction was stirred for approximately 5 hours at room temperature before dilution with ethyl acetate and filtration through Solka Flok. The desired product was isolated as a yellow oil, 0.1321 g, 81% yield and was used without further purification. MS (E/I): 425 (M+H).

General Procedure for the Preparation of Sulfonamides and Amides—Standard Procedure D

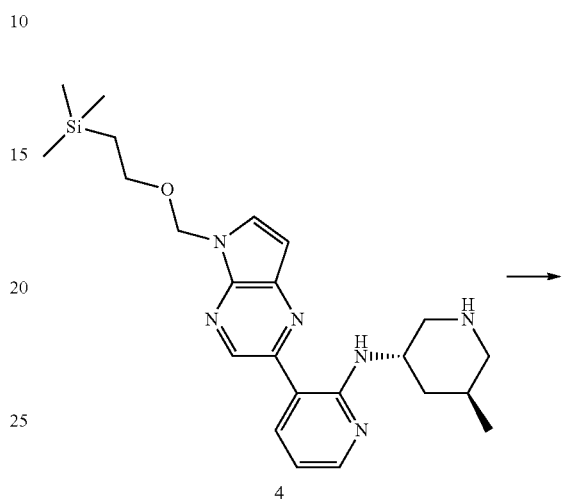

4

R = SO$_2$R' or C═OCH$_3$

To a solution of amine (4) (0.107 mmol, 0.0453 g) in dichloromethane (1 mL) under argon was added triethylamine (0.128 mmol, 0.0130 g, 0.018 mL, 1.2 eq). The reaction mixture was subsequently cooled to 0° C. and methanesulfonyl chloride (0.128 mmol, 0.0147 g, 0.010 mL, 1.2 eq) (or various other sulfonyl chlorides or acetic anhydride) was added via syringe. The reaction was slowly warmed to ambient temperature and stirred overnight before being diluted with water/dichloromethane and extracting twice with dichloromethane. The combined organic layers were dried over MgSO$_4$, filtered and concentrated in vacuo. The crude product was purified by preparative TLC (60% EtOAc/Hex-

General Procedure for the Removal of SEM Protecting Group—Standard Procedure E

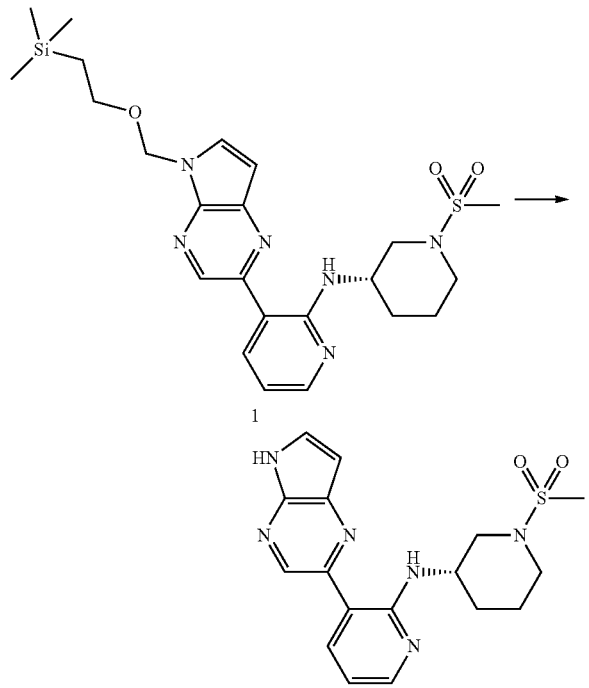

To a solution of SEM protected pyrrolopyrazine, 1 (0.0146 g, 0.029 mmol) in dichloromethane (1 mL) was added 1 mL of trifluoroacetic acid. The reaction mixture was stirred at ambient temperature for approximately 3 hours before concentration of the reaction mixture in vacuo. The resultant residue was azeotroped with chloroform twice to ensure the complete removal of trifluoroacetic acid. The residue was then dissolved in a 4:1:1 mixture of methanol/water/triethylamine respectively (3 mL total volume). The reaction mixture was stirred overnight at room temperature before concentration in vacuo and purification via preparative thin layer chromatography (30% magic base in dichloromethane). The desired product was isolated as an off-white solid, 0.0068 g, 63% yield.

EXAMPLES

Example 1

Preparation of ((S)-1-Methanesulfonyl-piperidin-3-yl)-[3-(5H-pyrrolo[2,3-b]pyrazin-2-yl)-pyridin-2-yl]-amine Using standard procedures A, B, E the product was isolated as an off-white solid, 0.0068 g, 63% yield (final step). $^1$H NMR (300 MHz, CHLOROFORM-d) δ ppm 1.63-2.03 (m, 4H) 2.80 (s, 3H) 2.99-3.22 (m, 1H) 3.45 (d, J=3.78 Hz, 2H) 3.50 (m, 1H) 4.44-4.62 (m, 1H) 6.67 (dd, J=7.55, 4.91 Hz, 1H) 6.89 (d, J=3.40 Hz, 1H) 7.63 (d, J=3.78 Hz, 1H) 7.96 (dd, J=7.55, 1.89 Hz, 1H) 8.19 (dd, J=4.91, 1.51 Hz, 1H) 8.71 (s, 1H) 9.39 (br s, 1H) 9.41 (br. s, 1H). MS (E/I): 373 (M+H).

Example 2

Preparation of ((R)-1-Methanesulfonyl-piperidin-3-yl)-[3-(5H-pyrrolo[2,3-b]pyrazin-2-yl)-pyridin-2-yl]-amine Using standard procedures B, C, D, E the product was isolated as a yellow solid, 0.0067 g, 69% yield (final step). $^1$H NMR (300 MHz, CHLOROFORM-d) δ ppm 1.66-2.06 (m, 4H) 2.80 (s, 3H) 3.03-3.17 (m, 1H) 3.45 (d, J=4.15 Hz, 2H) 3.47-3.59 (m, 1H) 4.44-4.62 (m, 1H) 6.67 (dd, J=7.74, 4.72 Hz, 1H) 6.90 (dd, J=3.59, 2.08 Hz, 1H) 7.57-7.69 (m, 1H) 7.96 (dd, J=7.55, 1.89 Hz, 1H) 8.19 (dd, J=4.91, 1.89 Hz, 1H) 8.71 (s, 1H) 8.99 (br. s., 1H) 9.40 (d, J=7.18 Hz, 1H). MS (E/I): 373 (M+H).

Example 3

Preparation of 1-{(R)-3-[3-(5H-Pyrrolo[2,3-b]pyrazin-2-yl)-pyridin-2-ylamino]-piperidin-1-yl}-ethanone Using standard procedures B, C, D, E the product was isolated as a yellow solid, 0.0092 g, 84% yield (final step). $^1$H NMR (300 MHz, CHLOROFORM-d) δ ppm 1.74 (s, 4H) 2.05 (s, 3H) 3.31-3.51 (m, 1H) 3.75 (d, J=3.02 Hz, 2H) 3.96 (ddd, J=12.65, 4.72, 4.53 Hz, 1H) 4.30-4.50 (m, 1H) 6.69 (dd, J=7.55, 4.91 Hz, 1H) 6.78 (dd, J=3.78, 1.89 Hz, 1H) 7.55-7.65 (m, 1H) 7.96 (dd, J=7.74, 1.70 Hz, 1H) 8.19 (dd, J=4.72, 1.70 Hz, 1H) 8.70 (s, 1H) 9.24 (d, J=7.55 Hz, 1H) 9.63 (br. s., 1H). MS (E/I): 337 (M+H).

Example 4

Preparation of 4-[3-(5H-Pyrrolo[2,3-b]pyrazin-2-yl)-pyridin-2-ylamino]-piperidine-1-carboxylic acid methyl ester Using standard procedures B, C, D, E the product was isolated as a yellow solid, 0.019 g, 79% yield (final step). $^1$H NMR (300 MHz, CHLOROFORM-d) δ ppm 1.57 (d, J=9.44 Hz, 2H) 2.03-2.23 (m, 2H) 3.22 (ddd, J=13.50, 10.29, 3.40 Hz, 2H) 3.72 (s, 3H) 4.00 (br. s., 2H) 4.25-4.44 (m, 1H) 6.67 (dd, J=7.55, 4.91 Hz, 1H) 6.71 (dd, J=3.40, 1.89 Hz, 1H) 7.63-7.69 (m, 1H) 7.91 (dd, J=7.55, 1.51 Hz, 1H) 8.19 (dd, J=4.91, 1.89 Hz, 1H) 8.69 (s, 1H) 8.86 (d, J=7.18 Hz, 1H) 9.82 (br. s., 1H). IR (KBr): 3426, 3215, 2924, 2855, 1700, 1593, 1516, 1480, 1448, 1411, 1384, 1298, 1273, 1221, 1148, 1089, 1030, 882, 766, 734 cm$^{-1}$. MS (E/I): 353 (M+H).

Example 5

Preparation of 1-{4-[3-(5H-Pyrrolo[2,3-b]pyrazin-2-yl)-pyridin-2-ylamino]-piperidin-1-yl}-ethanone Using standard procedures B, C, D, E the product was isolated as a yellow solid, 0.0141 g, 66% yield (final step). $^1$H NMR (300 MHz, CHLOROFORM-d) δ ppm 1.48-1.68 (m, 2H) 2.11-2.16 (m, 3H) 2.17-2.32 (m, 2H) 3.08-3.25 (m, 1H) 3.29-3.43 (m, 1H) 3.72-3.83 (m, 1H) 4.25-4.48 (m, 2H) 6.68 (dd, J=7.55, 4.91 Hz, 1H) 6.70-6.72 (m, 1H) 7.62-7.68 (m, 1H) 7.92 (dd, J=7.55, 1.89 Hz, 1H) 8.19 (dd, J=4.91, 1.89 Hz, 1H) 8.69 (s, 1H) 8.87 (d, J=7.18 Hz, 1H) 9.60 (br. s., 1H). MS (E/I): 337 (M+H).

Example 6

Preparation of [(R)-1-(Propane-2-sulfonyl)-piperidin-3-yl]-[3-(5H-pyrrolo[2,3-b]pyrazin-2-yl)-pyridin-2-yl]-amine Using standard procedures B, C, D, E the product was isolated as a yellow solid, 0.0184 g, 85% yield (final step). $^1$H NMR (300 MHz, CHLOROFORM-d) δ ppm 1.18-1.39 (m, 6H) 1.63-2.02 (m, 4H) 3.17 (dt, J=13.60, 6.80 Hz, 1H) 3.26-3.55 (m, 3H) 3.68 (dd, J=12.09, 3.02 Hz, 1H) 4.45 (ddd, J=6.61, 3.21, 3.02 Hz, 1H) 6.67 (dd, J=7.55, 4.91 Hz, 1H) 6.86 (dd, J=3.59, 1.70 Hz, 1H) 7.57-7.70 (m, 1H) 7.93 (dd, J=7.55, 1.51 Hz, 1H) 8.18 (dd, J=4.91, 1.51 Hz, 1H) 8.69 (s, 1H) 9.13 (d, J=7.55 Hz, 1H) 9.67 (br. s., 1H). IR (KBr): 3420, 2927, 2852, 1593, 1576, 1559, 1507, 1479, 1437, 1385, 1321, 1267, 1221, 1164, 1135, 1053, 1005, 952, 886, 737 cm$^{-1}$. MS (E/I): 401 (M+H).

Example 7

Preparation of ((3S,5S)-1-Methanesulfonyl-5-methyl-piperidin-3-yl)-[3-(5H-pyrrolo[2,3-b]pyrazin-2-yl)-pyridin-2-yl]-amine Using standard procedures B, C, D, E the product was isolated as a light yellow solid, 0.0046 g, 27% yield (final step). $^1$H NMR (300 MHz, CHLOROFORM-d) δ ppm 0.94 (d, J=6.42 Hz, 3H) 1.29 (td, J=12.46, 3.40 Hz, 2H) 2.01-2.27 (m, 1H) 2.28-2.43 (m, 1H) 2.78 (s, 3H) 2.96 (dd, J=11.71, 2.64 Hz, 1H) 3.76-3.99 (m, 2H) 4.65 (dt, J=7.55, 3.02 Hz, 1H) 6.66 (dd, J=7.55, 4.91 Hz, 1H) 6.96 (dd, J=3.78, 1.89 Hz, 1H) 7.56-7.64 (m, 1H) 7.98 (dd, J=7.55, 1.89 Hz, 1H) 8.17 (dd, J=4.91, 1.89 Hz, 1H) 8.71 (s, 1H) 9.34 (br. s., 1H) 9.75 (d, J=7.93 Hz, 1H). MS (E/I): 387 (M+H).

Example 8

Preparation of [(3S,5S)-5-Methyl-1-(propane-1-sulfonyl)-piperidin-3-yl]-[3-(5H-pyrrolo[2,3-b]pyrazin-2-yl)-pyridin-2-yl]-amine Using standard procedures B, C, D, E the product was isolated as a yellow solid, 0.0186 g. $^1$H NMR (300 MHz, CHLOROFORM-d) δ ppm 0.86-1.00 (m, 6H) 1.22-1.39 (m, 1H) 1.73-1.92 (m, 2H) 2.02-2.30 (m, 2H) 2.43 (t, J=11.14 Hz, 1H) 2.75-2.92 (m, 2H) 3.04 (dd, J=12.09, 2.27 Hz, 1H) 3.77-4.03 (m, 2H) 4.55-4.72 (m, 1H) 6.66 (dd, J=7.55, 4.91 Hz, 1H) 6.96 (dd, J=3.40 Hz, 1H) 7.61 (d, J=3.40 Hz, 1H) 7.98 (dd, J=7.74, 1.70 Hz, 1H) 8.18 (dd, J=4.91, 1.51 Hz, 1H) 8.72 (s, 1H) 9.25 (br. s., 1H) 9.69 (d, J=7.55 Hz, 1H). IR (KBr): 3421, 2925, 1594, 1576, 1509, 1480, 1439, 1384, 1330, 1294, 1220, 1169, 1142, 1045, 996, 923, 886, 761, 735, 644 cm$^{-1}$. MS (E/I): 415 (M+H). MP=178-180° C.

Example 9

Preparation of [(3S,5S)-5-Methyl-1-(2-methyl-propane-1-sulfonyl)-piperidin-3-yl]-[3-(5H-pyrrolo[2,3-b]pyrazin-2-yl)-pyridin-2-yl]-amine Using standard procedures B, C, D, E the product was isolated as a yellow solid, 0.0281 g, 74% yield (final step). $^1$H NMR (300 MHz, CHLOROFORM-d) δ ppm 0.93 (d, J=6.42 Hz, 3H) 1.03 (dd, J=6.20 Hz, 6H) 1.19-1.37 (m, 1H) 2.02-2.34 (m, 3H) 2.39 (t, J=11.14 Hz, 1H) 2.72 (dd, J=6.61, 1.70 Hz, 2H) 3.00 (dd, J=11.90, 2.45 Hz, 1H) 3.75-4.02 (m, 2H) 4.55-4.72 (m, 1H) 6.65 (dd, J=7.74, 4.72 Hz, 1H) 6.96 (d, J=3.78 Hz, 1H) 7.61 (d, J=3.40 Hz, 1H) 7.98 (dd, J=7.74, 1.70 Hz, 1H) 8.18 (dd, J=4.91, 1.51 Hz, 1H) 8.72 (s, 1H) 9.73 (d, J=7.93 Hz, 2H). IR (KBr): 3420, 2959, 1594, 1576, 1512, 1481, 1439, 1385, 1329, 1221, 1169, 1144, 1046, 1030, 997, 924, 885, 764, 681, 643 cm$^{-1}$. MS (E/I): 429 (M+H). MP=215-218° C.

Example 10

Preparation of [(3S,5S)-5-Methyl-1-(propane-2-sulfonyl)-piperidin-3-yl]-[3-(5H-pyrrolo[2,3-b]pyrazin-2-yl)-pyridin-2-yl]-amine Using standard procedures B, C, D, E the product was isolated as a yellow solid, 0.0082 g, 80% yield (final step). $^1$H NMR (400 MHz, CHLOROFORM-d) δ ppm 0.93 (d, J=6.57 Hz, 3H) 1.29 (d, J=6.57 Hz, 3H) 1.25 (d, J=7.07 Hz, 3H) 1.32-1.42 (m, 1H) 1.99-2.24 (m, 2H) 2.49-2.61 (m, 1H) 3.07-3.22 (m, 2H) 3.80-4.01 (m, 2H) 4.61 (dd, J=6.82, 3.79 Hz, 1H) 6.65 (dd, J=7.58, 5.05 Hz, 1H) 6.97 (d, J=3.54 Hz, 1H) 7.60 (d, J=3.54 Hz, 1H) 7.96 (dd, J=7.83, 1.77 Hz, 1H) 8.18 (dd, J=4.80, 1.77 Hz, 1H) 8.70 (s, 1H) 9.17 (br. s., 1H) 9.50 (d, J=7.58 Hz, 1H). MS (E/I): 415 (M+H).

Example 11

Preparation of [(S)-1-(2-Methyl-propane-1-sulfonyl)-piperidin-3-yl]-[3-(5H-pyrrolo[2,3-b]pyrazin-2-yl)-pyridin-2-yl]-amine Using standard procedures A, B, E the product was isolated as a yellow solid, 0.0169 g, 57% yield (final step). $^1$H NMR (300 MHz, CHLOROFORM-d) δ ppm 1.07 (d, J=3.78 Hz, 3H) 1.05 (d, J=4.15 Hz, 3H) 1.63-1.81 (m, 1H) 1.81-2.06 (m, 3H) 2.29 (dt, J=13.22, 6.61 Hz, 1H) 2.76 (d, J=6.42 Hz, 2H) 3.17 (d, J=8.69 Hz, 1H) 3.36-3.59 (m, 3H) 4.44-4.64 (m, 1H) 6.67 (dd, J=7.74, 5.10 Hz, 1H) 6.89 (dd, J=3.40, 1.89 Hz, 1H) 7.57-7.68 (m, 1H) 7.96 (dd, J=7.74, 1.70 Hz, 1H) 8.18 (dd, J=4.91, 1.89 Hz, 1H) 8.70 (s, 1H) 9.42 (br. s., 1H) 9.75 (br. s., 1H). MS (E/I): 415 (M+H). MP=150-152° C.

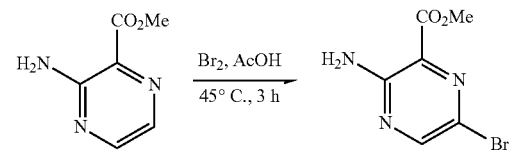 [SMILES: COC(=O)c1nccnc1N ; COC(=O)c1nc(Br)cnc1N]

Methyl 3-amino-2-pyrazinecarboxylate (5 g, 32.65 mmol) was dissolved in AcOH (25 mL) at 45° C. To this solution was added a solution of bromine (5.74 g, 35.91 mmol) in AcOH (5 mL). The reaction mixture was stirred at rt for 30 min. The reaction was followed by TLC and showed the presence of starting material. A solution of Bromine (2 g, 13.05 mmol) in AcOH (5 mL) was then added. After stirring at rt for 2 h, the reaction mixture was treated with water. The precipitate was collected by filtration and washed with water. The crude product was triturated with hexane, decanted and dried under reduced pressure to provide 6.5 g (85%) of a brown solid. MS m/z (ES): 231 (M+H)$^+$.

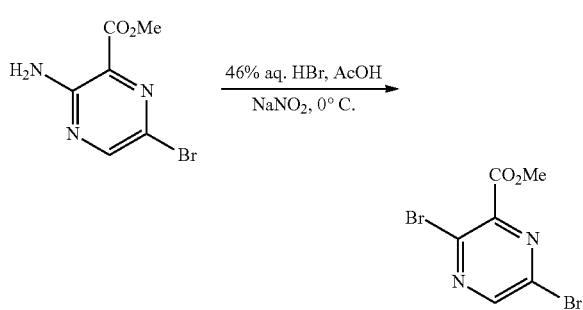

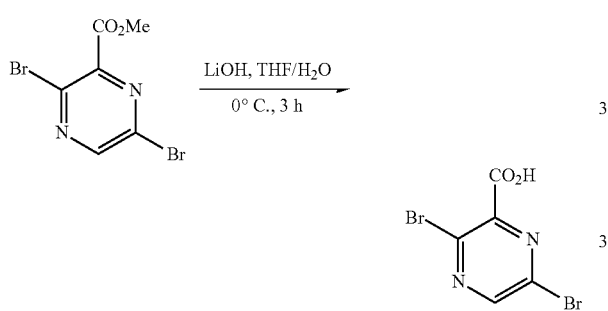

46% aq. HBr (30 mL) was added to a solution of the pyrazine (5 g, 21.55 mmol) in AcOH (20 mL) at 0° C. After stirring at 0° C. for 45 min, a solution of NaNO$_2$ (5.2 g, 75.42 mmol) in water (10 mL) was slowly added. After stirring at 0° C. for 15 min, the starting material was consumed by TLC. The reaction mixture was quenched upon addition of an aq. solution of NaHSO$_3$ (108 mmol) at 0° C. to provide a precipitate. The precipitate was collected by filtration and dried to provide a 2.6 g (41%) of a brown solid. MS m/z (ES): 294 (M+H)$^+$.

A solution of LiOH (121 mg, 5.07 mmol) in water (1 mL) was slowly added to a solution the pyrazine ester (500 mg, 1.67 mmol) in 1:1 THF/water (8 mL) at 0° C. After stirring at 0° C. for 45 min. The solvent was removed under reduced pressure. The residue was dissolved in a mixture of DCM and 1N aq. HCl. The organic layer was separated and the aqueous extracted twice with DCM. The combined organic extracts were dried (Na$_2$SO$_4$), filtered and concentrated to afford 350 mg (74%) of a cream colored solid. MS m/z (ES): 282 (M+H)$^+$.

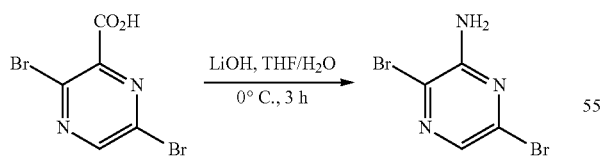

Diphenylphosphoryl azide (488 mg, 1.77 mmol) and triethylamine (180 mg, 1.77 mmol) were added to a solution of the acid (500 mg, 1.77 mmol) in tert-butanol (12 mL). The reaction mixture was stirred at reflux for 18 h and then quenched with water. The volatiles were removed under reduced pressure. The residue was dissolved in 4:1 TFA/DCM (5 mL) and stirred at rt for 1 h. The volatiles were removed under reduced pressure. The residue was dissolved in DCM and washed with 1N aq. NaOH. The combined organic extracts were dried (Na$_2$SO$_4$), filtered and concentrated. The crude residue was purified by SiO$_2$ chromatography eluting with an EtOAc/hexane gradient to afford 120 mg (27%) of bromoanisol as a colorless oil. MS m/z (ES): 253 (M+H)$^+$.

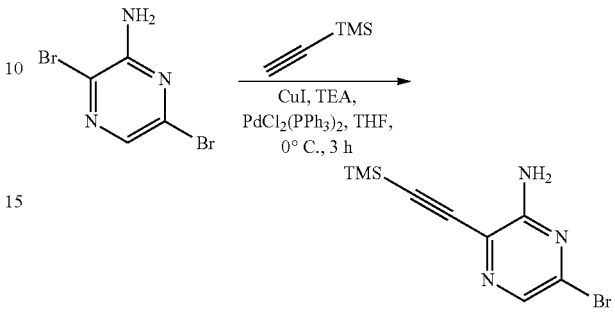

The bromopyrazine (3 g, 11.87 mmol) was dissolved in THF (60 mL) and the resultant solution was purged with argon. Triethylamine (1.44 g, 14.24 mmol), CuI (180 mg) and PdCl—(PPh$_3$)$_2$ (83 mg, 0.118 mmol) were added. The reaction mixture was cooled to 0° C. Trimethylsilylacetylene (1.28 g, 13.05 mmol) was slowly added and the reaction was left to warm up to rt for 2 h. The reaction mixture was diluted with water and filtered through celite. The crude mixture was extracted three times with EtOAc. The organic layer was separated, dried (Na$_2$SO$_4$), filtered and concentrated. The crude residue was purified by SiO$_2$ chromatography eluting with an EtOAc/hexane gradient to afford 3.3 g (51%) of alkyne as a yellow solid.

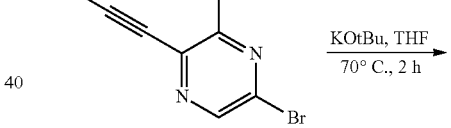

A solution of potassium tert-butoxyde (2.65 g, 23.7 mmol) in THF (30 mL) was added to a solution of the alkyne (3.2 g, 11.85 mmol) in THF at rt. After stirring at 0° C. for 4 h, the reaction mixture was concentrated, diluted with ethyl acetate and filtered through celite. The filtrate was washed with water. The combined organic extracts were dried (Na$_2$SO$_4$), filtered and concentrated. The crude residue was purified by SiO$_2$ chromatography eluting with 1:1 DCM/hexane to afford 1.2 g (51%) of bromoanisol as a colorless oil. MS m/z (ES): 199 (M+H)$^+$.

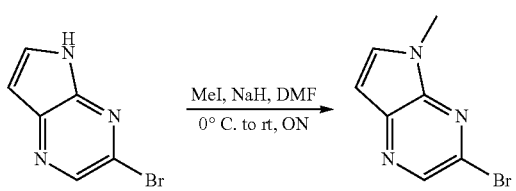

A round bottomed flask charged with NaH (181 mg, 60% in mineral oil) was washed with hexanes. The hexanes was removed and DMF (8 mL) was added. A solution of the pyrrolopyrazine (990 mg, 5.05 mmol) in DMF (7 mL) was slowly added at 0° C. After stirring at 0° C. for 10 min, methyl iodide (716 mg, 5.05 mmol) was slowly added. The reaction mixture was left to warm up to rt overnight. The volatiles were removed under reduced pressure. The crude residue was purified by SiO$_2$ chromatography eluting with an EtOAc/hexane gradient to afford 0.68 g (71%) of pyrrolopyrazine as a pale yellow solid. MS m/z (ES): 211 (M+H)$^+$.

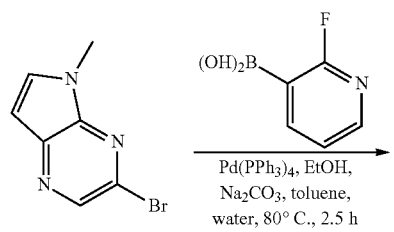

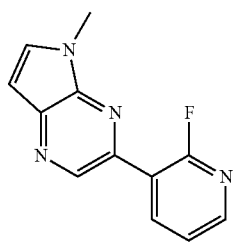

A round bottomed flask was charged with the pyrrolopyrazine (60 mg, 0.282 mmol), 2-fluoropyridine-3-boronic acid (48 mg, 0.339 mmol) and Na$_2$CO$_3$ (90 mg, 0.85 mmol) and the solids were suspended/dissolved in a mixture of 1.5 ml of toluene, 1 ml of H$_2$O and 0.5 ml of ethanol and the resulting mix was purged with argon for 20 minutes. Pd(PPh$_3$)$_4$ (98 mg, 0.084 mmol) was added to the reaction vessel and the system purged again for 10 minutes. The reaction mixture was heated at 80° C. for 2.5 h. The reaction was cooled to rt and filtered through a celite pad. The filtrate was diluted with water and extracted with EtOAc. The organic layer was isolated and the aqueous layer was back extracted with EtOAc. The combined organics were separated, dried (Na$_2$SO$_4$), filtered and concentrated to provide the desired coupling product 150 mg. MS m/z (ES): 229 (M+H)$^+$.

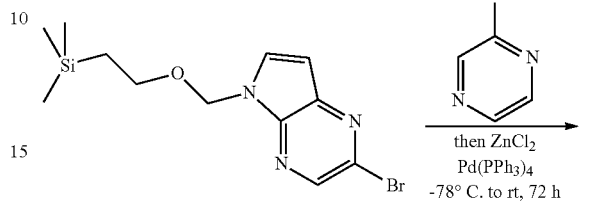

n-Butyllithium (2.5M in hexanes, 1.05 mL, 2.58 mmol) was added to a solution of 2,2,6,6-tetramethylpiperidine (462 μL, 2.73 mmol) in THF (10 mL) at −78° C. The reaction mixture was stirred at 0° C. for 20 min. A solution of 2-fluoropyrazine (224 mg, 2.28 mmol) in THF was added at −78° C. After stirring at −78° C. for 5 min, ZnCl$_2$ (0.5 M in THF, 11 mL, 5.32 mmol) was then added. The reaction mixture was stirred at −78° C. for 30 min and then at 0° C. for 1 h. A solution of the bromide (500 mg, 1.52 mmol) and Pd(PPh$_3$)$_4$ (352 mg, 0.304 mmol) in THF (20 mL) was then added. The reaction mixture was stirred at rt for 3 days. A sat. aq. solution of EDTA was added. After stirring at rt for 15 min, a sat. aq. solution of NaHCO$_3$ was added. The reaction mixture was extracted with DCM. The combined organics were separated, dried (MgSO$_4$), filtered and concentrated. The crude residue was purified by SiO$_2$ chromatography eluting with 20:80 EtOAc/hexane to afford 200 mg (38%) of pyrazine as a yellow oil. MS m/z (ES): 346 (M+H)$^+$.

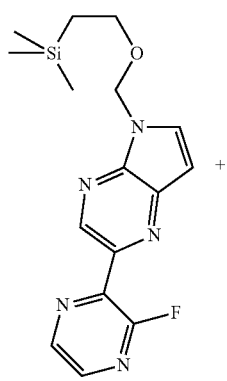

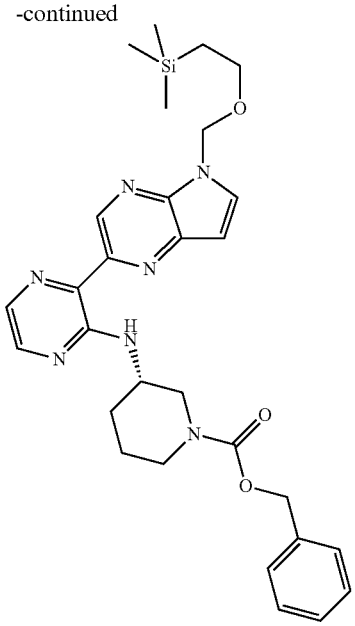

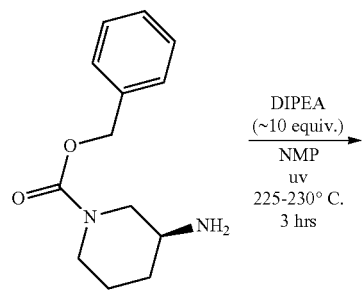

To a microwave reaction vessel was added 1 (200 mg, 0.58 mmol), 2 (200 mg, 0.85 mmol), Hunig's base (1 mL, 5.74 mmol), and NMP (0.5 mL). Reaction vessel flushed with argon and sealed. The suspension was heated at 230° C. under microwave irradiation for 3 hr. Water was added to the light green biphasic mixture and the mixture was extracted with ethyl acetate. The combined organics were separated, dried (MgSO$_4$), filtered and concentrated. The crude residue was purified by SiO$_2$ chromatography eluting a EtOAc/hexane gradient to afford 330 mg (99%) of pyrazine as a yellow oil. MS m/z (ES): 560 (M+H)$^+$.

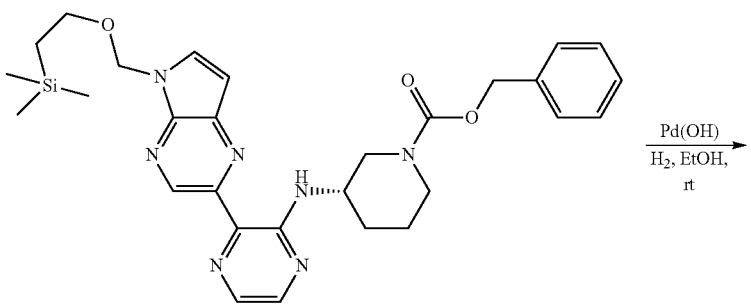

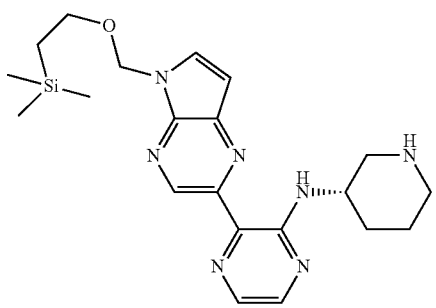

113

To a round bottomed flask charged with the carbamate (330 mg, 0.58 mmol) and Pd(OH) (100 mg) was added ethanol (50 mL). The reaction vessel was subsequently evacuated (×3) and filled with hydrogen gas (via balloon). The reaction was stirred for approximately 5 hours at room temperature before dilution with ethyl acetate and filtration through Solka Flok. The filtrate was concentrated to afford 210 mg (81%) of the piperidine as a yellow oil. MS m/z (ES): 426 (M+H).

Example 12

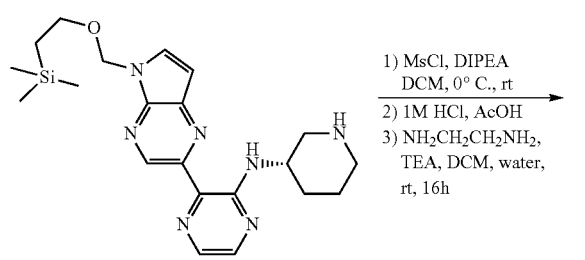

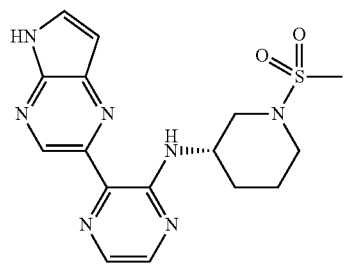

Methanesulfonyl chloride (30 µL, 0.368 mmol) was added to a solution of the amine (120 mg, 0.28 mmol) and diisopropylethylamine (150 µL, 0.86 mmol) in DCM (2 mL) at 0° C. The reaction was slowly warmed to ambient temperature and stirred overnight before being diluted with water/dichloromethane and extracting twice with dichloromethane. The combined organic layers were dried over MgSO$_4$, filtered and concentrated. The residue was dissolved in 5 ml of 1M HCl in HOAc was stirred at 60° C. for 3 h. The solvent was removed under vacuum and the residue was treated with toluene and concentrated to dryness. This procedure was repeated three times and the residue was left under high vacuum for one hour. The residue was taken into 5 ml of a 8:1:1 mixture of MeOH/H$_2$O/Et$_3$N containing ethylenediamine (0.150 ml, 2.31 mmol) and stirred at rt for 16 h. The reaction mixture was concentrated and purified by preparative TLC eluting with 95:5 DCM/MeOH to afford 10 mg (9.5%) of the desired product as a yellow solid. MS m/z (ES): 374 (M+H).

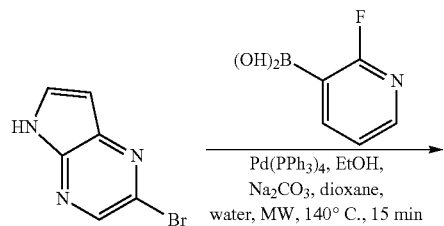

114

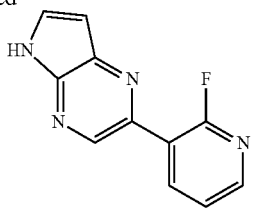

To a 25 mL microwave vial was added 2-bromo-5H-pyrrolo[2,3-b]pyrazine (0.5 g, 2.52 mmol), 2-fluoropyridin-3-ylboronic acid (600 mg, 4.26 mmol) and sodium carbonate (803 mg, 7.57 mmol) in dioxane (10.0 ml), water (5.00 ml), and EtOH (2.5 ml). The reaction mixture was bubbled through with argon for 10 mins. Pd(PPh$_3$)$_4$ (292 mg, 0.252 mmol). The reaction was bubbled through with argon for 5 mins. The vial was capped and heated in the microwave at 140° C. for 15 min. The reaction mixture was diluted with EtOAc and water. The combined organics were separated, dried (MgSO$_4$), filtered and concentrated. The crude residue dissolved in DCM and treated with silica. The solvent was evaporated and the crude absorbed in silica was purified by SiO$_2$ chromatography eluting with EtOAc/hexane gradient (0% to 60%) to afford 410 mg (76%) of pyrrolopyridine as a light yellow solid. MS m/z (ES): 215 (M+H)$^+$.

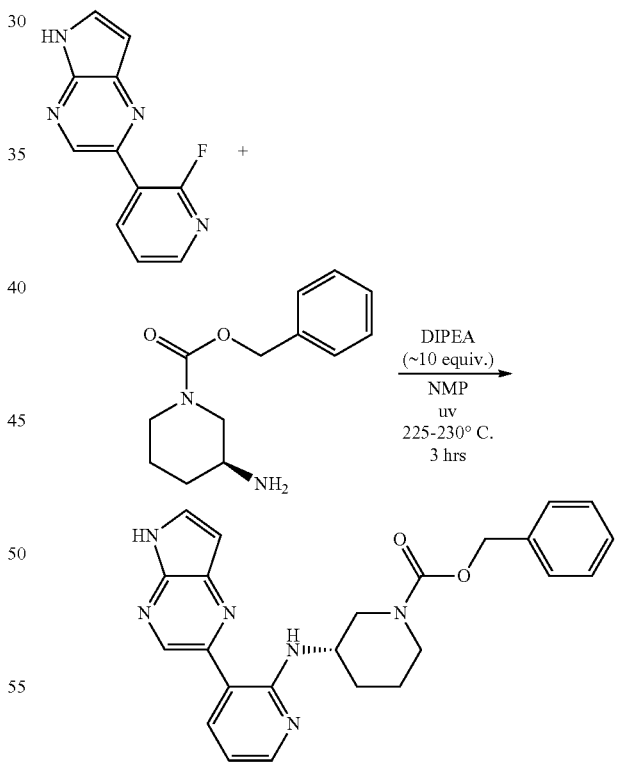

To a 2 mL microwave vial was added 2-(2-fluoropyridin-3-yl)-5H-pyrrolo[2,3-b]pyrazine (395 mg, 1.84 mmol), (S)-benzyl 3-aminopiperidine-1-carboxylate (670 mg, 2.86 mmol), DIPEA (237 mg, 1.83 mmol) and NMP (1.0 ml). The vial was capped and heated at 230° C. under microwave irradiation for 45 min. The reaction mixture was diluted with water and ethyl acetate. The combined organics were separated, dried (Na$_2$SO$_4$), filtered and concentrated. The crude residue was purified by SiO₂ chromatography eluting a EtOAc/hexane gradient to afford 347 mg (44%) of aminopyridine as a yellow glassy oil. MS m/z (ES): 429 (M+H)⁺.

Example 13

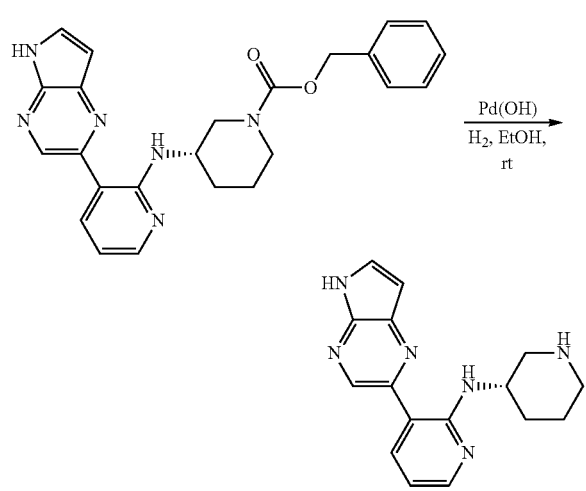

To a round bottomed flask charged with (S)-benzyl 3-(3-(5H-pyrrolo[2,3-b]pyrazin-2-yl)pyridin-2-ylamino)piperidine-1-carboxylate (140 mg, 0.327 mmol) and Pd(OH) (24 mg) was added ethanol (5 mL). The reaction vessel was subsequently evacuated and filled with hydrogen gas (via balloon). The reaction was stirred for approximately 6 hours at room temperature. Another portion of Pd(OH) (30 mg) was added. After stirring at rt for 2 h under 1 atm of H₂, the reaction mixture was filtered through celite. The filtrate was concentrated to afford 95 mg of the piperidine. MS m/z (ES): 295 (M+H)⁺.

Example 14

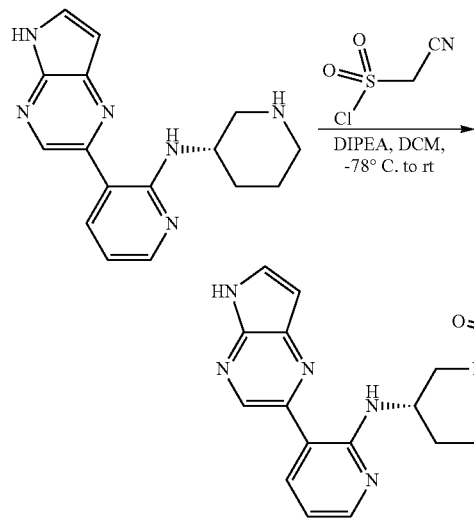

Cyanomethanesulfonyl chloride (50 mg, 0.510 mmol) was added to a solution of the amine (100 mg, 0.34 mmol) and diisopropylethylamine (360 µL, 2.07 mmol) in DCM (5 mL) at −78° C. The reaction was slowly warmed up to ambient temperature over a period of 2 h. The crude reaction mixture was loaded onto a preparative TLC, which was eluted 80:20 EtOAc/hexane to afford 15 mg (11%) of the desired product as a yellow solid. MS m/z (ES): 398 (M+H).

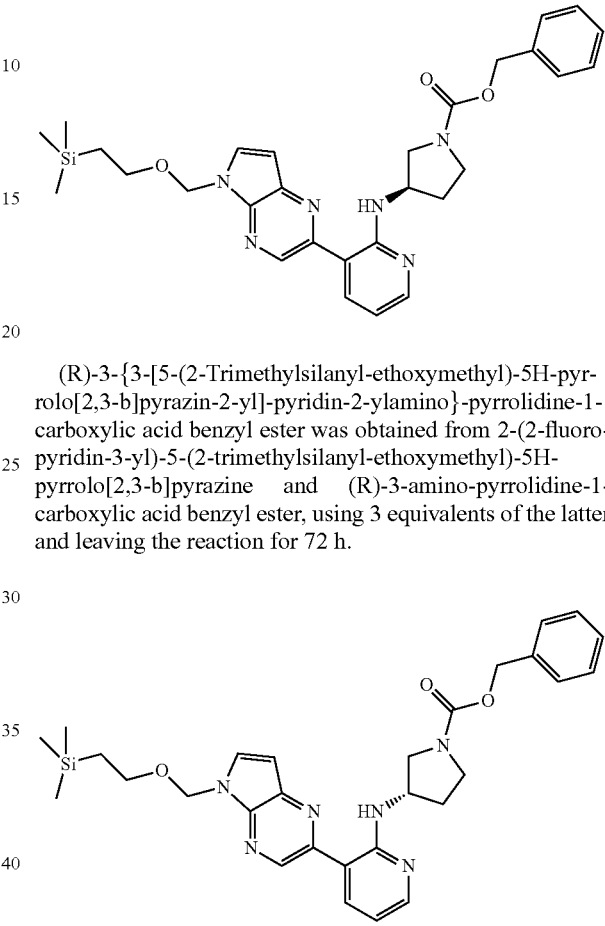

(R)-3-{3-[5-(2-Trimethylsilanyl-ethoxymethyl)-5H-pyrrolo[2,3-b]pyrazin-2-yl]-pyridin-2-ylamino}-pyrrolidine-1-carboxylic acid benzyl ester was obtained from 2-(2-fluoropyridin-3-yl)-5-(2-trimethylsilanyl-ethoxymethyl)-5H-pyrrolo[2,3-b]pyrazine and (R)-3-amino-pyrrolidine-1-carboxylic acid benzyl ester, using 3 equivalents of the latter and leaving the reaction for 72 h.

(S)-3-{3-[5-(2-Trimethylsilanyl-ethoxymethyl)-5H-pyrrolo[2,3-b]pyrazin-2-yl]-pyridin-2-ylamino}-pyrrolidine-1-carboxylic acid benzyl ester was obtained from 2-(2-fluoropyridin-3-yl)-5-(2-trimethylsilanyl-ethoxymethyl)-5H-pyrrolo[2,3-b]pyrazine and (S)-3-amino-pyrrolidine-1-carboxylic acid benzyl ester, using 3 equivalents of the latter and leaving the reaction for 72 h.

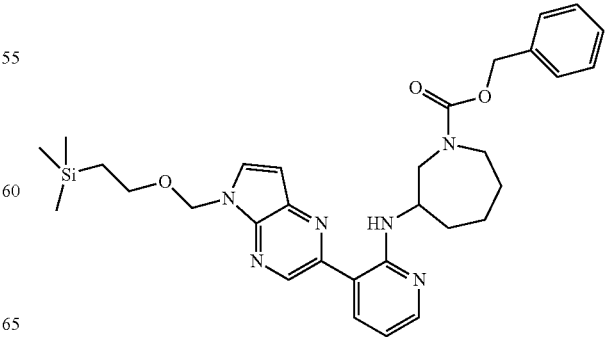

3-{3-[5-(2-Trimethylsilanyl-ethoxymethyl)-5H-pyrrolo[2,3-b]pyrazin-2-yl]-pyridin-2-ylamino}-azepane-1-carboxylic acid benzyl ester was obtained from 2-(2-fluoropyridin-3-yl)-5-(2-trimethylsilanyl-ethoxymethyl)-5H-pyrrolo[2,3-b]pyrazine and 3-amino-azepane-1-carboxylic acid benzyl ester, leaving the reaction for 96 h.

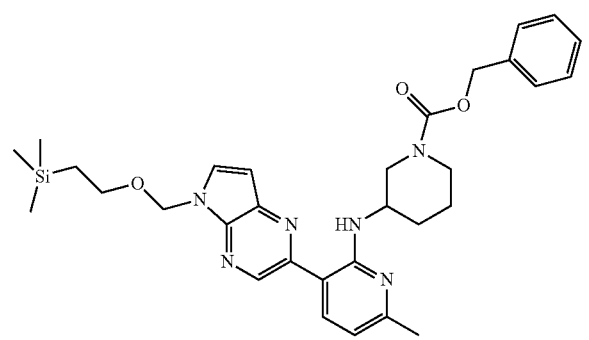 [SMILES: Cc1ccc(-c2cnc3c(ccn3COCC[Si](C)(C)C)n2)c(NC2CCCN(C(=O)OCc3ccccc3)C2)n1]

3-{6-Methyl-3-[5-(2-trimethylsilanyl-ethoxymethyl)-5H-pyrrolo[2,3-b]pyrazin-2-yl]-pyridin-2-ylamino}-piperidine-1-carboxylic acid benzyl ester was obtained from 2-(2-fluoro-6-methyl-pyridin-3-yl)-5-(2-trimethylsilanyl-ethoxymethyl)-5H-pyrrolo[2,3-b]pyrazine and 3-amino-piperidine-1-carboxylic acid benzyl ester using 2.5 equivalents of the latter and leaving the reaction for 72 h.

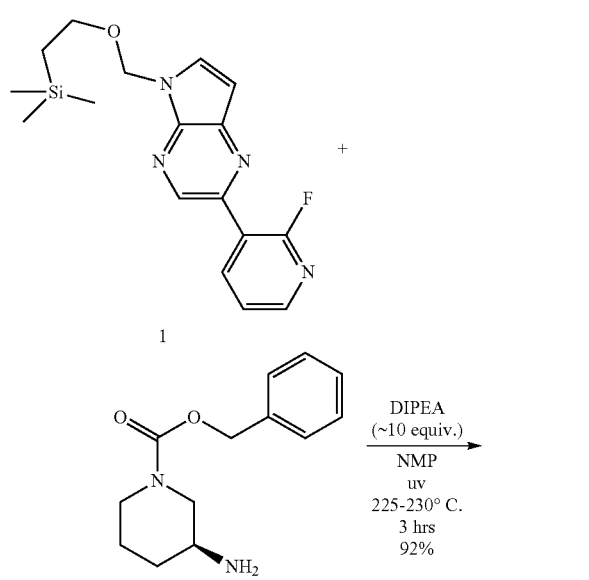

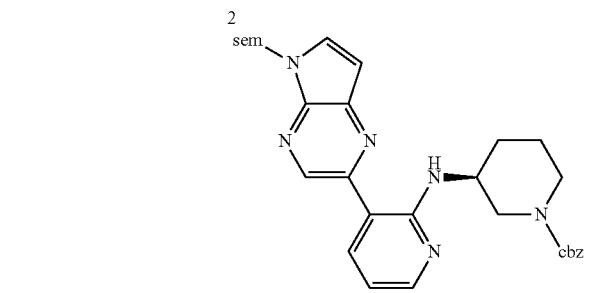

To microwave reaction vessel was added 1 (1.916 g, 5.6 mmol), 2 (1.955 g, 8.3 mmol), Hunig's base (10 mL, 57.4 mmol), and NMP (2 mL). Reaction vessel flushed with argon and sealed. The suspension was heated at 225° C. under microwave irradiation for 1 hr. The reaction was then heated at 230° C. under microwave irradiation for 2 hr. Water (25 mL) was added to the light green biphasic mixture and the mixture was extracted with ethyl acetate (3×25 mL). The combined organic layers was washed with water then brine, dried on Na$_2$SO$_4$, and concentrated. The viscous oil was purified by silica column chromatography (0% to 50% ethyl acetate in hexanes) to give a yellow glassy solid (2.851 g, 92%).

Example 15

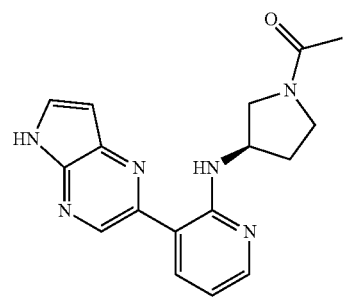 [SMILES: CC(=O)N1CC[C@@H](Nc2ncccc2-c2cnc3[nH]ccc3n2)C1]

1-{(R)-3-[3-(5H-Pyrrolo[2,3-b]pyrazin-2-yl)-pyridin-2-ylamino]-pyrrolidin-1-yl}-ethanone was prepared from 1-((R)-3-{3-[5-(2-trimethylsilanyl-ethoxymethyl)-5H-pyrrolo[2,3-b]pyrazin-2-yl]-pyridin-2-ylamino}-pyrrolidin-1-yl)-ethanone, following the general synthetic procedures described in the above Examples.

Example 16

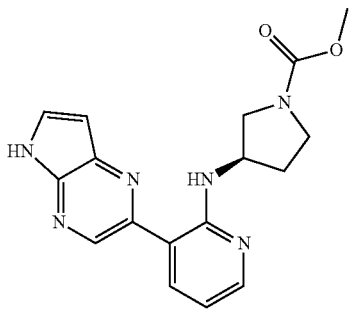 [SMILES: COC(=O)N1CC[C@@H](Nc2ncccc2-c2cnc3[nH]ccc3n2)C1]

(R)-3-[3-(5H-Pyrrolo[2,3-b]pyrazin-2-yl)-pyridin-2-ylamino]-pyrrolidine-1-carboxylic acid methyl ester was obtained from (R)-3-{3-[5-(2-trimethylsilanyl-ethoxymethyl)-5H-pyrrolo[2,3-b]pyrazin-2-yl]-pyridin-2-ylamino}-pyrrolidine-1-carboxylic acid methyl ester following the general synthetic procedures described in the above Examples.

Example 17

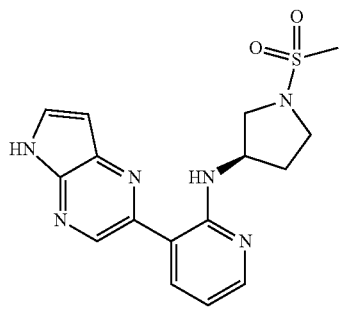 [SMILES: CS(=O)(=O)N1CC[C@@H](Nc2ncccc2-c2cnc3[nH]ccc3n2)C1]

((R)-1-Methanesulfonyl-pyrrolidin-3-yl)-[3-(5H-pyrrolo[2,3-b]pyrazin-2-yl)-pyridin-2-yl]-amine was obtained from ((R)-1-methanesulfonyl-pyrrolidin-3-yl)-{3-[5-(2-trimethylsilanyl-ethoxymethyl)-5H-pyrrolo[2,3-b]pyrazin-2-yl]-pyridin-2-yl}-amine following the general synthetic procedures described in the above Examples.

Example 18

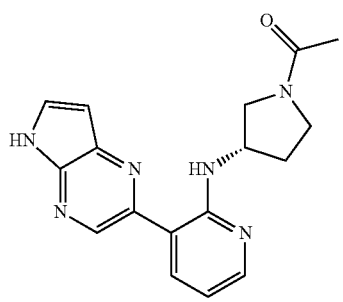 [SMILES: CC(=O)N1CC[C@H](Nc2ncccc2-c2cnc3[nH]ccc3n2)C1]

1-{(S)-3-[3-(5H-Pyrrolo[2,3-b]pyrazin-2-yl)-pyridin-2-ylamino]-pyrrolidin-1-yl}-ethanone was prepared from 1-((S)-3-{3-[5-(2-trimethylsilanyl-ethoxymethyl)-5H-pyrrolo[2,3-b]pyrazin-2-yl]-pyridin-2-ylamino}-pyrrolidin-1-yl)-ethanone, following the general synthetic procedures described in the above Examples.

Example 19

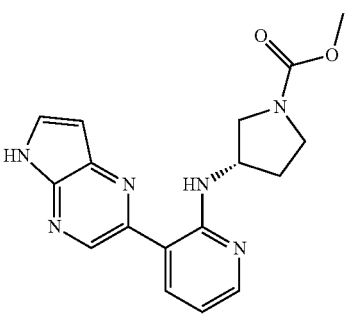 [SMILES: COC(=O)N1CC[C@H](Nc2ncccc2-c2cnc3[nH]ccc3n2)C1]

(S)-3-[3-(5H-Pyrrolo[2,3-b]pyrazin-2-yl)-pyridin-2-ylamino]-pyrrolidine-1-carboxylic acid methyl ester was obtained from (S)-3-{3-[5-(2-trimethylsilanyl-ethoxymethyl)-5H-pyrrolo[2,3-b]pyrazin-2-yl]-pyridin-2-ylamino}-pyrrolidine-1-carboxylic acid methyl ester following the general synthetic procedures described in the above Examples.

Example 20

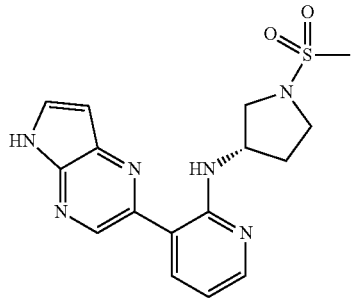 [SMILES: CS(=O)(=O)N1CC[C@H](Nc2ncccc2-c2cnc3[nH]ccc3n2)C1]

((S)-1-Methanesulfonyl-pyrrolidin-3-yl)-[3-(5H-pyrrolo[2,3-b]pyrazin-2-yl)-pyridin-2-yl]-amine was obtained from ((S)-1-methanesulfonyl-pyrrolidin-3-yl)-{3-[5-(2-trimethylsilanyl-ethoxymethyl)-5H-pyrrolo[2,3-b]pyrazin-2-yl]-pyridin-2-yl}-amine following the general synthetic procedures described in the above Examples.

Example 21

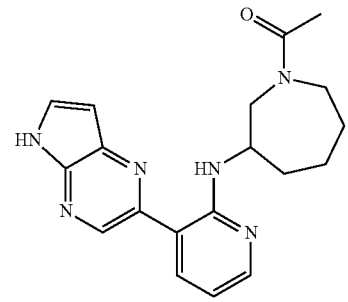 [SMILES: CC(=O)N1CCCCC(Nc2ncccc2-c2cnc3[nH]ccc3n2)C1]

1-{3-[3-(5H-Pyrrolo[2,3-b]pyrazin-2-yl)-pyridin-2-ylamino]-azepan-1-yl}-ethanone was prepared from 1-(3-{3-[5-(2-trimethylsilanyl-ethoxymethyl)-5H-pyrrolo[2,3-b]pyrazin-2-yl]-pyridin-2-ylamino}-azepan-1-yl)-ethanone, following the general synthetic procedures described in the above Examples.

Example 22

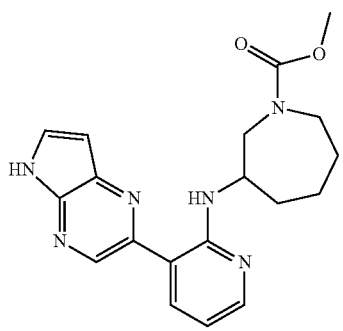 [SMILES: COC(=O)N1CCCCC(Nc2ncccc2-c2cnc3[nH]ccc3n2)C1]

3-[3-(5H-Pyrrolo[2,3-b]pyrazin-2-yl)-pyridin-2-ylamino]-azepane-1-carboxylic acid methyl ester was prepared from 3-{3-[5-(2-trimethylsilanyl-ethoxymethyl)-5H-pyrrolo[2,3-b]pyrazin-2-1]-pyridin-2-ylamino}-azepane-1-carboxylic acid methyl ester, following the general synthetic procedures described in the above Examples.

Example 23

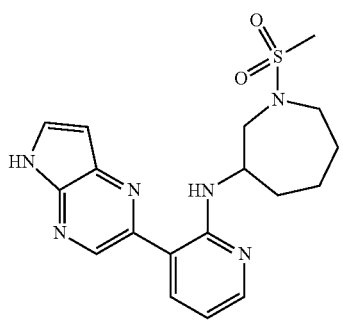 [SMILES: CS(=O)(=O)N1CCCCC(Nc2ncccc2-c2cnc3[nH]ccc3n2)C1]

(1-Methanesulfonyl-azepan-3-yl)-[3-(5H-pyrrolo[2,3-b]pyrazin-2-yl)-pyridin-2-yl]-amine was prepared from (1-methanesulfonyl-azepan-3-yl)-{3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 24

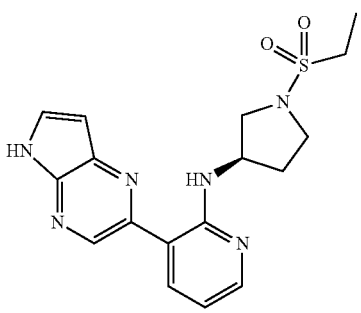 [SMILES: CCS(=O)(=O)N1CC[C@@H](Nc2ncccc2-c2cnc3[nH]ccc3n2)C1]

((R)-1-Ethanesulfonyl-pyrrolidin-3-yl)-[3-(5H-pyrrolo[2,3-b]pyrazin-2-yl)-pyridin-2-yl]-amine was prepared from ((R)-1-ethanesulfonyl-pyrrolidin-3-yl)-{3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 25

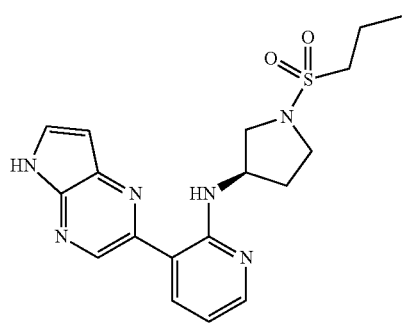 [SMILES: CCCS(=O)(=O)N1CC[C@@H](Nc2ncccc2-c2cnc3[nH]ccc3n2)C1]

[(R)-1-(Propane-1-sulfonyl)-pyrrolidin-3-yl]-[3-(5H-pyrrolo[2,3-b]pyrazin-2-yl)-pyridin-2-yl]-amine was prepared from [(R)-1-(propane-1-sulfonyl)-pyrrolidin-3-yl]-{3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 26

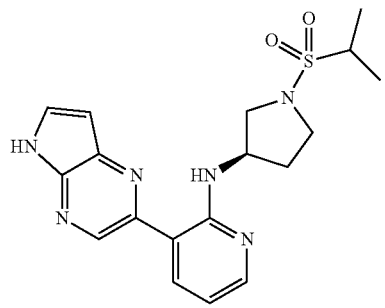 [SMILES: CC(C)S(=O)(=O)N1CC[C@@H](Nc2ncccc2-c2cnc3[nH]ccc3n2)C1]

[(R)-1-(Propane-2-sulfonyl)-pyrrolidin-3-yl]-[3-(5H-pyrrolo[2,3-b]pyrazin-2-yl)-pyridin-2-yl]-amine was prepared from [(R)-1-(Propane-2-sulfonyl)-pyrrolidin-3-yl]-{3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 27

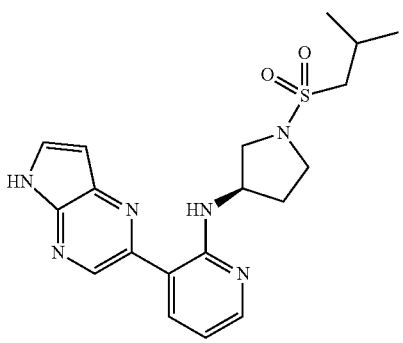 [SMILES: CC(C)CS(=O)(=O)N1CC[C@@H](Nc2ncccc2-c2cnc3[nH]ccc3n2)C1]

[(R)-1-(2-Methyl-propane-1-sulfonyl)-pyrrolidin-3-yl]-[3-(5H-pyrrolo[2,3-b]pyrazin-2-yl)-pyridin-2-yl]-amine was prepared from [(R)-1-(2-methyl-propane-1-sulfonyl)-pyrrolidin-3-yl]-{3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 28

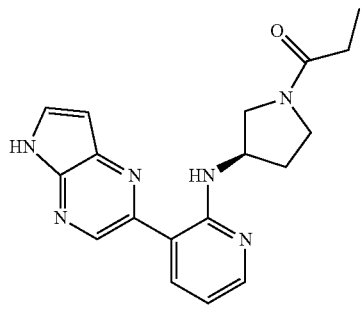 [SMILES: CCC(=O)N1CC[C@@H](Nc2ncccc2-c2cnc3[nH]ccc3n2)C1]

1-{(R)-3-[3-(5H-Pyrrolo[2,3-b]pyrazin-2-yl)-pyridin-2-ylamino]-pyrrolidin-1-yl}-propan-1-one was prepared from 1-((R)-3-{3-[5-(2-trimethylsilanyl-ethoxymethyl)-5H-pyrrolo[2,3-b]pyrazin-2-yl]-pyridin-2-ylamino}-pyrrolidin-1-yl)-propan-1-one, following the general synthetic procedures described in the above Examples.

Example 29

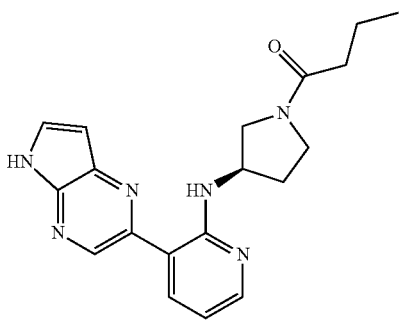 [SMILES: CCCC(=O)N1CC[C@@H](Nc2ncccc2-c2cnc3[nH]ccc3n2)C1]

1-{(R)-3-[3-(5H-Pyrrolo[2,3-b]pyrazin-2-yl)-pyridin-2-ylamino]-pyrrolidin-1-yl}-butan-1-one was prepared from 1-((R)-3-{3-[5-(2-trimethylsilanyl-ethoxymethyl)-5H-pyrrolo[2,3-b]pyrazin-2-yl]-pyridin-2-ylamino}-pyrrolidin-1-yl)-butanan-1-one, following the general synthetic procedures described in the above Examples.

Example 30

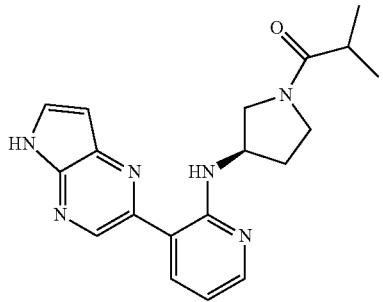 [SMILES: CC(C)C(=O)N1CC[C@@H](Nc2ncccc2-c2cnc3[nH]ccc3n2)C1]

2-Methyl-1-{(R)-3-[3-(5H-pyrrolo[2,3-b]pyrazin-2-yl)-pyridin-2-ylamino]-pyrrolidin-1-yl}-propan-1-one was prepared from 2-methyl-1-((R)-3-{3-[5-(2-trimethylsilanyl-ethoxymethyl)-5H-pyrrolo[2,3-b]pyrazin-2-yl]-pyridin-2-ylamino}-pyrrolidin-1-yl)-butanan-1-one, following the general synthetic procedures described in the above Examples.

Example 31

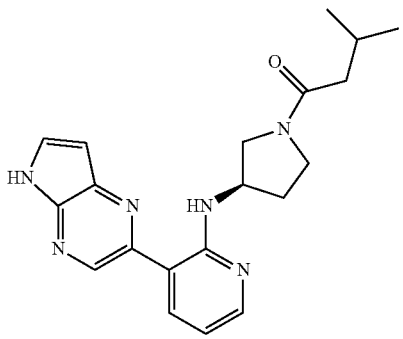 [SMILES: CC(C)CC(=O)N1CC[C@@H](Nc2ncccc2-c2cnc3[nH]ccc3n2)C1]

3-Methyl-1-{(R)-3-[3-(5H-pyrrolo[2,3-b]pyrazin-2-yl)-pyridin-2-ylamino]-pyrrolidin-1-yl}-propan-1-one was prepared from 3-methyl-1-((R)-3-{3-[5-(2-trimethylsilanyl-ethoxymethyl)-5H-pyrrolo[2,3-b]pyrazin-2-yl]-pyridin-2-ylamino}-pyrrolidin-1-yl)-butanan-1-one, following the general synthetic procedures described in the above Examples.

Example 32

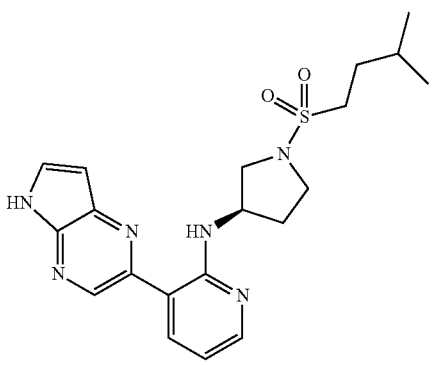 [SMILES: CC(C)CCS(=O)(=O)N1CC[C@@H](Nc2ncccc2-c2cnc3[nH]ccc3n2)C1]

[(R)-1-(3-Methyl-butane-1-sulfonyl)-pyrrolidin-3-yl]-[3-(5H-pyrrolo[2,3-b]pyrazin-2-yl)-pyridin-2-yl]-amine was prepared from [(R)-1-(3-methyl-butane-1-sulfonyl)-pyrrolidin-3-yl]-{3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 33

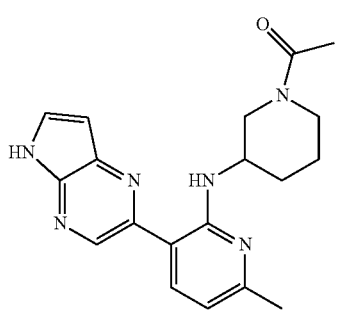 [SMILES: CC(=O)N1CCCC(Nc2nc(C)ccc2-c2cnc3[nH]ccc3n2)C1]

1-{3-[6-Methyl-3-(5H-pyrrolo[2,3-b]pyrazin-2-yl)-pyridin-2-ylamino]-piperidin-1-yl}-ethanone was prepared from 1-(3-{6-methyl-3-[5-(2-trimethylsilanyl-ethoxymethyl)-5H-pyrrolo[2,3-b]pyrazin-2-yl]-pyridin-2-ylamino}-piperidin-1-yl)-ethanone, following the general synthetic procedures described in the above Examples.

Example 34

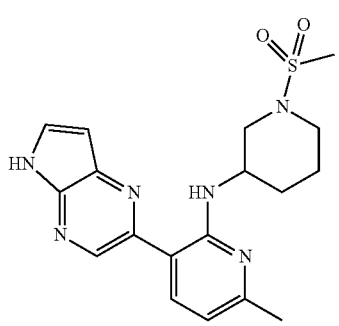 [SMILES: Cc1ccc(-c2cnc3[nH]ccc3n2)c(NC2CCCN(S(C)(=O)=O)C2)n1]

(1-Methanesulfonyl-piperidin-3-yl)-[6-methyl-3-(5H-pyrrolo[2,3-b]pyrazin-2-yl)-pyridin-2-yl]-amine was prepared from (1-methanesulfonyl-piperidin-3-yl)-{6-methyl-3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 35

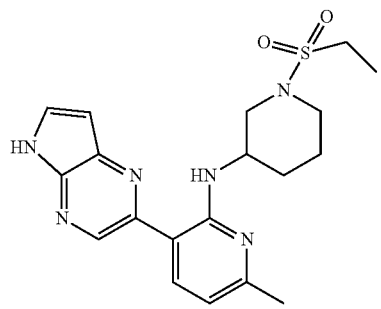 [SMILES: CCS(=O)(=O)N1CCCC(Nc2nc(C)ccc2-c2cnc3[nH]ccc3n2)C1]

(1-Ethanesulfonyl-piperidin-3-yl)-[6-methyl-3-(5H-pyrrolo[2,3-b]pyrazin-2-yl)-pyridin-2-yl]-amine was prepared from (1-ethanesulfonyl-piperidin-3-yl)-{6-methyl-3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 36

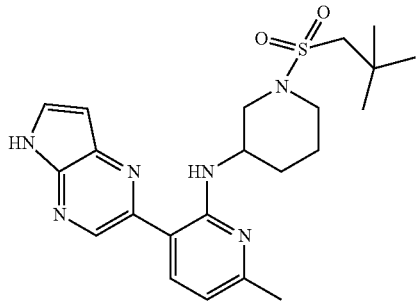 [SMILES: Cc1ccc(-c2cnc3[nH]ccc3n2)c(NC2CCCN(S(=O)(=O)CC(C)(C)C)C2)n1]

[1-(2,2-Dimethyl-propane-1-sulfonyl)-piperidin-3-yl]-[6-methyl-3-(5H-pyrrolo[2,3-b]pyrazin-2-yl)-pyridin-2-yl]-amine was prepared from [1-(2,2-dimethyl-propane-1-sulfonyl)-piperidin-3-yl]-{6-methyl-3-[5-(2-trimethylsilanyl-ethoxymethyl)-5H-pyrrolo[2,3-b]pyrazin-2-yl]-pyridin-2-yl}-amine, following the general synthetic procedures described in the above Examples.

Example 37

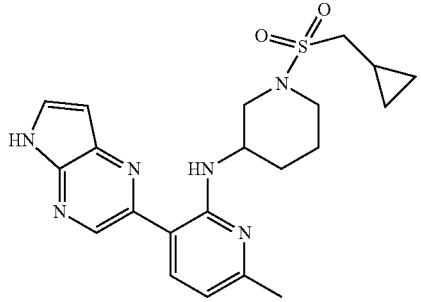 [SMILES: Cc1ccc(-c2cnc3[nH]ccc3n2)c(NC2CCCN(S(=O)(=O)CC3CC3)C2)n1]

(1-Cyclopropylmethanesulfonyl-piperidin-3-yl)-[6-methyl-3-(5H-pyrrolo[2,3-b]pyrazin-2-yl)-pyridin-2-yl]-amine was prepared from (1-cyclopropylmethanesulfonyl-piperidin-3-yl)-{6-methyl-3-[5-(2-trimethylsilanyl-ethoxymethyl)-5H-pyrrolo[2,3-b]pyrazin-2-yl]-pyridin-2-yl}-amine using 20 equivalents of tetrabutyl ammonium fluoride 1 M solution in THF, and 20 equivalents of ethylenediamine, and warming the mixture at 70° C. for 5 h.

Example 38

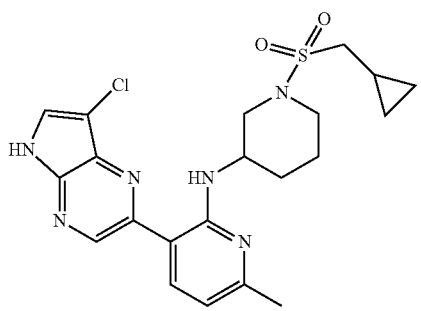 [SMILES: Cc1ccc(-c2cnc3[nH]cc(Cl)c3n2)c(NC2CCCN(S(=O)(=O)CC3CC3)C2)n1]

[3-(7-Chloro-5H-pyrrolo[2,3-b]pyrazin-2-yl)-6-methyl-pyridin-2-yl]-(1-cyclopropylmethanesulfonyl-piperidin-3-yl)-amine was prepared from {3-[7-chloro-5-(2-trimethylsilanyl-ethoxymethyl)-5H-pyrrolo[2,3-b]pyrazin-2-yl]-6-methyl-pyridin-2-yl}-(1-cyclopropylmethanesulfonyl-piperidin-3-yl)-amine, following the general synthetic procedures described in the above Examples.

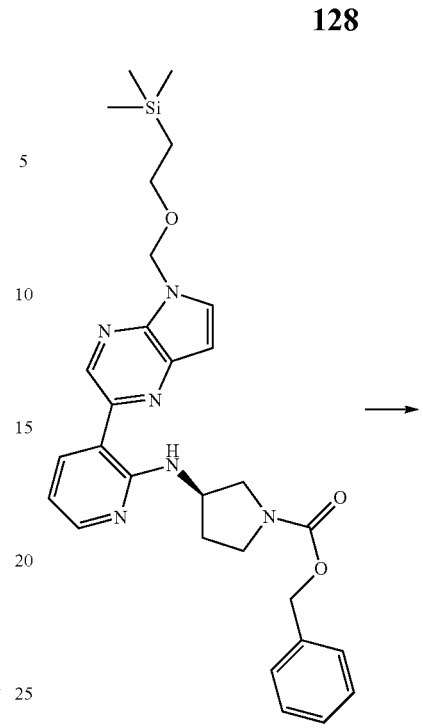

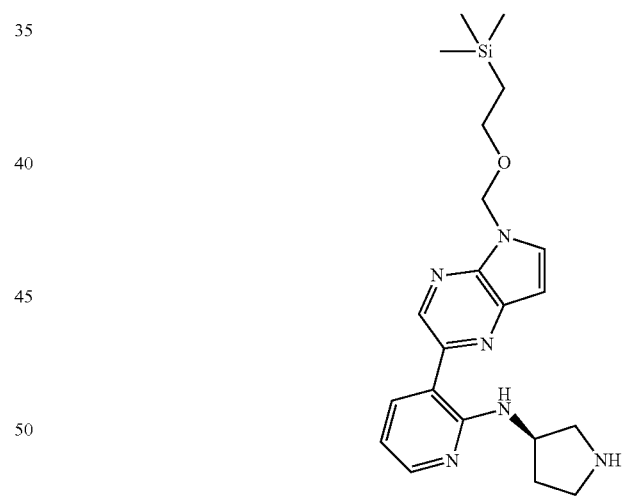

(R)-3-{3-[5-(2-Trimethylsilanyl-ethoxymethyl)-5H-pyrrolo[2,3-b]pyrazin-2-yl]-pyridin-2-ylamino}-pyrrolidine-1-carboxylic acid benzyl ester (0.535 g, 0.98 mmol) was dissolved in 20 ml of EtOH and the flask was flushed with argon. 20% Pd(OH)$_2$/C (0.105 g) was added and the system was flushed with argon again and at last was flushed with hydrogen. A hydrogen balloon was placed on the flask, with a needle, so that the gas bubbled directly into the solution at atmospheric pressure and the reaction was left for 2 h. The catalyst was removed by filtration and the solution was concentrated to dryness, giving 0.330 g (81%) of (R)-pyrrolidin-3-yl-{3-[5-(2-trimethylsilanyl-ethoxymethyl)-5H-pyrrolo[2,3-b]pyrazin-2-yl]-pyridin-2-yl}-amine which was used as is in the following steps.

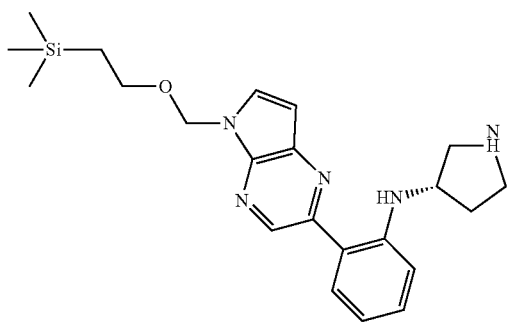 [SMILES: C[Si](C)(C)CCOCn1ccc2nc(-c3ccccc3N[C@H]3CCNC3)cnc21]

(S)-pyrrolidin-3-yl-{3-[5-(2-trimethylsilanyl-ethoxymethyl)-5H-pyrrolo[2,3-b]pyrazin-2-yl]-pyridin-2-yl}-amine was prepared from (S)-3-{3-[5-(2-Trimethylsilanyl-ethoxymethyl)-5H-pyrrolo[2,3-b]pyrazin-2-yl]-pyridin-2-ylamino}-pyrrolidine-1-carboxylic acid benzyl ester, following the general synthetic procedures described in the above Examples.

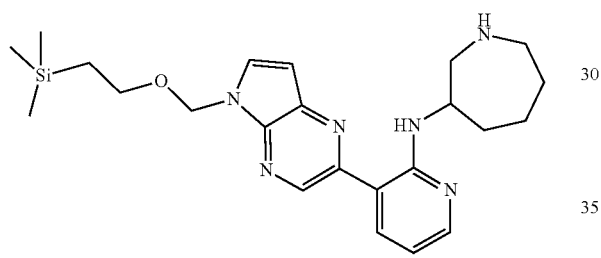

Azepan-3-yl-{3-[5-(2-trimethylsilanyl-ethoxymethyl)-5H-pyrrolo[2,3-b]pyrazin-2-yl]-pyridin-2-yl}-amine was prepared from 3-{3-[5-(2-Trimethylsilanyl-ethoxymethyl)-5H-pyrrolo[2,3-b]pyrazin-2-yl]-pyridin-2-ylamino}-azepane-1-carboxylic acid benzyl ester, following the general synthetic procedures described in the above Examples.

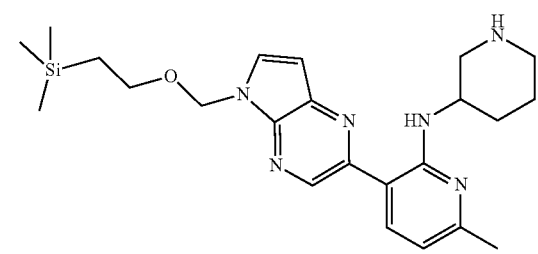 [SMILES: Cc1ccc(-c2cnc3c(ccn3COCC[Si](C)(C)C)n2)c(NC2CCCNC2)n1]

{6-Methyl-3-[5-(2-trimethylsilanyl-ethoxymethyl)-5H-pyrrolo[2,3-b]pyrazin-2-yl]-pyridin-2-yl}-piperidin-3-yl-amine was prepared from 3-{6-Methyl-3-[5-(2-trimethylsilanyl-ethoxymethyl)-5H-pyrrolo[2,3-b]pyrazin-2-yl]-pyridin-2-ylamino}-piperidine-1-carboxylic acid benzyl ester, following the general synthetic procedures described in the above Examples.

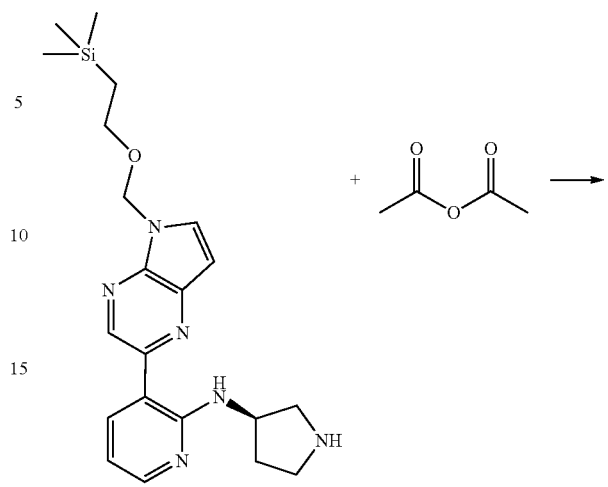

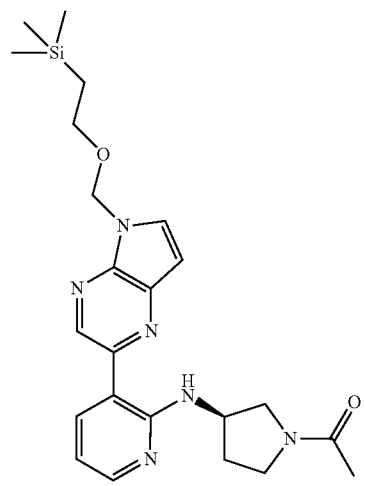

Acetic anhydride (0.04 ml, 0.38 mmol) was added to a solution of (R)-pyrrolidin-3-yl-{3-[5-(2-trimethylsilanyl-ethoxymethyl)-5H-pyrrolo[2,3-b]pyrazin-2-yl]-pyridin-2-yl}-amine (0.110 g, 0.27 mmol) in 1.5 ml of DCM and 0.090 ml of pyridine. The resulting mixture was stirred at RT overnight before being quenched with 1 ml of MeOH. After letting stirred for 10 minutes, the solvent was removed under vacuum and the residue was partitioned in DCM, and aqueous 1M HCl. The aqueous layer was back extracted twice with DCM and the combined organics were dried over MgSO4, filtered and concentrated. The crude was purified by SiO2 chromatography using DCM to 15% Magic (DCM:MeOH:NH4OH; 60:10:1) in DCM giving 0.102 g (84%) of 1-OR)-3-{3-[5-(2-trimethylsilanyhethoxymethyl)-5H-pyrrolo[2,3-b]pyrazin-2-yl]-pyridin-2-ylamino}-pyrrolidin-1-yl)-ethanone.

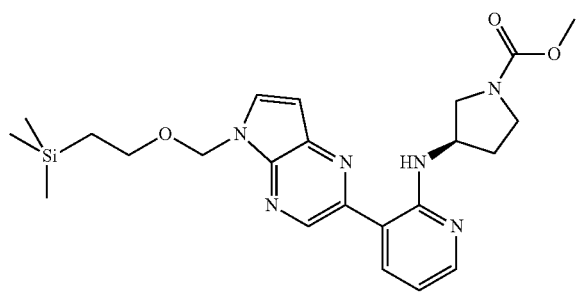

(R)-3-{3-[5-(2-Trimethylsilanyl-ethoxymethyl)-5H-pyrrolo[2,3-b]pyrazin-2-yl]-pyridin-2-ylamino}-pyrrolidine-1-carboxylic acid methyl ester was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and methylchloroformate using DIPEA as base and following the general synthetic procedures described in the above Examples.

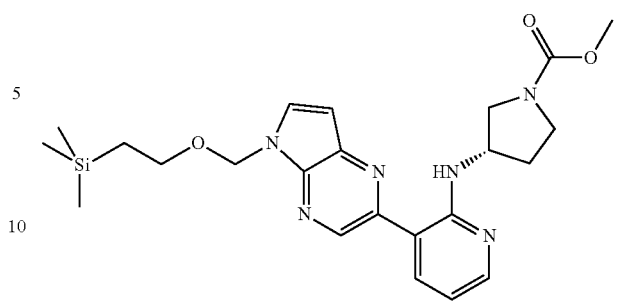

(S)-3-{3-[5-(2-Trimethylsilanyl-ethoxymethyl)-5H-pyrrolo[2,3-b]pyrazin-2-yl]-pyridin-2-ylamino}-pyrrolidine-1-carboxylic acid methyl ester was prepared from (S)-pyrrolidin-3-yl-{3-[5-(2-trimethylsilanyl-ethoxymethyl)-5H-pyrrolo[2,3-b]pyrazin-2-yl]-pyridin-2-yl}-amine and methylchloroformate, using DIPEA as base and following the general synthetic procedures described in the above Examples.

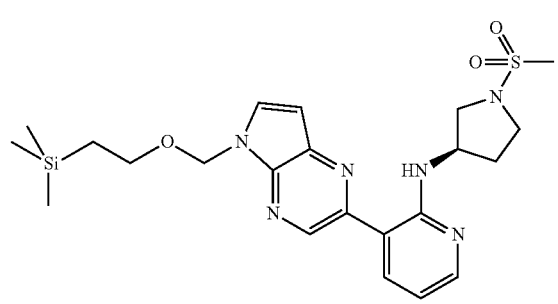

((R)-1-Methanesulfonyl-pyrrolidin-3-yl)-{3-[5-(2-trimethylsilanyl-ethoxymethyl)-5H-pyrrolo[2,3-b]pyrazin-2-yl]-pyridin-2-yl}-amine was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and methanesulfonyl chloride using DIPEA as base and following the general synthetic procedures described in the above Examples.

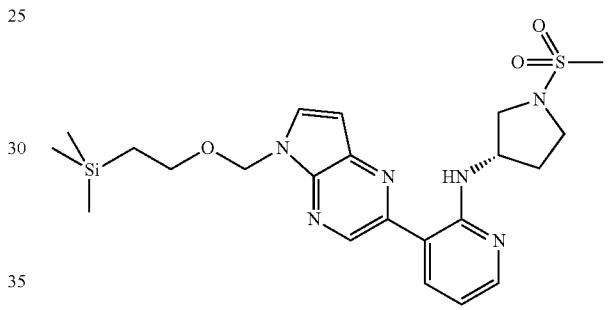

((S)-1-Methanesulfonyl-pyrrolidin-3-yl)-{3-[5-(2-trimethylsilanyl-ethoxymethyl)-5H-pyrrolo[2,3-b]pyrazin-2-yl]-pyridin-2-yl}-amine was prepared from (S)-pyrrolidin-3-yl-{3-[5-(2-trimethylsilanyl-ethoxymethyl)-5H-pyrrolo[2,3-b]pyrazin-2-yl]-pyridin-2-yl}-amine and methanesulfonyl chloride, using DIPEA as base and following the general synthetic procedures described in the above Examples.

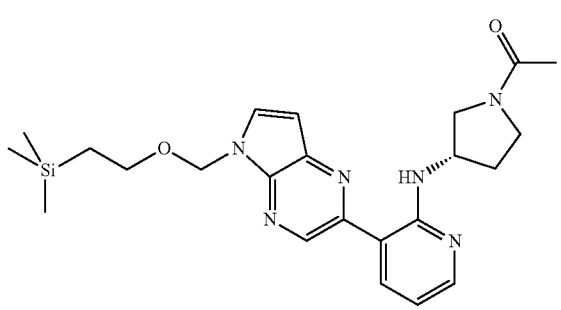 [SMILES: CC(=O)N1CC[C@H](Nc2ncccc2-c2cnc3c(ccn3COCC[Si](C)(C)C)n2)C1]

1-((S)-3-{3-[5-(2-Trimethylsilanyl-ethoxymethyl)-5H-pyrrolo[2,3-b]pyrazin-2-yl]-pyridin-2-ylamino}-pyrrolidin-1-yl)-ethanone was prepared from (S)-pyrrolidin-3-yl-{3-[5-(2-trimethylsilanyl-ethoxymethyl)-5H-pyrrolo[2,3-b]pyrazin-2-yl]-pyridin-2-yl}-amine and acetic anhydride following the general synthetic procedures described in the above Examples.

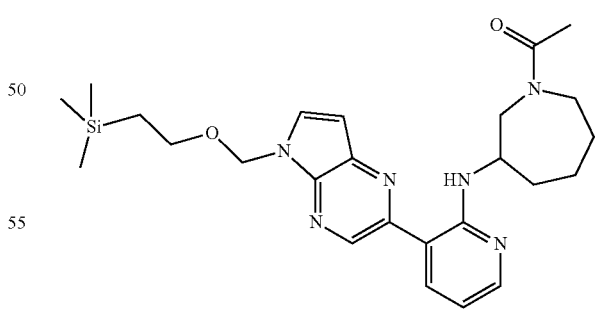

1-(3-{3-[5-(2-Trimethylsilanyl-ethoxymethyl)-5H-pyrrolo[2,3-b]pyrazin-2-yl]-pyridin-2-ylamino}-azepan-1-yl)-ethanone was prepared from azepan-3-yl-{3-[5-(2-trimethylsilanyl-ethoxymethyl)-5H-pyrrolo[2,3-b]pyrazin-2-yl]-pyridin-2-yl}-amine and acetic anhydride, following the general synthetic procedures described in the above Examples.

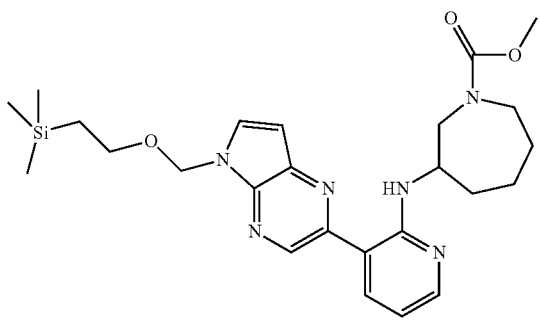

3-{3-[5-(2-Trimethylsilanyl-ethoxymethyl)-5H-pyrrolo [2,3-b]pyrazin-2-1]-pyridin-2-ylamino}-azepane-1-carboxylic acid methyl ester was prepared from azepan-3-yl-{3-[5-(2-trimethylsilanyl-ethoxymethyl)-5H-pyrrolo[2,3-b]pyrazin-2-yl]-pyridin-2-yl}-amine and methyl chloroformate, using 4 equivalents of DIPEA as base and following the general synthetic procedures described in the above Examples.

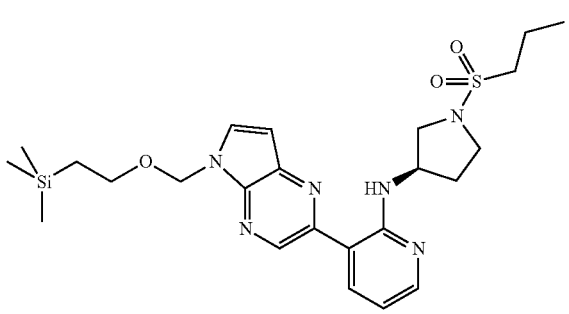

[(R)-1-(Propane-1-sulfonyl)-pyrrolidin-3-yl]-{3-[5-(2-trimethylsilanyl-ethoxymethyl)-5H-pyrrolo[2,3-b]pyrazin-2-yl]-pyridin-2-yl}-amine was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and propane-1-sulfonyl chloride, following the general synthetic procedures described in the above Examples.

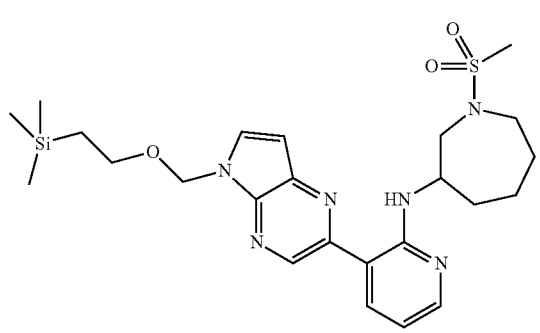 [SMILES: C[Si](C)(C)CCOCn1ccc2nc(-c3cccnc3NC3CCCCN(S(C)(=O)=O)C3)cnc21]

(1-Methanesulfonyl-azepan-3-yl)-{3-[5-(2-trimethylsilanyl-ethoxymethyl)-5H-pyrrolo[2,3-b]pyrazin-2-yl]-pyridin-2-yl}-amine was prepared from azepan-3-yl-{3-[5-(2-trimethylsilanyl-ethoxymethyl)-5H-pyrrolo[2,3-b]pyrazin-2-yl]-pyridin-2-yl}-amine and methanesulfonyl chloride, using 4 equivalents of DIPEA as base and following the general synthetic procedures described in the above Examples.

[(R)-1-(Propane-2-sulfonyl)-pyrrolidin-3-yl]-{3-[5-(2-trimethylsilanyl-ethoxymethyl)-5H-pyrrolo[2,3-b]pyrazin-2-yl]-pyridin-2-yl}-amine was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and propane-2-sulfonyl chloride, following the general synthetic procedures described in the above Examples.

((R)-1-Ethanesulfonyl-pyrrolidin-3-yl)-{3-[5-(2-trimethylsilanyl-ethoxymethyl)-5H-pyrrolo[2,3-b]pyrazin-2-yl]-pyridin-2-yl}-amine was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and ethanesulfonyl chloride, following the general synthetic procedures described in the above Examples.

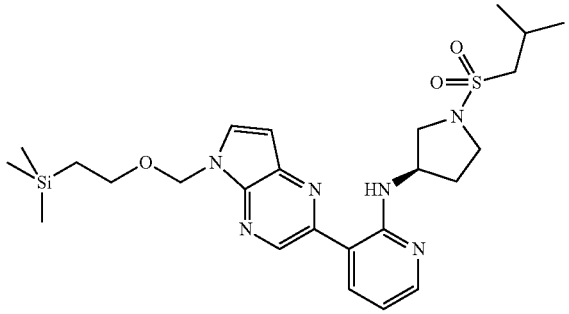 [SMILES: CC(C)CS(=O)(=O)N1CC[C@@H](Nc2ncccc2-c2cnc3c(ccn3COCC[Si](C)(C)C)n2)C1]

[(R)-1-(2-Methyl-propane-1-sulfonyl)-pyrrolidin-3-yl]-{3-[5-(2-trimethylsilanyl-ethoxymethyl)-5H-pyrrolo[2,3-b]pyrazin-2-yl]-pyridin-2-yl}-amine was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and 2-methyl-propane-1-sulfonyl chloride, following the general synthetic procedures described in the above Examples.

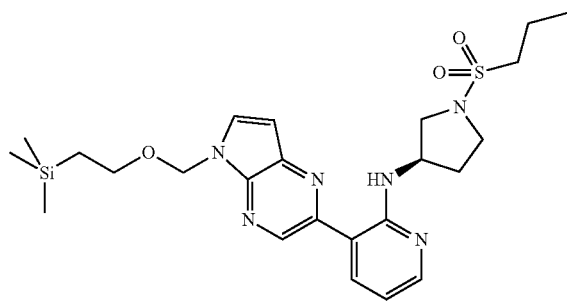 [SMILES: CCCS(=O)(=O)N1CC[C@@H](Nc2ncccc2-c2cnc3c(ccn3COCC[Si](C)(C)C)n2)C1]

1-((R)-3-{3-[5-(2-Trimethylsilanyl-ethoxymethyl)-5H-pyrrolo[2,3-b]pyrazin-2-yl]-pyridin-2-ylamino}-pyrrolidin-1-yl)-propan-1-one was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and propionyl chloride, following the general synthetic procedures described in the above Examples.

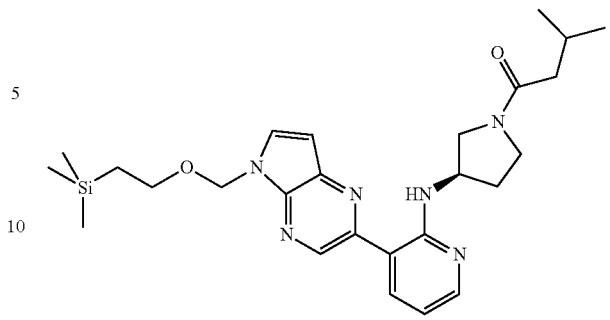

3-Methyl-1-((R)-3-{3-[5-(2-trimethylsilanyl-ethoxymethyl)-5H-pyrrolo[2,3-b]pyrazin-2-yl]-pyridin-2-ylamino}-pyrrolidin-1-yl)-butan-1-one was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and isovaleryl chloride, following the general synthetic procedures described in the above Examples.

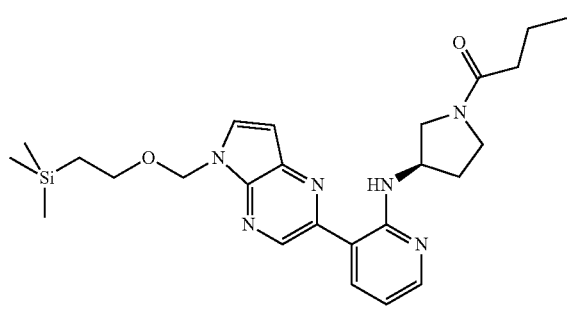 [SMILES: CCCC(=O)N1CC[C@@H](Nc2ncccc2-c2cnc3c(ccn3COCC[Si](C)(C)C)n2)C1]

1-((R)-3-{3-[5-(2-Trimethylsilanyl-ethoxymethyl)-5H-pyrrolo[2,3-b]pyrazin-2-yl]-pyridin-2-ylamino}-pyrrolidin-1-yl)-butan-1-one was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and butyryl chloride, following the general synthetic procedures described in the above Examples.

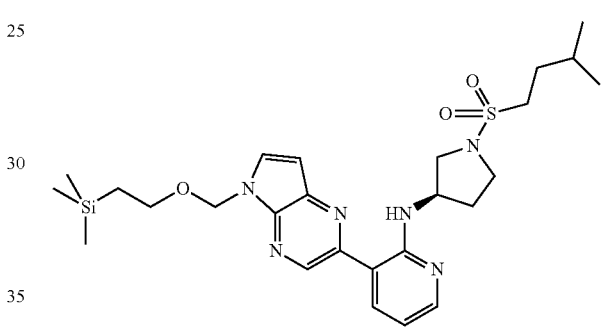

[(R)-1-(3-Methyl-butane-1-sulfonyl)-pyrrolidin-3-yl]-{3-[5-(2-trimethylsilanyl-ethoxymethyl)-5H-pyrrolo[2,3-b]pyrazin-2-yl]-pyridin-2-yl}-amine was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and 3-methyl-butane-1-sulfonyl chloride, following the general synthetic procedures described in the above Examples.

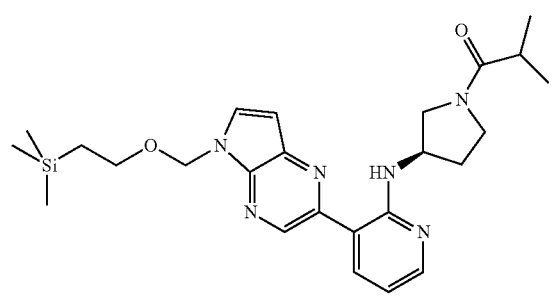 [SMILES: CC(C)C(=O)N1CC[C@@H](Nc2ncccc2-c2cnc3c(ccn3COCC[Si](C)(C)C)n2)C1]

2-Methyl-1-((R)-3-{3-[5-(2-trimethylsilanyl-ethoxymethyl)-5H-pyrrolo[2,3-b]pyrazin-2-yl]-pyridin-2-ylamino}-pyrrolidin-1-yl)-propan-1-one was prepared from (R)-pyrrolidin-3-yl-{3-[5-(2-trimethylsilanyl-ethoxymethyl)-5H-pyrrolo[2,3-b]pyrazin-2-yl]-pyridin-2-yl}-amine and isobutyryl chloride, following the general synthetic procedures described in the above Examples.

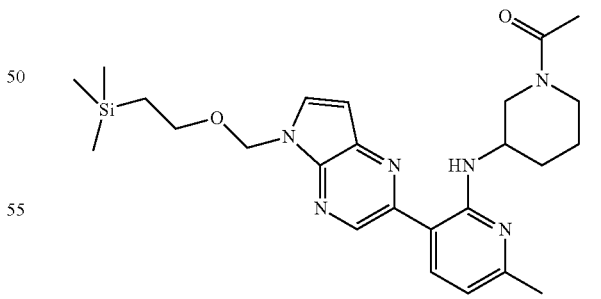

1-(3-{6-Methyl-3-[5-(2-trimethylsilanyl-ethoxymethyl)-5H-pyrrolo[2,3-b]pyrazin-2-yl]-pyridin-2-ylamino}-piperidin-1-yl)-ethanone was prepared from {6-methyl-3-[5-(2-trimethylsilanyl-ethoxymethyl)-5H-pyrrolo[2,3-b]pyrazin-2-yl]-pyridin-2-yl}-piperidin-3-yl-amine and acetic anhydride, following the general synthetic procedures described in the above Examples.

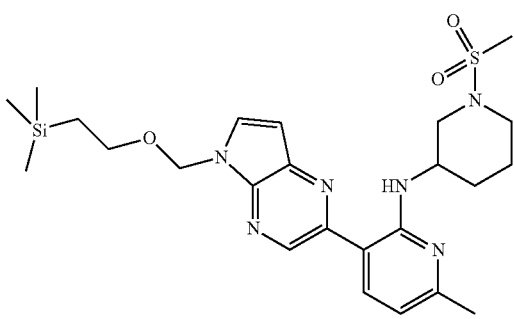

(1-Methanesulfonyl-piperidin-3-yl)-{6-methyl-3-[5-(2-trimethylsilanyl-ethoxymethyl)-5H-pyrrolo[2,3-b]pyrazin-2-yl]-pyridin-2-yl}-amine was prepared from {6-methyl-3-[5-(2-trimethylsilanyl-ethoxymethyl)-5H-pyrrolo[2,3-b]pyrazin-2-yl]-pyridin-2-yl}-piperidin-3-yl-amine, and methanesulfonyl chloride, using 4 equivalents of DIPEA as base and following the general synthetic procedures described in the above Examples.

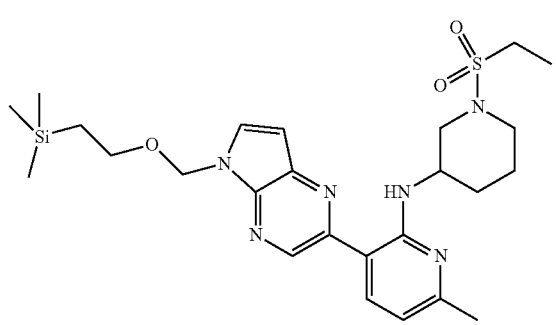 [SMILES: CCS(=O)(=O)N1CCCC(Nc2nc(C)ccc2-c2cnc3c(ccn3COCC[Si](C)(C)C)n2)C1]

(1-Ethanesulfonyl-piperidin-3-yl)-{6-methyl-3-[5-(2-trimethylsilanyl-ethoxymethyl)-5H-pyrrolo[2,3-b]pyrazin-2-yl]-pyridin-2-yl}-amine was prepared from {6-methyl-3-[5-(2-trimethylsilanyl-ethoxymethyl)-5H-pyrrolo[2,3-b]pyrazin-2-yl]-pyridin-2-yl}-piperidin-3-yl-amine, and ethanesulfonyl chloride, using 3 equivalents of DIPEA as base and following the general synthetic procedures described in the above Examples.

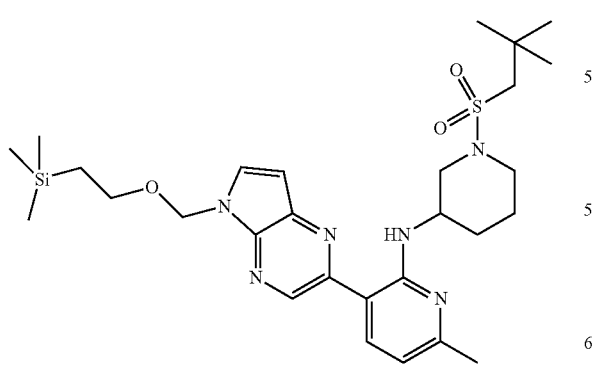

[1-(2,2-Dimethyl-propane-1-sulfonyl)-piperidin-3-yl]-{6-methyl-3-[5-(2-trimethylsilanyl-ethoxymethyl)-5H-pyrro[2,3-b]pyrazin-2-yl]-pyridin-2-yl}-amine was prepared from {6-methyl-3-[5-(2-trimethylsilanyl-ethoxymethyl)-5H-pyrrolo[2,3-b]pyrazin-2-yl]-pyridin-2-yl}-piperidin-3-yl-amine, and 2,2-dimethyl-propane-1-sulfonyl chloride, using 3 equivalents of DIPEA as base and following the general synthetic procedures described in the above Examples.

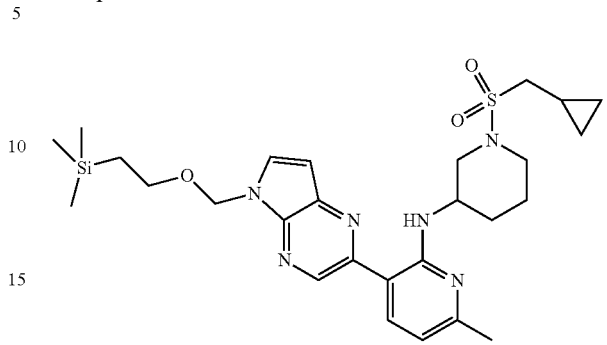

(1-Cyclopropylmethanesulfonyl-piperidin-3-yl)-{6-methyl-3-[5-(2-trimethylsilanyl-ethoxymethyl)-5H-pyrrolo[2,3-b]pyrazin-2-yl]-pyridin-2-yl}-amine was prepared from {6-methyl-3-[5-(2-trimethylsilanyl-ethoxymethyl)-5H-pyrrolo[2,3-b]pyrazin-2-yl]-pyridin-2-yl}-piperidin-3-yl-amine, and cyclopropyl methanesulfonyl chloride, using 3 equivalents of DIPEA as base and following the general synthetic procedures described in the above Examples.

Example 39

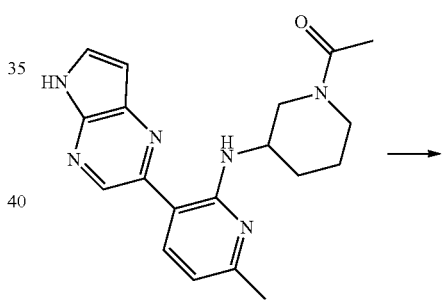

→

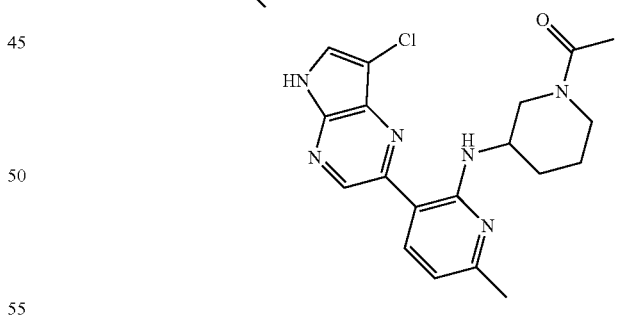

To a solution of 1-{(R)-3-[3-(5H-pyrrolo[2,3-b]pyrazin-2-yl)-pyridin-2-ylamino]-pyrrolidin-1-yl}-butan-1-one (0.070 g, 0.2 mmol) in 1.5 ml of DMF and 1.5 ml of DCM was added NCS (0.032 g, 0.24 mmol) and the mixture was stirred at RT overnight. LCMS showed only partial conversion, therefore another 0.015 g (0.12 mmol) of NCS were added and the reaction left for additional 24 h. The reaction was quenched by diluting it with DCM and adding brine. The organic layer was dried over MgSO4, filtered and concentrated. The crude was purified by SiO2 chromatography using DCM to 30% Magic (DCM:MeOH:NH4OH; 60:10:1) in DCM to give 0.015 mg (19.5%) of 1-{3-[3-(7-chloro-5H-pyrrolo[2,3-b]pyrazin-2-yl)-6-methyl-pyridin-2-ylamino]-piperidin-1-yl}-ethanone as a yellow powder.

Example 40

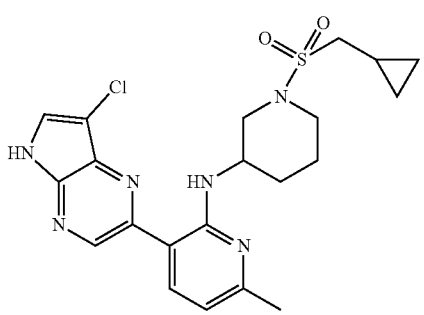 [SMILES: Cc1ccc(-c2cnc3[nH]cc(Cl)c3n2)c(NC2CCCN(S(=O)(=O)CC3CC3)C2)n1]

{3-[7-Chloro-5-(2-trimethylsilanyl-ethoxymethyl)-5H-pyrrolo[2,3-b]pyrazin-2-yl]-6-methyl-pyridin-2-yl}-(1-cyclopropylmethanesulfonyl-piperidin-3-yl)-amine was prepared from (1-cyclopropylmethanesulfonyl-piperidin-3-yl)-{6-methyl-3-[5-(2-trimethylsilanyl-ethoxymethyl)-5H-pyrrolo[2,3-b]pyrazin-2-yl]-pyridin-2-yl}-amine, following the general synthetic procedures described in the above Examples.

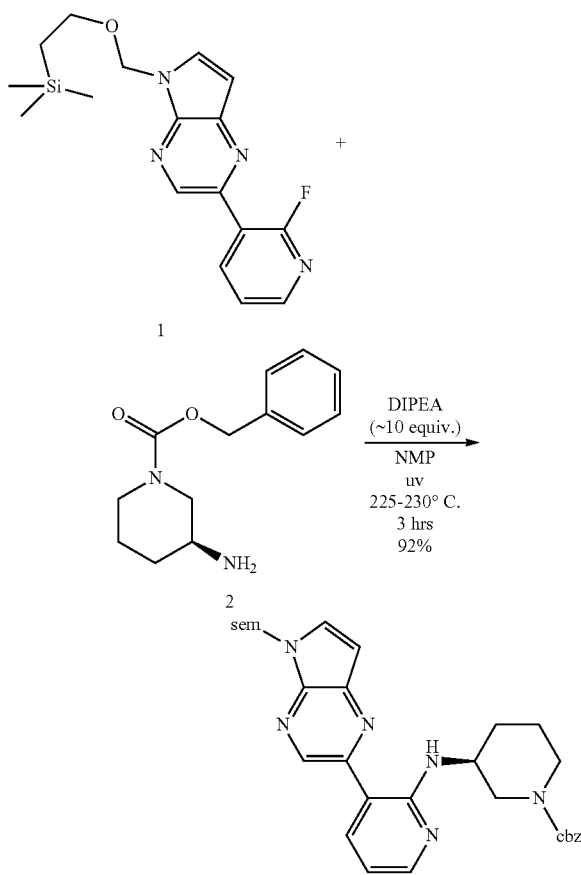

To microwave reaction vessel was added 1 (1.916 g, 5.6 mmol), 2 (1.955 g, 8.3 mmol), Hunig's base (10 mL, 57.4 mmol), and NMP (2 mL). Reaction vessel flushed with argon and sealed. The suspension was heated at 225° C. under microwave irradiation for 1 hr. The reaction was then heated at 230° C. under microwave irradiation for 2 hr. Water (25 mL) was added to the light green biphasic mixture and the mixture was extracted with ethyl acetate (3×25 mL). The combined organic layers was washed with water then brine, dried on $Na_2SO_4$, and concentrated. The viscous oil was purified by silica column chromatography (0% to 50% ethyl acetate in hexanes) to give a yellow glassy solid (2.851 g, 92%).

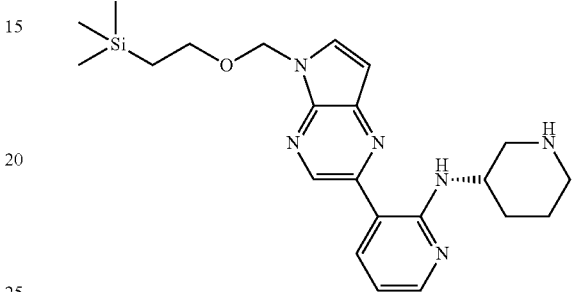

CBZ Deprotection:

A par flask was charged with (S)-3-{3-[5-(2-trimethylsilanyl-ethoxymethyl)-5H-pyrrolo[2,3-b]pyrazin-2-yl]-pyridin-2-ylamino}-piperidine-1-carboxylic acid benzyl ester (3.134 g, 5.61 mmol) and Pearlman's catalyst (0.301 g, 20 wt. %). The solids were suspended in ethanol (20 mL) under nitrogen atmosphere. The system was evacuated and placed under hydrogen atmosphere (3 atm). The reaction was shaken on the par for 1.5 hr. The reaction mixture was filtered through pad of solka floc. The pad was washed with ethanol. The filtrate was concentrated to give material as a crude solid (1.895 g, 80%). The crude material was taken on to next reaction without purification.

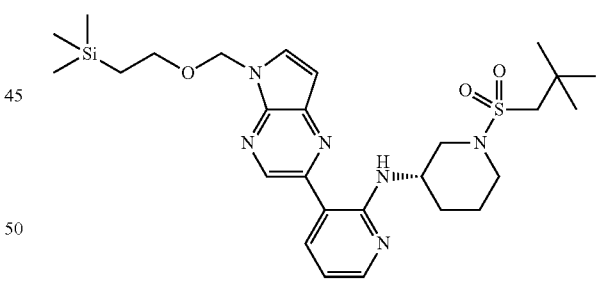

T-Butylmethyl Sulfonamide w/sem:

A test-tube reaction vessel was charged with (S)-piperidin-3-yl-{3-[5-(2-trimethylsilanyl-ethoxymethyl)-5H-pyrrolo[2,3-b]pyrazin-2-yl]-pyridin-2-yl}-amine (3.20 mL, 0.704 mmol, 0.22 M in dichloromethane) and diisopropyethylamine (0.18 mL, 1.05 mmol). The reaction was placed under Ar and sealed. The solution was cooled in an ice bath (0° C.). 2,2-Dimethylbutyl sulfonyl chloride (0.121 g, 0.70 mmol) was added dropwise to the cooled solution. The reaction was allowed to warm to room temperature. Stirring was continued at room temperature for 18 hrs. Water was added to the reaction mixture and extracted with dichloromethane. The combined organics were dried on sodium sulfate and concentrated to give a crude solid. The crude material was purified by column chromatography (silica, 0% to 5% methanol in dichloromethane) to give the product as a glassy yellow solid (0.102 g, 30%).

Example 41

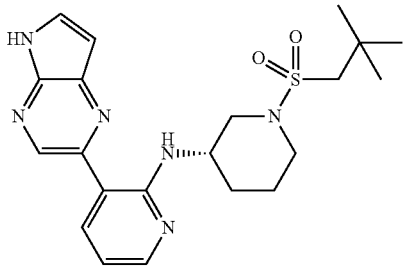 [SMILES: CC(C)(C)CS(=O)(=O)N1CCC[C@H](Nc2ncccc2-c2cnc3[nH]ccc3n2)C1]

Deprotected T-Butyl System:

A microwave reaction vessel was charged with [(S)-1-(2,2-dimethyl-propane-1-sulfonyl)-piperidin-3-yl]-{3-[5-(2-trimethylsilanyl-ethoxymethyl)-5H-pyrrolo[2,3-b]pyrazin-2-yl]-pyridin-2-yl}-amine (0.101 g, 0.181 mmol), tetrabutylammonium fluoride (0.9 mL, 1M in THF, 0.9 mmol), and ethylenediamine (0.06 mL, 0.90 mmol) dissolved in THF (1 mL). The reaction was placed under Ar and the vessel sealed. The reaction was heated to 180° C. by microwave irradiation for 30 min. Then the reaction mixture was concentrated to give a crude yellow oil. Water was added to give a suspension. A crude solid was isolated by filtration and the crude solid purified by column chromatography (silica, 0 to 5% MeOH (with 0.5% NH$_4$OH) in CH$_2$Cl$_2$) to give the product as a yellow solid (61.3 mg, 79%).

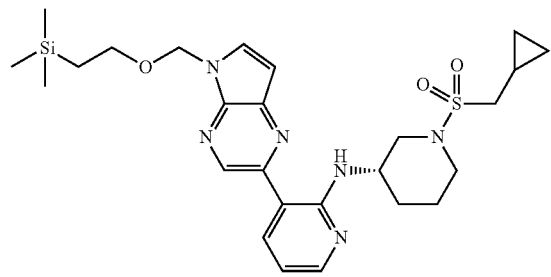 [SMILES: C[Si](C)(C)CCOCn1ccc2nc(-c3cccnc3N[C@H]3CCCN(S(=O)(=O)CC4CC4)C3)cnc21]

Cyclopropylmethyl Sulfonamide w/sem:

A test-tube reaction vessel was charged with (S)-piperidin-3-yl-{3-[5-(2-trimethylsilanyl-ethoxymethyl)-5H-pyrrolo[2,3-b]pyrazin-2-yl]-pyridin-2-yl}-amine (3.20 mL, 0.704 mmol, 0.22 M in dichloromethane) and diisopropyethylamine (0.18 mL, 1.05 mmol). The reaction was placed under Ar and sealed. The solution was cooled in an ice bath (0° C.). Cyclopropylmethyl sulfonyl chloride (0.110 g, 0.70 mmol) was added dropwise to the cooled solution. The reaction was allowed to warm to room temperature. Stirring was continued at room temperature for 18 hrs. Water was added to the reaction mixture and extracted with dichloromethane. The combined organics were dried on sodium sulfate and concentrated to give a crude solid. The crude material was purified by column chromatography (silica, 0% to 5% methanol (with 0.5% NH$_4$OH) in dichloromethane) to give the product as a glassy yellow solid (0.253 g, 66%).

Example 42

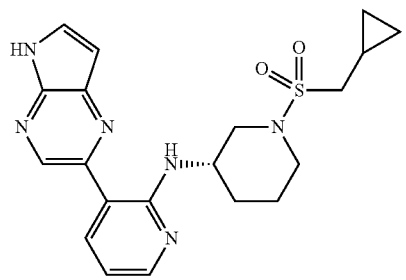 [SMILES: O=S(=O)(CC1CC1)N1CCC[C@H](Nc2ncccc2-c2cnc3[nH]ccc3n2)C1]

Deprotected Cyclopropyl Methyl System

A round bottom flask was charged with ((S-1-cyclopropylmethanesulfonyl-piperidin-3-yl-{3-[5-(2-trimethylsilanyl-ethoxymethyl)-5H-pyrrolo[2,3-b]pyrazin-2-yl)-amine (0.147 g, 0.271 mmol), tetrabutylammonium fluoride (1.3 mL, 1M in THF, 1.3 mmol), and ethylenediamine (0.09 mL, 1.34 mmol) dissolved in THF (1 mL). The reaction mixture was heated to reflux and stirred for 24 hrs. Then the reaction was concentrated and the residue was purified by column chromatography (silica, 0 to 5% of MeOH (with 0.5% NH$_4$OH) in CH$_2$Cl$_2$) as a yellow solid. The solid was recrystallized (methanol) to give the product as a pale yellow crystalline solid (36.9 mg, 33%).

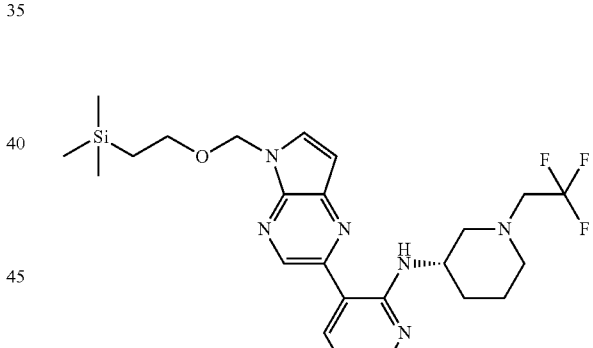

Trifluoroethyl w/SEM:

A round bottom flask was charged with [(S)-1-(2,2,2-trifluoro-ethyl)piperidin-3-yl]-{3-[5-(2-trimethylsilanyl-ethoxymethyl)-5H-pyrrolo[2,3-b]pyrazin-2-yl]-pyridin-2-yl}-amine (3.0 mL, 0.22 M in THF, 0.66 mmol) was cooled in a 0° C. bath. To the cooled solution was added diisopropylethyl amine (0.17 mL, 2.54 mmol). Then 2,2,2-trifluoroethyl trifluoromethansulfonate (0.170 g, 0.732 mmol) was added dropwise to the cooled solution. The reaction was allowed to warm to room temperature and stirring was continued for 20 hrs. An additional diisopropylethyl amine (0.17 mL, 2.54 mmol) was added. The reaction was allowed to stir at room temperature for an additional 20 hrs. The reaction was diluted with dichloromethane (20 mL) and washed with saturated sodium bicarbonate. The organic layer was separated, dried on Na$_2$SO$_4$, and concentrated. The residue was purified by column chromatography (silica, 0 to 100% ethyl acetate in hexanes) to give the product as a yellow viscous oil (0.171 g, 79%).

Example 43

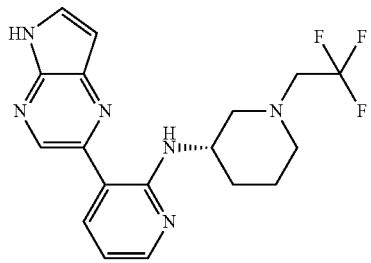 [SMILES: FC(F)(F)CN1CCC[C@H](Nc2ncccc2-c2cnc3[nH]ccc3n2)C1]

Deprotected Trifluoroethyl System:

A microwave reaction vessel was charged with [(S)-1-(2,2,2-trifluoro-ethyl)-piperidin-3-yl]-{3-[5-(2-trimethylsilanyl-ethoxymethyl)-5H-pyrrolo[2,3-b]pyrazin-2-yl]-pyridin-2-yl}-amine (0.135 g, 0.266 mmol), tetrabutylammonium fluoride (1.3 mL, 1M in THF, 1.3 mmol), and ethylenediamine (0.09 mL, 1.34 mmol) dissolved in THF (1 mL). The reaction was placed under Ar and the vessel sealed. The reaction was heated to 180° C. by microwave irradiation for 30 min. Water was added to the reaction mixture and extracted with ethyl acetate. The organic layers were combined, dried on $Na_2SO_4$, and concentrated. The residue was purified by column chromatography (silica, 0 to 5% MeOH (with 0.5% $NH_4OH$) in $CH_2Cl_2$) to give the product as a yellow solid (88.2 mg, 88%).

Example 44

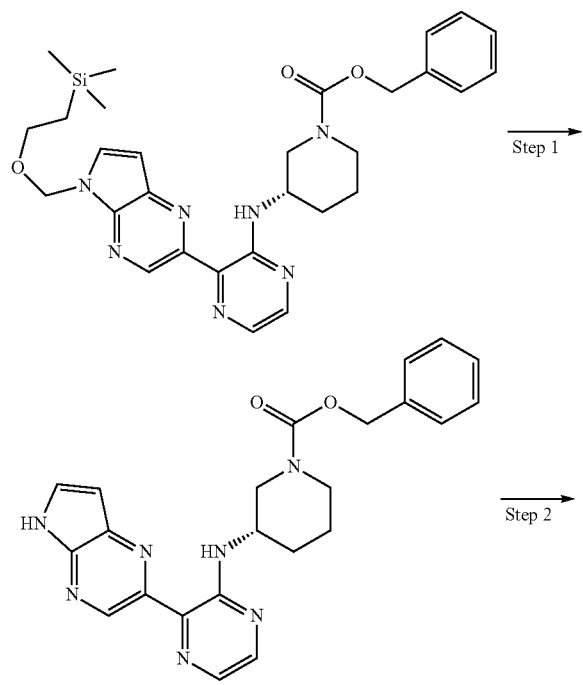

-continued

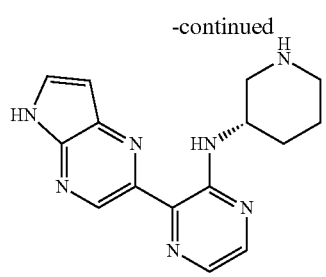

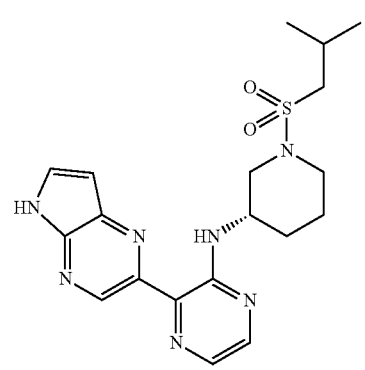 [SMILES: CCCS(=O)(=O)N1CCC[C@H](Nc2ncccc2-c2cnc3[nH]cnc3n2)C1]

Step 1

Tetrabutylammonium fluoride (1M solution in THF) (10.7 ml, 10.7 mmol) was added to (S)-benzyl 3-(3-(5-(2-(trimethylsilyl)ethoxy)methyl)-5H-pyrrolo[2,3-b]pyrazin-2-yl)pyrazin-2-ylamino)piperidine-1-carboxylate (1 g, 1.79 mmol). The reaction mixture was heated to 40° C. and stirred for 70 h. The reaction mixture was diluted with $H_2O$. The aqueous layer was back-extracted with EtOAc (2×50 mL). The organic phase was washed with water. The organic layers were dried over $MgSO_4$ and concentrated in vacuo. The crude material was purified by flash chromatography (silica gel, 80 g, 10% to 40% EtOAc in hexanes) to provide 700 mg of product (91%) as a light yellow oil. MS m/z (ES): 430 $(M+H)^+$.

Step 2

A solution of (S)-benzyl 3-(3-(5H-pyrrolo[2,3-b]pyrazin-2-yl)pyrazin-2-ylamino)piperidine-1-carboxylate (850 mg, 1.98 mmol) in MeOH (20 mL) was added to a 200 mL round-bottomed flask containing $Pd(OH)_2$ (500 mg, 1.98 mmol). The reaction flask was filled with hydrogen (balloon). The reaction mixture was stirred at rt for 3 h under hydrogen (1 atm). The reaction mixture was filtered through celite. The crude reaction mixture was concentrated in vacuo to provide 300 mg (51%) of the product as a yellow foam. MS m/z (ES): 296 $(M+H)^+$.

Step 3

2-methylpropane-1-sulfonyl chloride (119 mg, 99.4 μl, 762 μmol) was added to a solution of (S)—N-(piperidin-3-yl)-3-(5H-pyrrolo[2,3-b]pyrazin-2-yl)pyrazin-2-amine (150 mg, 508 μmol) and N-ethyl-N-isopropylpropan-2-amine (197 mg, 265 μl, 1.52 mmol) in DCM (20 ml) at 0° C. The reaction mixture was left to warm up to rt and stirred for 15 h. The reaction mixture was diluted with $H_2O$. The aqueous layer was back-extracted with EtOAc (2×25 mL). The combined organic extracts were dried over $MgSO_4$ and concentrated under reduced pressure. The crude mixture was purified by preparative TLC using 10% of MeOH in DCM to provide 11 mg (5%) of the product as a yellow semisolid. MS m/z (ES): 416 (M+H)+.

Example 45

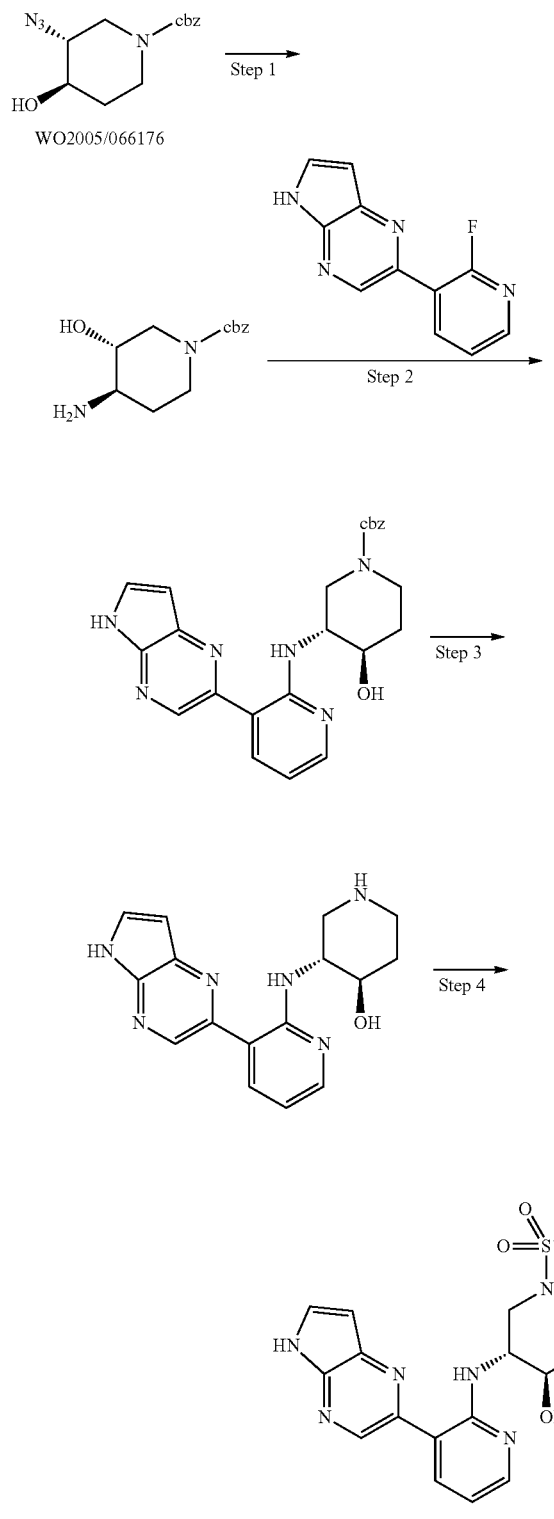

Step 1

In a 250 mL round-bottomed flask, (3R,4R)-benzyl 3-azido-4-hydroxypiperidine-1-carboxylate (900 mg, 3.26 mmol) and triphenylphosphine (1.71 g, 6.51 mmol) were combined with water (2.5 ml) and THF (25 mL) to give a light yellow solution. The reaction mixture was heated to 70° C. and stirred for 15 h. The reaction mixture was poured into 75 mL EtOAc and extracted with 1 M HCl (2×20 mL). The aqueous layer basified to pH 10 with aq NaOH and then was back-extracted with EtOAc (3×50 mL). The organic layers were dried over MgSO4 and concentrated in vacuo to provide 500 mg (61%) of the desired amino alcohol as a white solid. MS m/z (ES): 251 (M+H)+.

Step 2

To a 5 mL microwave vial was added 2-(2-fluoropyridin-3-yl)-5H-pyrrolo[2,3-b]pyrazine (342 mg, 1.6 mmol), 2-(2-fluoropyridin-3-yl)-5H-pyrrolo[2,3-b]pyrazine (342 mg, 1.6 mmol) in NMP. The vial was capped and heated in the microwave at 190° C. for 3 h. The reaction mixture was poured into 50 mL H2O and extracted with EtOAc (2×100 mL). The organic layers were dried over MgSO4 filtered, and concentrated in vacuo. The crude material was purified by flash chromatography (silica gel, 80 g, 0% to 10% MeOH in DCM) to afford 200 mg (22%) of the desired aminopyridine as an off white solid. MS m/z (ES): 445 (M+H)+.

Step 3

In a 500 mL round-bottomed flask, palladium hydroxide (63.2 mg, 450 µmol) and (3R,4R)-benzyl 3-(3-(5H-pyrrolo[2,3-b]pyrazin-2-yl)pyridin-2-ylamino)-4-hydroxypiperidine-1-carboxylate (200 mg, 0.45 mmol) were combined with ethanol to give a black suspension. The reaction mixture was heated to 25° C. and stirred for 2 h under hydrogen balloon. The reaction mixture was filtered through celite. The crude reaction mixture was concentrated in vacuo to provide 120 mg (86%) of the desired piperidine as a yellow solid. The crude was used in the next step as is. MS m/z (ES): 311 (M+H)+.

Step 4

In a 25 mL round-bottomed flask, (3R,4R)-3-(3-(5H-pyrrolo[2,3-b]pyrazin-2-yl)pyridin-2-ylamino)piperidin-4-ol (60 mg, 193 µmol) was combined with pyridine to give a light yellow solution. Methanesulfonyl chloride (26.6 mg, 18.0 µl, 232 µmol) was added at 0° C. The reaction mixture was heated to 25° C. and stirred for 20 h. The reaction mixture was treated with a drop of ammonia and silica. The crude material was preabsorb in silica and loaded in a 25 g silica column. The crude material was purified by flash chromatography (silica gel, 0% to 10% MeOH in DCM) to afford 10 mg (13%) of the product as a yellow solid. MS m/z (ES): 389 (M+H)+.

Example 46

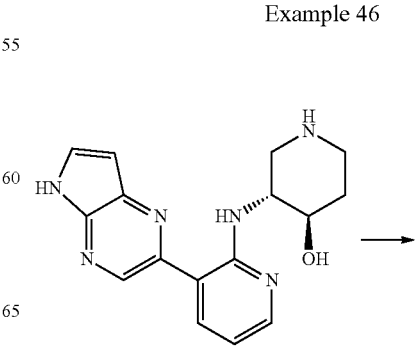

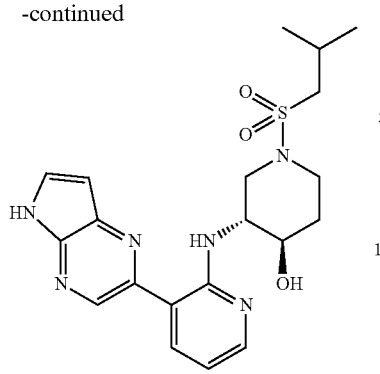

In a 25 mL round-bottomed flask, (3R,4R)-3-(3-(5H-pyrrolo[2,3-b]pyrazin-2-yl)pyridin-2-ylamino)piperidin-4-ol (60 mg, 193 μmol) was combined with pyridine (5 ml) to give a light yellow solution. 2-Methylpropane-1-sulfonyl chloride (36.3 mg, 30.3 μl, 232 μmol) was added at 0° C. The reaction mixture was heated to 25° C. and stirred for 20 h. The reaction mixture was treated with a drop of ammonia and silica. The crude material was preabsorb in silica and loaded in a 25 g silica column. The crude material was purified by flash chromatography (silica gel, 0% to 10% MeOH in DCM) to afford 30 mg (36%) of the product as a yellow solid. MS m/z (ES): 431 (M+H)⁺.

Example 47

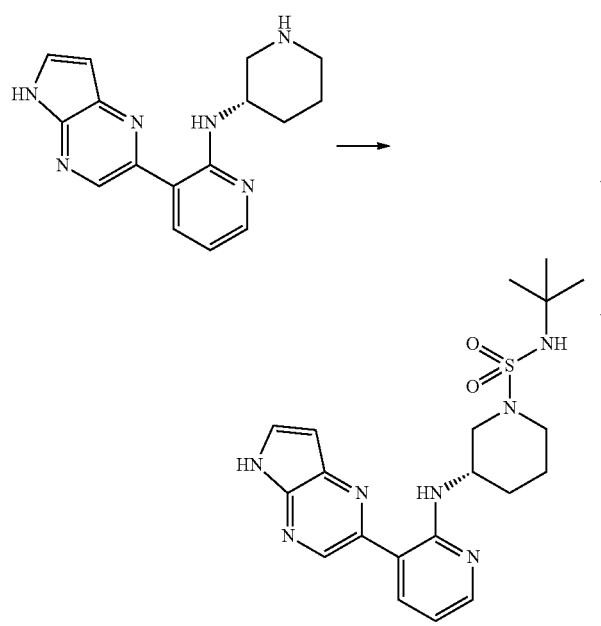

In a 10 mL round-bottomed flask, diisopropylethyl amine (94.8 mg, 128 μl, 734 μmol) and (S)—N-(piperidin-3-yl)-3-(5H-pyrrolo[3,2-b]pyrazin-2-yl)pyridin-2-amine (108 mg, 367 mmol) were combined with THF (5 ml) to give a light yellow solution. tert-Butylsulfamoyl chloride (75.6 mg, 440 μmol) was added. The reaction mixture was heated to 25° C. and stirred for 4 h. The reaction mixture was treated with a drop of ammonia and silica. The crude material was preabsorb in silica and loaded in a 25 g silica column. The crude material was purified by flash chromatography (silica gel, 0% to 10% MeOH in DCM) to afford 30 mg (19%) of the product as a yellow solid. MS m/z (ES): 430 (M+H)⁺.

Example 48

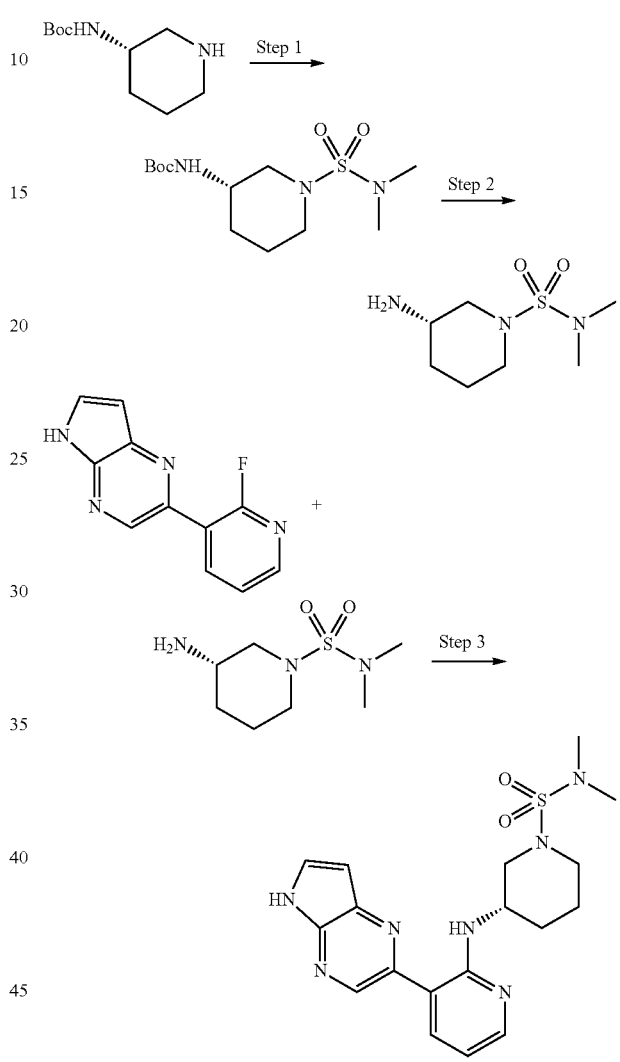

Step 1 and 2

In a 100 mL round-bottomed flask, (S)-tert-butyl piperidin-3-ylcarbamate (400 mg, 2.00 mmol) and N-ethyl-N-isopropylpropan-2-amine (516 mg, 696 μl, 3.99 mmol) were combined with DCM to give a colorless solution. Dimethylsulfamoyl chloride (344 mg, 257 μl, 2.4 mmol) was added at 0° C. The reaction mixture was heated to 25° C. and stirred for 16 h. The reaction mixture was poured into 100 mL H₂O and extracted with EtOAc (2×100 mL). The organic layers were dried over MgSO₄ and concentrated in vacuo. The crude was used as is. To a 20 mL microwave vial was added (S)-tert-butyl 1-(N,N-dimethylsulfamoyl)piperidin-3-ylcarbamate crude from the previous reaction and trifluoroisopropanol (10 ml). The vial was capped and heated in the microwave at 150° C. for 2 h. The crude reaction mixture was concentrated in vacuo. The reaction mixture was poured into 50 mL of EtOAc and extracted with 1 M HCl (2×25 mL). The aqueous layer was basified and back-extracted with EtOAc (2×50 mL). The organic layers were dried over MgSO$_4$ and concentrated in vacuo to afford 65 mg (18%) of the product as a yellow oil. MS m/z (ES): 208 (M+H)$^+$.

Step 3

To a 2 mL microwave vial was added 2-(2-fluoropyridin-3-yl)-5H-pyrrolo[2,3-b]pyrazine (100 mg, 467 µmol), (S)-3-amino-N,N-dimethylpiperidine-1-sulfonamide (65 mg, 314 mmol) in NMP. The vial was capped and heated in the microwave at 190° C. for 3 h. The reaction mixture was poured into 20 mL H$_2$O and extracted with EtOAc (2×50 mL). The organic layers were dried over MgSO$_4$ and concentrated in vacuo. The crude material was purified by flash chromatography (silica gel, 80 g, 0% to 10% MeOH in DCM) to afford 35 mg (28%) of the product as a yellow solid. MS m/z (ES): 402 (M+H)$^+$.

Example 49

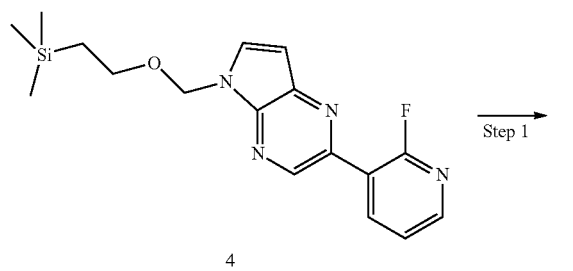

4

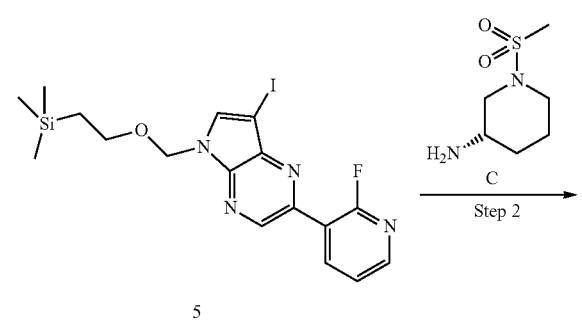

5

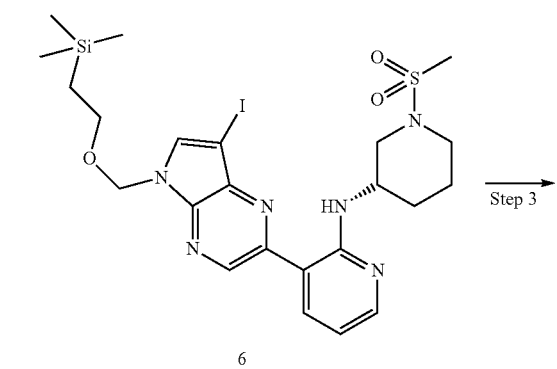

6

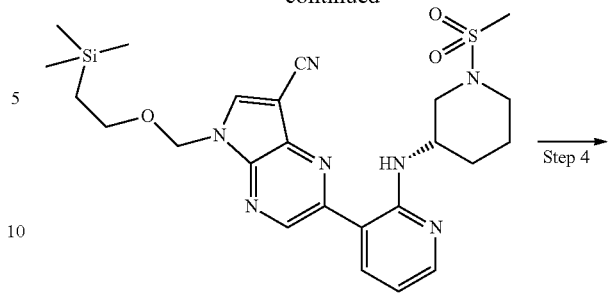

7

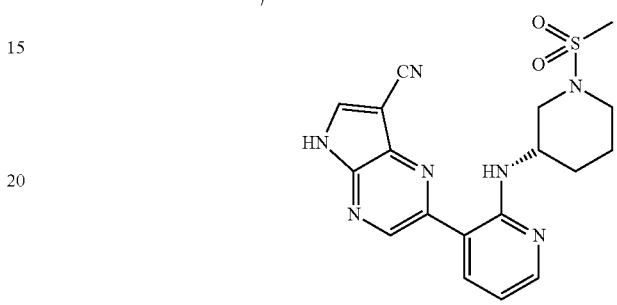

Step 1

To a stirred solution of 4 (1.5 g, 4.36 mmol) in acetone (20 mL), N-Iodo succinimide (1.47 g, 6.54 mmol) was added. The reaction mixture was stirred at 25° C. for 16 h. Acetone was evaporated under reduced pressure and the crude mass was purified by column chromatography (silica gel, 100-200 mesh) eluting with 10% ethyl acetate in hexane to get pure 5 (1.4 g, 68%). MS m/z (ES): 471 (M+H)$^+$.

Step 2

To a stirred solution of 5 (200 mg, 0.425 mmol) in DIPEA (2 mL) and NMP (0.7 mL) in a sealed tube, compound C (473 mg, 1.702 mmol) was added and heated at 140° C. for 16 h. The reaction mixture was diluted with ethyl acetate and washed with water. The organic layer was dried over anhydrous sodium sulfate and evaporated under reduced pressure. The crude material was purified by column chromatography (silica gel, 100-200 mesh) eluting with 20% ethyl acetate in hexane to afford pure 6 (140 mg, 52%). MS m/z (ES): 629 (M+H)$^+$.

Step 3

To a stirred solution of 6 (200 mg, 0.31 mmol) in 1% water in DMF (10 mL), zinc cyanide (36.4 mg, 0.31 mmol) was added. Reaction mixture was degassed followed by back-filled with argon for 15 min and then purged with argon for 30 min. DPPF (1.6 mg, 0.003 mmol) and Pd$_2$(dba)$_3$ (13.7 mg, 0.015 mmol) were added to the reaction mixture and heated at 120° C. for 1.5 h. DMF was evaporated under reduced pressure and crude mass was purified by column chromatography using (silica gel, 100-200 mesh) and eluting with 30% ethyl acetate in hexane to provide 7 (100 mg, 61%). MS m/z (ES): 528 (M+H)$^+$.

Step 4

A stirred solution of 7 (90 mg, 0.17 mmol) in 1M HCl in acetic acid (2.5 mL) was heated at 45° C. for 3 h. Acetic acid was evaporated under reduced pressure and crude was dissolved in mixed solvent of methanol:water:TEA (8:1:1) (3 mL). Ethylene diamine (0.058 mL, 0.854 mmol) was added to the reaction mixture and was stirred at 25° C. for 16 h. After complete consumption of starting material (monitored by TLC and LCMS), the solvent was evaporated under reduced pressure and the crude was purified by column chromatography using (silica gel, 100-200 mesh) and eluting with 2% methanol in methylene dichloride to afford C014-01 (30.9 mg, 45%). MS m/z (ES): 398 (M+H)⁺.

Example 50

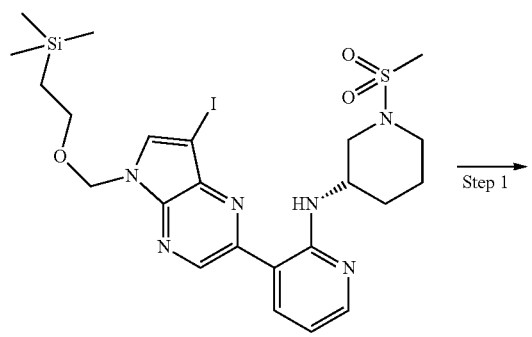

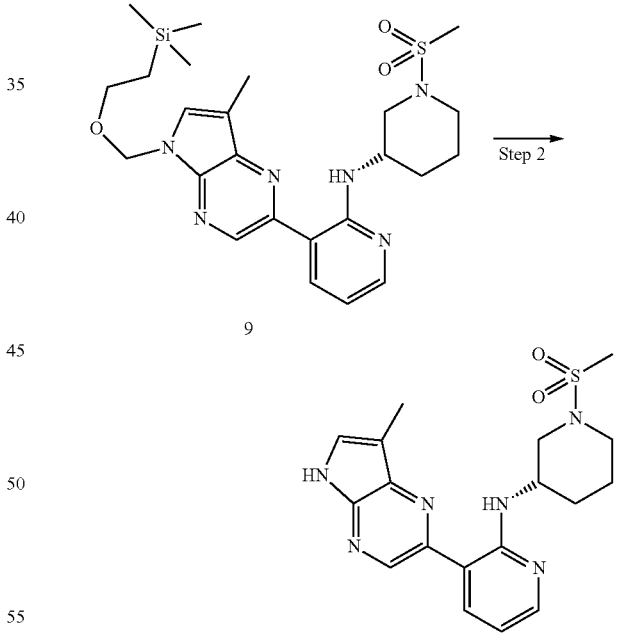

Step 1

To a stirred solution of 6 (200 mg, 0.318 mmol) in a mixture of toluene:water: (25:1) (8 mL), cyclopropyl boronic acid (86 mg, 0.6369 mmol), K₃PO₄ (130 mg, 0.955 mmol), and tricyclohexyl phosphine (17.86 mg, 0.0637 mmol) were added. The reaction mixture was degassed followed by back-filled with argon for 15 min and then purged with argon for 30 min. Pd(OAc)₂ (14.3 mg, 0.0637 mmol) was added into the reaction mixture and heated at 90° C. for 4 h under argon atmosphere. After complete consumption of starting material (monitored by TLC and LCMS) reaction mixture was filtered through a sintered funnel using celite bed and washed with ethyl acetate. The organic layer was extracted with ethyl acetate, washed with water, dried over Na₂SO₄ and evaporated under reduced pressure. The crude material was purified by column chromatography (silica gel, 100-200 mesh) eluting with 20% ethyl acetate in hexane to provide pure 8 (80 mg, 46%). MS m/z (ES): 543 (M+H)⁺.

Step 2

A stirred solution of 8 (120.6 mg, 0.22 mmol) in 1M HCl in acetic acid (3.5 mL) was heated at 45° C. for 3 h. Acetic acid was evaporated under reduced pressure and the crude was dissolved in mixed solvent of methanol:water:TEA (8:1:1) (4 mL). Ethylene diamine (0.065 mL, 1.107 mmol) was added to the reaction mixture which was stirred at 25° C. for 16 h. After complete consumption of starting material (monitored by TLC and LCMS) solvent was evaporated under reduced pressure and crude was purified by column chromatography using (silica gel, 100-200 mesh) and eluting with 2% methanol in methylene dichloride to provide the product (25.5 mg, 28%). MS m/z (ES): 413 (M+H)⁺.

Example 51

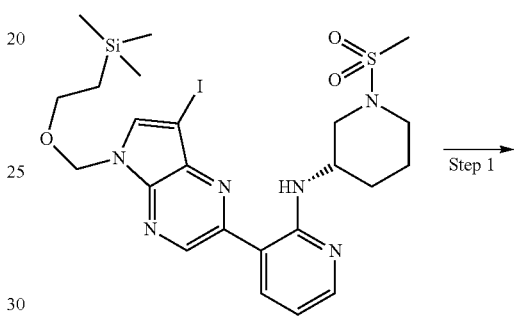

Step 1

To a stirred solution of 6 (200 mg, 0.318 mmol) in 1,4-dioxane (8 mL) in a sealed tube, methyl boronic acid (28.66 mg, 0.477 mmol), Cs₂CO₃ (310 mg, 0.956 mmol), and DPPF (35.28 mg, 0.064 mmol) were added. The reaction mixture was purged with argon for 30 min. Pd₂(dba)₃ (43.7 mg, 0.048 mmol) was added into the reaction mixture and heated at 120° C. for 5 h under argon atmosphere. After complete consumption of starting material (monitored by TLC and LCMS), the reaction mixture was filtered through celite and washed with ethyl acetate. The organic layer was extracted with ethyl acetate, washed with water, dried over anhy Na$_2$SO$_4$ and evaporated under reduced pressure. The crude material was purified by column chromatography (silica gel, 100-200 mesh) eluting with 15% ethyl acetate in hexane to get pure 9 (105 mg, 64%). MS m/z (ES): 629 (M+H)$^+$.

Step 2

A stirred solution of 9 (100 mg, 0.194 mmol) in 1M HCl in acetic acid (4 mL) was heated at 45° C. for 3 h. Acetic acid was evaporated under reduced pressure and crude was dissolved in mixed solvent of methanol:water:TEA (8:1:1) (3 mL). Ethylene diamine (0.062 mL, 0.97 mmol) was added to the reaction mixture which was stirred at 25° C. for 16 h. After complete consumption of starting material (monitored by TLC and LCMS), the solvent was evaporated under reduced pressure and the crude was purified by column chromatography using (silica gel, 100-200 mesh) and eluting with 2% methanol in methylene dichloride to get C014-03 (24.8 mg, 33%). MS m/z (ES): 387 (M+H)$^+$.

Example 52

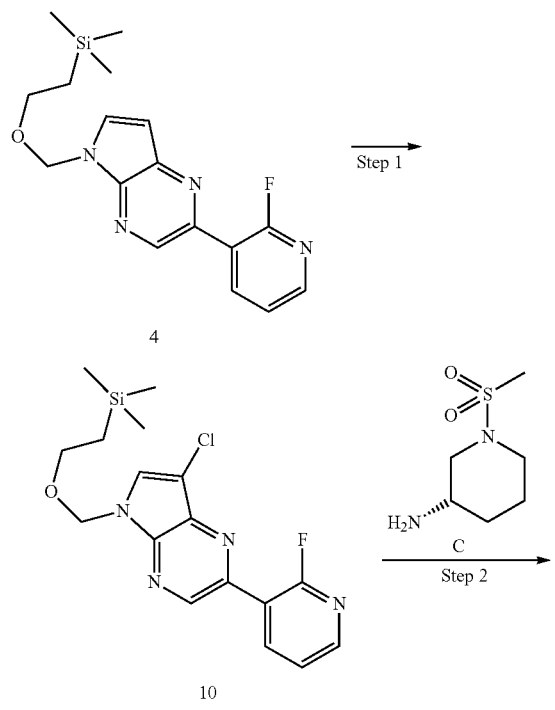

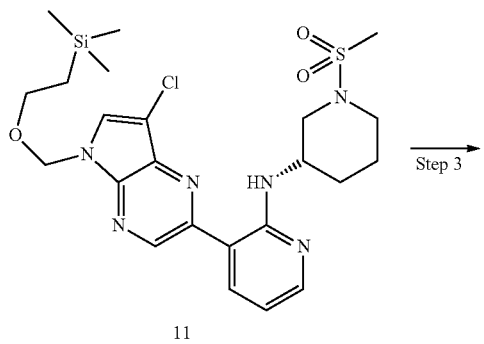

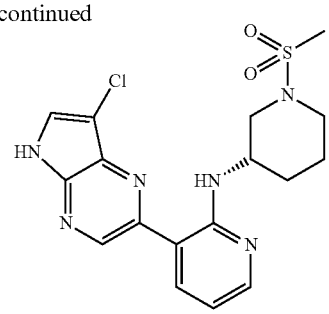

Step 1

To a stirred solution of 4 (500 mg, 0.726 mmol) in dry acetone (8 mL), N-chlorosuccinimide (145.5 mg, 1.09 mmol) was added. The reaction mixture was refluxed for 6 h. Acetone was evaporated under reduced pressure and crude mass was purified by column chromatography (silica gel, 100-200 mesh) eluting with 10% ethyl acetate in hexane to afford pure 10 (400 mg, 72%). MS m/z (ES): 379 (M+H)$^+$.

Step 2

To a stirred solution of 10 (300 mg, 0.396 mmol) in DIPEA (2.5 mL) and NMP (0.7 mL) in a sealed tube, compound C (440 mg, 1.58 mmol) was added and heated at 140° C. for 16 h. The reaction mixture was diluted with ethyl acetate and washed with water. The organic layer was dried over anhydrous sodium sulfate and evaporated under reduced pressure. The crude material was purified by column chromatography (silica gel, 100-200 mesh) eluting with 20% ethyl acetate in hexane to get pure 11 (170 mg, 40%). MS m/z (ES): 538 (M+H)$^+$.

Step 3

A stirred solution of 11 (160 mg, 0.298 mmol) in 1M HCl in acetic acid (5 mL) was heated at 45° C. for 3 h. Acetic acid was evaporated under reduced pressure and the crude was dissolved in mixed solvent of methanol:water:TEA (8:1:1) (5 mL). Ethylene diamine (0.1 mL, 1.49 mmol) was added to the reaction mixture which was stirred at 25° C. for 16 h. After complete consumption of starting material (monitored by TLC and LCMS), the solvent was evaporated under reduced pressure and the crude was purified by column chromatography using (silica gel, 100-200 mesh) and eluting with 2% methanol in methylene dichloride to afford the product (59.2 mg, 49%). MS m/z (ES): 407 (M+H)$^+$.

Example 53

155

-continued

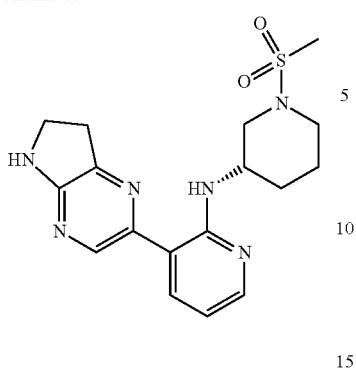

Raney-Ni (350 mg) was added to a stirred solution of 13 (90 mg, 0.242 mmol) in absolute ethanol (15 mL). The reaction mixture was subjected to hydrogenation in Parr-autoclave at 95° C. under 75 Psi pressure for 20 h. After complete consumption of starting material (monitored by TLC and LCMS), the reaction mixture was filtered through sintered funnel using celite bed and bed was washed with ethanol. The filtrate was evaporated under reduced pressure and the crude was purified by preparative-TLC to get the product (19.3 mg, 21%). MS m/z (ES): 375 (M+H)$^+$.

Example 54

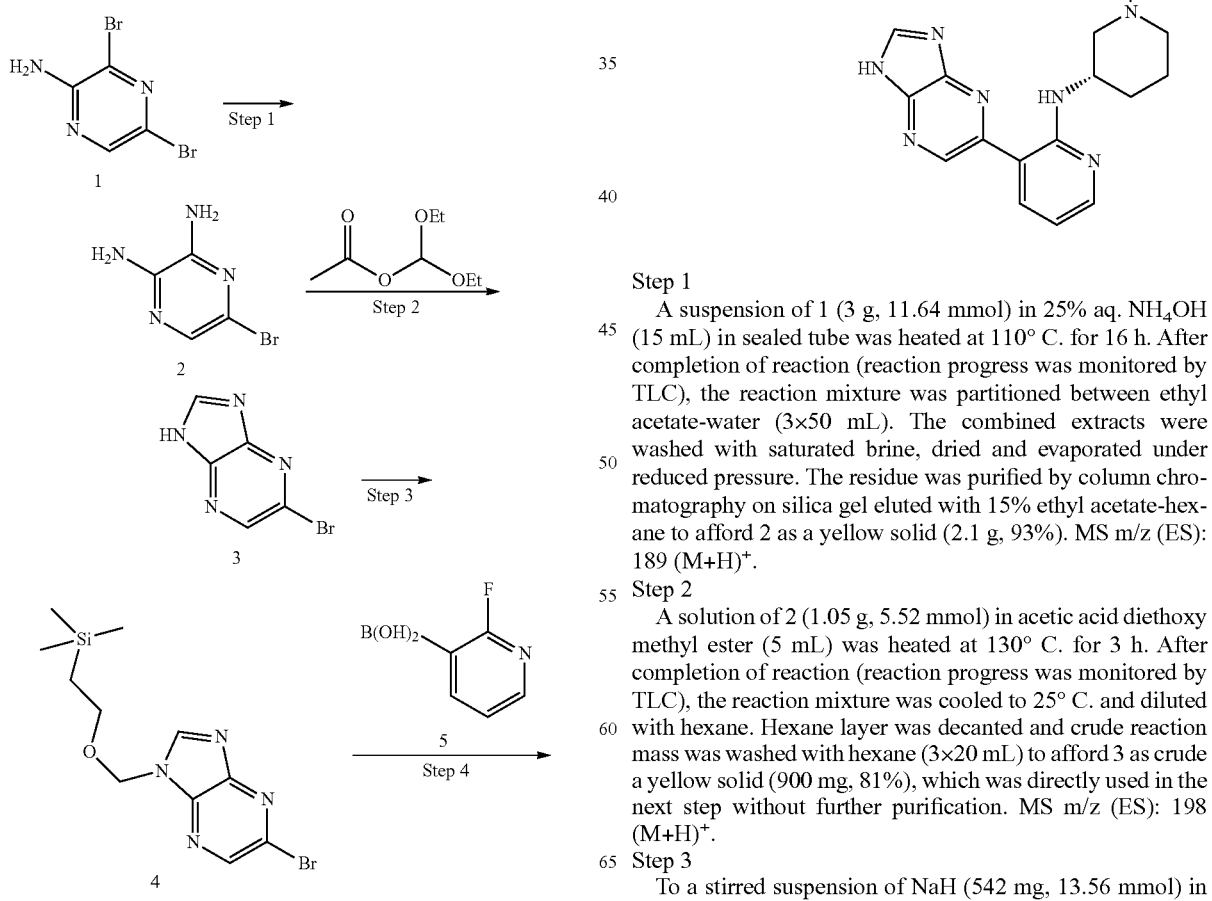

156

-continued

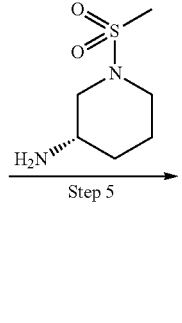

Step 1

A suspension of 1 (3 g, 11.64 mmol) in 25% aq. NH$_4$OH (15 mL) in sealed tube was heated at 110° C. for 16 h. After completion of reaction (reaction progress was monitored by TLC), the reaction mixture was partitioned between ethyl acetate-water (3×50 mL). The combined extracts were washed with saturated brine, dried and evaporated under reduced pressure. The residue was purified by column chromatography on silica gel eluted with 15% ethyl acetate-hexane to afford 2 as a yellow solid (2.1 g, 93%). MS m/z (ES): 189 (M+H)$^+$.

Step 2

A solution of 2 (1.05 g, 5.52 mmol) in acetic acid diethoxy methyl ester (5 mL) was heated at 130° C. for 3 h. After completion of reaction (reaction progress was monitored by TLC), the reaction mixture was cooled to 25° C. and diluted with hexane. Hexane layer was decanted and crude reaction mass was washed with hexane (3×20 mL) to afford 3 as crude a yellow solid (900 mg, 81%), which was directly used in the next step without further purification. MS m/z (ES): 198 (M+H)$^+$.

Step 3

To a stirred suspension of NaH (542 mg, 13.56 mmol) in anhydrous DMF (15 ml), a solution of 3 (1.8 g, 9.04 mmole)

in anhydrous DMF (10 mL) was added at −5 to 0° C. and the reaction mixture was allowed to stir at 25° C. for 30 min. The reaction mixture was cooled to −5 to 0° C. and SEM-Cl (1.92 mL, 10.85 mmol) was slowly added. The reaction was stirred at 25° C. for 2 h. After completion of reaction (reaction progress monitored by TLC), DMF was distilled off and the crude product was purified by column chromatography on silica gel eluting with 7% ethyl acetate-hexane to afford pure 4 (1.8 g, 60%). MS m/z (ES): 329 (M+H)$^+$.

Step 4

A suspension of 7 (1.7 g, 5.16 mmol), 2-fluoropyridine-3-boronic acid 5 (873 mg, 6.2 mmol), sodium carbonate (1.64 g, 15.5 mmol) in toluene (12 mL), water (6 mL), and ethanol (3 mL) was degassed thoroughly, followed by back filling with argon, purged with argon for 20 min. Pd(PPh$_3$)$_4$ (1.79 g, 1.55 mmol, 0.3 eqv) was added to the reaction mixture and purged again with argon. The reaction was stirred at 90° C. for 4 h. After completion of reaction (reaction progress monitored by TLC), the reaction mixture was cooled to RT diluted with water and extracted with ethyl acetate. The combined organic extracts were dried and concentrated under reduced pressure. The crude product was purified by column chromatography on silica gel eluting with 18% ethyl acetate in hexane to afford pure 6 (1.2 g, 67%). MS m/z (ES): 346 (M+H)$^+$.

Step 5

Compound 6 (200 mg, 0.579 mmol) and compound 10-02 (704.92 mg, 2.32 mmol) were taken in a sealed tube and DIPEA (1.5 mL), NMP (0.15 mL) were added. The reaction mixture was heated in a sealed tube at 140° C. for 16 hours. After completion of reaction (reaction progress monitored by TLC), the reaction mixture was diluted with water and extracted with ethyl acetate, dried and concentrated under reduced pressure. The crude product was purified by column chromatography on silica gel with 40% ethyl acetate in hexane to afford pure 11-02A (85 mg, 69%) and recovered 120 mg of compound 6. MS m/z (ES): 532 (M+H)$^+$.

Step 6

A solution of 11-02A (80 mg, 0.15 mmol) in 1M HCl in acetic acid (10.0 eqv) was heated at 60° C. for 2 hours. After completion of reaction (reaction progress was monitored by TLC), the reaction mixture was neutralized with 1 M sodium hydroxide solution and extracted with ethyl acetate (3×15 mL). The organic phase was dried and evaporated. The resulting crude was dissolved in methanol:water:TEA (8:1:1) (3 mL). Ethylene diamine (5 eqv) was added and the reaction stirred at 25° C. for 16 hours. After completion of reaction (reaction progress was monitored by LCMS), the solvent was evaporated under reduced pressure. The crude product was purified by biotage column chromatography on silica gel with 50% ethyl acetate in hexane to afford the product. (18.7 mg, 31%). MS m/z (ES): 402 (M+H)$^+$.

Example 55

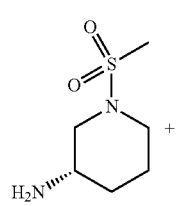

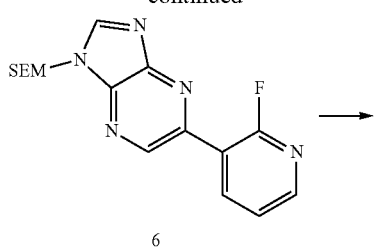

6

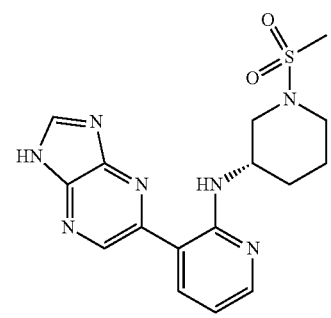

Compound 6 (200 mg, 0.579 mmol) and the amine (524 mg, 2.32 mmol) were taken in sealed tube. DIPEA (2.0 mL) and NMP (0.5 mL) were added. The reaction mixture was heated in a sealed tube at 160° C. for 16 hours. After completion of reaction (reaction progress monitored by TLC), the reaction mixture was diluted with water and extracted with ethyl acetate, organic layer was dried and solvent was concentrated under reduced pressure. The crude product was purified by biotage column chromatography on silica gel with 50% ethyl acetate in hexane to afford the product. (45 mg, 21%). MS m/z (ES): 374 (M+H)$^+$.

Example 56

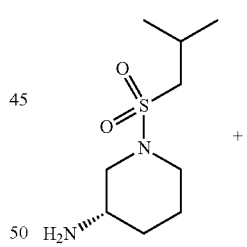

+

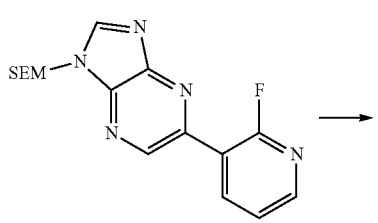

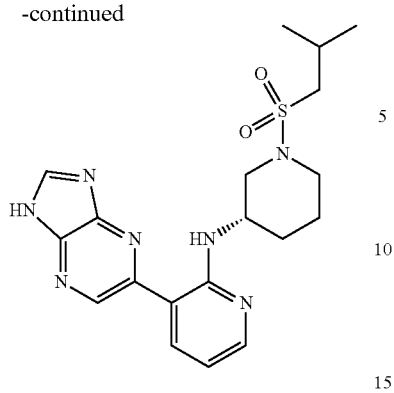

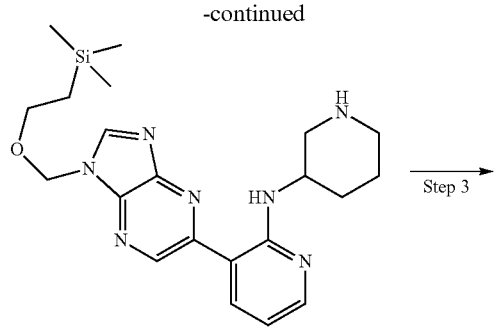

14

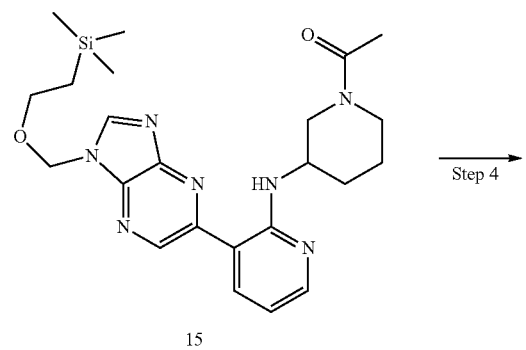

15

Compound 6 (150 mg, 3.0 mmol) and the amine (556.5 mg, 1.74 mmol) were taken in sealed tube and DIPEA (2.5 mL), NMP (0.15 mL) were added, and reaction mixture heated in a sealed tube at 140° C. for 16 h. After completion of reaction (reaction progress monitored by TLC), the reaction mixture was diluted with water and extracted with ethyl acetate, dried over Na$_2$SO$_4$ and concentrated under reduced pressure. The crude product was purified by column chromatography on silica gel with 40% ethyl acetate in hexane to afford the product (7.8 mg, 19%). MS m/z (ES): 416 (M+H)$^+$.

Example 57

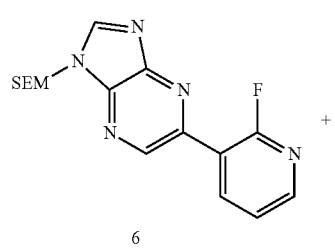

6

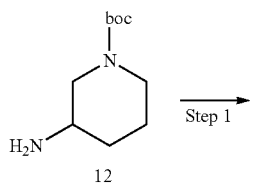

12

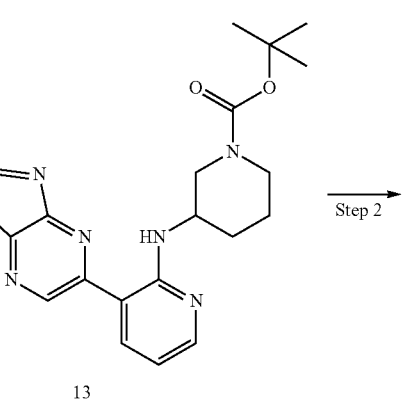

13

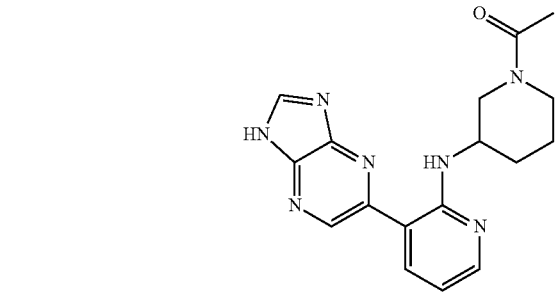

Step 1

Compound 6 (500 mg, 1.45 mmol) and compound 12 (1.16 g, 5.80 mmol, 4.0 eqv) were loaded in a sealed tube. TEA (0.75 mL, 5.80 mmol) and 1,4-dioxane (5 mL) were added. The reaction mixture was heated in a sealed tube at 150° C. for 48 h. After completion of reaction (reaction progress monitored by TLC), the reaction mixture was diluted with water and extracted with ethyl acetate, dried and concentrated under reduced pressure. The crude product was purified by column chromatography on silica gel with 20% ethyl acetate in hexane to afford pure 13 (380 mg, 83%) and recovered 200 mg of compound 6. MS m/z (ES): 526 (M+H)$^+$.

Step 2

To a solution of compound 13 (200 mg, 0.47 mmol) in DCM, TFA (20 eqv) was added at 0° C. reaction mixture was stirred at 25° C. for 16 h. After complete consumption of SM (reaction monitored by LCMS), the solvent was concentrated under reduced pressure. The crude product was carried to next step with out further purification. MS m/z (ES): 426 (M+H)$^+$.

Step 3

To a solution of compound 14 (crude of previous step) in DCM (6 mL), pyridine (148.52 mg, 1.88 mmol, 4.0 eqv), was added and then allowed to stir at 25° C. for 15 min. The reaction mixture was cooled to 0° C. Acetic anhydride (62.4 mg, 0.612 mmol) was added. The reaction mixture stirred at 25° C. for 16 hours. After completion of reaction (reaction progress monitored by TLC), the reaction mixture was diluted with DCM and washed with water. The combined organic layers were dried and concentrated under reduced pressure. The crude product was purified by column chromatography on silica gel with 20% ethyl acetate in hexane to afford pure 15 (70 mg, 31%). MS m/z (ES): 468 (M+H)⁺.

Step 4

A solution of compound 15 in 1M HCl in acetic acid (10.0 eqv) was heated at 60° C. for 2 h. After completion of reaction (reaction progress was monitored by TLC), the reaction was neutralized with 1 M sodium hydroxide solution and extracted with ethyl acetate (2×25 mL). The organic phase was dried and evaporated. The resulting crude was dissolved in methanol:water:TEA (8:1:1). Ethylene diamine (5 eqv) was added and the reaction stirred at 25° C. for 16 h. After completion of reaction (reaction progress was monitored by LCMS), the solvent was evaporated under reduced pressure. The crude product was purified by column chromatography on silica gel with 20% ethyl acetate in hexane to afford the product (12.6 mg). MS m/z (ES): 438 (M+H)⁺.

Example 58

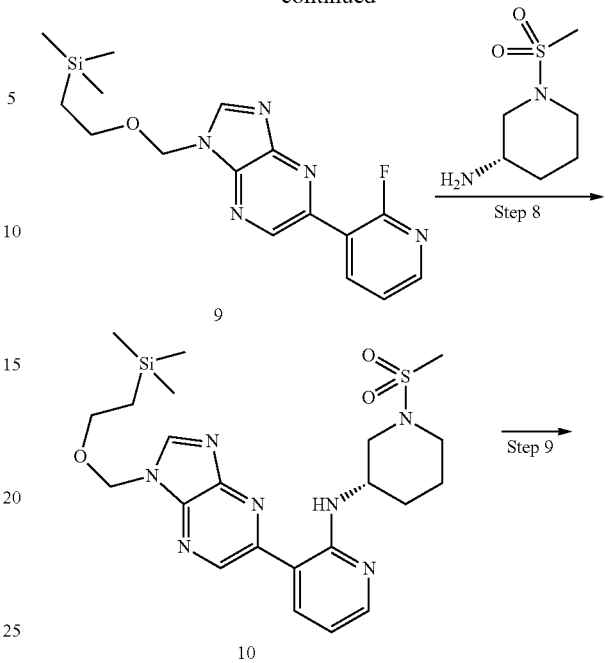

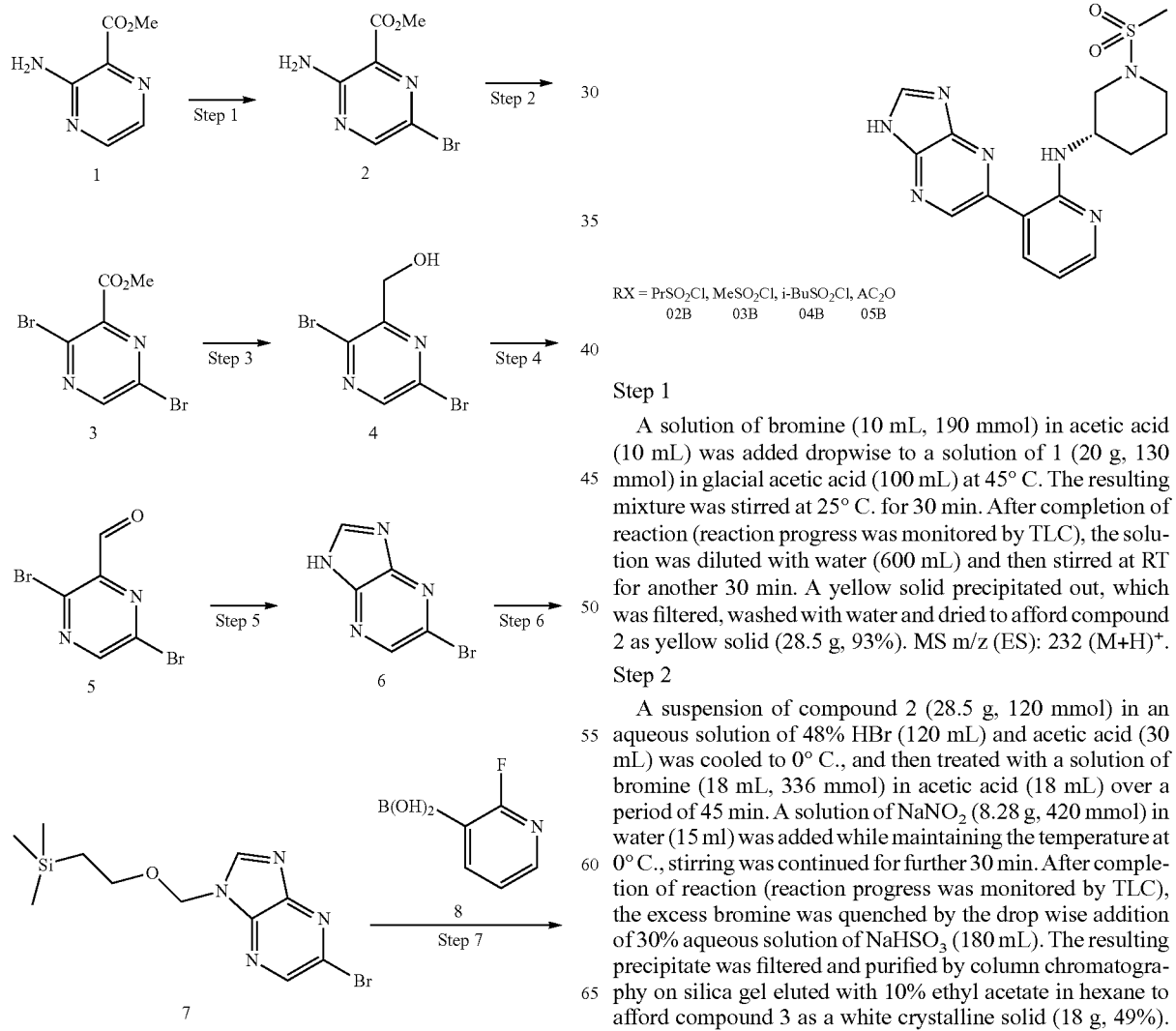

Step 1

A solution of bromine (10 mL, 190 mmol) in acetic acid (10 mL) was added dropwise to a solution of 1 (20 g, 130 mmol) in glacial acetic acid (100 mL) at 45° C. The resulting mixture was stirred at 25° C. for 30 min. After completion of reaction (reaction progress was monitored by TLC), the solution was diluted with water (600 mL) and then stirred at RT for another 30 min. A yellow solid precipitated out, which was filtered, washed with water and dried to afford compound 2 as yellow solid (28.5 g, 93%). MS m/z (ES): 232 (M+H)⁺.

Step 2

A suspension of compound 2 (28.5 g, 120 mmol) in an aqueous solution of 48% HBr (120 mL) and acetic acid (30 mL) was cooled to 0° C., and then treated with a solution of bromine (18 mL, 336 mmol) in acetic acid (18 mL) over a period of 45 min. A solution of NaNO₂ (8.28 g, 420 mmol) in water (15 ml) was added while maintaining the temperature at 0° C., stirring was continued for further 30 min. After completion of reaction (reaction progress was monitored by TLC), the excess bromine was quenched by the drop wise addition of 30% aqueous solution of NaHSO₃ (180 mL). The resulting precipitate was filtered and purified by column chromatography on silica gel eluted with 10% ethyl acetate in hexane to afford compound 3 as a white crystalline solid (18 g, 49%). MS m/z (ES): 294 (M+H)⁺.

Step 3

DIBAL-H (12.65 mL, 12.65 mmol) was added dropwise to a stirred solution of 3 (1.5 g, 5.06 mmol) in dichloromethane (60 mL) at −78° C. The reaction mixture was stirred at the same temperature for 20 min. After completion of reaction (reaction progress was monitored by TLC), the reaction mixture was quenched with glacial acetic acid (1.5 mL) at −78° C. The resulting mixture was warmed to room temperature and the volatiles were removed by evaporation. The residue was dissolved in 3N HCl (10 mL) and extracted with dichloromethane (3×50 mL). The combined extracts were washed with brine and dried over $Na_2SO_4$. The solvent was removed under reduced pressure and purified by column chromatography on silica gel eluting with 15% ethyl acetate-hexane to afford 4 as a white solid (700 mg, 51%). MS m/z (ES): 266 $(M+H)^+$.

Step 4

To a stirred solution of 4 (1.0 g, 3.73 mmol) in dichloromethane (40 mL) was added activated MnO2 (1.94 g, 22.38 mmol). The reaction mixture was stirred at 25° C. for 24 h. After completion of reaction (reaction progress was monitored by GCMS), the reaction mixture was filtered through celite bed and washed with hot dichloromethane. Dichloromethane was evaporated to afford 5 as white solid (900 mg). This crude compound 5 was carried to next step without further purification. MS m/z (ES): 264 $(M+H)^+$.

Step 5

To a stirred solution of 5 (1.7 g, 3.75 mmol) in THF (40 mL) was added hydrazine (1M solution in THF) (37.5 mL, 37.5 mmol) and reaction heated to 60° C. for 6 h. After completion of reaction (reaction progress was monitored by GCMS), THF was evaporated and the crude was diluted with water, stirred 30 min at 25° C. and filtered to afford 6 as yellow solid (1.0 g). This crude 5 was carried to next step without further purification. MS m/z (ES): 198 $(M+H)^+$.

Step 6

To a stirred suspension of NaH (110.5 mg, 2.76 mmol) in anhydrous DMF (10 ml), a solution of 6 (500 mg, 2.51 mmol) in anhydrous DMF (5 mL) was added at −5 to 0° C. The reaction mixture was allowed to stir at 25° C. for 1 hour. The reaction mixture was cooled to −5 to 0° C. and SEM-Cl (0.48 mL, 2.76 mmol) was slowly added. The reaction mixture was stirred at 0° C. for 30 min. After completion of reaction (reaction progress monitored by TLC), the reaction mixture was poured into cold water and extracted with ethyl acetate. The organic phase was washed with saturated brine solution, dried over $Na_2SO_4$, concentrated and purified by column chromatography on silica gel with 7% ethyl acetate-hexane to afford pure 7 (300 mg, 36%). MS m/z (ES): 329 $(M+H)^+$.

Step 7

Compound 7 (600 mg, 1.81 mmol), 2-fluoropyridine-3-boronic acid 8 (307 mg, 2.18 mmol), and sodium carbonate (575 mg, 5.43 mmol) were suspended in a mixture of 24 mL of toluene, 12 mL of water, and 6 mL of ethanol. The resulting mixture was degassed thoroughly, followed by back filling with argon, then purged with argon for 20 min. $Pd(PPh_3)_4$ (627 mg, 0.54 mmol) was added to the reaction mixture and purged again with argon. The reaction was heated at 90° C. for 3 hours. After completion of reaction (reaction progress monitored by TLC), the reaction mixture was cooled to RT diluted with water and extracted with ethyl acetate. The combined organic layers were dried over $Na_2SO_4$, concentrated and purified by column chromatography on silica gel with 18% ethyl acetate in hexane to get pure compound 9 (450 mg, 71%). MS m/z (ES): 346 $(M+H)^+$.

Step 8

Compound 9 (170 mg, 0.49 mmol) and compound 13-03 (545 mg, 1.96 mmol) were taken in sealed tube and DIPEA (1.5 mL) and NMP (0.15 mL) were added. The reaction mixture was heated in a sealed tube at 140° C. for 16 h. After completion of reaction (reaction progress monitored by TLC), the reaction mixture was diluted with water and extracted with ethyl acetate, dried over $Na_2SO_4$, concentrated and purified by column chromatography on silica gel with 40% ethyl acetate in hexane to afford pure 10. (200 mg, 80%). MS m/z (ES): 504 $(M+H)^+$.

Step 9

A solution of 10 in 1M HCl in acetic acid (10.0 eqv) was heated at 60° C. for 2 hours. After completion of reaction (reaction progress was monitored by TLC), the reaction mixture was neutralized with 1 M sodium hydroxide solution and extracted with ethyl acetate (2×25 mL). The organic phase was dried over and evaporated. The resulting crude mixture was dissolved in methanol:water:triethylamine (8:1:1), then ethylene diamine (5 eqv) was added and stirred at 25° C. for 16 h. After completion of reaction (reaction progress was monitored by LCMS), the solvent was evaporated under reduced pressure. The resulting crude was purified by washing with methanol. (31%). MS m/z (ES): 374 $(M+H)^+$.

Example 59

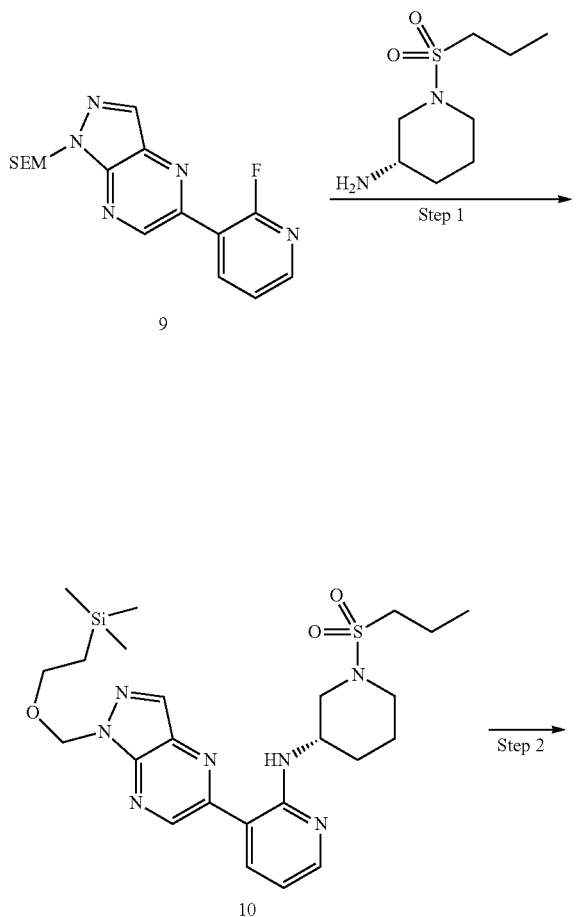

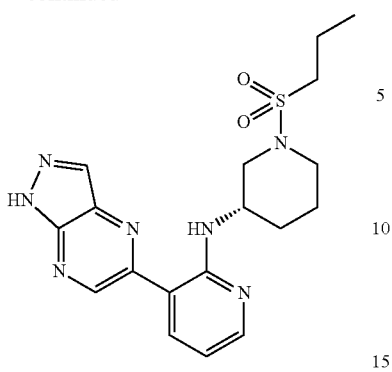

RX = PrSO₂Cl, MeSO₂Cl, i-BuSO₂Cl, AC₂O
  02B      03B       04B       05B

Step 1

Compound 9 (120 mg, 0.34 mmol) and the amine (1.39 mmol) were taken in sealed tube. DIPEA (1.5 mL) and NMP (0.15 mL) were added. The reaction mixture was heated in a sealed tube at 140° C. for 16 h. After completion of reaction (reaction progress monitored by TLC), the reaction mixture was diluted with water and extracted with ethyl acetate, dried over Na₂SO₄, concentrated and purified by column chromatography on silica gel with 40% ethyl acetate in hexane to afford pure 10 (160 mg, 86%). MS m/z (ES): 532 (M+H)⁺.

Step 2

A solution of 10 in 1M HCl in acetic acid (10.0 eqv) was heated at 60° C. for 2 hours. After completion of reaction (reaction progress was monitored by TLC), the reaction mixture was neutralized with 1 M sodium hydroxide solution and extracted with ethyl acetate (2×25 mL). The organic phase was dried and evaporated. The resulting crude was dissolved in methanol:water:triethylamine (8:1:1), then ethylene diamine (5 eqv) was added and stirred at 25° C. for 16 h. After completion of reaction (reaction progress was monitored by LCMS), the solvent was evaporated under reduced pressure. The resulting crude was purified by washing with methanol (40%). MS m/z (ES): 402 (M+H)⁺.

Example 60

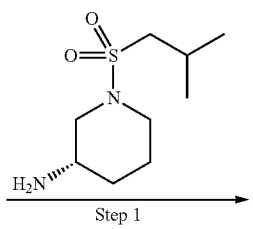

9

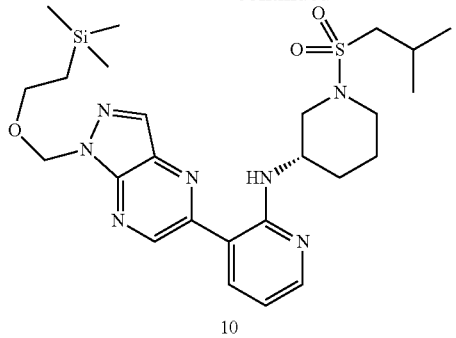

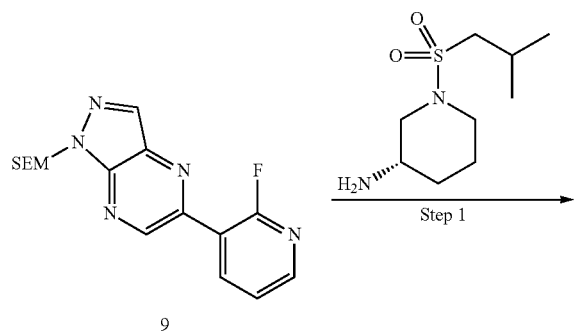

RX = PrSO₂Cl, MeSO₂Cl, i-BuSO₂Cl, AC₂O
  02B      03B       04B       05B

Step 1

Compound 9 (120 mg, 0.34 mmol) and the amine (1.39 mmol) were taken in sealed tube. DIPEA (1.5 mL) and NMP (0.15 ml) were added. The reaction mixture heated in a sealed tube at 140° C. for 16 hours. After completion of reaction (reaction progress monitored by TLC), the reaction mixture was diluted with water and extracted with ethyl acetate. The organic phase was dried over Na₂SO₄, concentrated and purified by column chromatography on silica gel with 40% ethyl acetate in hexane to afford pure 10. (170 mg, 89%). MS m/z (ES): 546 (M+H)⁺.

Step 2

A solution of 10 in 1M HCl in acetic acid (10.0 eqv) was heated at 60° C. for 2 hours. After completion of reaction (reaction progress was monitored by TLC), the reaction mixture was neutralized with 1M aqueous sodium hydroxide and extracted with ethyl acetate (2×25 mL). The organic phase was over Na₂SO₄ and evaporated. The resulting crude was dissolved in a mixture of methanol:water:triethylamine (8:1:1). Ethylene diamine (5 eqv) was added and the mixture was stirred at 25° C. for 16 h. After completion of reaction (reaction progress was monitored by LCMS) solvent was evaporated under reduced pressure. The crude material was purified by washing with methanol (12%). MS m/z (ES): 416 (M+H)+.

Example 61

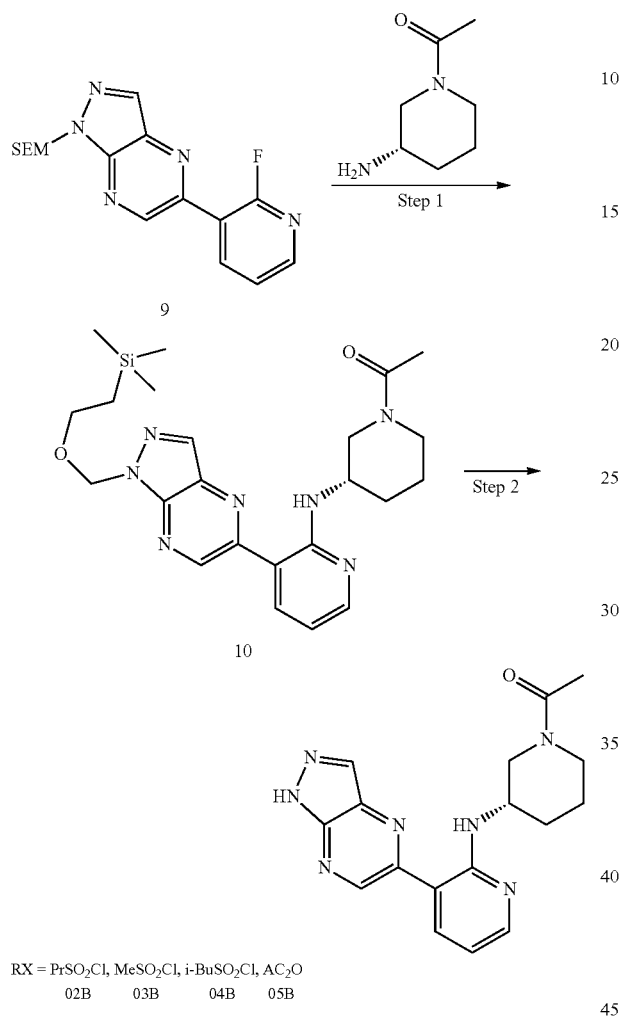

RX = PrSO₂Cl, MeSO₂Cl, i-BuSO₂Cl, AC₂O
02B      03B      04B      05B

Step 1

Compound 9 (120 mg, 0.34 mmol) and the amine (1.39 mmol) were taken in sealed tube. DIPEA (1.5 mL) and NMP (0.15 mL) were added. The reaction mixture was heated in a sealed tube at 140° C. for 16 hours. After completion of reaction (reaction progress monitored by TLC), the reaction mixture was diluted with water and extracted with ethyl acetate. The organic phase was dried over Na₂SO₄, concentrated and purified by column chromatography on silica gel eluting with 40% ethyl acetate in hexane to afford pure 10. (140 mg, 86%). MS m/z (ES): 468 (M+H)+.

Step 2

A solution of 10 in 1M HCl in acetic acid (10.0 eqv) was heated at 60° C. for 2 hours. After completion of reaction (reaction progress was monitored by TLC), the reaction mixture was neutralized with 1 M sodium hydroxide solution and extracted with ethyl acetate (2×25 mL). The organic phase was dried and evaporated. The resulting crude was dissolved in methanol:water:triethylamine (8:1:1). Ethylene diamine (5 eqv) was added and the reaction was stirred at 25° C. for 16 h. After completion of reaction (reaction progress was monitored by LCMS), the solvent was evaporated under reduced pressure. The crude material was purified by washing with methanol (41%). MS m/z (ES): 338 (M+H)+.

Example 62

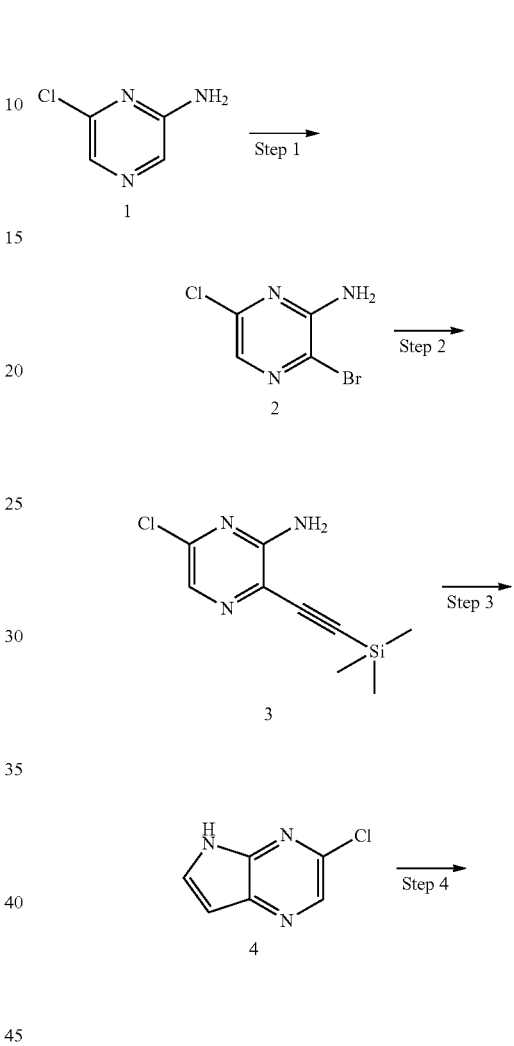

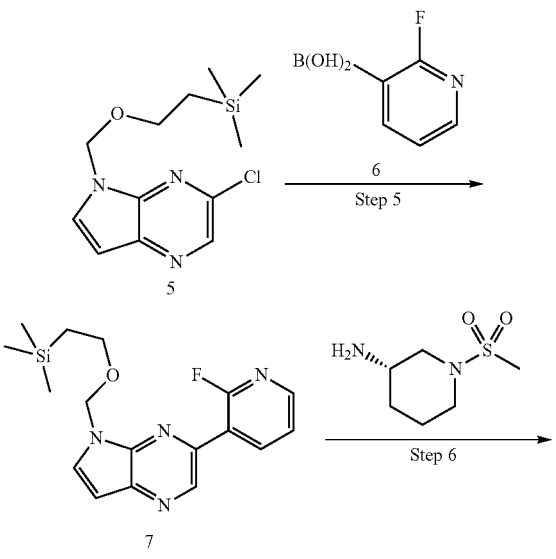

-continued

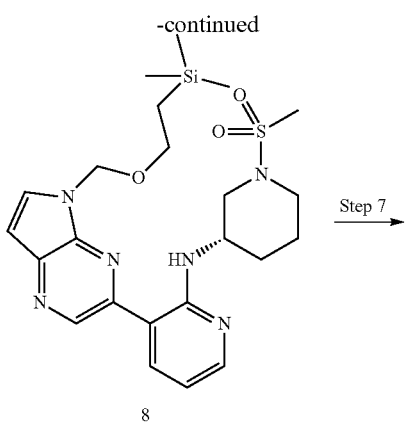

8

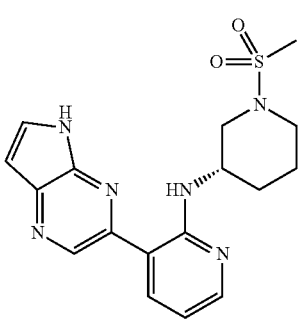

RX = PrSO₂Cl, MeSO₂Cl, i-BuSO₂Cl, AC₂O
  02Cl       03Cl      04Cl        05Cl

Step 1

To a solution of 1 (10.0 g, 77.19 mmol) in CHCl₃ (300 mL), N-bromo succinimide (13.73 g, 77.19 mmol) was slowly added in portions at reflux. The reaction was stirred at reflux for 1.5 h. TLC (100% DCM) showed complete consumption of SM. The reaction mixture was cooled to 25° C., washed with water (3×200 mL), dried over Na₂SO₄, and concentrated under reduced pressure to afford crude compound 2. This material was purified by column chromatography over silica gel (100-200 mesh) eluting with DCM to afford 2 as cream colored solid (5.0 g, 31%). MS m/z (ES): 207 (M+H)⁺.

Step 2

A solution of 2 (10.0 g, 47.97 mmol) in anhydrous THF (150 mL) was degassed and purged with argon gas for 20 min. Triethylamine (13.47 mL, 95.94 mmol), CuI (910 mg, 4.79 mmol), and Pd(PPh₃)₂Cl₂ (1.01 g, 1.43 mmol) were added at 0° C. Ethynyl trimethyl silane (5.18 g, 52.77 mmol) was added very slowly. The reaction was stirred at 25° C. for 1.5 h. TLC (20% EA/Hexane) revealed complete consumption of starting material. The reaction mixture was filtered through a celite bed, filtrate was diluted with water (100 mL) and extracted with EtOAc (3×100 ml). The combined organic layers were dried and concentrated under reduced pressure to afford crude compound 3. This material was purified by column chromatography over silica gel (100-200 mesh) using EtOAc/Hexane as (20~30%) as eluting solvent, afforded 3 as a pale yellow solid (6.0 g, 55%). MS m/z (ES): 226 (M+H)⁺.

Step 3

A solution of 3 (6.0 g, 26.57 mmol) in anhydrous THF (130 mL) was cooled to 0° C., tBuOK (5.96 g, 53.15 mmol) suspended in THF (30 mL). The reactions mixture was stirred for 30 min and then refluxed for 2.5 h. TLC (30% EA/Hexane) revealed complete consumption of starting material. The reaction mixture was cooled to 25° C., filtered through celite bed. The filtrate collected was concentrated under reduced pressure to afford crude compound 4. This was purified by column chromatography over silica gel (100-200 mesh) eluting with EtOAc/Hexane as (2560%) to provide 4 as a brown solid (2.51 g, 61%). MS m/z (ES): 154 (M+H)⁺.

Step 4

A suspension of NaH (370 mg, 15.62 mmol) in DMF (15 mL) was cooled to 0° C. and treated with 4 (1.6 g, 10.41 mmol) dissolved in DMF (15 mL). The reaction mixture was stirred 20 min at 25° C. The reaction mixture was again cooled to 0° C., SEM-Cl (2.2 mL, 12.50 mmol) was added slowly, and allowed to stir at 25° C. for 2 h. TLC (20% EA/Hexane) indicates complete consumption of starting material. The solvent was distilled off and the residue was purified by column chromatography over silica gel (100-200 mesh) eluting with EtOAc/Hexane (5-10%) to provide 5 as a brown oily liquid (2.0 g, 67%). MS m/z (ES): 284 (M+H)⁺.

Step 5

To a solution of 5 (2.0 g, 7.05 mmol) in a mixed solvent of toluene:ethanol:water (4:1:2), Na₂CO₃ (2.24 g, 21.15 mmol) and boronic acid 6 (1.19 g, 8.46 mmol) were added. The reaction mixture was thoroughly degassed, and the flask filled with argon for 15 min, and then purged with argon for 20 minutes. Pd(PPh₃)₄ (2.44 g, 2.11 mmol) was added in to reaction mixture and heated to 90° C. for 2 h. TLC (20% EA/Hexane) revealed complete consumption of starting material. The reaction mixture was cooled, diluted with water and extracted with ethyl acetate (3×100 mL). The combined organic layers were dried and concentrated under reduced pressure to afford crude 7. The crude material was purified by column chromatography over silica gel (100-200 mesh) eluting with EtOAc/Hexane (15~25%) to afford 7 as a yellow solid (1.1 g, 45%). MS m/z (ES): 345 (M+H)⁺.

Step 6

Compound 7 (150 mg) was dissolved in a mixture of DIPEA (0.75 mL, 10.0 eqv) and N-methylpyrrolidone (5 drops) in a seal tube, compound 11-03 (310 mg, 4.0 eqv) was added. The seal tube was heated at 170° C. for 16 h. TLC (40% EA/Hexane) indicates complete consumption of starting material. The reaction mixture was cooled to rt, diluted with water, extracted with ethyl acetate (3×20 mL). The organic layers were washed with a solution of brine (30 ml) and dried and concentrated under vacuum to afford crude 8. This was purified by biotage column using EtOAc/Hexane (15~30%) as eluting solvent, afforded pure 8 (150 mg, 71%) as a pale yellow oily liquid. MS m/z (ES): 503 (M+H)⁺.

Step 7

A solution of 8 (170 mg, 0.338 mmol) in 1M HCl in AcOH (10 mL) was heated at 60° C. for 3 h, TLC (40% EA/Hexane) indicated complete consumption of SM. The reaction mixture was cooled to rt and evaporated. The residue was dissolved in MeOH:TEA:EtOH:H₂O (8:1:1). Ethylene diamine (5 eqv) was added and the reaction mixture was stirred for 16 h at 25° C. The reaction was monitored by LCMS and TLC (5% MeOH/DCM). After complete consumption of starting material, the solvent was evaporated under reduced pressure and the residue was purified by biotage column using MeOH/

DCM (1-3%) as eluting solvent, afforded pure product as a pale yellow solid (21.9 mg, 17%). MS m/z (ES): 373 (M+H)+.

Example 63

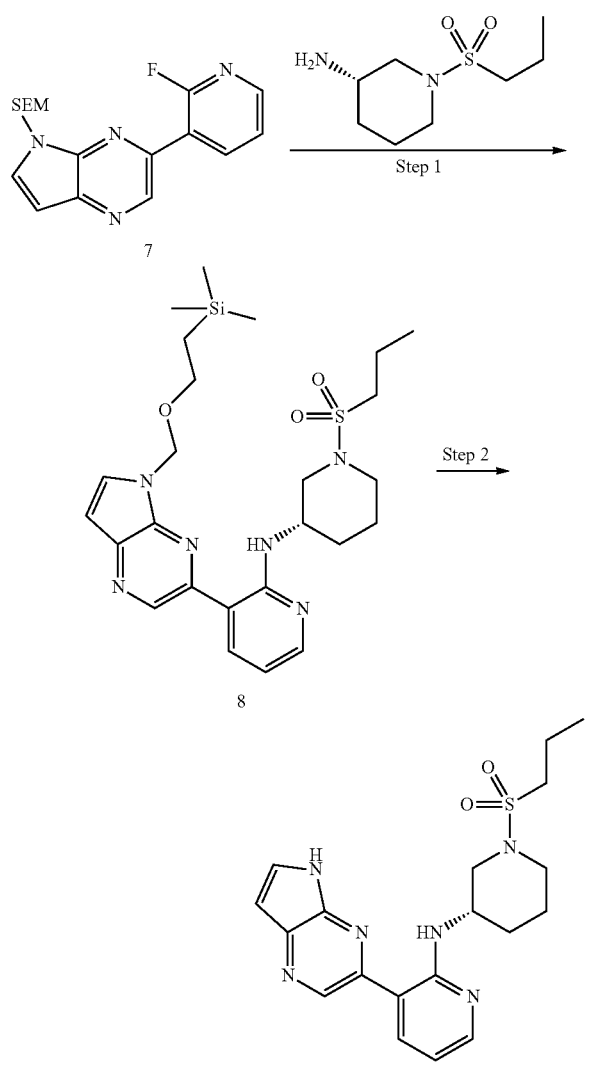

Step 1

Compound 7 (150 mg) was dissolved in a mixture of DIPEA (0.75 mL, 10.0 eqv) and N-methylpyrrolidone (5 drops) in a seal tube. The amine (350 mg, 4.0 eq.) was added and the sealed tube was heated at 170° C. for 16 h. TLC (40% EA/Hexane) indicates complete consumption of starting material. The reaction mixture was cooled, diluted with water, and extracted with ethyl acetate (3×20 mL). The organic layers were washed with brine solution (30 ml) and dried over Na₂SO₄, and concentrated under vacuum to afford crude 12-02. This material was purified by biotage column eluting with EtOAc/Hexane (15~30%) to afford pure 8 (110 mg, 47%) as a pale yellow oily liquid. MS m/z (ES): 531 (M+H)+.

Step 2

A solution of 8 (110 mg, 0.207 mmol) in 1M HCl in AcOH (10 mL) was heated at 60° C. for 3 h, TLC (40% EA/Hexane) indicated complete consumption of SM. The reaction mixture was cooled to rt. The solvent was evaporated and the residue was dissolved in MeOH:TEA:EtOH:H₂O (8:1:1). Ethylene diamine (5 eqv) was added and stirred for 16 h at 25° C. The reaction was monitored by LCMS and TLC (5% MeOH/DCM). After complete consumption of starting material, the solvent was evaporated under reduced pressure and the residue was purified by biotage column eluting with MeOH/DCM (1-3%) to afford pure product as a pale yellow solid (24.8 mg, 30%). MS m/z (ES): 401 (M+H)+.

Example 64

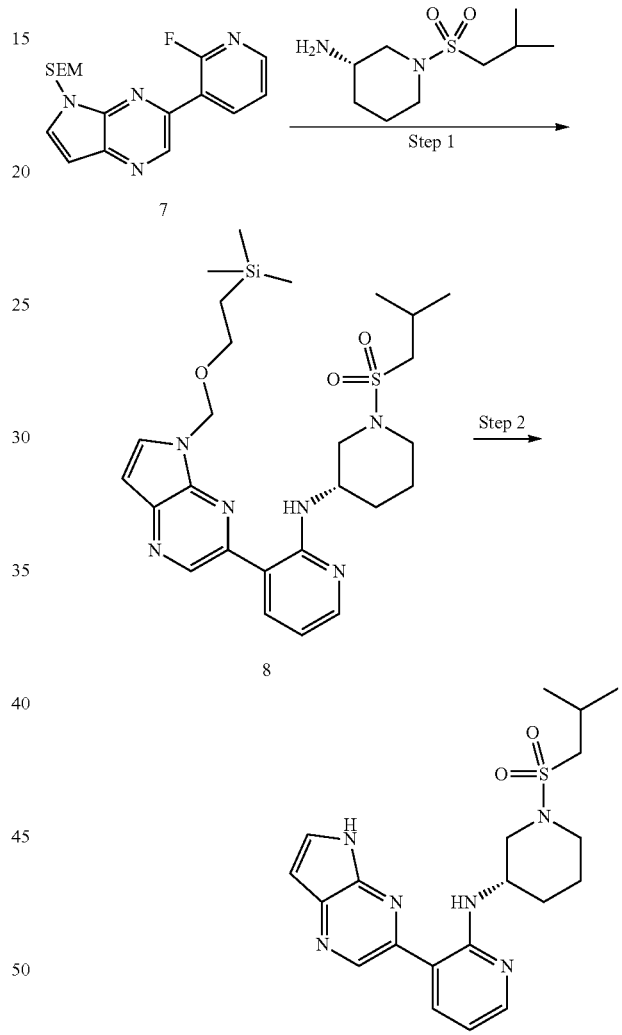

Step 1

Compound 7 (150 mg) was dissolved in a mixture of DIPEA (0.75 mL) and N-methyl pyrrolidone (5 drops) in a sealed tube. The amine (380 mg) was added and the seal tube was heated at 170° C. for 16 h. TLC (40% EA/Hexane) indicates complete consumption of starting material. The reaction mixture was cooled to rt, diluted with water, and extracted with ethyl acetate (3×20 mL). The combined organic layers were washed with brine (30 ml) and dried over Na₂SO₄, and evaporated to afford crude 12-04. This was purified by biotage column eluting with EtOAc/Hexane (15~30%) to afford pure 8 (200 mg, 86%) as a pale yellow oily liquid. MS m/z (ES): 545 (M+H)+.

Step 2

A solution of 8 (200 mg, 0.367 mmol) in 1(M) HCl in AcOH (10 mL) was heated at 60° C. for 3 h, TLC (40% EA/Hexane) indicated complete consumption of SM. The reaction mixture was cooled to rt. The solvent was evaporated and the residue was dissolved in a mixture of MeOH:TEA:EtOH:$H_2O$ (8:1:1). Ethylene diamine (5 eqv) was added and the reaction was stirred for 16 h at 25° C. The reaction was monitored by LCMS and TLC (5% MeOH/DCM). After complete consumption of starting material, the solvent was evaporated and the residue was purified by biotage column eluting with MeOH/DCM (1~3%) to afford pure product as a pale yellow solid (25.2 mg, 16%). MS m/z (ES): 415 (M+H)$^+$.

Example 65

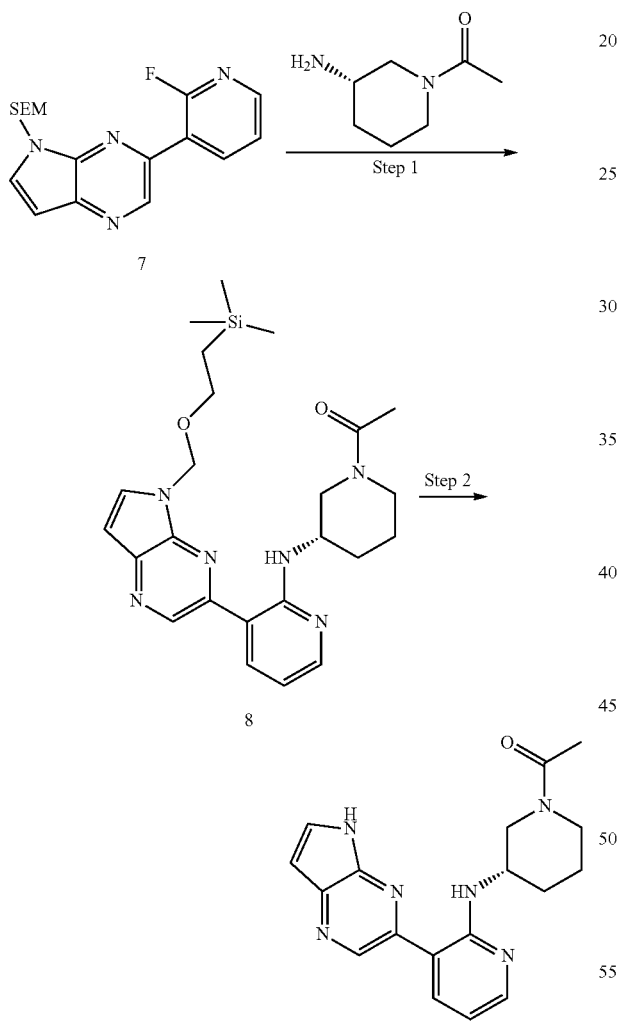

Step 1

Compound 7 (150 mg) was dissolved in a mixture of DIPEA (0.75 mL, 10.0 eqv) and N-methylpyrrolidone (5 drops) in a sealed tube. The amine (240 mg) was added and the seal tube was heated at 170° C. for 16 h. TLC (40% EA/Hexane) indicates complete consumption of starting material. The reaction mixture was cooled, diluted with water, and extracted with ethyl acetate (3×20 mL). The combined organic layers were washed with brine (30 ml) and dried over $Na_2SO_4$, and concentrated under reduced pressure to afford crude 12-05. This material was purified by biotage column eluting with EtOAc/Hexane (15~30%) to afford pure 8 (110 mg, 55%) as a pale yellow sticky solid. MS m/z (ES): 467 (M+H)$^+$.

Step 2

A solution of 8 (140 mg, 0.299 mmol) in 1M HCl in AcOH (10 mL) was heated at 60° C. for 3 h, TLC (40% EA/Hexane) revealed complete consumption of SM. The reaction mixture was cooled and the solvent was removed under reduced pressure. The residue was dissolved in MeOH:TEA:EtOH:$H_2O$ (8:1:1). Ethylene diamine (5 eqv) was added and the reaction was stirred for 16 h at 25° C. The reaction was monitored by LCMS and TLC (5% MeOH/DCM). After complete consumption of starting material, the solvent was evaporated and the residue was purified by biotage column eluting with MeOH/DCM (1-3%) to afford pure product as a pale yellow solid (17.4 mg, 53%). MS m/z (ES): 367 (M+H)$^+$.

Example 66

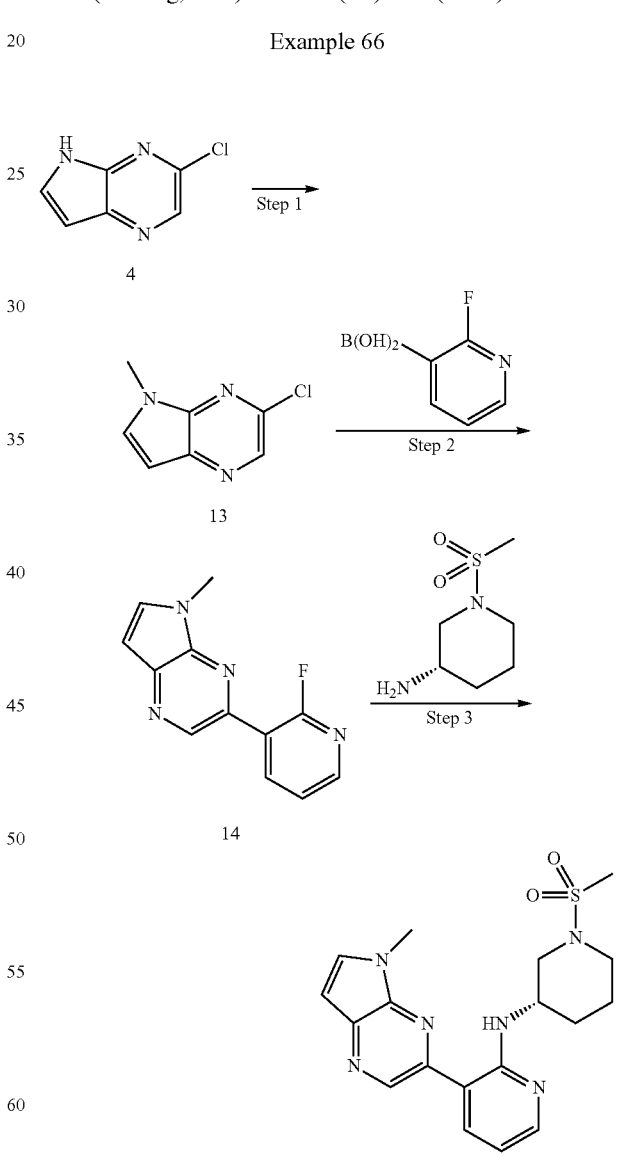

Step 1

A suspension of NaH (180 mg, 7.57 mmol) in DMF (8 mL) was cooled to 0° C. 4 (900 mg, 5.04 mmol) dissolved in DMF (7 mL) was added very slowly, and the reaction was then stirred for 20 min at 25° C. MeI (0.31 mL, 5.04 mmol) was slowly added at 0° C. and the reaction was allowed to stir at 25° C. for 2 h. TLC (20% EA/Hexane) revealed complete consumption of starting material. The solvent was evaporated and the residue was purified by column chromatography over silica gel (100-200 mesh) eluting with EtOAc/Hexane (5~7%) to afford 13 (680 mg, 70%) as a pale yellow solid. MS m/z (ES): 168 (M+H)+.

Step 2

Boronic acid 6 (390 mg, 2.82 mmol) was added to a solution of 13 (500 mg, 2.35 mmol) in a mixed solvent of toluene: ethanol:water (4:1:2). Na₂CO₃ (750 mg, 7.07 mmol) was also added. The reaction mixture was thoroughly degassed and purged with argon for 20 minutes. Pd (PPh₃)₄ (810 mg, 0.70 mmol) was added and the reaction was heated at 90° C. for 2 h. TLC (50% EA/Hexane) indicated complete consumption of starting material. The reaction mixture was cooled to 25° C., diluted with water and extracted with ethyl acetate (3×50 mL). The combined organic layers were dried and concentrated under reduced pressure to afford crude 14. The crude material was purified by column chromatography over silica gel (100-200 mesh) eluting with EtOAc/Hexane (10~25%) to afford 14 as a pale yellow solid (300 mg, 50%). MS m/z (ES): 228 (M+H)+.

Step 3

Compound 14 (50 mg, 0.22 mmol) and compound 11-03 (150 mg, 0.84 mmol) were taken in a sealed tube. DIPEA (0.37 mL) and NMP (5 drops) were added. The reaction mixture was heated in a sealed tube at 170° C. for 16 h. The reaction mixture was diluted with water and extracted with ethyl acetate (3×20 mL). The combined organic layers were washed with brine (30 mL), dried over Na₂SO₄, and concentrated under reduced pressure. The crude product was purified by biotage column chromatography on silica gel eluting with 40% ethyl acetate in hexane to afford the product (37.6 mg, 44%) as a yellow solid. MS m/z (ES): 387 (M+H)+.

Example 67

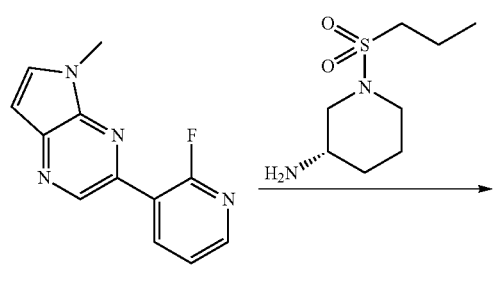

14

Compound 14 (50 mg, 0.22 mmol) and the amine (180 mg, 0.87 mmol) were taken in a sealed tube. DIPEA (0.37 mL) and NMP (5 drops) were added. The reaction mixture was heated in a sealed tube at 170° C. for 16 h. The reaction mixture was diluted with water and extracted with ethyl acetate (3×20 mL). The combined organic extracts were washed with brine (30 mL), dried over Na₂SO₄, and concentrated under reduced pressure. The crude product was purified by biotage column chromatography on silica gel eluting with 40% ethyl acetate in hexane to afford the product (7.3 mg, 8%) as a yellow solid. MS m/z (ES): 414 (M+H)+.

Example 68

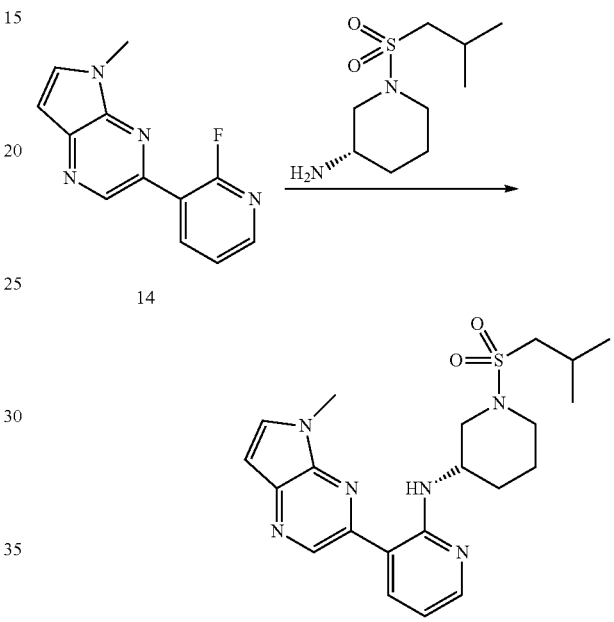

14

Compound 14 (65 mg, 0.28 mmol) and the amine (250 mg, 1.13 mmol) were taken in sealed tube. DIPEA (0.49 mL) and NMP (5 drops) were added. The reaction mixture was heated in a sealed tube at 170° C. for 16 h. The reaction mixture was diluted with water and extracted with ethyl acetate (3×20 mL). The combined organic extracts were washed with brine (30 mL), dried over Na₂SO₄, and concentrated under reduced pressure. The crude product was purified by biotage column chromatography on silica gel eluting with 40% ethyl acetate in hexane to afford product (27.8 mg, 23%) as a yellow solid. MS m/z (ES): 428 (M+H)+.

Example 69

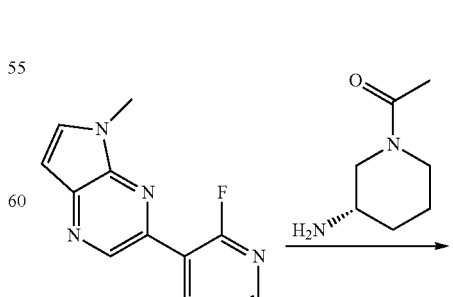

14

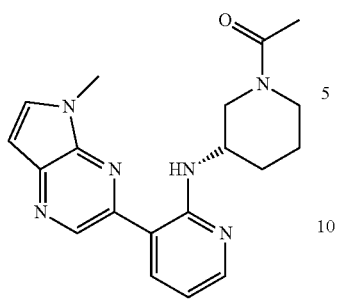

Compound 14 (60 mg, 0.26 mmol) and the amine (150 mg, 1.05) were taken in a sealed tube. DIPEA (0.45 mL) and NMP (5 drops) were added. The reaction mixture was heated in a sealed tube at 170° C. for 16 h. After completion of reaction (reaction progress monitored by TLC), the reaction mixture was diluted with water and extracted with ethyl acetate (3×20 mL). The combined organic extracts were washed with brine (30 mL), dried over $Na_2SO_4$, and concentrated under reduced pressure. The crude product was purified by biotage column chromatography on silica gel eluting with 40% ethyl acetate in hexane to afford product (22.4 mg, 24%) as a yellow solid. MS m/z (ES): 351 (M+H)$^+$.

Example 70

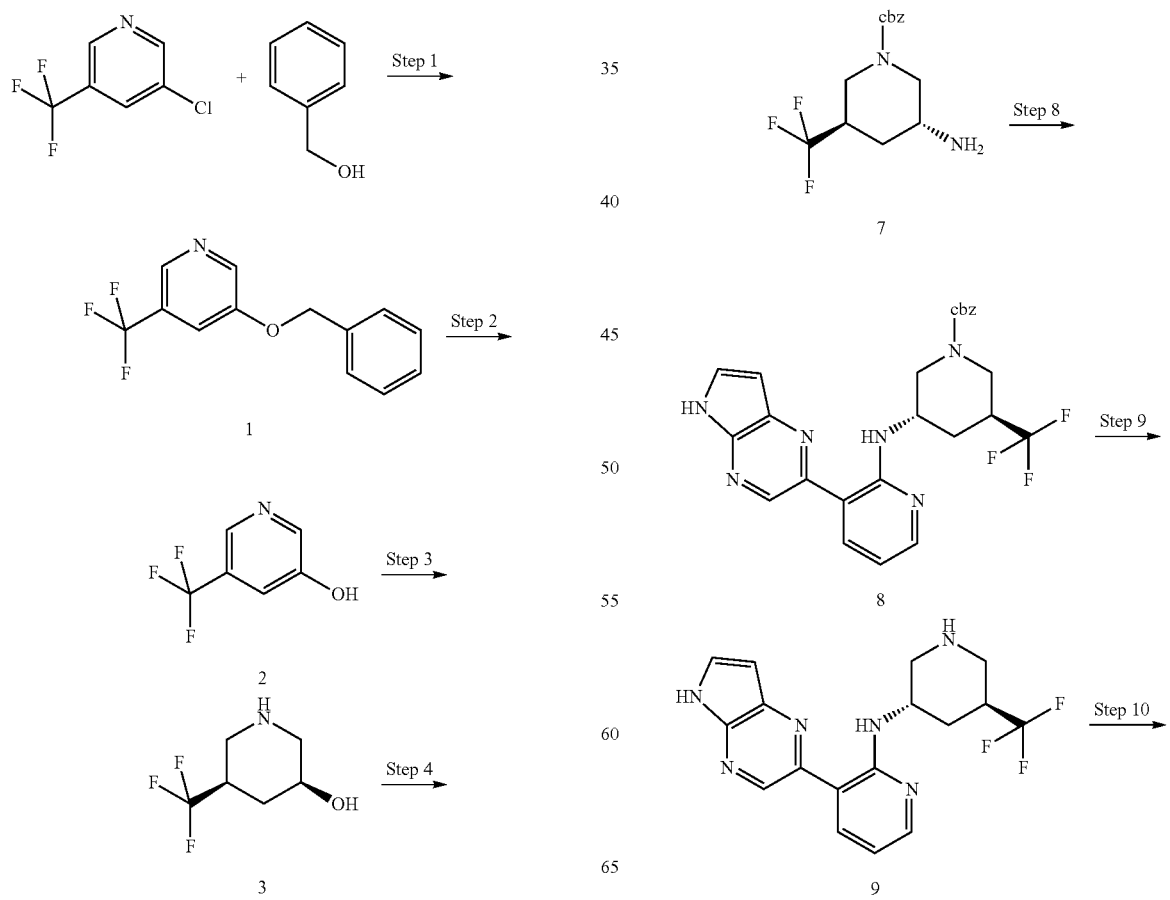

-continued

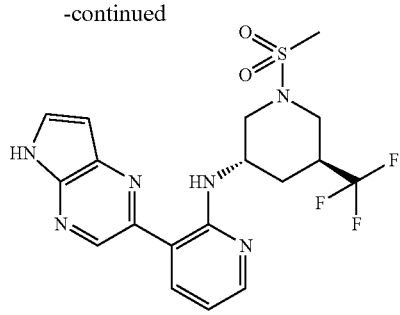

Step 1

3-Chloro-5-(trifluoromethyl)pyridine (9.1 g, 50 mmol) was dissolved in DMF (45 mL), NaH (2.40 g, 60 percent) and phenylmethanol (5 mL) was added slowly. The mixture was stirred for 2 hours at 40° C. The solvent was then evaporated in vacuo and the mixture diluted with chloroform, washed with saturated $NaHCO_3$ and a brine solution. The organic layer was then dried over $MgSO_4$, the resulting crude material was purified by column chromatography (petroleum ether/ethyl acetate=10:1 to 4:1) to yield compound 1 (11.7 g, 94%).

Step 2

Compound 1 (19.5 g, 77 mmol) was dissolved in 100 mL of methanol and hydrogenated over Pd/C (5 percent, 975 mg) at 1 atm $H_2$ for 16 hours. The catalyst was removed by filtration, and the solvent was evaporated. The residue was purified by flash chromatography on silica gel to give compound 2 (11.4 g, 92%).

Step 3

To a solution of 5-(trifluoromethyl)pyridin-3-ol (16.3 g, 0.1 mol) in MeOH (120 mL), 2 N HCl (12 mL) and $PtO_2$ (2.25 g, 10 mmol) was added under $N_2$. The solution was then placed on a parr shaker, purged and shaken under 60 PSI of $H_2$ gas for 2 hours. The resulting mixture was diluted with 5 mL of water and the catalyst was filtered on a bed of celite. The solvents were removed and the product Co-evaporated with acetonitrile, get the product (6.8 g, 40%).

Step 4

To a solution of cis-5-(trifluoromethyl)piperidin-3-ol (3.4 g, 20 mmol) in 30 mL of dioxane under $N_2$, a solution of $K_2CO_3$ (5.5 g, 40 mmol) in water (40 mL) was added at RT. The mixture was then cooled to 5° C., and CbzCl (3.2 mL, 22.6 mmol) in 35 mL of dioxane was added dropwise. The reaction was allowed to stand at RT for 2.5 h. The dioxane was evaporated off, and the aqueous mixture was extracted with methylene chloride. The extracts were washed with water and brine, and dried over $Na_2SO_4$, after evaporation to dryness, the residue was purified by column chromatography to give Compound 4 (3.7 g, 61%).

Step 5

Methanesulfonyl chloride (6 mL, 73 mmol) was added dropwise over 10 minutes to a stirred solution of Compound 4 (20 g, 66 mmol) and $Et_3N$ (18 mL, 132 mmol) in dichloromethane (30 mL) at 0° C. After stirring for 3 hours at RT, the reaction was quenched by addition of water. The organic phase was washed with brine, dried over $Na_2SO_4$, filtered and evaporated in vacuo to give product (15.5 g, 62%).

Step 6

A mixture of compound 5 (2.5 g, 6.5 mmol) and $NaN_3$ (1.3 g, 20 mmol) in DMF (50 mL) was heated to 105° C. for 20 h. The reaction mixture was poured on water and extracted with EA. The combined organic extracts were washed with brine, and dried over $Na_2SO_4$, and evaporated. The residue was purified by column chromatography (petroleum ether/ethyl acetate=5:1) to give Compound 6 (1.7 g, 79%).

Step 7

To a stirred solution of Compound 6 (30 g, 93 mmol) in THF (70 mL)-$H_2O$ (7 mL) was added $Ph_3P$ (36 g, 137 mmol), the mixture stirred under reflux for 16 hours, added $Na_2SO_4$, filtered and evaporated. The crude mixture was purified by column chromatography (petroleum ether/ethyl acetate=5:1) to give 5.0 g of trans-benzyl 3-amino-5-(trifluoromethyl)piperidine-1-carboxylate and as a yellow oil (18%).

Analysis $^1$H NMR (300 MHz, $CDCl_3$) δ: 7.31-7.38 (5H, m), 5.10-5.16 (2H, br), 4.05-4.17 (1H, m), 3.77-3.81 (1H, m), 3.25-3.35 (1H, m), 2.85-3.30 (2H, m), 2.69-2.71 (1H, m), 1.77-1.83 (2H, m). LC-MS: 303 $[M+1]^+$.

Step 8

To a 10 mL microwave vial was added 2-(2-fluoropyridin-3-yl)-5H-pyrrolo[2,3-b]pyrazine (433 mg, 2.02 mmol), (3S,5S)-3-amino-5-trifluoromethyl-piperidine-1-carboxylic acid benzyl ester (650 mg, 2.15 mmol), DIPEA (784 mg, 6.07 mmol) and NMP (4.0 ml). The vial was capped and heated at 230° C. under microwave irradiation for 45 min. The reaction mixture was diluted with water and ethyl acetate. The combined organics were separated, dried ($Na_2SO_4$), filtered and concentrated. The crude residue was purified by $SiO_2$ chromatography eluting a EtOAc/hexane gradient to afford 147 mg (15%) of aminopyridine as a yellow glassy oil. MS m/z (ES): 497 $(M+H)^+$.

Step 9

To a round bottomed flask charged with (3S,5S)-3-[3-(5H-Pyrrolo[2,3-b]pyrazin-2-yl)-pyridin-2-ylamino]-5-trifluoromethyl-piperidine-1-carboxylic acid benzyl ester (147 mg, 0.296 mmol) and $Pd(OH)_2$ (75 mg) was added ethanol (16 mL). The reaction vessel was subsequently evacuated and filled with hydrogen gas (via balloon). The reaction was stirred for approximately 6 hours at room temperature. Upon completion, the reaction mixture was filtered through celite. The filtrate was concentrated to afford 106 mg (98%) of the piperidine. MS m/z (ES): 363 $(M+H)^+$.

Step 10

A solution of methanesulfonyl chloride (1 mL, 1M in DCM, 0.124 mmol) was added to a solution of the amine (52 mg, 0.118 mmol) and triethylamine (17 μL, 0.124 mmol) in DCM (5 mL) at 0° C. The reaction was slowly warmed up to ambient temperature over a period of 2 h. The reaction mixture was concentrated. The crude residue was dissolved in MeOH (4 mL). To the solution was added a large excess of $K_2CO_3$ and the reaction mixture was heated at 140° C. under microwave irradiation for 5 min. The reaction mixture was diluted with water and ethyl acetate. The combined organics were separated, dried ($Na_2SO_4$), filtered and concentrated which was eluted 80:20 EtOAc/hexane to afford 20.4 mg (39%) of the desired product as a yellow solid. MS m/z (ES): 441 (M+H).

Example 71

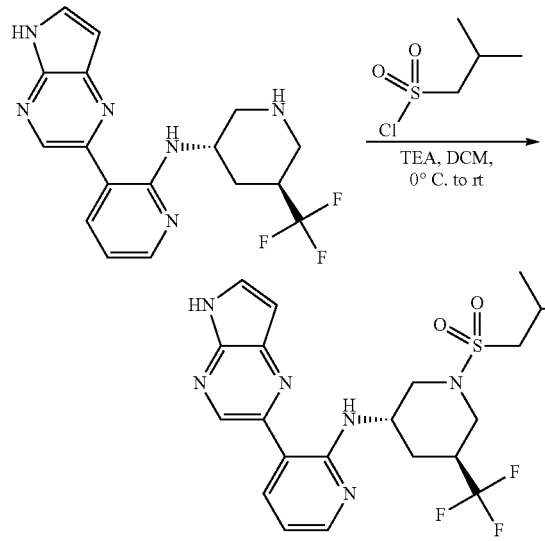

[(3S,5S)-1-(2-Methyl-propane-1-sulfonyl)-5-trifluoromethyl-piperidin-3-yl]-[3-(5H-pyrrolo[2,3-b]pyrazin-2-yl)-pyridin-2-yl]-amine was obtained from [3-(5H-pyrrolo[2,3-b]pyrazin-2-yl)-pyridin-2-yl]-((3S,5S)-5-trifluoromethyl-piperidin-3-yl)-amine and isobutylsulfonyl chloride following the general synthetic procedures described in the above Examples. MS m/z (ES): 483 (M+H)

Example 72

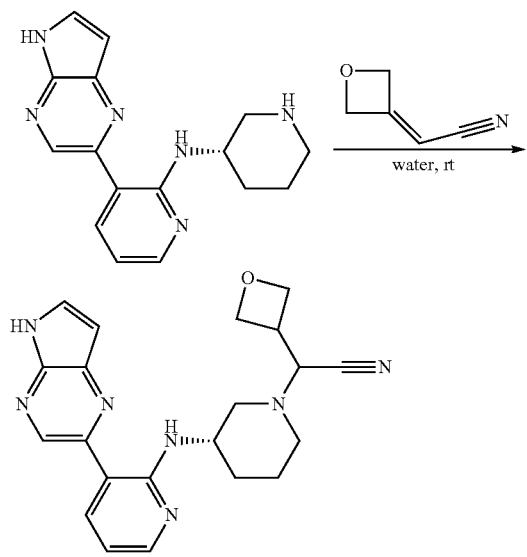

2-(Oxetan-3-ylidene)acetonitrile (20.0 mg, 0.21 mmol) was combined with the amine (30.9 mg, 0.10 mmol) in water (0.60 mL) at ambient temperature. The reaction was rapidly stirred at ambient temperature over a period of 1 h. The reaction mixture was diluted with water and extracted with ethyl acetate. The organics were combined and concentrated to give a crude solid. The crude reaction mixture was purified by flash chromatography (silica gel, 0% to 100% ethyl acetate in hexanes) to give 20.5 mg (50%) of the desired product as a yellow solid. MS m/z (ES): 390 (M+H)

Example 73

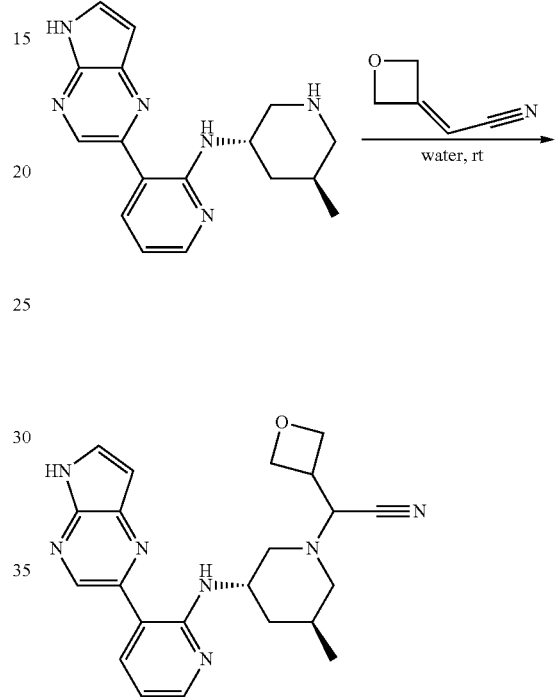

{(3S,5S)-3-Methyl-5-[3-(5H-pyrrolo[2,3-b]pyrazin-2-yl)-pyridin-2-ylamino]-piperidin-1-yl}-oxetan-3-yl-acetonitrile was obtained from ((3S,5S)-5-methyl-piperidin-3-yl)-[3-(5H-pyrrolo[2,3-b]pyrazin-2-yl)-pyridin-2-yl]-amine and 2-(oxetan-3-ylidene)acetonitrile following the general synthetic procedures described in the above Examples for (3-{(S)-3-[3-(5H-Pyrrolo[2,3-b]pyrazin-2-yl)-pyridin-2-ylamino]-piperidin-1-yl}-oxetan-3-yl)-acetonitrile (I-117). MS m/z (ES): 404 (M+H)

Example 74

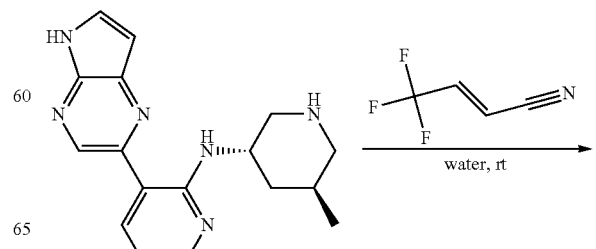

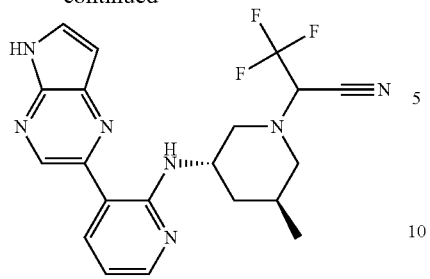

3,3,3-Trifluoro-2-{(3S,5S)-3-methyl-5-[3-(5H-pyrrolo[2,3-b]pyrazin-2-yl)-pyridin-2-ylamino]-piperidin-1-yl}-propionitrile was obtained from ((3S,5S)-5-methyl-piperidin-3-yl)-[3-(5H-pyrrolo[2,3-b]pyrazin-2-yl)-pyridin-2-yl]-amine and (E)-4,4,4-trifluorobut-2-enenitrile following the general synthetic procedures described in the example for (3-{(S)-3-[3-(5H-Pyrrolo[2,3-b]pyrazin-2-yl)-pyridin-2-ylamino]-piperidin-1-yl}-oxetan-3-yl)-acetonitrile. The crude reaction mixture was loaded onto a preparative TLC, which was eluted with 50:50 EtOAc/hexane to afford 4.6 mg (9%) of the desired product as a yellow solid. MS m/z (ES): 416 (M+H).

Example 75

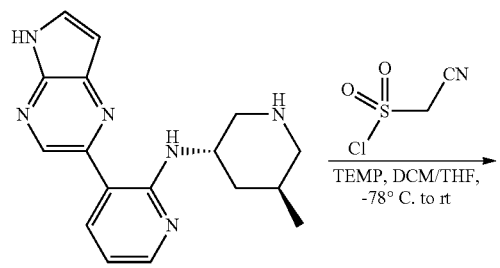

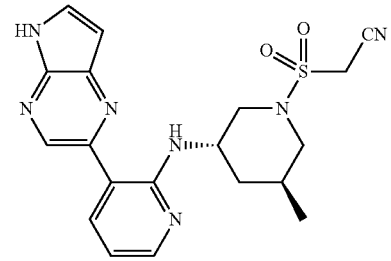

Cyanomethanesulfonyl chloride (0.1 M THF, 24 mg, 0.211 mmol) was added dropwise to a suspension of the amine (65 mg, 0.211 mmol) and 2,2,6,6-tetramethylpiperidine (215 μL, 1.26 mmol) in THF (0.10 mL), DCM (5 mL), and NMP (5 drops) at −10° C. The reaction was slowly warmed up to ambient temperature over a period of 2 h. Additional 2,2,6,6-tetramethylpiperidine (72 μL, 0.42 mmol) was added. The reaction was allowed to stir at ambient temperature for 1.5 h. The crude reaction mixture was diluted with ethyl acetate (10 mL) and washed with water (2×2 mL). The organic layer was dried over sodium sulfate and concentrated in vacuo. The crude material was loaded onto a preparative TLC, which was eluted 20:10 EtOAc/hexane to afford 3 mg (4%) of the desired product as a yellow solid. MS m/z (ES): 412 (M+H).

Example 76

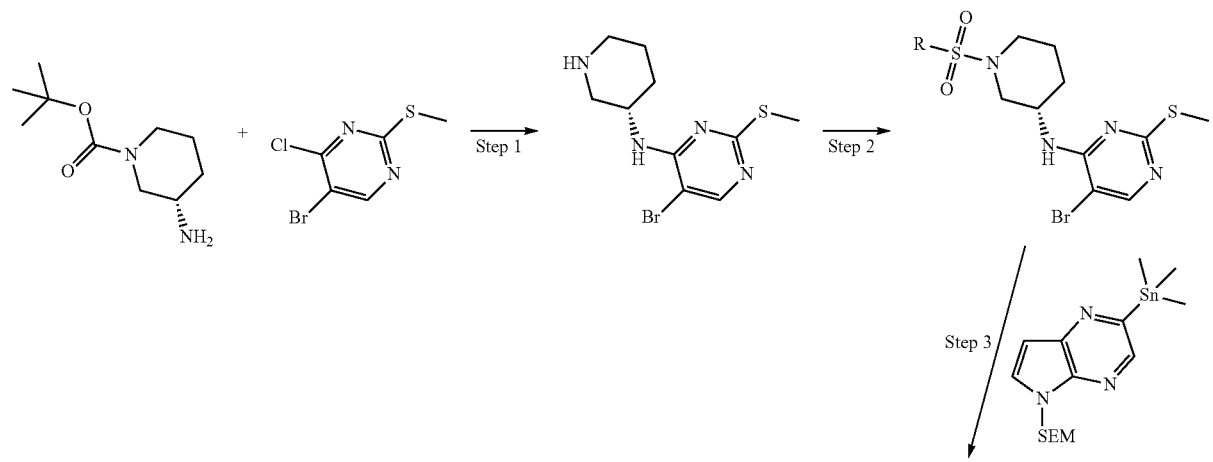

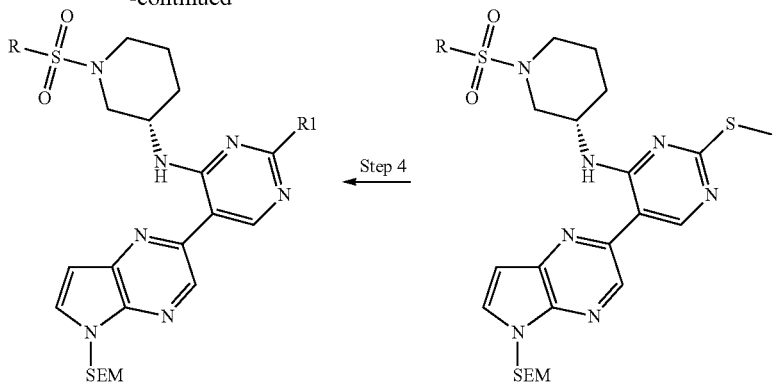
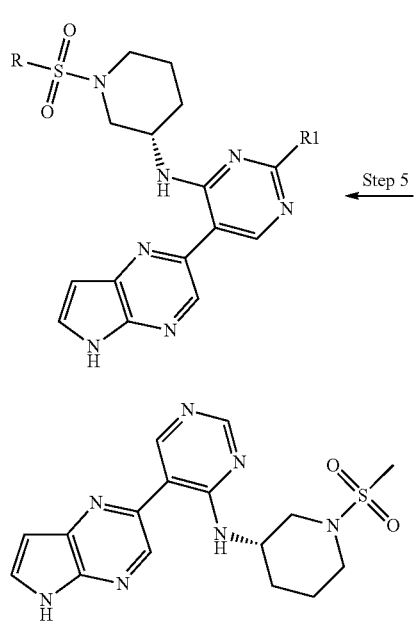

((S)-1-Methanesulfonyl-piperidin-3-yl)-[5-(5H-pyrrolo[2,3-b]pyrazin-2-yl)-pyrimidin-4-yl]-amine The General Procedure is According to that of the Above Scheme Step 1

A solution of 5-bromo-4-chloro-2-(methylthio)pyrimidine (4.8 g, 20 mmol), (S)-tert-butyl 3-aminopiperidine-1-carboxylate (4.8 g, 240 mmol) and diisopropylethylamine (6.2 g, 480 mmol) in dichloroethane (120 ml) was stirred at room temperature for 14 hours and then at 70° C. for 16 hours. Another equivalent of both (S)-tert-butyl 3-aminopiperidine-1-carboxylate and diisopropylethylamine were added and heating was continued at 80° C. for 6 hours. The reaction was cooled, washed with aqueous ammonium chloride, dried (MgSO$_4$) and evaporated to give an oil that was purified by flash chromatography (0-50% ethyl acetate/dichloromethane) to give (S)-3-aminopiperidine-1-carboxylic acid tert-butyl ester as an oil. The oil was diluted with dichloromethane (100 ml) cooled to 5° C. and treated with trifluoroacetic acid (40 ml). After stirring at room temperature for 5 hours, all solvent was evaporated. The residue was dissolved in dichloromethane (150 ml) and washed with cold dilute aqueous sodium hydroxide. The organics were dried (MgSO$_4$) and evaporated to give an oil that solidified on standing in ether/hexane to give (5-bromo-2-methylsulfanyl-pyrimidin-4-yl)-(S)-piperidin-3-yl-amine. MS (ES+): 304

Step 2

A solution of (5-bromo-2-methylsulfanyl-pyrimidin-4-yl)-(S)-piperidin-3-yl-amine (2.9 g, 9.6 mmol) and diisopropylethylamine (3.7 g, 28 mmol) in dichloromethane (50 ml) was cooled to 5° C. and treated with a solution of methanesulfonyl chloride (1.21 g, 10.5 mmol) in dichloromethane (20 ml). This was stirred at room temperature for 14 hours, washed with water, dried (MgSO$_4$) and evaporated to give (5-bromo-2-methylsulfanyl-pyrimidin-4-yl)-((S)-1-methanesulfonyl-piperidin-3-yl)-amine as a white solid. MS (ES+): 382 (2602-33).

Step 3

A degassed toluene solution of 2-bromo-5-(2-(trimethylsilyl)ethoxy)methyl)-5H-pyrrolo[2,3-b]pyrazine (200 mg, 0.61 mmol) and 1,1,1,2,2,2-hexamethyldistannane (220 mg, 0.67 mmol) was treated with tetrakistriphenylphosphine palladium (0) (35 mg, 0.03 mmol) and heated to 95-100° C. for 2 hours. When LCMS indicated conversion to the tin product, 5-(2-trimethylsilanyl-ethoxymethyl)-2-trimethylstannanyl-5H-pyrrolo[2,3-b]pyrazine, (MS (ES+): 412), the reaction was treated with (5-bromo-2-methylsulfanyl-pyrimidin-4-yl)-((S)-1-methanesulfonyl-piperidin-3-yl)-amine (80 mg, 0.21 mmol) and additional tetrakistriphenylphosphine palladium (0) (35 mg, 0.03 mmol) and heated to 100° C. for 16 hours. The reaction was cooled, filtered through celite, evaporated and purified by flash chromatography (60% ethyl acetate/hexane+2% triethylamine) to give 60 mg of ((S)-1-methanesulfonyl-piperidin-3-yl)-{2-methylsulfanyl-5-[5-(2-trimethylsilanyl-ethoxymethyl)-5H-pyrrolo[2,3-b]pyrazin-2-yl]-pyrimidin-4-yl}-amine. MS (ES+): 550.

Step 4

((S)-1-methanesulfonyl-piperidin-3-yl)-{2-methylsulfanyl-5-[5-(2-trimethylsilanyl-ethoxymethyl)-5H-pyrrolo[2,3-b]pyrazin-2-yl]-pyrimidin-4-yl}-amine (400 mg, 0.728 mmol) was dissolved in dioxane (10 ml), ethanol (2 ml) and water (2 ml) and treated with 2 g of Raney Nickel (2000). This was refluxed for 16 hours. The reaction was filtered, evaporated and purified by silica gel chromatography (5% methanol/methylene chloride to give ((S)-1-methanesulfonyl-piperidin-3-yl)-{5-[5-(2-trimethylsilanyl-ethoxymethyl)-5H-pyrrolo[2,3-b]pyrazin-2-yl]-pyrimidin-4-yl}-amine (~80 mg). MS (ES+): 504.

Step 5

((S)-1-methanesulfonyl-piperidin-3-yl)-{5-[5-(2-trimethylsilanyl-ethoxymethyl)-5H-pyrrolo[2,3-b]pyrazin-2-yl]-pyrimidin-4-yl}-amine (40 mg) was dissolved in 50% trifluoroacetic acid/dichloromethane at 5° C. and stirred at 15° C. for 2 hours. All solvent was evaporated and the residue treated with a solution of methanol (5 ml), methylene chloride (15 ml) and triethylamine (3 ml). This was stirred for 4 hours. Solvent was evaporated and the residue triturated with ethyl acetate. The salts were filtered and the solution was washed with water/brine, dried (MgSO$_4$) and concentrated in vacuo. The residue was triturated with ether to give 20 mg (65%) of a solid, ((S)-1-methanesulfonyl-piperidin-3-yl)-[5-(5H-pyrrolo[2,3-b]pyrazin-2-yl)-pyrimidin-4-yl]-amine. MS (ES+): 374.

Example 77

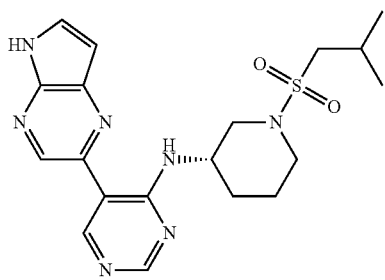

[(S)-1-(2-Methyl-propane-1-sulfonyl)-piperidin-3-yl]-[5-(5H-pyrrolo[2,3-b]pyrazin-2-yl)-pyrimidin-4-yl]-amine Step 1

A solution of (5-bromo-2-methylsulfanyl-pyrimidin-4-yl)-(S)-piperidin-3-yl-amine (1.0 g, 3.3 mmol) from Scheme 1, step 1, Example 76 and diisopropylethylamine (1.6 ml, 6.6 mmol) in dichloromethane (15 ml) was cooled to 5° C. and treated with a solution of 2-methylpropane-1-sulfonyl chloride (0.52 g, 3.3 mmol) in dichloromethane (2 ml) similar to step 2. This was stirred at room temperature for 16 hours, washed with water, dried (MgSO$_4$) and evaporated to give an oil. This was purified by silica gel chromatography (50-80% ethyl acetate/hexane) to give 1.0 g (65%) (5-bromo-2-methylsulfanyl-pyrimidin-4-yl)-[(S)-1-(2-methyl-propane-1-sulfonyl)-piperidin-3-yl]-amine. MS (ES+): 424

Step 2

Starting with (5-bromo-2-methylsulfanyl-pyrimidin-4-yl)-[(S)-1-(2-methyl-propane-1-sulfonyl)-piperidin-3-yl]-amine from above and 5-(2-trimethylsilanyl-ethoxymethyl)-2-trimethylstannanyl-5H-pyrrolo[2,3-b]pyrazine described in step 3 of Example 76, and using similar synthetic procedures of steps 4-5 described herein from Example 76, gave [(S)-1-(2-methyl-propane-1-sulfonyl)-piperidin-3-yl]-[5-(5H-pyrrolo[2,3-b]pyrazin-2-yl)-pyrimidin-4-yl]-amine. MS (ES+): 416.

Example 78

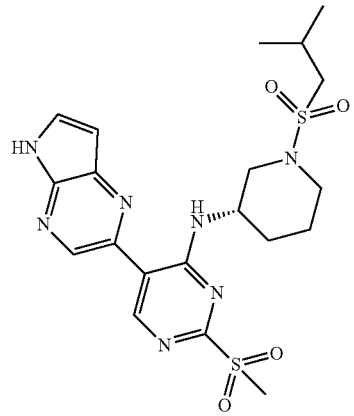 [SMILES: CC(C)CS(=O)(=O)N1CCC[C@H](Nc2nc(S(C)(=O)=O)ncc2-c2cnc3[nH]ccc3n2)C1]

N*4*-[(S)-1-(2-Methyl-propane-1-sulfonyl)-piperidin-3-yl]-5-(5H-pyrrolo[2,3-b]pyrazin-2-yl)-pyrimidine-2,4-diamine Step 1

A solution of [(S)-1-(2-methyl-propane-1-sulfonyl)-piperidin-3-yl]-{2-methylsulfanyl-5-[5-(2-trimethylsilanyl-ethoxymethyl)-5H-pyrrolo[2,3-b]pyrazin-2-yl]-pyrimidin-4-yl}-amine (650 mg, 1.1 mmol) prepared in step 2 of Example 77 above in tetrahydrofuran (5 ml) and methanol (8 ml) was treated with a solution of potassium peroxymonosulfate dissolved in water (4 ml) at 5° C. and stirred at room temperature for 16 hours. The reaction mixture was diluted with water and extracted into dichloromethane (2×). The organic layers were dried (MgSO$_4$) and concentrated in vacuo. Purification was by chromatography (silica gel, 40 g, 5% methanol/dichloromethane) which gave {2-methanesulfonyl-5-[5-(2-trimethysilanyl-ethoxymethyl)-5H-pyrrolo[2,3-b]pyrazin-2-yl]-pyrimidin-4-yl}-[(S)-1-(2-methyl-propane-1-sulfonyl)-piperidin-3-yl]-amine as a foam ~450 mg. MS (ES+): 623.

Step 2

In a 10 mL sealed tube {2-methanesulfonyl-5-[5-(2-trimethysilanyl-ethoxymethyl)-5H-pyrrolo[2,3-b]pyrazin-2-yl]-pyrimidin-4-yl}-[(S)-1-(2-methyl-propane-1-sulfonyl)-piperidin-3-yl]-amine (38 mg, 609 µmol) and ammonium hydroxide (450 mg, 0.5 ml, 12.8 mmol) were combined with 1,4-dioxane (2 ml) to give a light yellow solution. The reaction mixture was heated to 90° C. and stirred for 6 h. It was concentrated and diluted with water, extracted with ethyl acetate (2×20 ml). The organic layers were dried (MgSO$_4$) and concentrated to give N*4*-[(S)-1-(2-methyl-propane-1-sulfonyl)-piperidin-3-yl]-5-[5-(2-trimethylsilanyl-ethoxymethyl)-5H-pyrrolo[2,3-b]pyrazin-2-yl]-pyrimidine-2,4-diamine as a yellow foaming solid. MS (ES+): 561.

Step 3

N*4*-[(S)-1-(2-methyl-propane-1-sulfonyl)-piperidin-3-yl]-5-[5-(2-trimethylsilanyl-ethoxymethyl)-5H-pyrrolo[2,3-b]pyrazin-2-yl]-pyrimidine-2,4-diamine was de-protected in a manner similar to step 5, Example 1 to give N*4*-[(S)-1-

(2-Methyl-propane-1-sulfonyl)-piperidin-3-yl]-5-(5H-pyr-rolo[2,3-b]pyrazin-2-yl)-pyrimidine-2,4-diamine. MS (ES+): 431.

Example 79

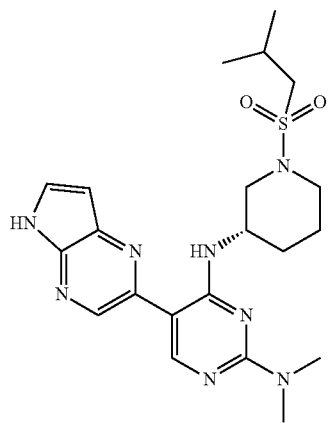 [SMILES: CC(C)CS(=O)(=O)N1CCC[C@H](Nc2nc(N(C)C)ncc2-c2cnc3[nH]ccc3n2)C1]

N*2*,N*2*-Dimethyl-N*4*-[(S)-1-(2-methyl-pro-pane-1-sulfonyl)-piperidin-3-yl]-5-(5H-pyrrolo[2,3-b]pyrazin-2-yl)-pyrimidine-2,4-diamine
RO5514181-000-001

From {2-methanesulfonyl-5-[5-(2-trimethysilanyl-ethoxymethyl)-5H-pyrrolo[2,3-b]pyrazin-2-yl]-pyrimidin-4-yl}-[(S)-1-(2-methyl-propane-1-sulfonyl)-piperidin-3-yl]-amine derived from Example 3, step 1, dimethylamine was used to displace the methylsulfone similar to examples above and the de-protection step was similar to step 5 of Example 76 to give N*2*,N*2*-dimethyl-N*4*-[(S)-1-(2-methyl-pro-pane-1-sulfonyl)-piperidin-3-yl]-5-(5H-pyrrolo[2,3-b]pyrazin-2-yl)-pyrimidine-2,4-diamine. MS (ES+): 459.

Example 80

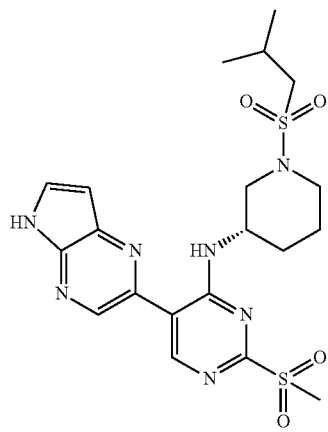

[2-Methanesulfonyl-5-(5H-pyrrolo[2,3-b]pyrazin-2-yl)-pyrimidin-4-yl]-[(S)-1-(2-methyl-propane-1-sulfonyl)-piperidin-3-yl]-amine From {2-methanesulfonyl-5-[5-(2-trimethysilanyl-ethoxymethyl)-5H-pyrrolo[2,3-b]pyrazin-2-yl]-pyrimidin-4-yl}-[(S)-1-(2-methyl-propane-1-sulfonyl)-piperidin-3-yl]-amine from step 1, Example 3, and the de-protection step was similar to step 5 of Example 76 to give [2-methanesulfonyl-5-(5H-pyrrolo[2,3-b]pyrazin-2-yl)-pyrimidin-4-yl]-[(S)-1-(2-methyl-propane-1-sulfonyl)-piperidin-3-yl]-amine. MS (ES+): 494.

Example 81

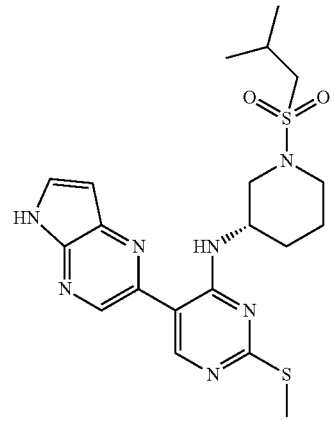 [SMILES: CSc1ncc(-c2cnc3[nH]ccc3n2)c(N[C@H]2CCCN(S(=O)(=O)CC(C)C)C2)n1]

[(S)-1-(2-Methyl-propane-1-sulfonyl)-piperidin-3-yl]-[2-methylsulfanyl-5-(5H-pyrrolo[2,3-b]pyrazin-2-yl)-pyrimidin-4-yl]-amine

[(S)-1-(2-methyl-propane-1-sulfonyl)-piperidin-3-yl]-{2-methylsulfanyl-5-[5-(2-trimethylsilanyl-ethoxymethyl)-5H-pyrrolo[2,3-b]pyrazin-2-yl]-pyrimidin-4-yl}-amine (650 mg, 1.1 mmol) from step 2 of Example 2 was de-protected in a step similar to step 5 of Example 76 to give [(S)-1-(2-methyl-propane-1-sulfonyl)-piperidin-3-yl]-[2-methylsulfa-nyl-5-(5H-pyrrolo[2,3-b]pyrazin-2-yl)-pyrimidin-4-yl]-amine. MS (ES+): 462.

Example 82

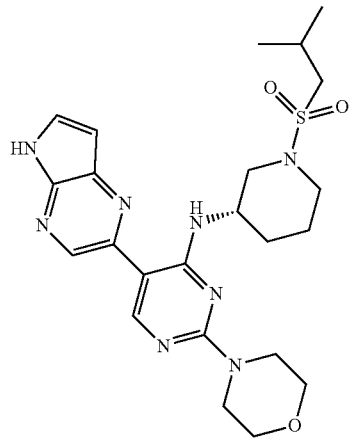 [SMILES: CC(C)CS(=O)(=O)N1CCC[C@H](Nc2nc(N3CCOCC3)ncc2-c2cnc3[nH]ccc3n2)C1]

[(S)-1-(2-Methyl-propane-1-sulfonyl)-piperidin-3-yl]-[2-morpholin-4-yl-5-(5H-pyrrolo[2,3-b]pyrazin-2-yl)-pyrimidin-4-yl]-amine In a dioxane solution of {2-methanesulfonyl-5-[5-(2-trimethysilanyl-ethoxymethyl)-5H-pyrrolo[2,3-b]pyrazin-2-yl]-pyrimidin-4-yl}-[(S)-1-(2-methyl-propane-1-sulfonyl)-piperidin-3-yl]-amine from Example 3, step 1, morpholine was used to displace the methylsulfone similar to examples above and the de-protection step was similar to step 5 of Example 76 to give [(S)-1-(2-methyl-propane-1-sulfonyl)-piperidin-3-yl]-[2-morpholin-4-yl-5-(5H-pyrrolo[2,3-b]pyrazin-2-yl)-pyrimidin-4-yl]-amine. MS (ES+): 501.

Example 83

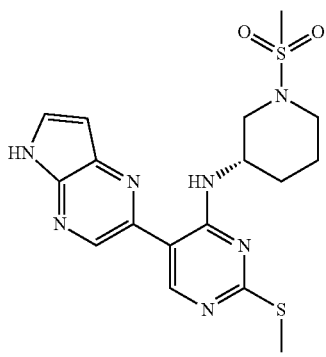 [SMILES: CSc1ncc(-c2cnc3[nH]ccc3n2)c(N[C@H]2CCCN(S(C)(=O)=O)C2)n1]

((S)-1-Methanesulfonyl-piperidin-3-yl)-[2-methylsulfanyl-5-(5H-pyrrolo[2,3-b]pyrazin-2-yl)-pyrimidin-4-yl]-amine The product of step 3, Example 76, ((S)-1-methanesulfonyl-piperidin-3-yl)-{2-methylsulfanyl-5-[5-(2-trimethylsilanyl-ethoxymethyl)-5H-pyrrolo[2,3-b]pyrazin-2-yl]-pyrimidin-4-yl}-amine was de-protected in a manner similar to step 5 of Example 76 to give ((S)-1-methanesulfonyl-piperidin-3-yl)-[2-methylsulfanyl-5-(5H-pyrrolo[2,3-b]pyrazin-2-yl)-pyrimidin-4-yl]-amine. MS (ES+): 420.

Example 84

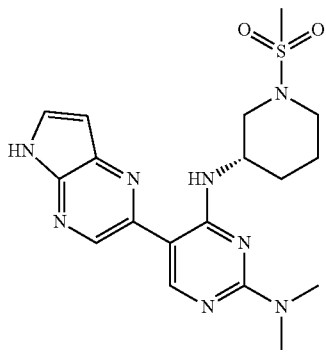

N*4*-((S)-1-Methanesulfonyl-piperidin-3-yl)-N*2*,N*2*-dimethyl-5-(5H-pyrrolo[2,3-b]pyrazin-2-yl)-pyrimidine-2,4-diamine Step 1

A solution of ((S)-1-methanesulfonyl-piperidin-3-yl)-{2-methylsulfanyl-5-[5-(2-trimethylsilanyl-ethoxymethyl)-5H-pyrrolo[2,3-b]pyrazin-2-yl]-pyrimidin-4-yl}-amine, derived from Example 76, step 3 (180 mg, 0.33 mmol) in methylene chloride (25 ml) was cooled to 10° C. and treated with m-chloroperbenzoic acid (113 mg, 0.66 mmol) for 1 hour at room temperature. The reaction mixture was washed with aqueous sodium thiosulfate, dried and concentrated. The crude material was purified by flash chromatography (0-40% ethyl acetate/dichloromethane) to give ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine as a yellow solid (190 mg, 84%) MS (ES+): 581. This was taken to the next step.

Step 2

Dimethylamine was used to displace the methylsulfone from above similar to examples above and the de-protection step was similar to step 5 of Example 76 to give N*4*-((S)-1-methanesulfonyl-piperidin-3-yl)-N*2*,N*2*-dimethyl-5-(5H-pyrrolo[2,3-b]pyrazin-2-yl)-pyrimidine-2,4-diamine. MS (ES+): 417.

Example 85

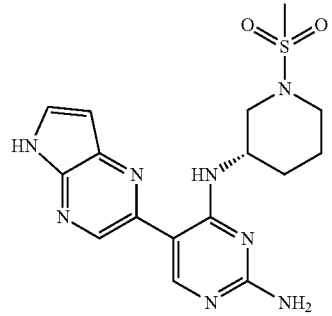 [SMILES: CS(=O)(=O)N1CCC[C@H](Nc2nc(N)ncc2-c2cnc3[nH]ccc3n2)C1]

N*4*-((S)-1-Methanesulfonyl-piperidin-3-yl)-5-(5H-pyrrolo[2,3-b]pyrazin-2-yl)-pyrimidine-2,4-diamine A suspension of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine from Example 84, step 1 in ammonium hydroxide in dioxane was heated at 90° C. for 6 hours. The reaction was concentrated and diluted with water and extracted with EtOAc (2×20 ml). The organic layers were dried over MgSO₄ and concentrated in vacuo to give a yellow foaming solid. MS (ES+): 561. The de-protection step was similar to step 5 of Example 76 to give N*4*-((S)-1-methanesulfonyl-piperidin-3-yl)-5-(5H-pyrrolo[2,3-b]pyrazin-2-yl)-pyrimidine-2,4-diamine. MS (ES+): 389.

193

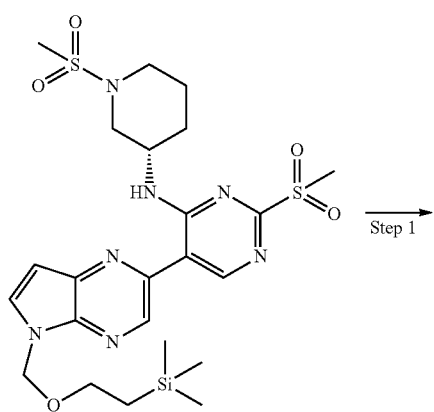

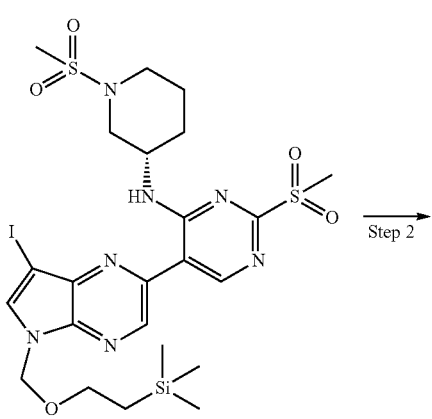

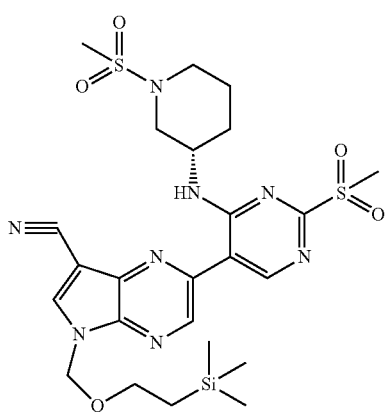

194

Example 86

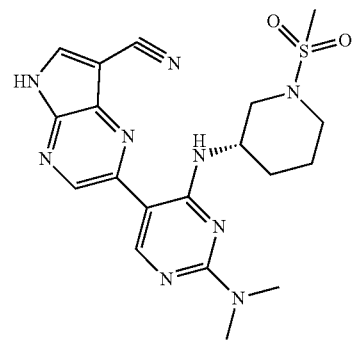 [SMILES: CN(C)c1ncc(-c2cnc3[nH]cc(C#N)c3n2)c(N[C@H]2CCCN(S(C)(=O)=O)C2)n1]

2-[2-Dimethylamino-4-((S)-1-methanesulfonyl-piperidin-3-ylamino)-pyrimidin-5-yl]-5H-pyrrolo[2,3-b]pyrazine-7-carbonitrile Step 1

A solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1 (70 mg, 0.12 mmol) in acetone (0.5 ml) was treated with N-Iodosuccinimide (41 mg, 0.18 mmol) and stirred at 20° C. for 16 hours. The crude reaction mixture was concentrated in vacuo and was purified by silica gel chromatography (0% to 40% ethyl acetate/dichloromethane) to give 67 mg (79%) of {5-[7-Iodo-5-(2-trimethylsilanyl-ethoxymethyl)-5H-pyrrolo[2,3-b]pyrazin-2-yl]-2-methanesulfonyl-pyrimidin-4-yl}-((S)-1-methanesulfonyl-piperidin-3-yl)-amine. MS (ES+): 708.

Step 2

A solution of {5-[7-Iodo-5-(2-trimethylsilanyl-ethoxymethyl)-5H-pyrrolo[2,3-b]pyrazin-2-yl]-2-methanesulfonyl-pyrimidin-4-yl}-((S)-1-methanesulfonyl-piperidin-3-yl)-amine (65 mg, 0.091 mmol) and dicyanozinc (11 mg, 0.092 mmol) was combined with dimethylformamide (0.5 ml) (1% water) and the solution thoroughly degassed. To this was added 1,1'-bis(diphenylphosphino)ferrocene (dppf) (1.0 mg, 1.84 µmol) and Tris(dibenzylideneacetone)dipalladium(0) ($Pd_2(dba)_3$) (4.2 mg, 4.6 µmol) and the mixture was heated to 120° C. for 1.5 hours. This was cooled, diluted with brine and water, extracted with ethyl acetate, dried and purified by flash chromatography (silica gel, 0% to 50% ethyl acetate/dichloromethane) to give 2-[2-methanesulfonyl-4-((S)-1-methanesulfonyl-piperidin-3-ylamino)-pyrimidin-5-yl]-5-(2-trimethylsilanyl-ethoxymethyl)-5H-pyrrolo[2,3-b]pyrazine-7-carbonitrile (35 mg, 63%). MS: (ES+): 607.

Step 3

In a dioxane 2-[2-methanesulfonyl-4-((S)-1-methanesulfonyl-piperidin-3-ylamino)-pyrimidin-5-yl]-5-(2-trimethylsilanyl-ethoxymethyl)-5H-pyrrolo[2,3-b]pyrazine-7-carbonitrile derived from step 2 above, dimethylamine was used to displace the methylsulfone similar to examples above and the de-protection step was similar to Scheme 1, step 5 to give 2-[2-dimethylamino-4-((S)-1-methanesulfonyl-piperidin-3-ylamino)-pyrimidin-5-yl]-5H-pyrrolo[2,3-b]pyrazine-7-carbonitrile. MS: (ES+): 442.

Example 87

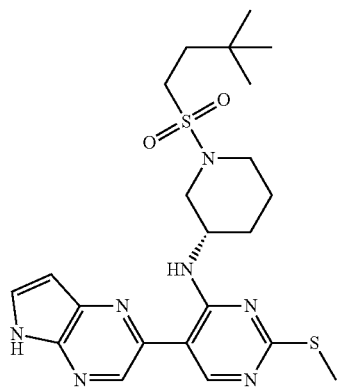 [SMILES: CSc1ncc(-c2cnc3[nH]ccc3n2)c(N[C@H]2CCCN(S(=O)(=O)CCC(C)(C)C)C2)n1]

[(S)-1-(3,3-Dimethylbutane-1-sulfonyl)-piperidin-3-yl]-[2-methylsulfanyl-5-(5H-pyrrolo[2,3-b]pyrazin-2-yl)-pyrimidin-4-yl]-amine From (5-bromo-2-methylsulfanyl-pyrimidin-4-yl)-((S)-1-methanesulfonyl-piperidin-3-yl)-amine, Example 76, step 2 using 3,3-dimethyl-1-butanesulfonyl chloride (prepared according to *Journal of Organic Chemistry* (1956), 21 385-7), to give (5-Bromo-2-methylsulfanyl-pyrimidin-4-yl)-[(S)-1-(3,3-dimethyl-butane-1-sulfonyl)-piperidin-3-yl]-amine and followed by steps 3-5 as in Example 76 gave [(S)-1-(3,3-dimethylbutane-1-sulfonyl)-piperidin-3-yl]-[2-methylsulfanyl-5-(5H-pyrrolo[2,3-b]pyrazin-2-yl)-pyrimidin-4-yl]-amine. MS (ES+): 490.

Example 88

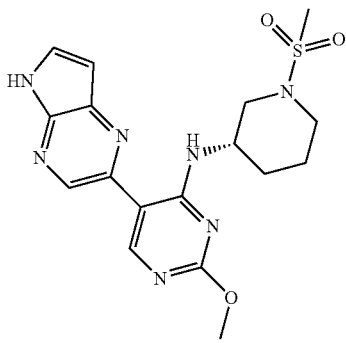 [SMILES: COc1ncc(-c2cnc3[nH]ccc3n2)c(N[C@H]2CCCN(S(C)(=O)=O)C2)n1]

((S)-1-Methanesulfonyl-piperidin-3-yl)-[2-methoxy-5-(5H-pyrrolo[2,3-b]pyrazin-2-yl)-pyrimidin-4-yl]-amine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, sodium methoxide/tetrahydrofuran was used to displace the methyl-sulfone similar to examples above and the de-protection step was similar to step 5 to give ((S)-1-methanesulfonyl-piperidin-3-yl)-[2-methoxy-5-(5H-pyrrolo[2,3-b]pyrazin-2-yl)-pyrimidin-4-yl]-amine. MS (ES+): 404.

Example 89

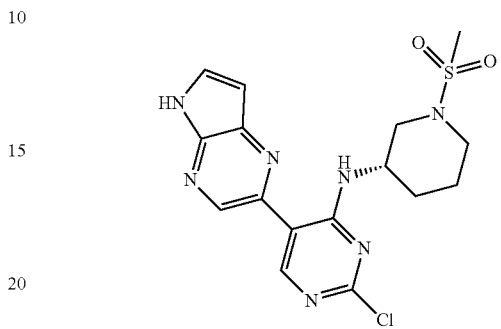

[2-Chloro-5-(5H-pyrrolo[2,3-b]pyrazin-2-yl)-pyrimidin-4-yl]-((S)-1-methanesulfonyl-piperidin-3-yl)-amine Step 1

A solution 5-bromo-2,4-dichloro-pyrimidine 4 g, 17.6 mmol), (S)-tert-butyl 3-aminopiperidine-1-carboxylate (3.6 g, 17.6 mmol) and diisopropylethylamine (3.1 ml, 18 mmol) in dichloroethane (200 ml) was warmed to 40-50° C. for 16 hours. The reaction was cooled and washed with water, dried (MgSO$_4$), and filtered. The oil was purified by silica gel chromatography (10-25% ethyl acetate/hexane) to give (S)-3-(5-bromo-2-chloro-pyrimidin-4-ylamino)-piperidine-1-carboxylic acid tert-butyl ester as an oil that was taken to the next step. The oil was diluted with dichloromethane (100 ml) cooled to 5° C. and treated with trifluoroacetic acid (40 ml). After stirring at room temperature for 5 hours, all solvent was evaporated. The residue was dissolved in chloroform (150 ml) and washed with cold dilute aqueous sodium carbonate. The organics were dried (MgSO$_4$) and evaporated to give an oil that solidified on standing in ether/hexane to give 3.5 g (68%) of (5-bromo-2-chloro-pyrimidin-4-yl)-(S)-piperidin-3-yl-amine as a solid. $^1$H NMR (300 MHz), dmso-d) δ ppm, 8.23 (s, 1H), 7.17 (s, 1H), 3.99 (m, 1H).

Step 2

A solution of (5-bromo-2-chloro-pyrimidin-4-yl)-(S)-piperidin-3-yl-amine (3.5 g, 12.2 mmol) and diisopropylamine (6 g, 46 mmol) in dichloromethane was cooled to 5° C. and treated with methansulfonyl chloride (2.1 g, 18 mmole). After stirring at 20° C. for 2 hours, the reaction was concentrated purified by silica gel chromatography to give 3.1 g (43% from step 1) of (5-Bromo-2-chloro-pyrimidin-4-yl)-((S)-3-methanesulfonyl-cyclohexyl)-amine.

Step 3

(5-Bromo-2-chloro-pyrimidin-4-yl)-((S)-3-methanesulfonyl-cyclohexyl)-amine from above was coupled with the tin reagent prepared in Example 76, step 3 followed by step 4-5 in Example 76 to give [2-Chloro-5-(5H-pyrrolo[2,3-b]

pyrazin-2-yl)-pyrimidin-4-yl]-((S)-1-methanesulfonyl-piperidin-3-yl)-amine. MS (ES+): 408.

Example 90

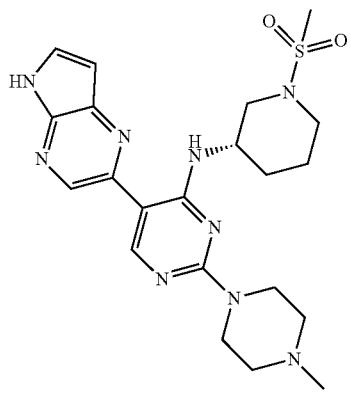 [SMILES: CN1CCN(c2ncc(-c3cnc4[nH]ccc4n3)c(N[C@H]3CCCN(S(C)(=O)=O)C3)n2)CC1]

((S)-1-Methanesulfonyl-piperidin-3-yl)-[2-(4-methyl-piperazin-1-yl)-5-(5H-pyrrolo[2,3-b]pyrazin-2-yl)-pyrimidin-4-yl]-amine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, N-methylpiperazine was used to displace the methylsulfone similar to examples above and the de-protection step was similar to step 5, Example 76, to give ((S)-1-methanesulfonyl-piperidin-3-yl)-[2-(4-methyl-piperazin-1-yl)-5-(5H-pyrrolo[2,3-b]pyrazin-2-yl)-pyrimidin-4-yl]-amine. MS (ES+): 472.

Example 91

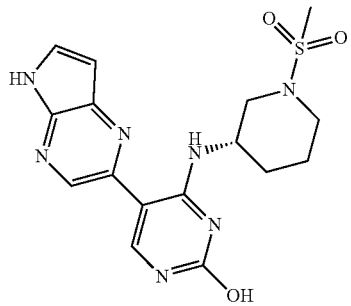 [SMILES: CS(=O)(=O)N1CCC[C@H](Nc2nc(O)ncc2-c2cnc3[nH]ccc3n2)C1]

4-((S)-1-Methanesulfonyl-piperidin-3-ylamino)-5-(5H-pyrrolo[2,3-b]pyrazin-2-yl)-pyrimidin-2-ol A solution of ((S)-1-methanesulfonyl-piperidin-3-yl)-[2-methoxy-5-(5H-pyrrolo[2,3-b]pyrazin-2-yl)-pyrimidin-4-yl]-amine (18 mg, 0.044 mmol) from Example 84, step 1, in water/dioxane was heated to 105° C. for 16 hr. Solvent was evaporated and the product purified by super critical chromatography (SFC) to give 4-((S)-1-methanesulfonyl-piperidin-3-ylamino)-5-(5H-pyrrolo[2,3-b]pyrazin-2-yl)-pyrimidin-2-ol. MS (ES+): 390.

Example 92

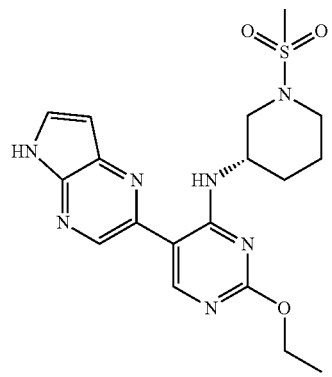 [SMILES: CCOc1ncc(-c2cnc3[nH]ccc3n2)c(N[C@H]2CCCN(S(C)(=O)=O)C2)n1]

[2-Ethoxy-5-(5H-pyrrolo[2,3-b]pyrazin-2-yl)-pyrimidin-4-yl]-((S)-1-methanesulfonyl-piperidin-3-yl)-amine In a tetrahydrofuran solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, sodium ethoxide/tetrahydrofuran was used to displace the methylsulfone similar to the example above and the de-protection step was similar to step 5, Example 76 to give [2-ethoxy-5-(5H-pyrrolo[2,3-b]pyrazin-2-yl)-pyrimidin-4-yl]-((S)-1-methanesulfonyl-piperidin-3-yl)-amine. MS (ES+): 418.

Example 93

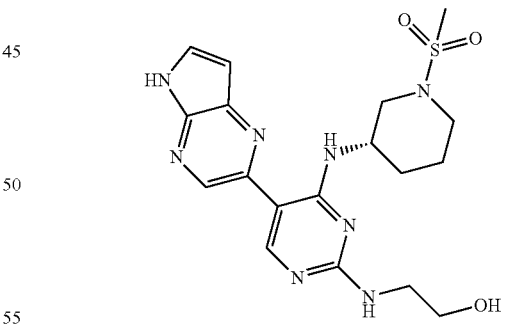

2-[4-((S)-1-Methanesulfonyl-piperidin-3-ylamino)-5-(5H-pyrrolo[2,3-b]pyrazin-2-yl)-pyrimidin-2-ylamino]-ethanol In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, ethanolamine was used to displace the methylsulfone similar to examples above and the de-protection step was similar to step 5, Example 76 to give 2-[4-((S)-1-methanesulfonyl-piperidin-3-ylamino)-5-(5H-pyrrolo[2,3-b]pyrazin-2-yl)-pyrimidin-2-ylamino]-ethanol. MS (ES+): 433.

Example 94

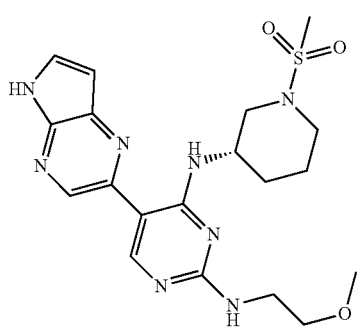

N*4*-((S)-1-Methanesulfonyl-piperidin-3-yl)-N*2*-(2-methoxy-ethyl)-5-(5H-pyrrolo[2,3-b]pyrazin-2-yl)-pyrimidine-2,4-diamine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1,2-methoxy-ethylamine was used to displace the methylsulfone similar to examples above and the de-protection step was similar to step 5 to give N*4*-((S)-1-Methanesulfonyl-piperidin-3-yl)-N*2*-(2-methoxy-ethyl)-5-(5H-pyrrolo[2,3-b]pyrazin-2-yl)-pyrimidine-2,4-diamine. MS (ES+): 447.

Example 95

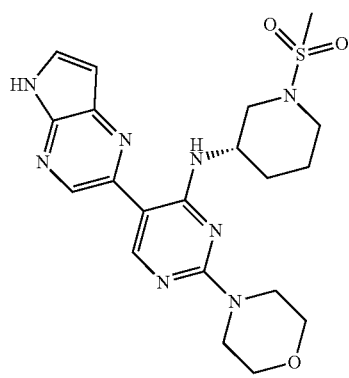

((S)-1-Methanesulfonyl-piperidin-3-yl)-[2-morpholin-4-yl-5-(5H-pyrrolo[2,3-b]pyrazin-2-yl)-pyrimidin-4-yl]-amine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, morpholine was used to displace the methylsulfone similar to examples above and the de-protection step was similar to step 5, Example 76 to give ((S)-1-methanesulfonyl-piperidin-3-yl)-[2-morpholin-4-yl-5-(5H-pyrrolo[2,3-b]pyrazin-2-yl)-pyrimidin-4-yl]-amine. MS (ES+): 459.

Example 96

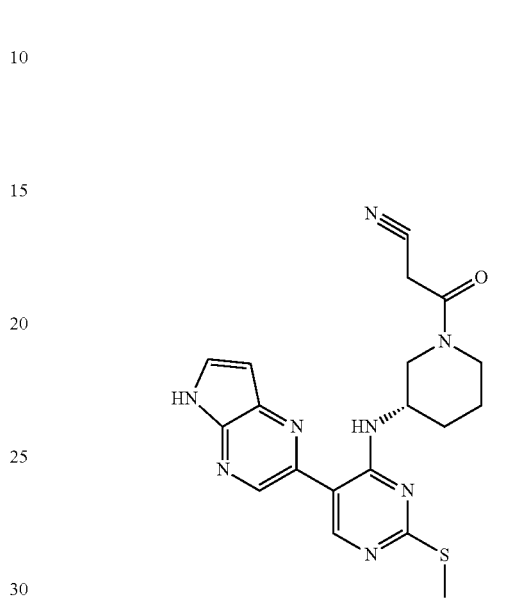

3-{(S)-3-[2-Methylsulfanyl-5-(5H-pyrrolo[2,3-b]pyrazin-2-yl)-pyrimidin-4-ylamino]-piperidin-1-yl}-3-oxo-propionitrile A tetrahydrofuran solution (6 ml) of (5-bromo-2-methylsulfanyl-pyrimidin-4-yl)-(S)-piperidin-3-yl-amine (from Example 76, step 1 above) (300 mg, 0.99 mmol), diazabicycloundecane (530 mg, 3.5 mmol) and ethyl 2-cyanoacetate was stirred at room temperature for 20 hours. The reaction was diluted with water and extracted with ethyl acetate (2×). The organics were dried and evaporated to give 3-[(S)-3-(5-bromo-2-methylsulfanyl-pyrimidin-4-ylamino)-piperidin-1-yl]-3-oxo-propionitrile as an oil. MS (ES+): 371.

The 3-[(S)-3-(5-bromo-2-methylsulfanyl-pyrimidin-4-ylamino)-piperidin-1-yl]-3-oxo-propionitrile from above (226 mg, 609 μmol) was cross-coupled with 5-(2-trimethylsilanyl-ethoxymethyl)-2-trimethylstannanyl-5H-pyrrolo[2,3-b]pyrazine prepared from 2-bromo-5-((2-(trimethylsilyl)ethoxy)methyl)-5H-pyrrolo[2,3-b]pyrazine (200 mg, 0.61 mmol) and tetrakistriphenylphosphine palladium (0) (35 mg, 0.03 mmol) in a manner similar to step 3, Example 76 to give 3-((S)-3-{2-methylsulfanyl-5-[5-(2-trimethylsilanyl-ethoxymethyl)-5H-pyrrolo[2,3-b]pyrazin-2-yl]-pyrimidin-4-ylamino}-piperidin-1-yl)-3-oxo-propionitrile (~40 mg). MS (ES+): 539.

The de-protection step was similar to step 5, Example 76, to give 3-{(S)-3-[2-methylsulfanyl-5-(5H-pyrrolo[2,3-b]pyrazin-2-yl)-pyrimidin-4-ylamino]-piperidin-1-yl}-3-oxo-propionitrile. MS (ES+): 409.

Example 97

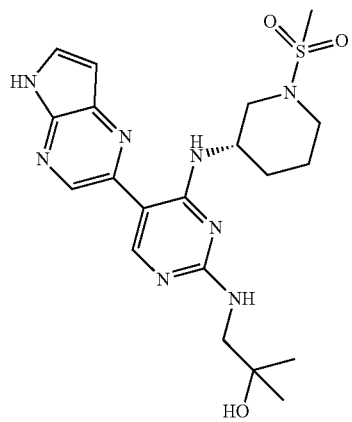

1-[4-((S)-1-Methanesulfonyl-piperidin-3-ylamino)-5-(5H-pyrrolo[2,3-b]pyrazin-2-yl)-pyrimidin-2-ylamino]-2-methyl-propan-2-ol In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1,1-amino-2-methylpropan-2-ol was used to displace the methylsulfone similar to examples above and the de-protection step was similar to step 5, Example 76 to give 1-[4-((S)-1-methane-sulfonyl-piperidin-3-ylamino)-5-(5H-pyrrolo[2,3-b]pyrazin-2-yl)-pyrimidin-2-ylamino]-2-methyl-propan-2-ol. MS (ES+): 461.

Example 98

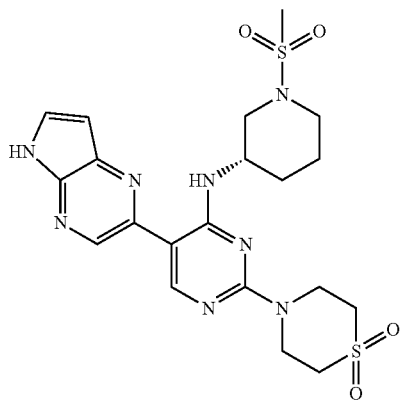 [SMILES: CS(=O)(=O)N1CCC[C@H](Nc2nc(N3CCS(=O)(=O)CC3)ncc2-c2cnc3[nH]ccc3n2)C1]

[2-(1,1-Dioxo-1lambda*6*-thiomorpholin-4-yl)-5-(5H-pyrrolo[2,3-b]pyrazin-2-yl)-pyrimidin-4-yl]-((S)-1-methanesulfonyl-piperidin-3-yl)-amine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, thiomorpholine 1,1-dioxide was used to displace the methylsulfone similar to examples above and the de-protection step was similar to step 5, Example 76, to give [2-(1,1-dioxo-1lambda*6*-thiomorpholin-4-yl)-5-(5H-pyrrolo[2,3-b]pyrazin-2-yl)-pyrimidin-4-yl]-((S)-1-methanesulfonyl-piperidin-3-yl)-amine. MS (ES+): 507.

Example 99

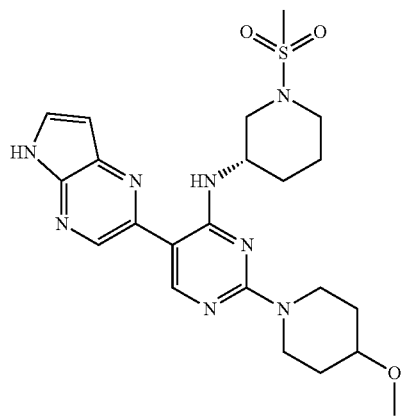

((S)-1-Methanesulfonyl-piperidin-3-yl)-[2-(4-methoxy-piperidin-1-yl)-5-(5H-pyrrolo[2,3-b]pyrazin-2-yl)-pyrimidin-4-yl]-amine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1,4-methoxy-piperidine was used to displace the methylsulfone similar to examples above and the de-protection step was similar to step 5, Example 76 to give ((S)-1-methanesulfonyl-piperidin-3-yl)-[2-morpholin-4-yl-5-(5H-pyrrolo[2,3-b]pyrazin-2-yl)-pyrimidin-4-yl]-amine. MS (ES+): 487.

Example 100

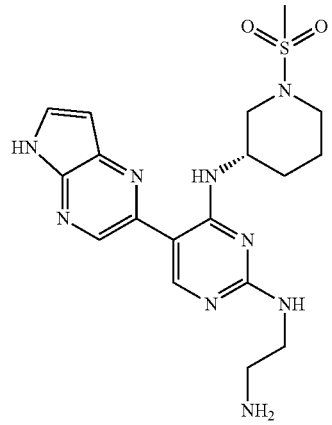 [SMILES: CS(=O)(=O)N1CCC[C@H](Nc2nc(NCCN)ncc2-c2cnc3[nH]ccc3n2)C1]

N*2*-(2-Amino-ethyl)-N*4*-((S)-1-methanesulfonyl-piperidin-3-yl)-5-(5H-pyrrolo[2,3-b]pyrazin-2-yl)-pyrimidine-2,4-diamine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, ethylenediamine was used to displace the methylsulfone similar to examples above and the de-protection step was similar to step 5, Example 76, to give N*2*-(2-amino-ethyl)-N*4*-((S)-1-methanesulfonyl-piperidin-3-yl)-5-(5H-pyrrolo[2,3-b]pyrazin-2-yl)-pyrimidine-2,4-diamine. MS: (ES+): 432.

Example 101

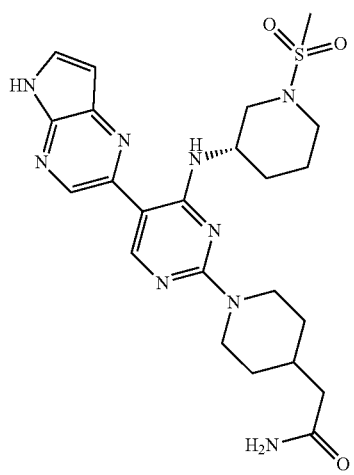

2-{1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetamide In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1,2-piperidin-4-yl-acetamide was used to displace the methylsulfone similar to examples above and the de-protection step was similar to step 5, Example 76, to give 2-{1-[4-((S)-1-Methanesulfonyl-piperidin-3-ylamino)-5-(5H-pyrrolo[2,3-b]pyrazin-2-yl)-pyrimidin-2-yl]-piperidin-4-yl}4-acetamide. MS: (ES+): 514.

Example 102

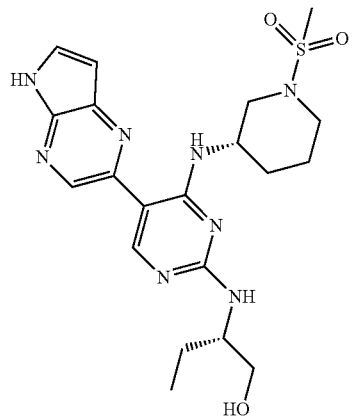

(S)-2-[4-((S)-1-Methanesulfonyl-piperidin-3-ylamino)-5-(5H-pyrrolo[2,3-b]pyrazin-2-yl)-pyrimidin-2-ylamino]-butan-1-ol In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, (S)-2-aminobutan-1-ol was used to displace the methylsulfone similar to examples above and the de-protection step was similar to step 5, Example 76, to give (S)-2-[4-((S)-1-methanesulfonyl-piperidin-3-ylamino)-5-(5H-pyrrolo[2,3-b]pyrazin-2-yl)-pyrimidin-2-ylamino]-butan-1-ol. MS: (ES+) 461.

Example 103

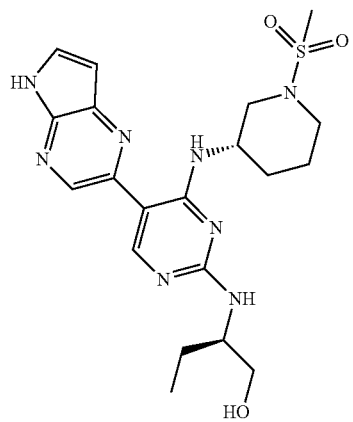

(R)-2-[4-((S)-1-Methanesulfonyl-piperidin-3-ylamino)-5-(5H-pyrrolo[2,3-b]pyrazin-2-yl)-pyrimidin-2-ylamino]-butan-1-ol In a dioxane solution of ((S)-1-methanesulfonyl-piperidin-3-yl)-{2-methanesulfonyl-5-[5-(2-trimethylsilanylethoxymethyl)-5H-pyrrolo[2,3-b]pyrazin-2-yl]-pyrimidin-4-yl}-amine derived from Example 84, step 1, (R)-2-aminobutan-1-ol was used to displace the methylsulfone similar to examples above and the de-protection step was similar to step 5, Example 76, to give (R)-2-[4-((S)-1-methanesulfonyl-piperidin-3-ylamino)-5-(5H-pyrrolo[2,3-b]pyrazin-2-yl)-pyrimidin-2-ylamino]-butan-1-ol. MS: (ES+) 461.

Example 104

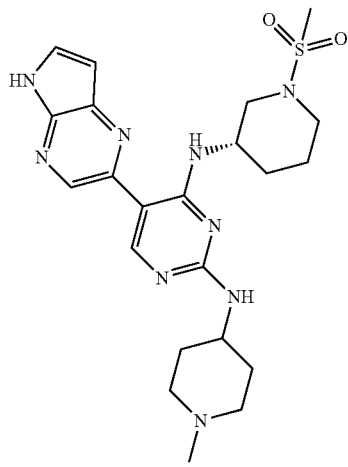

N*4*-((S)-1-Methanesulfonyl-piperidin-3-yl)-N*2*-(1-methyl-piperidin-4-yl)-5-(5H-pyrrolo[2,3-b]pyrazin-2-yl)-pyrimidine-2,4-diamine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1,1-methyl-piperidin-4-amino was used to displace the methylsulfone similar to examples above and the de-protection step was similar to step 5, Example 76, to give N*4*-((S)-1-methanesulfonyl-piperidin-3-yl)-N*2*-(1-methyl-piperidin-4-yl)-5-(5H-pyrrolo[2,3-b]pyrazin-2-yl)-pyrimidine-2,4-diamine. MS: (ES+) 486.

Example 105

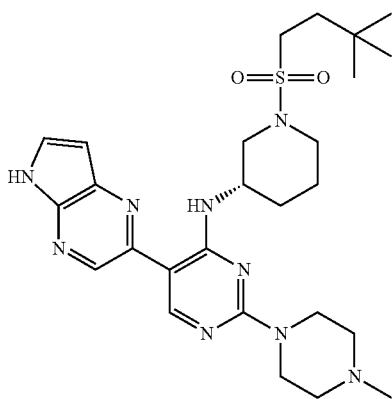 [SMILES: CN1CCN(c2ncc(-c3cnc4[nH]ccc4n3)c(N[C@H]3CCCN(S(=O)(=O)CCC(C)(C)C)C3)n2)CC1]

[(S)-1-(3,3-Dimethyl-butane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine From the intermediate derived in a similar manner as Example 3, step 1 (R=3,3-dimethylbutyl, 3,3-dimethyl-1-butanesulfonyl chloride, prepared according to *Journal of Organic Chemistry* (1956), 21 385-7), in dioxane 1-methylpiperazine was used to displace the methylsulfone similar to examples above and the de-protection step was similar to step 5, Example 76, to give [(S)-1-(3,3-dimethyl-butane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine. MS: (ES+): 542.

Example 106

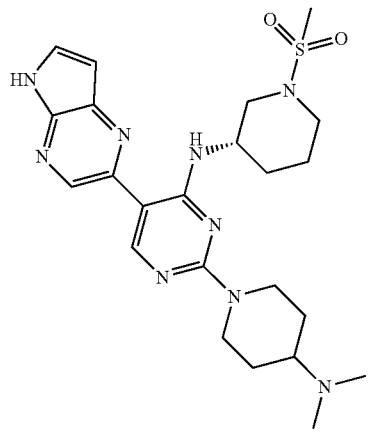

[2-(4-Dimethylamino-piperidin-1-yl)-5-(5H-pyrrolo[2,3-b]pyrazin-2-yl)-pyrimidin-4-yl]-((S)-1-methanesulfonyl-piperidin-3-yl)-amine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, dimethylpiperidin-4-ylamine was used to displace the methylsulfone similar to examples above and the de-protection step was similar to step 5, Example 76, to give [2-(4-dimethylamino-piperidin-1-yl)-5-(5H-pyrrolo[2,3-b]pyrazin-2-yl)-pyrimidin-4-yl]-((S)-1-methanesulfonyl-piperidin-3-yl)-amine. MS: (ES+): 500.

Example 107

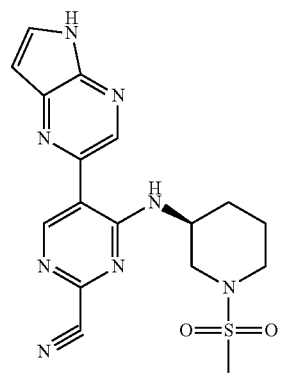

4-((S)-1-Methanesulfonyl-piperidin-3-ylamino)-5-(5H-pyrrolo[2,3-b]pyrazin-2-yl)-pyrimidine-2-carbonitrile A solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1 was treated with tetra-n-butyl ammonium cyanide in acetonitrile at 100° C. for 4 hours. Solvent was concentrated to dryness and purified by chromatography to give a protected intermediate that was de-protected similar to step 5, Example 76, to give 4-((S)-1-methanesulfonyl-piperidin-3-ylamino)-5-(5H-pyrrolo[2,3-b]pyrazin-2-yl)-pyrimidine-2-carbonitrile. MS: ES+: 399

Example 108

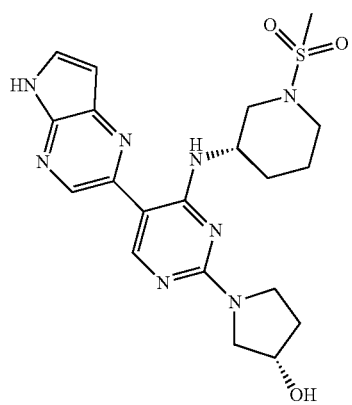 [SMILES: CS(=O)(=O)N1CCC[C@H](Nc2nc(N3CC[C@H](O)C3)ncc2-c2cnc3[nH]ccc3n2)C1]

(S)-1-[4-((S)-1-Methanesulfonyl-piperidin-3-ylamino)-5-(5H-pyrrolo[2,3-b]pyrazin-2-yl)-pyrimidin-2-yl]-pyrrolidin-3-ol In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, (S)-pyrrolidin-3-ol was used to displace the methylsulfone similar to examples above and the de-protection step was similar to step 5, Example 76, to give (R)-1-[4-((S)-1-methanesulfonyl-piperidin-3-ylamino)-5-(5H-pyrrolo[2,3-b]pyrazin-2-yl)-pyrimidin-2-yl]-pyrrolidin-3-ol. MS: (ES+): 459

Example 109

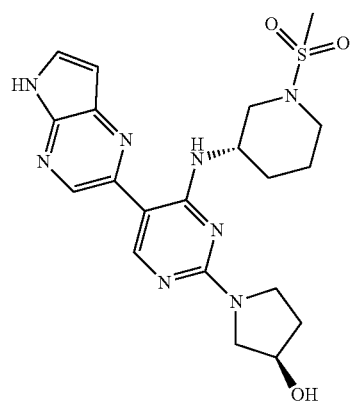 [SMILES: CS(=O)(=O)N1CCC[C@H](Nc2nc(N3CC[C@@H](O)C3)ncc2-c2cnc3[nH]ccc3n2)C1]

(R)-1-[4-((S)-1-Methanesulfonyl-piperidin-3-ylamino)-5-(5H-pyrrolo[2,3-b]pyrazin-2-yl)-pyrimidin-2-yl]-pyrrolidin-3-ol In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, (R)-pyrrolidin-3-ol was used to displace the methylsulfone similar to examples above and the de-protection step was similar to step 5, Example 76, to give (R)-1-[4-((R)-1-methanesulfonyl-piperidin-3-ylamino)-5-(5H-pyrrolo[2,3-b]pyrazin-2-yl)-pyrimidin-2-yl]-pyrrolidin-3-ol. MS: (ES+): 459

Example 110

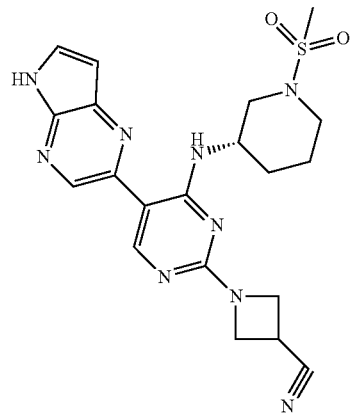 [SMILES: CS(=O)(=O)N1CCC[C@H](Nc2nc(N3CC(C#N)C3)ncc2-c2cnc3[nH]ccc3n2)C1]

1-[4-((S)-1-Methanesulfonyl-piperidin-3-ylamino)-5-(5H-pyrrolo[2,3-b]pyrazin-2-yl)-pyrimidin-2-yl]-azetidine-3-carbonitrile In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, azetidine-3-carbonitrile was used to displace the methylsulfone similar to examples above and the de-protection step was similar to step 5, Example 76, to give 1-[4-((S)-1-methanesulfonyl-piperidin-3-ylamino)-5-(5H-pyrrolo[2,3-b]pyrazin-2-yl)-pyrimidin-2-yl]-azetidine-3-carbonitrile. MS: (ES+): 454

Example 111

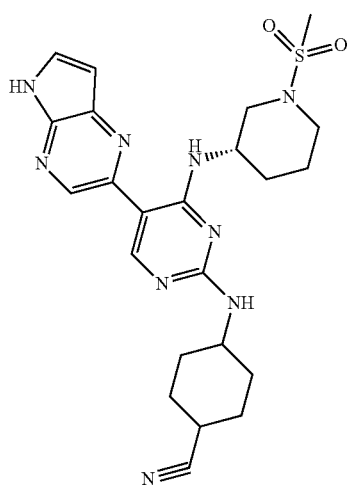 [SMILES: CS(=O)(=O)N1CCC[C@H](Nc2nc(NC3CCC(C#N)CC3)ncc2-c2cnc3[nH]ccc3n2)C1]

4-[4-((S)-1-Methanesulfonyl-piperidin-3-ylamino)-5-(5H-pyrrolo[2,3-b]pyrazin-2-yl)-pyrimidin-2-ylamino]-cyclohexanecarbonitrile In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, 4-amino-cyclohexanecarbonitrile was used to displace the methylsulfone similar to examples above and the de-protection step was similar to step 5, Example 76, to give 4-[4-((S)-1-Methanesulfonyl-piperidin-3-ylamino)-5-(5H-pyrrolo[2,3-b]pyrazin-2-yl)-pyrimidin-2-ylamino]-cyclohexanecarbonitrile. MS: (ES+): 496.

Example 112

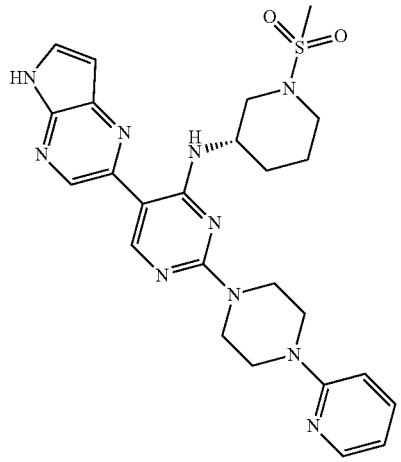 [SMILES: CS(=O)(=O)N1CCC[C@H](Nc2nc(N3CCN(c4ccccn4)CC3)ncc2-c2cnc3[nH]ccc3n2)C1]

((S)-1-Methanesulfonyl-piperidin-3-yl)-[2-(4-pyridin-2-yl-piperazin-1-yl)-5-(5H-pyrrolo[2,3-b]pyrazin-2-yl)-pyrimidin-4-yl]-amine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1,1-pyridin-2-yl-piperazine was used to displace the methylsulfone similar to examples above and the de-protection step was similar to step 5, Example 76, to give ((S)-1-methanesulfonyl-piperidin-3-yl)-[2-(4-pyridin-2-yl-piperazin-1-yl)-5-(5H-pyrrolo[2,3-b]pyrazin-2-yl)-pyrimidin-4-yl]-amine. MS: (ES+): 535

Example 113

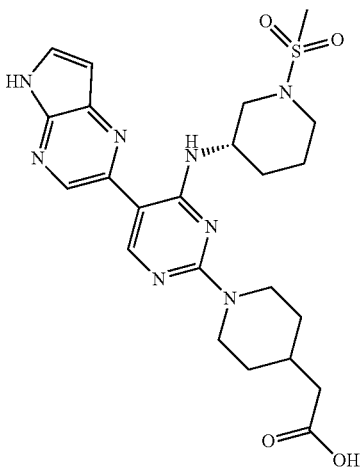 [SMILES: CS(=O)(=O)N1CCC[C@H](Nc2nc(N3CCC(CC(=O)O)CC3)ncc2-c2cnc3[nH]ccc3n2)C1]

{1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetic acid In a dioxane solution of ((S)-1-methanesulfonyl-piperidin-3-yl)-{2-methanesulfonyl-5-[5-(2-trimethylsilanylethoxymethyl)-5H-pyrrolo[2,3-b]pyrazin-2-yl]-pyrimidin-4-yl}-amine derived from Example 84, step 1, Piperidin-4-yl-acetic acid was used to displace the methylsulfone similar to examples above and the de-protection step was similar to step 5, Example 76, to give {1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetic acid. MS: (ES+): 515

Example 114

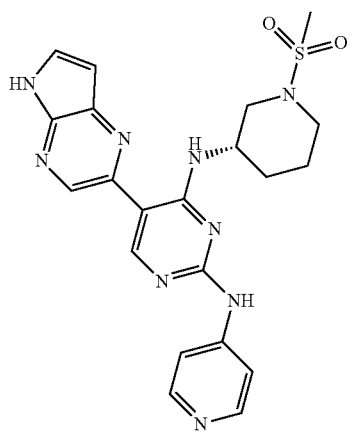 [SMILES: CS(=O)(=O)N1CCC[C@H](Nc2nc(Nc3ccncc3)ncc2-c2cnc3[nH]ccc3n2)C1]

N*4*-((S)-1-Methanesulfonyl-piperidin-3-yl)-N*2*-pyridin-4-yl-5-(5H-pyrrolo[2,3-b]pyrazin-2-yl)-pyrimidine-2,4-diamine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, pyridin-4-ylamine was used to displace the methylsulfone similar to examples above and the de-protection step was similar to step 5, Example 76, to give N*4*-((S)-1-methanesulfonyl-piperidin-3-yl)-N*2*-pyridin-4-yl-5-(5H-pyrrolo[2,3-b]pyrazin-2-yl)-pyrimidine-2,4-diamine. MS (ES+): 466.

Example 115

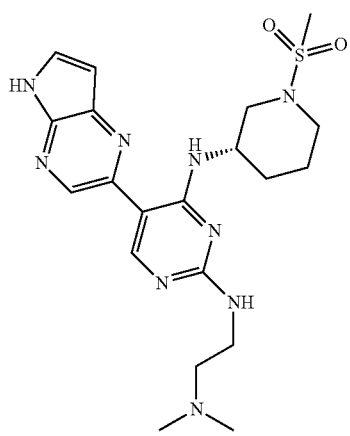 [SMILES: CN(C)CCNc1ncc(-c2cnc3[nH]ccc3n2)c(N[C@H]2CCCN(S(C)(=O)=O)C2)n1]

N*2*-(2-Dimethylamino-ethyl)-N*4*-((S)-1-methanesulfonyl-piperidin-3-yl)-5-(5H-pyrrolo[2,3-b]pyrazin-2-yl)-pyrimidine-2,4-diamine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, N*1*,N*1*-dimethyl-ethane-1,2-diamine was used to displace the methylsulfone similar to examples above and the de-protection step was similar to step 5, Example 76, to give N*2*-(2-dimethylamino-ethyl)-N*4*-((S)-1-methanesulfonyl-piperidin-3-yl)-5-(5H-pyrrolo[2,3-b]pyrazin-2-yl)-pyrimidine-2,4-diamine. MS (ES+): 460.

Example 116

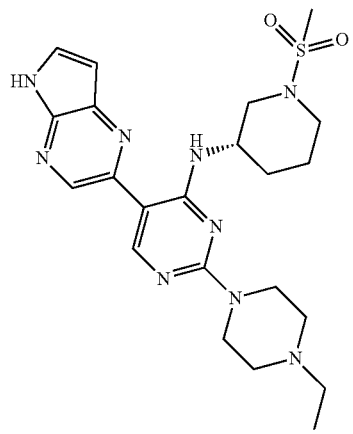 [SMILES: CCN1CCN(c2ncc(-c3cnc4[nH]ccc4n3)c(N[C@H]3CCCN(S(C)(=O)=O)C3)n2)CC1]

[2-(4-Ethyl-piperazin-1-yl)-5-(5H-pyrrolo[2,3-b]pyrazin-2-yl)-pyrimidin-4-yl]-((S)-1-methanesulfonyl-piperidin-3-yl)-amine In a dioxane solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1,1-ethyl-piperazine was used to displace the methylsulfone similar to examples above and the de-protection step was similar to step 5, Example 76, to give [2-(4-ethyl-piperazin-1-yl)-5-(5H- pyrrolo[2,3-b]pyrazin-2-yl)-pyrimidin-4-yl]-((S)-1-methanesulfonyl-piperidin-3-yl)-amine. MS (ES+): 486.

Example 117

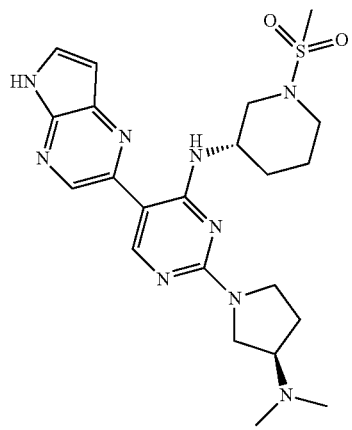 [SMILES: CN(C)[C@@H]1CCN(c2ncc(-c3cnc4[nH]ccc4n3)c(N[C@H]3CCCN(S(C)(=O)=O)C3)n2)C1]

[2-((R)-3-Dimethylamino-pyrrolidin-1-yl)-5-(5H-pyrrolo[2,3-b]pyrazin-2-yl)-pyrimidin-4-yl]-((S)-1-methanesulfonyl-piperidin-3-yl)-amine A solution of ((S)-1-methanesulfonyl-piperidin-3-yl)-{2-methanesulfonyl-5-[5-(2-trimethylsilanyl-ethoxymethyl)-5H-pyrrolo[2,3-b]pyrazin-2-yl]-pyrimidin-4-yl}-amine derived from Example 84, step 1, dimethyl-(R)-pyrrolidin-3-yl-amine was used to displace the methylsulfone similar to examples above and the de-protection step was similar to step 5, Example 76, to give [2-((R)-3-dimethylamino-pyrrolidin-1-yl)-5-(5H-pyrrolo[2,3-b]pyrazin-2-yl)-pyrimidin-4-yl]-((S)-1-methanesulfonyl-piperidin-3-yl)-amine. MS (ES+): 486.

Example 118

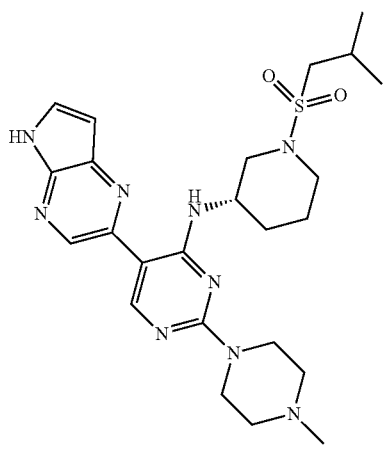 [SMILES: CC(C)CS(=O)(=O)N1CCC[C@H](Nc2nc(N3CCN(C)CC3)ncc2-c2cnc3[nH]ccc3n2)C1]

[2-(4-Methyl-piperazin-1-yl)-5-(5H-pyrrolo[2,3-b]pyrazin-2-yl)-pyrimidin-4-yl]-[(S)-1-(2-methyl-propane-1-sulfonyl)-piperidin-3-yl]-amine From dioxane solution Example 3, step 1 (R=isobutyl), 1-methyl-piperazine was used to displace the methylsulfone similar to examples above and the de-protection step was similar to step 5, Example 76, to give [2-(4-Methyl-piperazin-1-yl)-5-(5H-pyrrolo[2,3-b]pyrazin-2-yl)-pyrimidin-4-yl]-[(S)-1-(2-methyl-propane-1-sulfonyl)-piperidin-3-yl]-amine. MS (ES+): 514.

Scheme 3

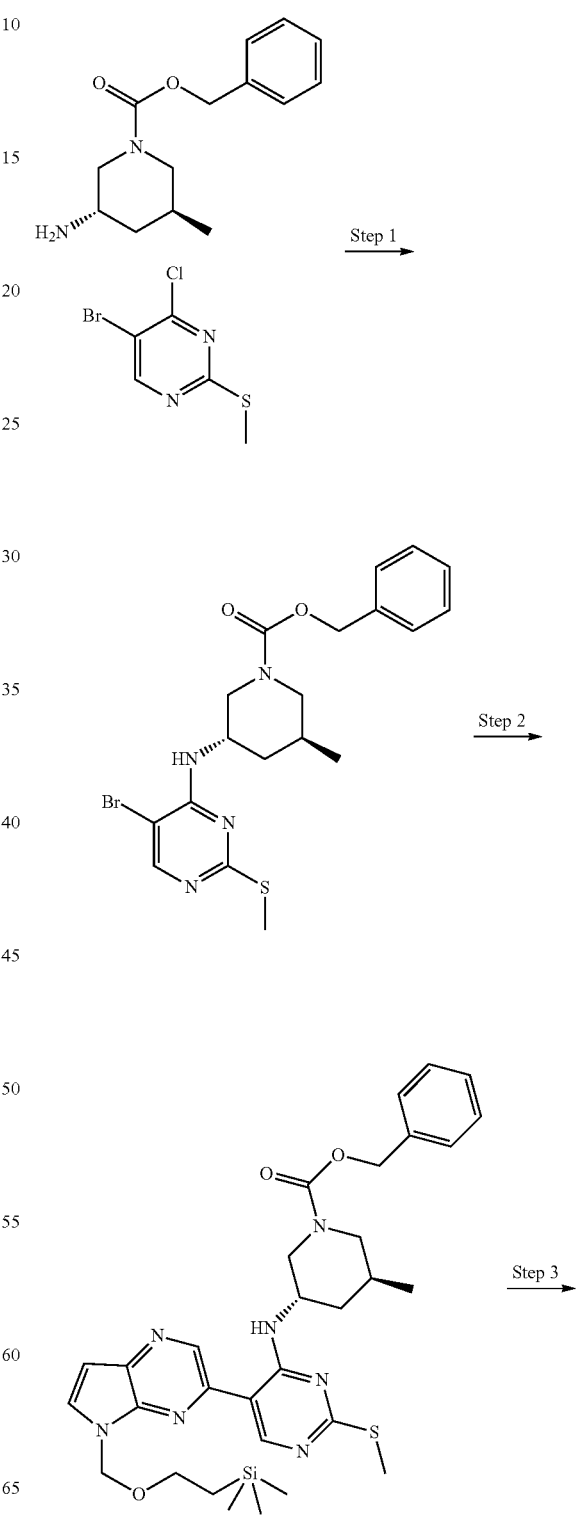

-continued

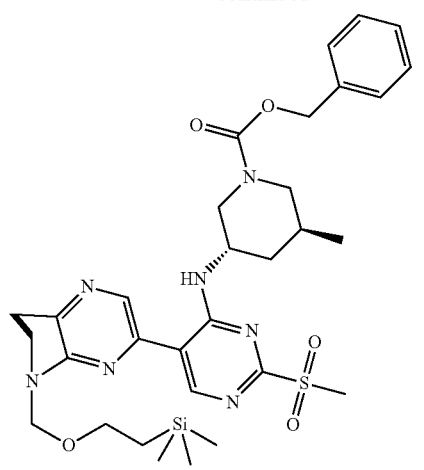

Step 4 →

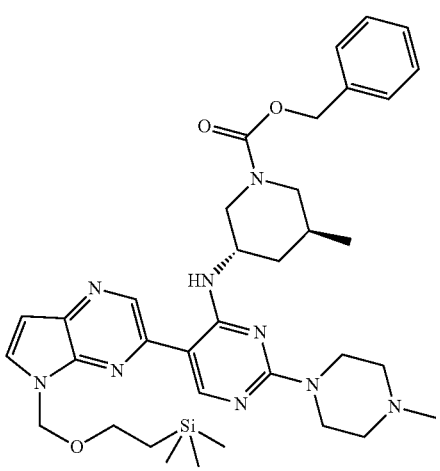

Step 5 →

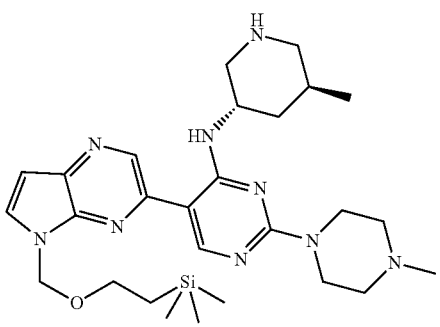

Step 6 →

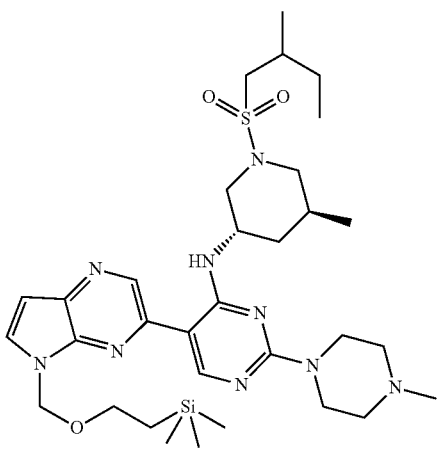

Step 7 →

-continued

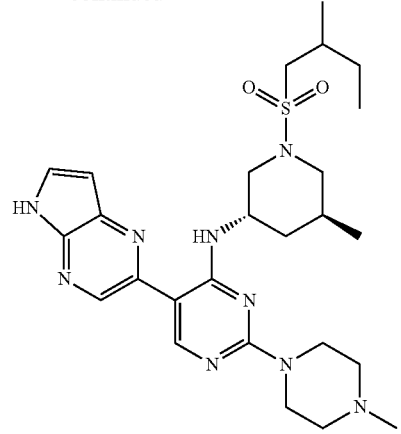

Example 119

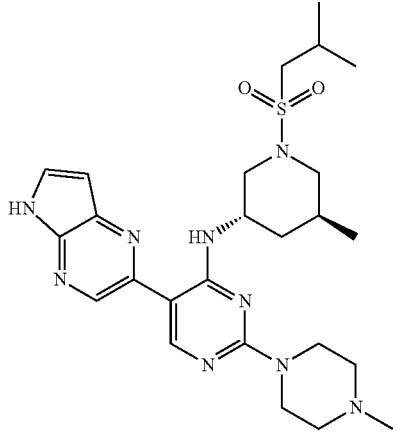 [SMILES: CC(C)CS(=O)(=O)N1C[C@@H](C)C[C@H](Nc2nc(N3CCN(C)CC3)ncc2-c2cnc3[nH]ccc3n2)C1]

[(3S,5S)-5-Methyl-1-(2-methyl-propane-1-sulfonyl)-piperidin-3-yl]-[2-(4-methyl-piperazin-1-yl)-5-(5H-pyrrolo[2,3-b]pyrazin-2-yl)-pyrimidin-4 yl]-amine Step 1

A solution of 5-bromo-4-chloro-2-(methylthio)pyrimidine (1.0 g, 4.2 mmol), (3S,5S)-benzyl 3-amino-5-methylpiperidine-1-carboxylate (2.7 g, 8.35 mmol) and triethylamine 1.3 g, 12.5 mmol) in dioxane (50 ml) were stirred for 16 hours. The reaction was concentrated and the residue dissolved in methylene chloride (50 ml) and washed with water. The organic layer was dried and concentrated and purified on a silica gel column with 10-20% ethyl acetate/dichloromethane as solvent to give (3S,5S)-3-(5-bromo-2-methylsulfanyl-pyrimidin-4-ylamino)-5-methyl-piperidine-1-carboxylic acid benzyl ester as a viscous oil. MS (ES+): 452.

Step 2

A degassed toluene (15 ml) solution of 2-bromo-5-((2-(trimethylsilyl)ethoxy)methyl)-5H-pyrrolo[2,3-b]pyrazine (1.0 g, 3.0 mmol), 1,1,1,2,2,2-hexamethyldistannane (1.0 g, 3.1 mmol), and tetrakis(triphenylphosphine)palladium(0) (176 mg, 0.15 mmol) was treated in a similar manner as Example 76, step 3. To this was added (3S,5S)-benzyl 3-(5-bromo-2-(methylthio)pyrimidin-4-ylamino)-5-methylpiperidine-1-carboxylate (1.37 g, 3.0 mmol) and another 176 mg of palladium catalyst and following Example 76, step 3. (3S, 5S)-3-methyl-5-{2-methylsulfany-l-5-[5-(2-trimethylsilanyl-ethoxymethyl)-5H-pyrrolo[2,3-b]pyrazin-2-yl]-pyrimidin-4-ylamino}-piperidine-1-carboxylic acid benzyl ester (660 mg, 35%) could be isolated as an oil and taken to the next step. (0227-160)

Step 3

In a 20 mL pear-shaped flask, (3S,5S)-3-methyl-5-{2-methylsulfany-l-5-[5-(2-trimethylsilanyl-ethoxymethyl)-5H-pyrrolo[2,3-b]pyrazin-2-yl]-pyrimidin-4-ylamino}-piperidine-1-carboxylic acid benzyl ester (200 mg, 323 µmol) was combined with dichloromethane (10 ml) and cooled to 0° C. M-chloroperbenzoic acid (111 mg, 645 µmmol) was added and reaction mixture was stirred at 0° C. for 30 min and at 20° C. for 40 min. The reaction was diluted with dichloromethane (20 ml) and washed with sodium thiosulfate (sat.) dried and purified by flash chromatography (0-40% ethyl acetate/methylene chloride to give (3S,5S)-3-{2-methanesulfonyl-5-[5-(2-trimethylsilanyl-ethoxymethyl)-5H-pyrrolo[2,3-b]pyrazin-2-yl]-pyrimidin-4-ylamino}-5-methyl-piperidine-1-carboxylic acid benzyl ester as a yellow solid (120 mg, 57%). MS (ES+): 652.

Step 4

In a dioxane solution of the intermediate derived from Example 40, step 3, N-methylpiperidine was used to displace the methylsulfone similar to examples above to give (3S,5S)-3-methyl-5-{2-(4-methyl-piperazin-1-yl)-5-[5-(2-trimethylsilanyl-ethoxymethyl)-5H-pyrrolo[2,3-b]pyrazin-2-yl]-pyrimidin-4-ylamino}-piperidine-1-carboxylic acid benzyl ester. MS (ES+): 672.

Step 5

A suspension of (3S,5S)-3-methyl-5-{2-(4-methyl-piperazin-1-yl)-5-[5-(2-trimethylsilanyl-ethoxymethyl)-5H-pyrrolo[2,3-b]pyrazin-2-yl]-pyrimidin-4-ylamino}-piperidine-1-carboxylic acid benzyl ester from step 4 above (120 mg, 179 µmol), K$_2$CO$_3$ (45.7 mg, 330 µmol) in ethanol (2 ml) was treated with palladium hydroxide (62.7 mg, 446 µmol) and hydrogenated at 1 atmosphere at 20° C. for 1.5 hours. The reaction mixture was filtered through celite, washed with ethanol and concentrated in vacuo to give {2-(4-2-methyl-piperazin-1-yl)-5-[5-(trimethylsilanyl-ethoxymethyl)-5H-pyrrolo[2,3-b]pyrazin-2-yl]-pyrimidin-4-yl}-((3S,5S)-5-methyl-piperidin-3-yl)-amine as a solid (65 mg, 67%). MS (ES+): 538.

Step 6

A solution of {2-(4-2-methyl-piperazin-1-yl)-5-[5-(trimethylsilanyl-ethoxymethyl)-5H-pyrrolo[2,3-b]pyrazin-2-yl]-pyrimidin-4-yl}-((3S,5S)-5-methyl-piperidin-3-yl)-amine (65 mg, 121 µmol) in methylene chloride (10 ml) was treated with isobutylchloride in a manner similar to step 2, Scheme 1. The crude reaction mixture was concentrated in vacuo diluted with methylene chloride and washed with water. The organic layer was dried, concentrated and purified by silica gel chromatography (0-10% methanol/methylene chloride) to give [(3S,5S)-5-methyl-1-(2-methyl-propane-1-sulfonyl)-piperidin-3-yl]-{2-(4-methyl-piperazin-1-yl)-5-[5-(2-trimethylsilanyl-ethoxymethyl)-5H-pyrrolo[2,3-b]pyrazin-2-yl]-pyrimidin-4-yl}-amine (68 mg, 81%). MS (ES+): 658.

Step 7

[(3S,5S)-5-methyl-1-(2-methyl-propane-1-sulfonyl)-piperidin-3-yl]-{2-(4-methyl-piperazin-1-yl)-5-[5-(2-trimethylsilanyl-ethoxymethyl)-5H-pyrrolo[2,3-b]pyrazin-2-yl]-pyrimidin-4-yl}-amine was deprotected in a manner similar to step 5, Scheme 1 to give [(3S,5S)-5-methyl-1-(2-methyl-propane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine (46 mg, 84%). MS (ES+): 528.

Example 120

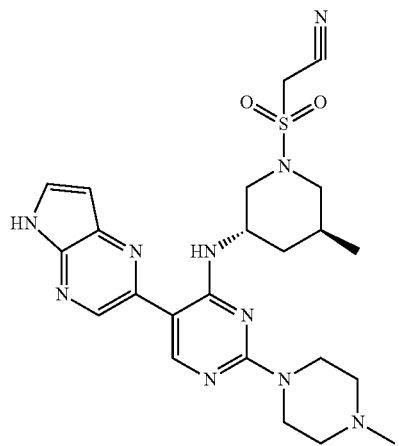 [SMILES: C[C@H]1C[C@H](Nc2nc(N3CCN(C)CC3)ncc2-c2cnc3[nH]ccc3n2)CN(S(=O)(=O)CC#N)C1]

{(3S,5S)-3-Methyl-5-[2-(4-methyl-piperazin-1-yl)-5-(5H-pyrrolo[2,3-b]pyrazin-2-yl)-pyrimidin-4-ylamino]-piperidine-1-sulfonyl}-acetonitrile The intermediate from step 5, Scheme 3, {2-(4-2-methyl-piperazin-1-yl)-5-[5-(trimethylsilanyl-ethoxymethyl)-5H-pyrrolo[2,3-b]pyrazin-2-yl]-pyrimidin-4-yl}-((3S,5S)-5-methyl-piperidin-3-yl)-amine (80 mg, 149 µmmol) was treated with 2-nitrilo-ethanesulfonyl chloride (104 mg, 744 µmmol) in a manner similar to step 2, Example 76, to give ((3S,5S)-3-methyl-5-{2-(4-methyl-piperazin-1-yl)-5-[5-(2-trimethylsilanyl-ethoxymethyl)-5H-pyrrolo[2,3-b]pyrazin-2-yl]-pyrimidin-4-ylamino}-piperidine-1-sulfonyl)-acetonitrile (65 mg, 68%). MS (ES+): 641.

((3S,5S)-3-methyl-5-{2-(4-methyl-piperazin-1-yl)-5-[5-(2-trimethylsilanyl-ethoxymethyl)-5H-pyrrolo[2,3-b]pyrazin-2-yl]-pyrimidin-4-ylamino}-piperidine-1-sulfonyl)-acetonitrile (~25 mg) was de-protected in a manner similar to step 5, Scheme 1 to give {(3S,5S)-3-Methyl-5-[2-(4-methylpiperazin-1-yl)-5-(5H-pyrrolo[2,3-b]pyrazin-2-yl)-pyrimidin-4-ylamino]-piperidine-1-sulfonyl}-acetonitrile (12 mg, 57%). MS (ES+): 511.

Example 121

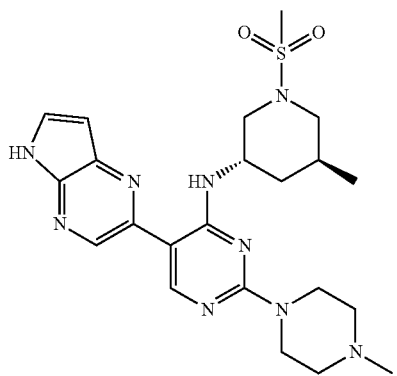

((3S,5S)-1-Methanesulfonyl-5-methyl-piperidin-3-yl)-[2-(4-methyl-piperazin-1-yl)-5-(5H-pyrrolo[2,3-b]pyrazin-2-yl)-pyrimidin-4-yl]-amine The intermediate from step 5, Scheme 3, {2-(4-2-methyl-piperazin-1-yl)-5-[5-(trimethylsilanyl-ethoxymethyl)-5H-pyrrolo[2,3-b]pyrazin-2-yl]-pyrimidin-4-yl}-((3S,5S)-5-methyl-piperidin-3-yl)-amine (56 mg, 104 μmol) was treated with methanesulfonyl chloride (60 mg, 520 μmol) in a manner similar to step 2, Example 76, to give ((3S,5S)-1-methanesulfonyl-5-methyl-piperidin-3-yl)-{2-(4-methyl-piperazin-1-yl)-5-[5-(2-trimethylsilanyl-ethoxymethyl)-5H-pyrrolo[2,3-b]pyrazin-2-yl]-pyrimidin-4-yl}-amine (36 mg, 56%). MS (ES+): 617. ((3S,5S)-1-methanesulfonyl-5-methyl-piperidin-3-yl)-{2-(4-methyl-piperazin-1-yl)-5-[5-(2-trimethylsilanyl-ethoxymethyl)-5H-pyrrolo[2,3-b]pyrazin-2-yl]-pyrimidin-4-yl}-amine (34 mg) was de-protected in a manner similar to step 5, Scheme 1, to give ((3S,5S)-1-Methanesulfonyl-5-methyl-piperidin-3-yl)-[2-(4-methyl-piperazin-1-yl)-5-(5H-pyrrolo[2,3-b]pyrazin-2-yl)-pyrimidin-4-yl]-amine (20 mg, 68%. MS (ES+): 486.

JAK Assay Information
Determination of $IC_{50}$ of Janus Kinase (JAK) Inhibition:
Enzymes and peptide substrate used are described below:
JAK1: Recombinant human kinase domain (866-1154) from Invitrogen (Cat # PV4774)
JAK3: Recombinant human kinase domain (810-1124) made in house by Roche Palo Alto
JAK2: Recombinant human kinase domain (808-1132) from Millipore (Cat #14-640)
Substrate: N-terminally biotinylated 14-mer peptide derived from activation loop of JAK1 with sequence of the peptide substrate: Biotin-KAIETDKEYYTVKD
Assay conditions used are described below:
Assay Buffer: JAK Kinase Buffer: 50 mM Hepes [pH 7.2], 10 mM $MgCl_2$, 1 mM DTT, 1 mg/ml BSA. The assay is carried out in this buffer.
Assay Format The kinase activity of all three JAK kinases is measured using a radioactive, end-point assay and with trace amounts of $^{33}P$-ATP. The assays are carried out in 96-well polypropylene plates.

Experimental Method

All concentrations are final in the reaction mixture and all incubations are carried at room temperature. Assay steps are described below:
1) Compounds are serially diluted in 100% DMSO typically at a 10× starting concentration of 1 mM. Final concentration of DMSO in the reaction is 10%.
2) Compounds are preincubated with enzyme (0.1 nM JAK3, 1 nM JAK2, 5 nM JAK1) for 10 minutes.
3) Reactions are initiated by the addition of a cocktail of the two substrates (ATP and peptide premixed in the JAK Kinase Buffer). In the JAK1/JAK2/JAK3 assays, ATP and the peptide are used at concentrations of 1.5 uM and 50 uM, respectively. The duration of the assay for JAK2 and JAK3 is 20 minutes. JAK1 assay is carried out for 45 minutes. With all three enzymes, reactions are terminated by the addition of 0.5M EDTA to a final concentration of 100 mM.
4) 25 ul of terminated reactions are transferred to 150 ul of a 7.5% (v/v) slurry of streptavidin-coated sepharose beads in $MgCl_2$- and $CaCl_2$-free 1× Phosphate Buffered Saline containing 50 mM of EDTA in 96-well, 1.2 um MultiScreen-BV filter plates.
5) After a 30-minute incubation, the beads are washed under vacuum with the following buffers:
  a. 3 to 4 washes with 200 ul of 2M NaCl.
  b. 3 to 4 washes with 200 ul of 2M NaCl plus 1% (v/v) phosphoric acid.
  c. 1 wash with water.
6) Washed plates are dried in a 60° C. oven for between 1 to 2 hours.
7) 70 ul of Microscint 20 scintillation fluid is added to each well of filter plates and after at least 30 minutes of incubation, radioactive counts are measured in a Perkin Elmer microplate scintillation counter.

Representative $IC_{50}$ results are in Table II below:

TABLE II

| Compound | Ic50 h-jak3(810-1124, pln 7-93)-baculovirus-c:no additive | Ic50 h-jak2-sf2I-c:no additive | Ki h-jak3(810-1124, pln 7-93)-baculovirus-c:no additive |
| --- | --- | --- | --- |
| I-1 | 0.03082 | 0.0822 | 0.015529 |
| I-2 | 0.00837 | 0.0292 | 0.004294 |
| I-3 | 0.048945 | 0.0926 | 0.025109 |
| I-4 | 0.335955 | 0.0986 | 0.172341 |
| I-5 | 0.010465 | 0.0296 | 0.005369 |
| I-6 | 0.01281 | 0.0228 | 0.006572 |
| I-7 | 0.312765 | 0.047 | 0.160445 |
| I-8 | 0.604935 | 0.0765 | 0.310324 |
| I-9 | 0.063455 | 0.0397 | 0.032552 |
| I-10 | 0.219795 | 0.0276 | 0.112752 |
| I-11 | 0.01794 | 0.0108 | 0.009203 |
| I-12 | 0.10739 | 0.0191 | 0.05509 |
| I-13 | 0.049305 | 0.0106 | 0.025293 |
| I-14 | 0.09868 | 0.0209 | 0.050622 |
| I-15 | 0.779215 | 0.7285 | 0.399728 |
| I-16 | 0.19188 | 0.2469 | 0.098432 |
| I-17 | 0.542035 | 0.3428 | 0.278057 |
| I-18 | 0.805155 | 0.5728 | 0.413034 |
| I-19 | 1.1565 | 0.662 | 0.593269 |
| I-20 | 0.194845 | 0.0847 | 0.099953 |
| I-21 | 0.7003 | 0.1214 | 0.359245 |
| I-22 | 0.21995 | 0.1684 | 0.176251 |
| I-23 | 10 | 0.1532 | |
| I-24 | 0.03714 | 0.1401 | 0.019053 |
| I-25 | 0.00776 | 0.0676 | 0.003981 |
| I-26 | 0.006695 | 0.07 | 0.003435 |
| I-27 | 0.546745 | 0.8108 | 0.280473 |
| I-28 | 0.02957 | 0.2226 | 0.015169 |

TABLE II-continued

| Compound | Ic50 h-jak3(810-1124, pln 7-93)-baculovirus-c:no additive | Ic50 h-jak2-sf2I-c:no additive | Ki h-jak3(810-1124, pln 7-93)-baculovirus-c:no additive |
|---|---|---|---|
| I-29 | 0.02038 | 0.1079 | 0.010455 |
| I-30 | 0.060745 | 0.0876 | 0.030373 |
| I-31 | 0.019375 | 0.0464 | 0.009688 |
| I-32 | 0.0024 | 0.0245 | 0.0012 |
| I-33 | 0.20579 | 0.035 | 0.102895 |
| I-34 | 0.050985 | 0.1612 | 0.025493 |
| I-35 | 0.039765 | 0.1669 | 0.019883 |
| I-36 | 0.016765 | 0.1338 | 0.008383 |
| I-37 | 0.03938 | 0.0089 | 0.01969 |
| I-38 | 0.00747 | 0.0413 | 0.00373 |
| I-39 | 0.06878 | 0.1466 | 0.03528 |
| I-40 | 0.03508 | 0.1543 | 0.01754 |
| I-41 | 0.04936 | 0.0359 | 0.02468 |
| I-42 | 0.00149 | 0.088 | 0.000748 |
| I-43 | 3.254865 | 1.9595 | 1.62743 |
| I-44 | 2.37006 | | 1.18503 |
| I-45 | 0.248435 | 0.8586 | 0.12585 |
| I-46 | 0.126905 | 0.8331 | 0.0651 |
| I-47 | 0.290615 | 1 | 0.14908 |
| I-48 | 1.031735 | 0.3102 | 0.52926 |
| I-49 | 1.28077 | 1 | 1.02631 |
| I-50 | 0.75233 | 0.5802 | 0.38593 |
| I-51 | 3 | 1 | |
| I-52 | 1 | 3 | |
| I-53 | 10 | 10 | |
| I-54 | 3 | 1.2305 | |
| I-55 | 10 | 10 | |
| I-56 | 0.02299 | 0.0797 | 0.01179 |
| I-57 | 1.102595 | 0.1915 | 0.56561 |
| I-58 | 10 | 10 | |
| I-59 | 4.678085 | | 2.33904 |
| I-60 | 0.01735 | 0.1236 | 0.00867 |
| I-61 | 0.011745 | 0.0367 | 0.00587 |
| I-62 | 0.021495 | 0.0384 | 0.01074 |
| I-63 | 0.00773 | 0.0398 | 0.00386 |
| I-64 | 0.004205 | 0.09 | 0.0021 |
| I-65 | 0.007615 | 0.0201 | 0.0038 |
| I-66 | 0.04782 | 0.1115 | 0.02391 |
| I-67 | 0.0647 | 0.2215 | 0.03235 |
| I-68 | 0.03661 | 0.1806 | 0.01878 |
| I-69 | 0.00196 | 0.0581 | 0.00098 |
| I-70 | 0.001155 | 0.0196 | 0.000578 |
| I-71 | 0.004965 | 0.0549 | 0.00248 |
| I-72 | 0.00188 | 0.0646 | 0.00094 |
| I-73 | 0.00897 | 0.0764 | 0.00448 |
| I-74 | 0.010505 | 0.049 | 0.00525 |
| I-75 | 0.04737 | 0.139 | 0.02368 |
| I-76 | 0.05674 | 0.1373 | 0.02837 |
| I-77 | 0.017875 | 0.0713 | 0.00893 |
| I-78 | 0.44839 | 0.3889 | 0.22419 |
| I-79 | 0.00242 | 0.0293 | 0.00121 |
| I-80 | 0.02712 | 0.0717 | 0.01356 |
| I-81 | 0.05241 | 0.1314 | 0.0262 |
| I-82 | 0.015593 | 0.0603 | 0.01055 |
| I-83 | 0.01721 | 0.1294 | 0.0086 |
| I-84 | 0.032625 | 0.1413 | 0.01631 |
| I-85 | 0.008045 | 0.0668 | 0.00402 |
| I-86 | 0.01071 | 0.0763 | 0.00535 |
| I-87 | 0.01863 | 0.1026 | 0.00931 |
| I-88 | 0.84448 | 0.223 | 0.42224 |
| I-89 | 0.03959 | 0.1769 | 0.01979 |
| I-90 | 0.049835 | 0.2551 | 0.02491 |
| I-91 | 0.030085 | 0.1067 | 0.01504 |
| I-92 | 0.050375 | 0.1665 | 0.02518 |
| I-93 | 0.0053 | 0.0221 | 0.00265 |
| I-94 | 0.01096 | 0.0432 | 0.00548 |
| I-95 | 0.00858 | 0.054 | 0.00429 |
| I-96 | 0.025065 | 0.1084 | 0.01253 |
| I-97 | 0.002185 | 0.0172 | 0.00109 |
| I-98 | 0.02582 | 0.1373 | 0.01291 |
| I-99 | 0.1607 | 0.6186 | 0.08035 |
| I-100 | 0.04262 | 0.1694 | 0.02131 |
| I-101 | 0.01512 | 0.1804 | 0.00756 |
| I-102 | 0.012505 | 0.0485 | 0.00625 |
| I-103 | 0.013595 | 0.1455 | 0.00679 |
| I-104 | 0.064865 | 0.1751 | 0.03243 |
| I-105 | 0.023355 | 0.1131 | 0.01167 |
| I-106 | 0.153085 | 0.6379 | 0.07654 |
| I-107 | 0.032685 | 0.1921 | 0.01634 |
| I-108 | 0.048555 | 0.2125 | 0.02427 |
| I-109 | 0.021635 | 0.0708 | 0.01081 |
| I-110 | 0.006755 | 0.0585 | 0.00337 |
| I-111 | 0.005185 | 0.0838 | 0.01631 |
| I-112 | 0.00415 | 0.0782 | 0.00207 |
| I-113 | 0.02678 | 0.2168 | 0.01339 |
| I-114 | 0.39098 | 0.5559 | 0.19549 |
| I-115 | 0.134655 | 0.4635 | 0.06732 |
| I-116 | 0.09996 | 0.2185 | 0.04998 |
| I-117 | 0.18972 | 0.5116 | 0.09486 |
| I-118 | 0.005205 | 0.0332 | 0.0026 |
| I-119 | 0.3222 | 0.2305 | 0.1611 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I

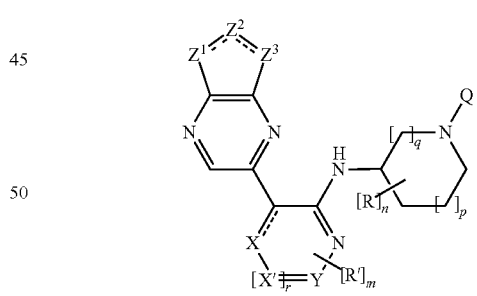

wherein:
R is lower alkyl, lower haloalkyl, lower alkoxy, hydroxy lower alkyl, hydroxy, or halogen;
n is 0 or 1;
$Z^1$ is NH;
$Z^2$ is CH;
$Z^3$ is $CR^1$;
$R^1$ is H, lower alkyl, cycloalkyl, cyano, cyano lower alkyl, or halogen;
X is CH, CR', or N;
X' is CH, CR', or N;
r is 0 or 1;

223

Y is CH, CR', or N;
R' is $R'^a$ or $R'^b$;
  $R'^a$ is halogen or cyano;
  $R'^b$ is lower alkyl, cycloalkyl, heterocycloalkyl, OR", SR", S(=O)$_2$R", or NR"R", optionally substituted with one or more $R'^c$;
    $R'^c$ is hydroxy, halogen, oxo, cyano, lower alkyl, cycloalkyl, heterocycloalkyl, heteroaryl, carboxy lower alkyl, amino, amino carboxy lower alkyl, lower alkyl amino, lower dialkyl amino, lower haloalkyl, or lower alkoxy;
m is 0 or 1;
R" is H, lower alkyl, hydroxy lower alkyl, heteroaryl, or lower alkoxy;
Q is H, S(=O)$_2$Q$^1$, C(=O)Q$^2$, C(=O)OQ$^3$, or Q$^4$;
  Q$^1$ is lower alkyl, cycloalkyl lower alkyl, lower alkyl amino, lower dialkyl amino, or cycloalkyl, optionally substituted with one or more $Q^{1'}$;
    each $Q^{1'}$ is independently halogen, lower alkyl, cyano, or lower alkoxy;
  Q$^2$ is lower alkyl, cycloalkyl lower alkyl, or cycloalkyl, optionally substituted with one or more $Q^{2'}$;
    each $Q^{2'}$ is independently halogen, lower alkyl, cyano, or lower alkoxy;
  Q$^3$ is lower alkyl, cycloalkyl lower alkyl, or cycloalkyl, optionally substituted with one or more $Q^{3'}$;
    each $Q^{3'}$ is independently halogen, lower alkyl, or lower alkoxy;
  Q$^4$ is lower alkyl, cycloalkyl lower alkyl, heterocycloalkyl, or cycloalkyl, optionally substituted with one or more $Q^{4'}$;
    each $Q^{4'}$ is independently halogen, cyano, cyano lower alkyl, lower alkyl, or lower alkoxy;
p is 0, 1, or 2;
q is 1 or 2;
each ==== represents a single bond or a double bond; and
with the proviso that the bonds between Z$^1$ and Z$^2$ and Z$^2$ and Z$^3$ are not both double bonds and are not both single bonds;
or a pharmaceutically acceptable salt thereof.

2. The compound of claim 1, having the Formula II

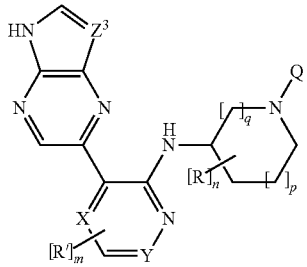

II wherein:
R is lower alkyl;
n is 0 or 1;
Z$^3$ is CR$^1$;
R$^1$ is H, lower alkyl, or halogen;
X is CH, CR', or N;
Y is CH, CR', or N;
R' is $R'^a$ or $R'^b$;
  $R'^a$ is halogen or cyano;
  $R'^b$ is lower alkyl, cycloalkyl, heterocycloalkyl, OR", SR", S(=O)$_2$R", or NR"R", optionally substituted with one or more $R'^c$;

224

$R'^c$ is hydroxy, halogen, oxo, cyano, lower alkyl, cycloalkyl, heterocycloalkyl, heteroaryl, carboxy lower alkyl, amino, amino carboxy lower alkyl, lower alkyl amino, lower dialkyl amino, lower haloalkyl, or lower alkoxy;
m is 0 or 1;
R" is H, lower alkyl, hydroxy lower alkyl, heteroaryl, or lower alkoxy;
Q is H, S(=O)$_2$Q$^1$, C(=O)Q$^2$, C(=O)OQ$^3$, or Q$^4$;
Q is H, S(=O)$_2$Q$^1$, C(=O)Q$^2$, C(=O)OQ$^3$, or Q$^4$;
  Q$^1$ is lower alkyl, cycloalkyl lower alkyl, lower alkyl amino, lower dialkyl amino, or cycloalkyl, optionally substituted with one or more $Q^{1'}$;
    each $Q^{1'}$ is independently halogen, lower alkyl, cyano, or lower alkoxy;
  Q$^2$ is lower alkyl, cycloalkyl lower alkyl, or cycloalkyl, optionally substituted with one or more $Q^{2'}$;
    each $Q^{2'}$ is independently halogen, lower alkyl, cyano, or lower alkoxy;
  Q$^3$ is lower alkyl, cycloalkyl lower alkyl, or cycloalkyl, optionally substituted with one or more $Q^{3'}$;
    each $Q^{3'}$ is independently halogen, lower alkyl, or lower alkoxy;
  Q$^4$ is lower alkyl, cycloalkyl lower alkyl, heterocycloalkyl, or cycloalkyl, optionally substituted with one or more $Q^{4'}$;
    each $Q^{4'}$ is independently halogen, cyano, cyano lower alkyl, lower alkyl, or lower alkoxy;
p is 0, 1, or 2;
q is 1 or 2; and
or a pharmaceutically acceptable salt thereof.

3. The compound of claim 2, wherein Z$^3$ is CH.
4. The compound of claim 3, wherein X is CH and Y is CH.
5. The compound of claim 4, wherein m is 0 and n is 0.
6. The compound of claim 5, wherein p is 1 and q is 1.
7. The compound of claim 5, wherein p is 0 and q is 1.
8. The compound of claim 6, wherein Q is S(=O)$_2$Q'.
9. The compound of claim 8, wherein Q$^1$ is lower alkyl.
10. The compound of claim 8, wherein Q$^1$ is cycloalkyl lower alkyl.
11. The compound of claim 7, wherein Q is S(=O)$_2$Q$^1$.
12. The compound of claim 11, wherein Q$^1$ is lower alkyl.
13. The compound of claim 6, wherein Q is C(=O)Q$^2$ and Q$^2$ is lower alkyl.
14. The compound of claim 7, wherein Q is C(=O)Q$^2$ and Q$^2$ is lower alkyl.
15. The compound of claim 6, wherein Q is C(=O)OQ$^3$ and Q$^3$ is lower alkyl.
16. The compound of claim 7, wherein Q is C(=O)OQ$^3$ and Q$^3$ is lower alkyl.
17. The compound of claim 4, wherein p is 1, q is 1, m is 1, n is 0, and R' is lower alkyl.
18. The compound of claim 4, wherein p is 1, q is 1, m is 0, n is 1, and R" is lower alkyl.
19. The compound of claim 17, wherein Q is S(=O)$_2$Q'.
20. The compound of claim 19, wherein Q$^1$ is lower alkyl.
21. The compound of claim 19, wherein Q$^1$ is cycloalkyl lower alkyl.
22. The compound of claim 18, wherein Q is S(=O)$_2$Q'.
23. The compound of claim 22, wherein Q$^1$ is lower alkyl.
24. The compound of claim 22, wherein Q$^1$ is cycloalkyl lower alkyl.
25. A compound selected from the group consisting of:
((S)-1-Methanesulfonyl-piperidin-3-yl)-[3-(5H-pyrrolo[2,3-b]pyrazin-2-yl)-pyridin-2-yl]-amine;
((R)-1-Methanesulfonyl-piperidin-3-yl)-[3-(5H-pyrrolo[2,3-b]pyrazin-2-yl)-pyridin-2-yl]-amine;

1-{(R)-3-[3-(5H-Pyrrolo[2,3-b]pyrazin-2-yl)-pyridin-2-ylamino]-pyrrolidin-1-yl}-ethanone;
(R)-3-[3-(5H-Pyrrolo[2,3-b]pyrazin-2-yl)-pyridin-2-ylamino]-pyrrolidine-1-carboxylic acid methyl ester;
((R)-1-Methanesulfonyl-pyrrolidin-3-yl)-[3-(5H-pyrrolo[2,3-b]pyrazin-2-yl)-pyridin-2-yl]-amine;
1-{(R)-3-[3-(5H-Pyrrolo[2,3-b]pyrazin-2-yl)-pyridin-2-ylamino]-piperidin-1-yl}-ethanone;
4-[3-(5H-Pyrrolo[2,3-b]pyrazin-2-yl)-pyridin-2-ylamino]-piperidine-1-carboxylic acid methyl ester;
1-{4-[3-(5H-Pyrrolo[2,3-b]pyrazin-2-yl)-pyridin-2-ylamino]-piperidin-1-yl}-ethanone;
1-{(S)-3-[3-(5H-Pyrrolo[2,3-b]pyrazin-2-yl)-pyridin-2-ylamino]-pyrrolidin-1-yl}-ethanone;
(S)-3-[3-(5H-Pyrrolo[2,3-b]pyrazin-2-yl)-pyridin-2-ylamino]-pyrrolidine-1-carboxylic acid methyl ester;
((S)-1-Methanesulfonyl-pyrrolidin-3-yl)-[3-(5H-pyrrolo[2,3-b]pyrazin-2-yl)-pyridin-2-yl]-amine;
1-{3-[3-(5H-Pyrrolo[2,3-b]pyrazin-2-yl)-pyridin-2-ylamino]-azepan-1-yl}-ethanone;
3-[3-(5H-Pyrrolo[2,3-b]pyrazin-2-yl)-pyridin-2-ylamino]-azepane-1-carboxylic acid methyl ester;
(1-Methanesulfonyl-azepan-3-yl)-[3-(5H-pyrrolo[2,3-b]pyrazin-2-yl)-pyridin-2-yl]-amine;
[(R)-1-(Propane-2-sulfonyl)-piperidin-3-yl]-[3-(5H-pyrrolo[2,3-b]pyrazin-2-yl)-pyridin-2-yl]-amine;
((R)-1-Ethanesulfonyl-pyrrolidin-3-yl)-[3-(5H-pyrrolo[2,3-b]pyrazin-2-yl)-pyridin-2-yl]-amine;
[(R)-1-(Propane-1-sulfonyl)-pyrrolidin-3-yl]-[3-(5H-pyrrolo[2,3-b]pyrazin-2-yl)-pyridin-2-yl]-amine;
[(R)-1-(Propane-2-sulfonyl)-pyrrolidin-3-yl]-[3-(5H-pyrrolo[2,3-b]pyrazin-2-yl)-pyridin-2-yl]-amine;
[(R)-1-(2-Methyl-propane-1-sulfonyl)-pyrrolidin-3-yl]-[3-(5H-pyrrolo[2,3-b]pyrazin-2-yl)-pyridin-2-yl]-amine;
1-{(R)-3-[3-(5H-Pyrrolo[2,3-b]pyrazin-2-yl)-pyridin-2-ylamino]-pyrrolidin-1-yl}-propan-1-one;
1-{(R)-3-[3-(5H-Pyrrolo[2,3-b]pyrazin-2-yl)-pyridin-2-ylamino]-pyrrolidin-1-yl}-butan-1-one;
2-Methyl-1-{(R)-3-[3-(5H-pyrrolo[2,3-b]pyrazin-2-yl)-pyridin-2-ylamino]-pyrrolidin-1-yl}-propan-1-one;
3-Methyl-1-{(R)-3-[3-(5H-pyrrolo[2,3-b]pyrazin-2-yl)-pyridin-2-ylamino]-pyrrolidin-1-yl}-butan-1-one;
((3S,5S)-1-Methanesulfonyl-5-methyl-piperidin-3-yl)-[3-(5H-Pyrrolo[2,3-b]pyrazin-2-yl)-pyridin-2-yl]-amine;
[(3S,5S)-5-Methyl-1-(propane-1-sulfonyl)-piperidin-3-yl]-[3-(5H-Pyrrolo[2,3-b]pyrazin-2-yl)-pyridin-2-yl]-amine;
[(3S,5S)-5-Methyl-1-(2-methyl-propane-1-sulfonyl)-piperidin-3-yl]-[3-(5H-Pyrrolo[2,3-b]pyrazin-2-yl)-pyridin-2-yl]-amine;
[(R)-1-(3-Methyl-butane-1-sulfonyl)-pyrrolidin-3-yl]-[3-(5H-pyrrolo[2,3-b]pyrazin-2-yl)-pyridin-2-yl]-amine;
[(3S,5S)-5-Methyl-1-(propane-2-sulfonyl)-piperidin-3-yl]-[3-(5H-pyrrolo[2,3-b]pyrazin-2-yl)-pyridin-2-yl]-amine;
[(S)-1-(2-Methyl-propane-1-sulfonyl)-piperidin-3-yl]-[3-(5H-pyrrolo[2,3-b]pyrazin-2-yl)-pyridin-2-yl]-amine;
1-{3-[6-Methyl-3-(5H-pyrrolo[2,3-b]pyrazin-2-yl)-pyridin-2-ylamino]-piperidin-1-yl}-ethanone;
(1-Methanesulfonyl-piperidin-3-yl)-[6-methyl-3-(5H-pyrrolo[2,3-b]pyrazin-2-yl)-pyridin-2-yl]-amine;
[(S)-1-(2,2-Dimethyl-propane-1-sulfonyl)-piperidin-3-yl]-[3-(5H-pyrrolo[2,3-b]pyrazin-2-yl)-pyridin-2-yl]-amine;
[3-(5H-Pyrrolo[2,3-b]pyrazin-2-yl)-pyridin-2-yl]-[(S)-1-(2,2,2-trifluoro-ethyl)-piperidin-3-yl]-amine;
(1-Ethanesulfonyl-piperidin-3-yl)-[6-methyl-3-(5H-pyrrolo[2,3-b]pyrazin-2-yl)-pyridin-2-yl]-amine;
(1-Cyclopropylmethanesulfonyl-piperidin-3-yl)-[6-methyl-3-(5H-pyrrolo[2,3-b]pyrazin-2-yl)-pyridin-2-yl]-amine;
[1-(2,2-Dimethyl-propane-1-sulfonyl)-piperidin-3-yl]-[6-methyl-3-(5H-pyrrolo[2,3-b]pyrazin-2-yl)-pyridin-2-yl]-amine;
(1-Methanesulfonyl-azepan-4-yl)-[3-(5H-pyrrolo[2,3-b]pyrazin-2-yl)-pyridin-2-yl]-amine;
((S)-1-Cyclopropylmethanesulfonyl-piperidin-3-yl)-[3-(5H-pyrrolo[2,3-b]pyrazin-2-yl)-pyridin-2-yl]-amine;
1-{3-[3-(7-Chloro-5H-pyrrolo[2,3-b]pyrazin-2-yl)-6-methyl-pyridin-2-ylamino]-piperidin-1-yl}-ethanone;
[3-(7-Chloro-5H-pyrrolo[2,3-b]pyrazin-2-yl)-6-methyl-pyridin-2-yl]-(1-cyclopropylmethanesulfonyl-piperidin-3-yl)-amine;
((S)-1-Methanesulfonyl-piperidin-3-yl)-[3-(5H-pyrrolo[2,3-b]pyrazin-2-yl)-pyrazin-2-yl]-amine;
{(S)-3-[3-(5H-Pyrrolo[2,3-b]pyrazin-2-yl)-pyridin-2-ylamino]-piperidine-1-sulfonyl}-acetonitrile;
[(S)-1-(2-Methyl-propane-1-sulfonyl)-piperidin-3-yl]-[3-(5H-pyrrolo[2,3-b]pyrazin-2-yl)-pyrazin-2-yl]-amine;
2-[2-((S)-1-Methanesulfonyl-piperidin-3-ylamino)-pyridin-3-yl]-5H-pyrrolo[2,3-b]pyrazine-7-carbonitrile;
((S)-1-Methanesulfonyl-piperidin-3-yl)-[3-(7-methyl-5H-pyrrolo[2,3-b]pyrazin-2-yl)-pyridin-2-yl]-amine;
[3-(7-Cyclopropyl-5H-pyrrolo[2,3-b]pyrazin-2-yl)-pyridin-2-yl]-((S)-1-methanesulfonyl-piperidin-3-yl)-amine;
[3-(7-Chloro-5H-pyrrolo[2,3-b]pyrazin-2-yl)-pyridin-2-yl]-((S)-1-methanesulfonyl-piperidin-3-yl)-amine;
(3R,4R)-1-(2-Methyl-propane-1-sulfonyl)-3-[3-(5H-pyrrolo[2,3-b]pyrazin-2-yl)-pyridin-2-ylamino]-piperidin-4-ol;
(3R,4R)-1-Methanesulfonyl-3-[3-(5H-pyrrolo[2,3-b]pyrazin-2-yl)-pyridin-2-ylamino]-piperidin-4-01;
(S)-3-[3-(5H-Pyrrolo[2,3-b]pyrazin-2-yl)-pyridin-2-ylamino]-piperidine-1-sulfonic acid dimethylamide;
(S)-3-[3-(5H-Pyrrolo[2,3-b]pyrazin-2-yl)-pyridin-2-ylamino]-piperidine-1-sulfonic acid tert-butylamide;
((S)-1-Methanesulfonyl-piperidin-3-yl)-[5-(5H-pyrrolo[2,3-b]pyrazin-2-yl)-pyrimidin-4-yl]-amine;
[(S)-1-(2-Methyl-propane-1-sulfonyl)-piperidin-3-yl]-[5-(5H-pyrrolo[2,3-b]pyrazin-2-yl)-pyrimidin-4-yl]-amine;
N4-[(S)-1-(2-Methyl-propane-1-sulfonyl)-piperidin-3-yl]-5-(5H-pyrrolo[2,3-b]pyrazin-2-yl)-pyrimidine-2,4-diamine;
N2,N2-Dimethyl-N-4-[(S)-1-(2-methyl-propane-1-sulfonyl)-piperidin-3-yl]-5-(5H-pyrrolo[2,3-b]pyrazin-2-yl)-pyrimidine-2,4-diamine;
[2-Methanesulfonyl-5-(5H-pyrrolo[2,3-b]pyrazin-2-yl)-pyrimidin-4-yl]-[(S)-1-(2-methyl-propane-1-sulfonyl)-piperidin-3-yl]-amine;
[(S)-1-(2-Methyl-propane-1-sulfonyl)-piperidin-3-yl]-[2-methylsulfanyl-5-(5H-pyrrolo[2,3-b]pyrazin-2-yl)-pyrimidin-4-yl]-amine;
[(S)-1-(2-Methyl-propane-1-sulfonyl)-piperidin-3-yl]-[2-morpholin-4-yl-5-(5H-pyrrolo[2,3-b]pyrazin-2-yl)-pyrimidin-4-yl]-amine;
((S)-1-Methanesulfonyl-piperidin-3-yl)-[2-methylsulfanyl-5-(5H-pyrrolo[2,3-b]pyrazin-2-yl)-pyrimidin-4-yl]-amine;
N4-((S)-1-Methanesulfonyl-piperidin-3-yl)-N2,N2-dimethyl-5-(5H-pyrrolo[2,3-b]pyrazin-2-yl)-pyrimidine-2,4-diamine;

N4-((S)-1-Methanesulfonyl-piperidin-3-yl)-5-(5H-pyrrolo[2,3-b]pyrazin-2-yl)-pyrimidine-2,4-diamine;
2-[2-Dimethylamino-4-((S)-1-methanesulfonyl-piperidin-3-ylamino)-pyrimidin-5-yl]-5H-pyrrolo[2,3-b]pyrazine-7-carbonitrile;
[(S)-1-(3,3-Dimethyl-butane-1-sulfonyl)-piperidin-3-yl]-[2-methylsulfanyl-5-(5H-pyrrolo[2,3-b]pyrazin-2-yl)-pyrimidin-4-yl]-amine;
((S)-1-Methanesulfonyl-piperidin-3-yl)-[2-methoxy-5-(5H-pyrrolo[2,3-b]pyrazin-2-yl)-pyrimidin-4-yl]-amine;
[2-Chloro-5-(5H-pyrrolo[2,3-b]pyrazin-2-yl)-pyrimidin-4-yl]-((S)-1-methanesulfonyl-piperidin-3-yl)-amine;
((S)-1-Methanesulfonyl-piperidin-3-yl)-[2-(4-methyl-piperazin-1-yl)-5-(5H-pyrrolo[2,3-b]pyrazin-2-yl)-pyrimidin-4-yl]-amine;
4-((S)-1-Methanesulfonyl-piperidin-3-ylamino)-5-(5H-pyrrolo[2,3-b]pyrazin-2-yl)-pyrimidin-2-ol;
[2-Ethoxy-5-(5H-pyrrolo[2,3-b]pyrazin-2-yl)-pyrimidin-4-yl]-((S)-1-methanesulfonyl-piperidin-3-yl)-amine;
2-[4-((S)-1-Methanesulfonyl-piperidin-3-ylamino)-5-(5H-pyrrolo[2,3-b]pyrazin-2-yl)-pyrimidin-2-ylamino]-ethanol;
N4-((S)-1-Methanesulfonyl-piperidin-3-yl)-N2-(2-methoxy-ethyl)-5-(5H-pyrrolo[2,3-b]pyrazin-2-yl)-pyrimidine-2,4-diamine;
((S)-1-Methanesulfonyl-piperidin-3-yl)-[2-morpholin-4-yl-5-(5H-pyrrolo[2,3-b]pyrazin-2-yl)-pyrimidin-4-yl]-amine;
3-{(S)-3-[2-Methylsulfanyl-5-(5H-pyrrolo[2,3-b]pyrazin-2-yl)-pyrimidin-4-ylamino]-piperidin-1-yl}-3-oxo-propionitrile;
1-[4-((S)-1-Methanesulfonyl-piperidin-3-ylamino)-5-(5H-pyrrolo[2,3-b]pyrazin-2-yl)-pyrimidin-2-ylamino]-2-methyl-propan-2-ol;
[2-(1,1-Dioxo-1λ6-thiomorpholin-4-yl)-5-(5H-pyrrolo[2,3-b]pyrazin-2-yl)-pyrimidin-4-yl]-((S)-1-methanesulfonyl-piperidin-3-yl)-amine;
((S)-1-Methanesulfonyl-piperidin-3-yl)-[2-(4-methoxy-piperidin-1-yl)-5-(5H-pyrrolo[2,3-b]pyrazin-2-yl)-pyrimidin-4-yl]-amine;
N2-(2-Amino-ethyl)-N4-((S)-1-methanesulfonyl-piperidin-3-yl)-5-(5H-pyrrolo[2,3-b]pyrazin-2-yl)-pyrimidine-2,4-diamine;
2-{1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetamide;
(S)-2-[4-((S)-1-Methanesulfonyl-piperidin-3-ylamino)-5-(5H-pyrrolo[2,3-b]pyrazin-2-yl)-pyrimidin-2-ylamino]-butan-1-ol;
(R)-2-[4-((S)-1-Methanesulfonyl-piperidin-3-ylamino)-5-(5H-pyrrolo[2,3-b]pyrazin-2-yl)-pyrimidin-2-ylamino]-butan-1-ol;
N4-((S)-1-Methanesulfonyl-piperidin-3-yl)-N2-(1-methyl-piperidin-4-yl)-5-(5H-pyrrolo[2,3-b]pyrazin-2-yl)-pyrimidine-2,4-diamine;
[(S)-1-(3,3-Dimethyl-butane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine;
[2-(4-Dimethylamino-piperidin-1-yl)-5-(5H-pyrrolo[2,3-b]pyrazin-2-yl)-pyrimidin-4-yl]-((S)-1-methanesulfonyl-piperidin-3-yl)-amine;
4-((S)-1-Methanesulfonyl-piperidin-3-ylamino)-5-(5H-pyrrolo[2,3-b]pyrazin-2-yl)-pyrimidine-2-carbonitrile;
(S)-1-[4-((S)-1-Methanesulfonyl-piperidin-3-ylamino)-5-(5H-pyrrolo[2,3-b]pyrazin-2-yl)-pyrimidin-2-yl]-pyrrolidin-3-ol;
(R)-1-[4-((S)-1-Methanesulfonyl-piperidin-3-ylamino)-5-(5H-pyrrolo[2,3-b]pyrazin-2-yl)-pyrimidin-2-yl]-pyrrolidin-3-ol;
1-[4-((S)-1-Methanesulfonyl-piperidin-3-ylamino)-5-(5H-pyrrolo[2,3-b]pyrazin-2-yl)-pyrimidin-2-yl]-azetidine-3-carbonitrile;
4-[4-((S)-1-Methanesulfonyl-piperidin-3-ylamino)-5-(5H-pyrrolo[2,3-b]pyrazin-2-yl)-pyrimidin-2-ylamino]-cyclohexanecarbonitrile;
((S)-1-Methanesulfonyl-piperidin-3-yl)-[2-(4-pyridin-2-yl-piperazin-1-yl)-5-(5H-pyrrolo[2,3-b]pyrazin-2-yl)-pyrimidin-4-yl]-amine;
{1-[4-((S)-1-Methanesulfonyl-piperidin-3-ylamino)-5-(5H-pyrrolo[2,3-b]pyrazin-2-yl)-pyrimidin-2-yl]-piperidin-4-yl}-acetic acid;
N4-((S)-1-Methanesulfonyl-piperidin-3-yl)-N2-pyridin-4-yl-5-(5H-pyrrolo[2,3-b]pyrazin-2-yl)-pyrimidine-2,4-diamine;
N2-(2-Dimethylamino-ethyl)-N4-((S)-1-methanesulfonyl-piperidin-3-yl)-5-(5H-pyrrolo[2,3-b]pyrazin-2-yl)-pyrimidine-2,4-diamine;
[2-(4-Ethyl-piperazin-1-yl)-5-(5H-pyrrolo[2,3-b]pyrazin-2-yl)-pyrimidin-4-yl]-((S)-1-methanesulfonyl-piperidin-3-yl)-amine;
[2-((R)-3-Dimethylamino-pyrrolidin-1-yl)-5-(5H-pyrrolo[2,3-b]pyrazin-2-yl)-pyrimidin-4-yl]-((S)-1-methanesulfonyl-piperidin-3-yl)-amine;
[2-(4-Methyl-piperazin-1-yl)-5-(5H-pyrrolo[2,3-b]pyrazin-2-yl)-pyrimidin-4-yl]-[(S)-1-(2-methyl-propane-1-sulfonyl)-piperidin-3-yl]-amine;
[(3S,5S)-5-Methyl-1-(2-methyl-propane-1-sulfonyl)-piperidin-3-yl]-[2-(4-methyl-piperazin-1-yl)-5-(5H-pyrrolo[2,3-b]pyrazin-2-yl)-pyrimidin-4-yl]-amine;
{(3S,5S)-3-Methyl-5-[2-(4-methyl-piperazin-1-yl)-5-(5H-pyrrolo[2,3-b]pyrazin-2-yl)-pyrimidin-4-ylamino]-piperidine-1-sulfonyl}-acetonitrile;
((3S,5S)-1-Methanesulfonyl-5-methyl-piperidin-3-yl)-[2-(4-methyl-piperazin-1-yl)-5-(5H-pyrrolo[2,3-b]pyrazin-2-yl)-pyrimidin-4-yl]-amine;
((3S,5S)-1-Methanesulfonyl-5-trifluoromethyl-piperidin-3-yl)-[3-(5H-pyrrolo[2,3-b]pyrazin-2-yl)-pyridin-2-yl]-amine;
[(3S,5S)-1-(2-Methyl-propane-1-sulfonyl)-5-trifluoromethyl-piperidin-3-yl]-[3-(5H-pyrrolo[2,3-b]pyrazin-2-yl)-pyridin-2-yl]-amine;
(3-{(S)-3-[3-(5H-Pyrrolo[2,3-b]pyrazin-2-yl)-pyridin-2-ylamino]-piperidin-1-yl}-oxetan-3-yl)-acetonitrile;
(3-{(3S,5S)-3-Methyl-5-[3-(5H-pyrrolo[2,3-b]pyrazin-2-yl)-pyridin-2-ylamino]-piperidin-1-yl}-oxetan-3-yl)-acetonitrile;
{(3S,5S)-3-Methyl-5-[3-(5H-pyrrolo[2,3-b]pyrazin-2-yl)-pyridin-2-ylamino]-piperidine-1-sulfonyl}-acetonitrile; and
4,4,4-Trifluoro-3-{(S)-3-[3-(5H-pyrrolo[2,3-b]pyrazin-2-yl)-pyridin-2-ylamino]-piperidin-1-yl}-butyronitrile.

26. A pharmaceutical composition comprising the compound of claim 1, admixed with at least one pharmaceutically acceptable carrier, excipient or diluent.

27. The pharmaceutical composition of claim 26, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

* * * * *